United States Patent
Stuhler

(10) Patent No.: US 11,427,644 B2
(45) Date of Patent: Aug. 30, 2022

(54) DUAL ANTIGEN-INDUCED BIPARTITE FUNCTIONAL COMPLEMENTATION

(71) Applicant: JULIUS-MAXIMILIANS-UNIVERSITÄT WÜRZBURG, Würzburg (DE)

(72) Inventor: Gernot Stuhler, Tübingen (DE)

(73) Assignee: Julius-Maxmillians-Universitat Wurzburg, Wursburg (DE)

( * ) Notice: Subject to any disclaimer, the term of this patent is extended or adjusted under 35 U.S.C. 154(b) by 587 days.

(21) Appl. No.: 16/289,798

(22) Filed: Mar. 1, 2019

(65) Prior Publication Data

US 2019/0284296 A1   Sep. 19, 2019
US 2021/0188997 A9   Jun. 24, 2021

Related U.S. Application Data

(63) Continuation of application No. 14/371,910, filed as application No. PCT/EP2013/050603 on Jan. 14, 2013, now abandoned.

(30) Foreign Application Priority Data

Jan. 13, 2012 (EP) .................................. 12151125

(51) Int. Cl.
| | |
|---|---|
| *A61K 39/395* | (2006.01) |
| *C07K 16/30* | (2006.01) |
| *C07K 16/46* | (2006.01) |
| *C07K 16/28* | (2006.01) |
| *G01N 33/574* | (2006.01) |
| *A61K 39/00* | (2006.01) |

(52) U.S. Cl.
CPC ............ *C07K 16/30* (2013.01); *C07K 16/289* (2013.01); *C07K 16/2833* (2013.01); *C07K 16/3061* (2013.01); *C07K 16/468* (2013.01); *G01N 33/574* (2013.01); *A61K 2039/505* (2013.01); *C07K 2317/34* (2013.01); *C07K 2317/56* (2013.01)

(58) Field of Classification Search
CPC .. C07K 16/30; C07K 16/289; C07K 16/2833; G01N 33/574
See application file for complete search history.

(56) References Cited

U.S. PATENT DOCUMENTS

| | | | |
|---|---|---|---|
| 5,091,513 | A | 2/1992 | Huston |
| 6,054,561 | A | 4/2000 | Ring |
| 8,076,459 | B2 | 12/2011 | Hofmeister |
| 8,623,356 | B2 | 1/2014 | Christopherson |
| 2009/0130106 | A1 | 5/2009 | Christopherson |

FOREIGN PATENT DOCUMENTS

| | | |
|---|---|---|
| EP | 1536005 | 6/2005 |
| EP | 1561759 | 8/2005 |
| EP | 2133093 | 12/2009 |
| WO | WO 93/15210 | 8/1993 |
| WO | WO 94/09131 | 4/1994 |
| WO | WO 2004/016782 | 2/2004 |
| WO | WO 2004/042404 | 5/2004 |
| WO | WO 2007/062466 | 6/2007 |
| WO | WO 2010/022225 | 2/2010 |

OTHER PUBLICATIONS

Brinkman et al., "The Making of Bispecific Antibodies", 2017 *MABS*, 9(2):182-212.
Hamel et al., "Relative Noncovalent Association Constant Between Immunoglobulin H and L Chains in Unrelated to their Expression or Antigen-Binding Activity", 1987 *The Journal of Immunology*, 139(9):3012-3020.
Hu et al., "Minibody: A Novel Engineered Anti-Carcinoembryonic Antigen Antibody Fragment (Single-Chain Fv-$C_H3$) Which Exhibits Rapid, High-Level Targeting of Xenografts", 1996 *Cancer Research*, 56:3055-61.
Manakas et al., Abstract of the Poster Presentation at The 42$^{nd}$ Lorne Conference on Protein Structure and Function 2017.
Jaehde, "Dosis-Individualisierung in der Krebs-Chemotherapie", 2006 *Pharm. Unserer Zeit* 2(35):150-6.
Rothlisberger et al., "Domain Interactions in the Fab Fragment: A Comparative Evaluation of the Single-Chain Fv and Fab Format Engineered with Variable Domains of Different Stability," 2006 *J. Mol. Biol.*, 347:773-789.
Shu et al., "Secretion of a Single-Gene-Encoded Immunoglobulin From Myeloma Cells", 1993 *Proc. Natl. Acad. Sci.*, 90:7995-7999.
Summons to Attend Oral Proceedings in EP 2802607, dated Mar. 25, 2019.
Anthony et al., "Production of stable anti-digoxin Fv in *Escherichia coli*," 1992 *Mol Immunol.* 29(10):1237-47.

(Continued)

*Primary Examiner* — Mark Halvorson
(74) *Attorney, Agent, or Firm* — Mueting Raasch Group

(57) ABSTRACT

The present invention relates to a set of polypeptides and its uses. In particular, the present invention relates to a set of polypeptides whereby this set comprises two polypeptides each of which comprises a targeting moiety "T" binding to an antigen "Λ" and a fragment of "F" of a functional domain, wherein said two polypeptides are not associated with each other in absence of a substrate that has "A" at (on) its surface and wherein, upon dimerization of "F", the resulting dimer becomes functional. Furthermore, medical and diagnostic uses of said set are described. Moreover, the present invention relates to nucleic acid molecule(s) encoding said set of polypeptides. The present invention also relates to a vector comprising the nucleotide sequence of nucleic acid molecule(s) encoding said set of polypeptides. Furthermore, the present invention relates to pharmaceutical compositions comprising said set of polypeptides. Moreover, the present invention relates to a kit comprising said set of polypeptides.

16 Claims, 30 Drawing Sheets

Figure 1A:
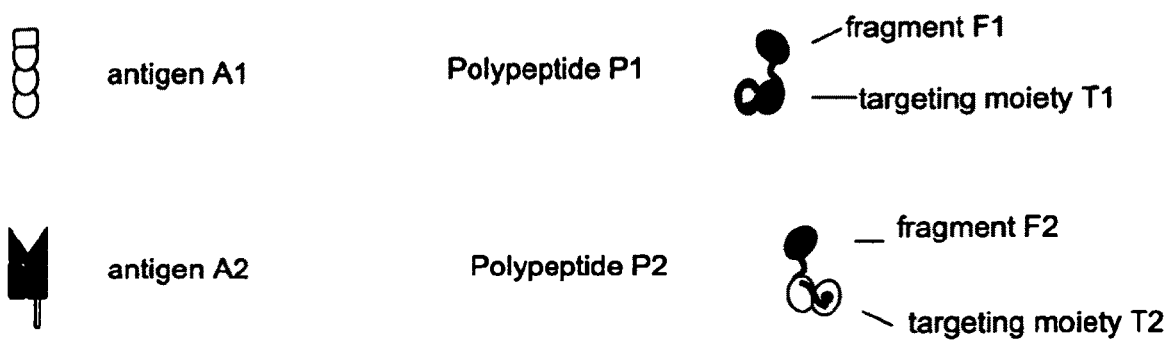

Specification includes a Sequence Listing.

(56) References Cited

OTHER PUBLICATIONS

Amit et al., "Three-dimensional structure of an antigen-antibody complex at 2.8 A resolution," 1986 *Science*, 233:747-753.
Balagurunathan et al., "Gene expression profiling-based identification of cell-surface targets for developing multimeric ligands in pancreatic cancer," 2008 *Mol Cancer Ther*, 7:3071-3080.
Banaszek et al., "Dual Antigen-Restricted Complementation of a Trispecific Antibody Construct for Targeted Immunotherapy of Blood Cancer," Abstracts for Talks and Posters, 8tth Fabisch-Symposium, 3$^{rd}$ Targeted Tumor Therapies, Berlin 2012, excerpt of https://fabisch.charite.de/AbstractsText.html, 4 pages.
Banaszek, "Dual Antigen-Restricted Complementation of a Two-Part Trispecific Antibody for Targeted Immunotherapy of Blood Cancer," Dissertation 2013.
Bargou et al., "Tumor regression in cancer patients by very low doses of a T cellengaging antibody," 2008 *Science*, 321(5891):974-977.
Barrett et al., "NCBI GEO: archive for functional genomics data sets—10 years on," 2011 *Nucleic Acids Res*, 39(Database issue):D1005-10.
"Bispecific Antibodies" by Roland E. Kontermann (editor), Springer Berlin Heidelberg; 1st Edition. (2011).
Bluemel et al., "Epitope distance to the target cell membrane and antigen size determine the potency of T cell-mediated lysis by BiTE antibodies specific for a large melanoma surface antigen," 2010 *Cancer Immunol Immunother*, 59(8):1197-209.
Cancer Genome Anatomy Project (CGAP); available on the worldwide web at cgap.nci.nih.gov/ (home page accessed Oct. 30, 2015).
Carter et al., "Identification and validation of cell surface antigens for antibody targeting in oncology," 2004 *Endocr Relat Cancer*, 11:659-87.
Chopra A. Gaussia princeps luciferase. Jan. 3, 20081 [Updated Feb. 28, 2008], In: Molecular Imaging and Contrast Agent Database (MICAD) [Internet], Bethesda (MD): National Center for Biotechnology Information (US); 2004-2013. Available from: http://www.ncbi.nlm.nih.gov/books/NBK23149/.
Colman et al., "Three-dimensional structure of a complex of antibody with influenza virus neuraminidase," 1987 *Nature*, 326:358-363.
David J. Dabbs, Diagnostic immunohistochemistry, Churchill Livingstone, 3rd edition (2010).
"Demibodies™: Dimerisation-activated therapeutic antibodies" datasheet [online], BIOLINK, Sydney, Australia, 2007 [retrieved on Jan. 1, 2007], Retrieved from the Internet:<URL: http://biolink.org.au/library/file/demibodies.pdf>; 2 pgs.
Essono et al., "A general method allowing the design of oligonucleotide primers to amplify the variable regions from immunoglobulin cDNA," 2003 *J Immunol Methods*, 279:251-266.
Frank et al., "The therapeutic promise of the cancer stem cell concept," 2010 *J Clin Invest*, 120:41-50.
Gene Expression Atlas of the European Bioinformatics Institute (EBI), available on the worldwide web at ebi.ac.uk/gxa/ (home page accessed Oct. 30, 2015).
Glockshuber et al., *Biochemistry* 29:13 62-13 67 (1990).
Goldenberg et al., "Cancer Imaging and Therapy with Bispecific Antibody Pretargeting," 2007 *Update Cancer Ther*, 2(1):19-31.
"Handbook of Practical Immunohistochemistry: Frequently Asked Questions" by F Lin and J Prichard, Springer New York, 1st edition (2011).
Heuser et al., "An anti-MUC1-antibody-interleukin-2 fusion protein that activates resting NK cells to lysis of MUC1-positive tumour cells," 2003, *Br. J. Cancer* 89(6): 1130-39.
Hochman et al., "An active antibody fragment (Fv) composed of the variable portions of heavy and light chains," 1973 *Biochemistry*, 12(6): 1130-5.
Hochman et al., "Folding and interaction of subunits at the antibody combining site," 1976 *Biochemistry*, 15(12):2706-10.

Horne et al., "Noncovalent association of heavy and light chains of human immunoglobulins. III. Specific interactions between $V_H$ and $V_L$," 1982 *J Immunol*. 129(2):660-4.
Human Cell Differentiation Molecules (HCDM); available on the worldwide web at hcdm.org/Home (home page accessed Oct. 30, 2015).
Inoue et al., "Gaussia luciferase for bioluminescence tumor monitoring in comparison with firefly luciferase," 2011 *Mol Imaging*, 10(5):377-85.
Jordan et al. "Evaluation of the potential use of hybrid LC-MS/MS for active drug quantification applying the 'free analyte QC concept',"2017 *Bioanalysis* 9(21): 1705-1717.
Kain et al., "Green fluorescent protein as a reporter of gene expression and protein localization," 1995 *Biotechniques*, 19(4):650-55 (abstract only).
Kawashima et al., EpCAM- and EGFR-targeted selective gene therapy for biliary cancers using Z33-fiber-modified adenovirus, Sep. 2011, Int. J. Cancer 129(5): 1244-53, (Published online Nov. 8, 2010).
Kerppola, "Visualization of molecular interactions using bimolecular fluorescence complementation analysis: characteristics of protein fragment complementation," 2009 *Chem Soc Rev*, 38:2876-86.
Kimura et al., 2D7 diabody bound to the alpha2 domain of HLA class I efficiently induces caspase-independent cell death against malignant and activated lymphoid cells, Dec. 2004, Biochem, Biophys. Res. Commun, 325(4):1201-9.
Kipriyanov et al., Generation and production of engineered antibodies, Jan. 2004, Mol, Biotechnol, 26(1):39-60.
Kreitman, "Immunotoxins for targeted cancer therapy," 2006 *AAPS J*, 8(3):E532-51.
Law et al., "Expression and characterization of recombinant soluble human CD3 molecules: presentation of antigenic epitopes defined on the native TCR-CD3 complex," 2002 *Int Immunol*, 14:389-400.
"Leukocyte and Stromal Cell Molecules: The CD Markers" by Zola H, Swart B, Nicholson I, and Voss E; John Wiley & Sons, 1st ed. (2007).
Linke et al., "Catumaxomab: clinical development and future directions," 2010 *MAbs*, 2:129-136.
Luker et al., "In vivo imaging of ligand receptor binding with Gaussia luciferase complementation," 2011 *Nature Medicine*, 18(1):172-177.
Mack et al., "A small bispecific antibody construct expressed as a functional single-chain molecule with high tumor cell cytotoxicity," 1995 *Proc Natl Acad Sci*, 92(15):7021-7025.
Maetzel et al., "Nuclear signalling by tumour-associated antigen EpCAM," 2009 *Nat Cell Biol*, 11 (2): 162-171.
Magde et al., "Thermodynamic Fluctuation in a Reacting System—Measurement by Fluorescence Correction Spectroscopy," 1972 *Physical Review Letters*, 29(11):705-708.
Masuda et al., "Loss or down-regulation of HLA class I expression at the allelic level in freshly isolated leukemic blasts." 2007 *Cancer Sci*. 98:102-108.
Miller et al., Design, construction, and in vitro analyses of multivalent antibodies, May 2003, *J. Immunol*. 170(9):4854-61.
Müller and Kontermann, "Bispecific antibodies for cancer immunotherapy: Current perspectives," 2010 *BioDrugs*, 24(2):89-98 (abstract only).
Munz et al., "Side-by-side analysis of five clinically tested anti-EpCAM monoclonal antibodies," 2010 *Cancer Cell Int*, 10:44.
Nagai et al., "A variant of yellow fluorescent protein with fast and efficient maturation for cell-biological applications," 2002 *Nat Biotechnol*, 20(1):87-90.
Ohiro et al., A homogeneous and noncompetitive immunoassay based on the enhanced fluorescence resonance energy transfer by leucine zipper interaction, Nov. 2002, Anal. Chem, 74(22):5786-92.
Ohmuro-Matsuyama (2012) Detection of Protein Phosphorylation by Open-Sandwich Immunoassay, Integrative Proteomics, Dr. Hon-Chiu Leung (Ed.), ISBN: 978-953-51-0070-6.
Orlandi et al., "Cloning immunoglobulin variable domains for expression by the polymerase chain reaction," 1989 *Proc Natl Acad Sci USA*, 86(10):3833-3837.

(56) References Cited

OTHER PUBLICATIONS

Ossenkoppele et al., "Review of the relevance of aberrant antigen expression by flow cytometry in myeloid neoplasms," 2011 *Br J Haematol*, 153(4):421-36.

Pastan et al., "Immunotoxin treatment of cancer," 2007 *Annu Rev Med*, 5 8:221-37.

PCT Patent Application No. PCT/EP2013/050603, filed Jan. 14, 2013, International Preliminary Report on Patentability dated Jul. 24, 2014, 12 pages.

Pezard et al., "Contribution of individual toxin components to virulence of *Bacillus anthracis*," 1991 *Infect Immun*, 59 (10):3472.

Pluckthun et al., "New protein engineering approaches to multivalent and bispecific antibody fragments," 1997 *Immunotech*, 3:83-105.

Pluckthun, "Mono- and bivalent antibody fragments produced in *Escherichia coli*: engineering, folding and antigen binding," 1992 *Immunological Reviews*, 130:151-188.

Polymenis et al., "Domain interactions and antigen binding of recombinant anti-Z-DNA antibody variable domains. The role of heavy and light chains measured by surface plasmon resonance," 1995 *J Immunol.* 154(5):2198-208.

Protein Surface Recognition: Approaches for Drug Discovery: Approaches for the Inhibition of Protein-Protein Interactions for Drug Discovery (Eds: Ernest Giralt, Mark Peczuh, Xavier Salvatella John Wiley & Sons; Nov. 12, 2010).

Protein-Protein Interactions: Methods and Applications: 261 (Methods in Molecular Biology); Haian Fu (Editor); Humana Press; 1 (Mar. 23, 2004).

Reichert et al., "The future of antibodies as cancer drugs," 2012 *Drug Discov Today*, 17:954-963.

Remy et al., "A highly sensitive protein-protein interaction assay based on Gaussia luciferase," 2006 *Nature Methods*, 3:977-979.

Rheinnecker et al., Multivalent antibody fragments with high functional affinity for a tumor-associated carbohydrate antigen, Oct. 1996, J. Immunol, 157(7):2989-97.

Santos et al., "Sensitive in vivo imaging of T cells using a membrane-bound Gaussia princeps luciferase," 2009 *Nat Med*, 15(3):338-44.

Seifert et al., The IgM CH2 domain as covalently linked homodimerization module for the generation of fusion proteins with dual specificity, Oct. 2012, Prot. Eng, Des. Sel. 25(10):603-12. (Published online Sep. 17, 2012.).

Singapore U.S. Appl. No. 11/201,403 997S filed Jan. 14, 2013; Written Opinion dated Jun. 2, 2015; 13 pages.

The Cancer Genome Characterization Initiative (CGCI); available on the worldwide web at cgap.nci.nih.gov/cgci.html (home page accessed Oct. 30, 2015).

Topp et al., "Targeted therapy with the T-cell-engaging antibody blinatumomab of chemotherapy-refractory minimal residual disease in B-lineage acute lymphoblastic leukemia patients results in high response rate and prolonged leukemia-free survival," 2011 *J Clin Oncol*, 29:2493-8.

Ueda et al., "Open sandwich ELISA: a novel immunoassay based on the interchain interaction of antibody variable region," 1996 *Nature Biotechnology*, 14(13):1714-1718.

UniProtKB/Swiss-Prot Accession No. P03276 (Human adenovirus 2 Penton protein), accessed on Oct. 30, 2015, at http://www.ncbi.nlm.nih.gov/protein/p03276.

UniProtKB/Swiss-Prot Accession No. P06473 (Human herpesvirus 5 strain AD 169 envelope glycoprotein B), accessed on Oct. 30, 2015, at http://www.ncbi.nlm.nih.gov/protein/p06473.

UniProtKB/Swiss-Prot Accession No. P13285 (Epstein-Barr virus latent membrane protein 2), accessed on Oct. 30, 2015, at http://www.ncbi.nlm.nih.gov/protein/p13285.

UniProtKB/Swiss-Prot Accession No. Q6TRB1 (Hepatitis C virus E2 polypeptide) accessed on Oct. 30, 2015, at http://www.ncbi.nlm.nih.gov/protein/q6trb1.

UniProtKB/Swiss-Prot Accession No. Q9JG36 (Hepatitis B virus HBS antigen), accessed on Oct. 30, 2015, at http://www.ncbi.nlm.nih.gov/protein/q9jg36.

UniProtKB/Swiss-Prot Accession No. Q78706 (Human immunodeficiency virus 1 (HIV-1) Gpl20 protein), accessed on Oct. 30, 2015, at http://www.ncbi.nlm.nih.gov/protein/q78706.

Van Beusechem et al., Efficient and selective gene transfer into primary human brain tumors by using single-chain antibody-targeted adenoviral vectors with native tropism abolished, Mar. 2002, J. Virol, 76(6):2753-62.

Van Dam et al., "Intraoperative tumor-specific fluorescence imaging in ovarian cancer by folate receptor-α a targeting: first in-human results," 2011 *Nat Med*, 17(10):1315-9.

Vassilopoulos et al., "Identification and characterization of cancer initiating cells from BRCA1 related mammary tumours using markers for normal mammary stem cells," 2008 *Int J Biol Sci*, 4:133-142.

Wang et al., "A new recombinant single chain trispecific antibody recruits T lymphocytes to kill CEA (carcinoma embryonic antigen) positive tumor cells in vitro efficiently." 2004 *J Biochem.* 135(4):555-65.

Wang et al., "Universal PCR amplification of mouse immunoglobulin gene variable regions: the design of degenerate primers and an assessment of the effect of DNA polymerase 3' to 5' exonuclease activity," 2000 *J Immunol Methods*, 233(1-2):167-177.

Ward et al., "Binding activities of a repertoire of single immunoglobulin variable domains secreted from *Escherichia coli*," 1989 *Nature* 341(6242):544-6.

Worn et al., "Stability engineering of antibody single-chain Fv fragments," 2001 *J Mol Biol*, 305:989-1010.

Xie et al., A new format of bispecific antibody: highly efficient heterodimerization, expression and tumor cell lysis, Jan. 2005, J. Immunol. Methods 296(1-2):95-101.

Zhao et al., Therapeutic applications of superantibodies, Sep. 2005, Drug Discover, Today 10(18):1231-36.

Zhou et al., "Surface antigen profiling of colorectal cancer using antibody microarrays with fluorescence multiplexing," 2010 *J Immunol Methods*, 355:40-51.

Zhu et al., "Remodeling domain interfaces to enhance heterodimer formation," 1997 *Protein Sci*, 6:781-8.

International Search Report (PCT/ISA/210) issued in connection with International Patent Application No. PCT/EP2013/050603, filed Jan. 14, 2013.

Written Opinion (PCT/ISA/237) issued in connection with International Patent Application No. PCT/EP2013/050603, filed Jan. 14, 2013.

International Preliminary Report on Patentability (PCT/IB/373) issued in connection with International Patent Application No. PCT/EP2013/050603, filed Jan. 14, 2013.

Notice of Opposition of a European Patent (in EP 2802607), dated Apr. 7, 2018.

Notice of Opposition of a European Patent (in EP 2802607), dated Mar. 7, 2018.

Results of Oral Proceedings for European Application No. 13 7043 69.1 dated Oct. 18, 2019 (15 pages).

D33-Abstract of the Poster Presentation at The 42nd Lorne Conference on Protein Structure and Function 2017 of Richard Christopherson (1 page).

D34-Adhmad et al., "scFv Antibody: Principles and Clinical Application," *Clinical and Developmental Immunology*, vol. 2012, pp. 1-15.

D35-Marks et al., "By-Passing Immunization, Human Antibodies from V-Gene Libraries Displayed on Phage," *J. Mol. Biol.*, 1991, pp. 581-597.

D36-Holliger et al., "Diabodies": Small Bivalent and Bispecific Antibody Fragments, *Proc. Natl. Acad. Sci.*, vol. 90, 1993, pp. 6444-6448.

D37-Rossi et al., "Pretargeting of Carcinoembryonic Antigen-Expressing Cancers with a Trivalent Bispecific Fusion Protein Produced in Myeloma Cells," *Clin. Cancer Res.*, 11(19), 2005, pp. 7122-7129.

D38-Declaration of Dr. Falk Nimmeijahn dated Aug. 15, 2019 (48 pages).

D41-Kontermann, Roland E., "Dual Targeting Strategies with Bispecific Antibodies," *Landes Bioscience*, 4(2), 2012, pp. 182-197.

(56) References Cited

OTHER PUBLICATIONS

D42-Muller et al., "Recombinant Bispecific Antibodies for Cellular Cancer Immunotherapy," *Curr. Opin. Mol. Ther.*, 9(4), 2007, pp. 319-326.

*85/71*  taFvCD3-HLA-A2-

*75/82*  taFvHLA-A2-CD3-

*42*  V$_L$CD3-scFvHLA-A2-

*45*  V$_H$CD3-scFvCD45(V$_L$-V$_H$)-

*55*  V$_H$CD3-scFvCD45(V$_H$-V$_L$)-

*80/78*  V$_H$CD3-scFvHLA-A2-

36   scFvCD3-FlagHis 4    scFvHLA-A2-mycHis

17   FlagHis-scFvCD45(V$_L$-V$_H$)

46   scFvCD45(V$_H$-V$_L$)-FlagHis

42   V$_L$CD3-scFvHLA-A2-mycHis

45   V$_H$CD3-scFvCD45(V$_L$-V$_H$)- FlagHis

55   V$_H$CD3-scFvCD45(V$_H$-V$_L$)- FlagHis

DUAL ANTIGEN-INDUCED BIPARTITE FUNCTIONAL COMPLEMENTATION

CONTINUING APPLICATION DATA

This application is a continuation application of U.S. application Ser. No. 14/371,910, filed Jul. 11, 2014, which is a U.S. National Stage Application of International Application No. PCT/EP2013/050603, filed Jan. 14, 2013, which was published in English on Jul. 18, 2013, as International Publication No. WO 2013/104804 A2. International Application No. PCT/EP2013/050603 claims priority to European Application No. 12151125.7 filed Jan. 13, 2012. A certified copy of European Application No. 12151125.7 filed Jan. 13, 2012, was provided in and is available in, U.S. patent application Ser. No. 14/371,910.

SEQUENCE LISTING

This application contains a Sequence Listing electronically submitted via EFS-Web to the United States Patent and Trademark Office as an ASCII text filed entitled "0258.000029US02_ST25.txt" having a size of 240 kilobytes and created on Feb. 28, 2019. The information contained in the Sequence Listing is incorporated by reference herein.

The present invention relates to a set of polypeptides and its uses. In particular, the present invention relates to a set of polypeptides whereby this set comprises two polypeptides each of which comprises a targeting moiety "T" binding to an antigen "A" and a fragment of "F" of a functional domain, wherein said two polypeptides are not associated with each other in absence of a substrate that has "A" at (on) its surface and wherein, upon dimerization of "F", the resulting dimer becomes functional. Furthermore, medical and diagnostic uses of said set are described. Moreover, the present invention relates to nucleic acid molecule(s) encoding said set of polypeptides. The present invention also relates to a vector comprising the nucleotide sequence of nucleic acid molecule(s) encoding said set of polypeptides. Furthermore, the present invention relates to pharmaceutical compositions comprising said set of polypeptides. Moreover, the present invention relates to a kit comprising said set of polypeptides.

The last years have seen a number of landmark papers reporting outstanding efficacy of bispecific antibody constructs for immune therapy of tumours in vitro and in pre-clinical and early clinical trials. Today, a substantial number of different bispecific constructs are available that differ in size, composition, pharmacokinetics and ability to directly eliminate neoplastic cells or to engage immune effector cells for tumour cell lysis.

Antibody-based cancer immune strategies are highly promising therapeutic options due to their excellent sensitivity and specificity towards target structures.

The modular structural and functional organisation of antibodies allows extensive manipulation by genetic engineering. Different immunoglobulin-like domains can be separated and/or joined without losing specific domain-associated functional features. Moreover, they can be combined and linked with heterologous protein domains but also with non-peptidic moieties. It is therefore possible to develop fusion constructs in a rational way devoid of the natural limitations of conventional antibodies.

Antibody-based fusion proteins can be generated with novel biological and/or pharmaceutical properties. There are promising efforts to modify the capability of the Fc domain to elicit ADCC (antibody dependent cell mediated cytotoxicity) and CDC (complement-dependent cytotoxicity) by mutagenesis, dependent on the intended application, either to reduce side effects (inhibitory mutations) or to enhance therapeutic efficacy (activating mutations). New applications that become possible by genetic engineering are even more variate when the antigen binding domain of antibodies is considered.

The antigen recognizing variable domains of the heavy ($V_H$) and light chain ($V_L$) of an antibody can be joined by a peptide linker via genetic engineering while preserving the antigen binding capability. Such antigen binding single chain variable fragments (scFvs) can be used as small antibody surrogates with high tissue penetrating capability and low serum retention time for clinical imaging procedures and radiotherapy and other applications. Importantly, these scFv moieties can be easily employed as antigen specific modules in the development of novel recombinant therapeutics.

Recent reports indicate a tremendous potential of recombinant bispecific antibodies in anti-tumour therapy. Such bispecific antibodies recognise two antigens, one of which is expressed by the tumour, whereas the other is usually found on an immune cell. Most bispecific antibodies in anti-tumour therapy target a tumour-associated lineage marker on the one hand and CD3ε, an invariant molecule of the T-cell receptor/CD3 complex on the other hand, thus recruiting T cells to destroy the tumour [Müller and Kontermann, Bispecific antibodies for cancer immunotherapy: Current perspectives. BioDrugs 2010, 24(2):89-98].

Despite the extensive options for manipulating antibody structure and function, the therapeutic efficacy of such antibody-based reagents is limited by the nature of the addressed antigen, the accessibility of the antigen in tumour and tumour-associated tissues and the aptitude of the antibody to elicit or mediate the desired cell death inducing function.

For example, when patients are treated with bispecific constructs directed against antigens also expressed on tissues with vital functions, severe side effects are observed. This is a severe problem, since, with the exception of an unknown number of individually mutated cell surface molecules and the monoclonal B- or T-cell receptor in case of lymphomas, tumour specific antigens that discriminate a transformed cell from its healthy progenitor are not available.

Since therapeutic concepts based on the use of bispecific antibodies usually rely on the recruitment of effector cells, it appears that the more effective the tool (bispecific construct), the more likely side effects do occur, and even minute expression of antigen on non-transformed tissue can cause uncontrollable off-target effects.

In 2008, SCIENCE published the first report on the clinical efficacy of the single-chain bispecific T cell engaging (BiTE) antibody MT103/blinatumomab; it induces remissions in about 80% of lymphoma patients relapsed or refractory to standard immune-chemotherapy at serum levels about 5 orders of magnitude lower than serum levels reported for the monoclonal antibody rituximab (Bargou, R. et al Science 321, 974-977, 2008). This publication and subsequent reports on confirmatory phase II trials in acute lymphatic leukemia (ALL) ushered in a new era of bispecific antibodies, until then in grave demise for almost two decades due to systemic toxicity and little or no therapeutic activity. Mainly in the wake of that SCIENCE paper, bispecific antibodies became a burgeoning field again in which more than 35 different formats were counted (Reichert, *Drug*

*Discov Today.* 17 (2012) 954-963). These formats differ in size and are optimized for affinity to the antigen, stability, ability to recruit effector cells (mostly T cells) and pharmacokinetics. Affinity or avidity of the constructs are manipulated by affinity maturation using diverse techniques or simply by joining multiple scFv domains in line in order to create a multivalent construct. Even trispecific antibodies are reported that are designed to display enhance binding capabilities by addressing two instead of one target molecule. Stability of the formats can be optimized by adding immunoglobulin-like domains in order to mimic naturally occurring antibodies and to simultaneously enhance pharmacokinetic properties like prolonged half life in serum and protection from proteolytic digestion by proteases. Moreover, stability of the formats can be enhanced by optimizing the production. Since linker sequences which are utilized to covalently join scFv domains often leads to aggregates, production lines have been established that first produce two or three polypeptides that can be easily reassembled in order to generate a functional drug. Such techniques utilize directed disulphid-bridges or crosslinking reagents to covalently join two different polypeptides. Other techniques make use of hetero- or homo-dimerization domains like leucine-zipper domains, Fc-domains and others like knob into hole technologies (see, for example, WO 2007/062466). Moreover, $V_H$ and $V_L$ interactions, which can be stabilized by the binding of the antigen, have been used in so called open-sandwich immunoassays for the detection of the antigen (Ueda, Nature Biotechnology 14 (1996), 1714-1718; Ohmuro-Matsuyama (2012) Detection of Protein Phosphorylation by Open-Sandwich Immunoassay, Integrative Proteomics, Dr. Hon-Chiu Leung (Ed.), ISBN: 978-953-51-0070-6; WO 2004/016782/EP-A1 1536005.)

However, bi/tri-specific and bi- or multivalent constructs described in the art have disadvantages. First, the absence of truly specific tumor antigens that can be addressed as target molecule. In fact, the more potent the bispecific antibody format, the more severe are collateral damages, because the target antigens addressed so far are differentiation antigens shared by tumours and non-malignant cells. In consequence, bi- or tri-specific formats of the prior art cannot discriminate malignant from non-malignant cells. In this respect, tri-specific constructs, developed for high avidity binding to target cells, may turn out to confer a high degree of off-target effects because binding of one target molecule in general suffice to recruit immune cells for destruction of a cell which express either target molecule. Thus, tri-specific construct enhance avidity on the cost of specificity. Recent multiparameter analyses indicate that tumor cells can be distinguished from their respective non-transformed tissues of origin because of the expression of aberrant antigen signatures. Today, these findings constitute an integral part of the World Health Organization (WHO) classification system of hematopoietic neoplasms, and also hold true for cancer and cancer stem or cancer initiating cells of other provenance. Thus, it would be advantageous to target cells that simultaneously express a combination of antigens that together signify a malignant state. None of the antibodies disclosed by prior art is able to discriminate between cells that express a combination of target antigens from single antigen positive cells. Second, a major problem of bi-specific antibody technologies using, for example, complete CD3 modules (e.g. a anti Cd3 scFv) is the inherent ability of these proteins to stimulate or pre-stimulate T cells irrespective of binding to the target antigen on target cells and many side effects observed so far appear to be associated with errant T cell function.

Thus, there is a need in the art for more specific treatment options in cancer treatment, in particular there is a need for improved ways to identify and/or eliminate cancer cells with higher specificity and reduce side-effects.

Similar needs exist in the field of allogeneic stem cell transplantation, i.e. the transplantation of stem cells obtained from another person to a patient. A patient suffering from relapsed or refractory leukaemia or another haematological disease may be treated by chemotherapy/irradiation (to eliminate the malignant haematopoietic cells) in combination with a transplantation of healthy haematopoietic cells from a donor. If elimination of malignant cells is incomplete, the tumour may grow back from the surviving malignant recipient cells despite the presence of healthy cells provided by the transplantation. As a result, survival rates among patients undergoing tumour treatment and allogeneic transplantation are significantly reduced.

However, it is difficult to eliminate (and, similarly, to identify) the surviving malignant cells with high specificity, and thus despite various attempts, good solutions to this problem have not been found. Accordingly, there exists a need in the art to provide improved ways to specifically identify and/or eliminate such malignant recipient cells with minimal side effects on other cells.

The graft (allogenic stem cells), given shortly after the conditioning therapy (radiation/chemotherapy) can replace and reconstitute hematopoiesis. The graft is harvested from either bone marrow or from stimulated peripheral blood cells and contains about one percent of hematopoetic stem cells which are the source of newly built blood cells. In addition, the graft normally contains a huge number of immune cells, especially T lymphocytes, that are part of the adoptive immune system and that can be very beneficial in cases where these T cells mount an immune attack against leukemic cells. This situation is well described and known as graft versus leukemia effect. On the other side, an errant immune response which directs T cells against the patient, known as graft versus host disease, is also frequently observed.

To minimize graft versus host disease, grafts are usually selected on the basis of HLA (human leukocyte antigen) or MHC (major histocompatibility complex). The closer the antigens between donor and recipient match the lower is the probability of severe graft versus host disease. However, for many patients, a full matched graft cannot be found. In these cases, a bone marrow or peripheral blood stem cells are utilized that differ in one or even more HLA molecules. These clinical situation requires a strict immunosuppressive regimen after transplantation to keep the T cell system strictly under control.

It is therefore one object of the present invention to provide for improved ways to specifically identify and/or eliminate specific kinds of cells. Moreover, it is an object of the present invention to provide for improved ways to specifically identify and/or eliminate cells that have a specific combination of two specific antigens at their cell surface. Furthermore, it is an object of the present invention to provide for improved ways to specifically identify and/or eliminate cancerous cells. Furthermore, it is an object of the present invention to provide for improved ways to specifically identify and/or eliminate cells that (1) are of a certain origin (such as, in the situation of a tissue or cell transplantation, cells originating from the recipient or from the donor) and that (2) belong to a specific cell type or cell lineage (such as haematopoietic cells).

The objects of the present invention are solved by a set of polypeptides comprising:
a first polypeptide P1 comprising
(i) a targeting moiety T1,
wherein said targeting moiety T1 specifically binds to an antigen A1, and
(ii) a fragment F1 of a functional domain F,
wherein neither said fragment F1 by itself nor said polypeptide P1 by itself is functional with respect to the function of said domain F,
and
a second polypeptide P2 comprising
(i) a targeting moiety T2,
wherein said targeting moiety T2 specifically binds to an antigen A2, and
(ii) a fragment F2 of said functional domain F,
wherein neither said fragment F2 by itself nor said polypeptide P2 by itself is functional with respect to the function of said domain F,
wherein said antigen A1 is different from said antigen A2,
wherein said polypeptide P1 and said polypeptide P2 are not associated with each other in the absence of a substrate that has both antigens A1 and A2 at or on its surface, more specifically a cell that carries both antigens A1 and A2 at or on its cell surface, and wherein, upon dimerization of said fragment F1 of said polypeptide P1 with said fragment F2 of said polypeptide P2, the resulting dimer is functional with respect to the function of said domain F.

The objects of the present invention are also solved by a set of polypeptides comprising:
a first polypeptide P1 comprising
(i) a targeting moiety T1,
wherein said targeting moiety T1 specifically binds to an antigen A1, and
(ii) a fragment F1 of a functional domain F,
wherein neither said fragment F1 by itself nor said polypeptide P1 by itself is functional with respect to the function of said domain F,
and
a second polypeptide P2 comprising
(i) a targeting moiety T2,
wherein said targeting moiety T2 specifically binds to an antigen A2, and
(ii) a fragment F2 of said functional domain F,
wherein neither said fragment F2 by itself nor said polypeptide P2 by itself is functional with respect to the function of said domain F,
wherein said antigen A1 is different from said antigen A2,
wherein
(a) said fragment F1 comprises a $V_L$ domain of an antibody and said fragment F2 comprises a $V_H$ domain of the same antibody; or wherein said fragment F1 comprises a $V_H$ domain of an antibody and said fragment F2 comprises a $V_L$ domain of the same antibody; or
(b) said fragment F1 comprises a $V_L$ domain of an antibody and said fragment F2 comprises a $V_H$ domain of the same antibody; or wherein said fragment F1 comprises a $V_H$ domain of an antibody and said fragment F2 comprises a $V_L$ domain of the same antibody; and
wherein said polypeptide P1 and said polypeptide P2 are not associated with each other in the absence of a substrate that has both antigens A1 and A2 at or on its surface, more specifically a cell that carries both antigens A1 and A2 at or on its cell surface, and
wherein, upon dimerization of said fragment F1 of said polypeptide P1 with said fragment F2 of said polypeptide P2, the resulting dimer is functional with respect to the function of said domain F.

The objects of the present invention are also solved by a set of polypeptides comprising:
a first polypeptide P1 comprising
(i) a targeting moiety T1,
wherein said targeting moiety T1 specifically binds to an antigen A1, and
(ii) a fragment F1 of a functional domain F,
wherein neither said fragment F1 by itself nor said polypeptide P1 by itself is functional with respect to the function of said domain F,
and
a second polypeptide P2 comprising
(i) a targeting moiety T2,
wherein said targeting moiety T2 specifically binds to an antigen A2, and
(ii) a fragment F2 of said functional domain F,
wherein neither said fragment F2 by itself nor said polypeptide P2 by itself is functional with respect to the function of said domain F,
wherein said antigen A1 is different from said antigen A2,
wherein
(c) said fragment F1 comprises a $V_L$ domain of an antibody and said fragment F2 comprises a $V_H$ domain of the same antibody; or wherein said fragment F1 comprises a $V_H$ domain of an antibody and said fragment F2 comprises a $V_L$ domain of the same antibody;
(d) said polypeptide P1 and said polypeptide P2 are not associated with each other in the absence of a substrate that has both antigens A1 and A2 at its surface, more specifically a cell that carries both antigens A1 and A2 at its cell surface; or
(e) said fragment F1 comprises a $V_L$ domain of an antibody and said fragment F2 comprises a $V_H$ domain of the same antibody; or wherein said fragment F1 comprises a $V_H$ domain of an antibody and said fragment F2 comprises a $V_L$ domain of the same antibody; and
wherein said polypeptide P1 and said polypeptide P2 are not associated with each other in the absence of a substrate that has both antigens A1 and A2 at its surface, more specifically a cell that carries both antigens A1 and A2 at its cell surface, and
wherein, upon dimerization of said fragment F1 of said polypeptide P1 with said fragment F2 of said polypeptide P2, the resulting dimer is functional with respect to the function of said domain F, and wherein said polypeptides P1 and P2, in particular said fragments F1 and F2, have, in the absence of a substrate or cell, with each other a dissociation constant $K_D$ in the range of $10^{-8}$ M to $10^{-2}$ M.

The present invention further refers to the following items:
1. A set of polypeptides comprising:
a first polypeptide P1 comprising
(i) a targeting moiety T1,
wherein said targeting moiety T1 specifically binds to an antigen A1, and
(ii) a fragment F1 of a functional domain F,
wherein neither said fragment F1 by itself nor said polypeptide P1 by itself is functional with respect to the function of said domain F,
and a second polypeptide P2 comprising
   (i) a targeting moiety T2,
      wherein said targeting moiety T2 specifically binds to an antigen A2, and
   (ii) a fragment F2 of said functional domain F,
wherein neither said fragment F2 by itself nor said polypeptide P2 by itself is functional with respect to the function of said domain F,
wherein said antigen A1 is different from said antigen A2,
wherein said polypeptide P1 and said polypeptide P2 are not associated with each other in the absence of a substrate that has both antigens A1 and A2 at its surface, more specifically a cell that carries both antigens A1 and A2 at its cell surface, and
wherein, upon dimerization of said fragment F1 of said polypeptide P1 with said fragment F2 of said polypeptide P2, the resulting dimer is functional with respect to the function of said domain F.

2. The set of polypeptides according to item 1, wherein a cell carrying both antigens A1 and A2 at its cell surface induces dimerization of the fragment F1 of said polypeptide P1 with the fragment F2 of said polypeptide P2, whereas a cell which does not carry both antigens A1 and A2 at its cell surface does not induce dimerization of the fragment F1 of said polypeptide P1 with the fragment F2 of said polypeptide P2.

3. The set of polypeptides according to item 1 or 2, wherein said targeting moiety T1 comprises an immunoglobulin module, preferably an immunoglobulin module I1 comprising a $V_L$ domain linked to a $V_H$ domain, more preferably an immunoglobulin module I1 that comprises a scFv (single-chain variant fragment) of an antibody, or an immunoglobulin module comprising a variable domain $V_HH$ of a llama antibody, camel antibody or shark antibody,
and/or said targeting moiety T2 comprises an immunoglobulin module, preferably an immunoglobulin module I2 comprising a $V_L$ domain linked to a $V_H$ domain, more preferably an immunoglobulin module I2 that comprises a scFv (single-chain variant fragment) of an antibody, or an immunoglobulin module comprising a variable domain $V_HH$ of a llama antibody, camel antibody or shark antibody,
or wherein said targeting moiety T1 and/or said targeting moiety T2 comprises an aptamer or a natural ligand of said antigen A1 or antigen A2, respectively 4. The set of polypeptides according to any of the preceding items, wherein said antigen A1 and/or said antigen A2 is an antigen expressed on the surface of cells of a tumour or on the surface of progenitor/precursor cells of a tumour, preferably an antigen expressed on the surface of cells of a haematologic tumour or an antigen expressed on the surface of cells of a non-haematologic tumour.

5. The set of polypeptides according to any of the preceding items, wherein the combination of antigen A1 and antigen A2 is only found on cancerous cells, and not on cells that are not cancerous, and wherein, preferably, the combination of antigen A1 and antigen A2 is specific for cancerous cells of a certain type of cancer.

6. The set of polypeptides according to any of the preceding items, wherein said antigen A1 is an MHC antigen, preferably an allelic variant of any of HLA-A, HLA-B, HLA-C, HLA-DQ, HLA-DR, or HLA-DM, more preferably an allelic variant of an MHC class I molecule, even preferably an allelic variant selected from the group consisting of HLA-A1, HLA-A2, HLA-A3, HLA-A25, HLA-B7, HLA-B8, HLA-B35, HLA-B44, HLA-Cw3, HLA-Cw4, and HLA-Cw7, and/or said antigen A2 is an antigen that is specific for a certain cell type or cell lineage.

7. The set of polypeptides according to any of the preceding items, wherein said functional domain F is an immunoglobulin module, preferably a scFv (single-chain variant fragment) of an antibody, or a fluorescent molecule, preferably GFP or a GFP variant, or a molecule capable of mediating bioluminescence, preferably *Gaussia luciferase*.

8. The set of polypeptides according to any of the preceding items, wherein said functional domain F is a domain that specifically binds to a carrier molecule, preferably a carrier molecule that is a peptide or a carbohydrate molecule, or an affinity tag, preferably an affinity tag selected from the group consisting of a FLAG-tag, a myc-tag, a glutathione-S-transferase (GST)-tag, a hemagglutinin (HA)-tag, a polyhistidine (His)-tag and a maltose binding protein (MBP)-tag.

9. The set of polypeptides according to any of the preceding items, wherein said functional domain F is a domain that specifically binds to a radioactive compound, a domain that specifically binds to a toxin molecule that by itself is not capable of penetrating through the cell membrane of a human cell and that is internalized into a human cell upon association with the cell membrane of said cell, a domain that specifically binds to a fluorescent molecule, or a domain that specifically binds to a molecule capable of mediating bioluminescence.

10. The set of polypeptides according to any of the preceding items, wherein said fragment F1 comprises a $V_L$ domain of an antibody and said fragment F2 comprises a $V_H$ domain of the same antibody, wherein, preferably, said antibody is an anti-CD3 antibody, or wherein said fragment F1 comprises a $V_H$ domain of an antibody and said fragment F2 comprises a $V_L$ domain of the same antibody, wherein, preferably, said antibody is an anti-CD3 antibody.

11. The set of polypeptides according to any of the preceding items for use in the treatment of a patient who is suffering from a tumour or for diagnostic use in a patient who is suffering from a tumour, preferably for use in the treatment of a patient who is suffering from a tumour and undergoing allogeneic tissue or cell transplantation or meant to undergo such transplantation or for diagnostic use in a patient who is suffering from a tumour and undergoing or meant to undergo allogeneic tissue or cell transplantation, wherein, preferably, said set of polypeptides is administered to said patient.

12. A nucleic acid molecule or a set of nucleic acid molecules encoding the set of polypeptides or one of the polypeptides of the set of polypeptides according to any of the preceding items.

13. A vector comprising the nucleotide sequence of the nucleic acid molecule according to item 12 or the sequence of one of the nucleic acid molecules of the set of nucleic acid molecules according to item 12.

14. A pharmaceutical composition comprising either the set of polypeptides according to any of items 1 to 11 or the nucleic acid molecule/set of nucleic acid molecules according to item 12 or the vector according to item 13, wherein, preferably, said pharmaceutical composition further comprises a pharmaceutically acceptable carrier.

15. A kit comprising the set of polypeptides according to any of items 1-11.

Preferably, said antigen A1 is a cell surface molecule.
Preferably, said antigen A2 is a cell surface molecule.

Preferably, said antigen A1 is specific for the malignant state of a cell. Preferably, said antigen A2 is specific for a certain cell type or cell lineage or for the malignant state of a cell. Preferably, said antigen A1 is specific for a malignant cell type. Preferably, said antigen A2 is specific for a malignant cell type.

In one aspect, the present invention relates to the set of polypeptides as defined and described herein, wherein, however, the antigen A1 is the same as the antigen A2. Hence, in such a set of polypeptides P1 and P2, the F1 fragment may be linked to the targeting moiety T1 and the F2 fragment may be linked to the targeting moiety T2, whereas both T1 and T2 specifically bind to the same antigen. In this context, the epitope on antigen A1, to which the targeting moiety T1 binds, may be the same or a different epitope as the epitope on the antigen A2, to which the targeting moiety T2 binds. In case the epitope on antigen A1 is the same as the epitope on the antigen A2, polypeptide P1 may comprise a targeting moiety which is identical to the targeting moiety comprised in P2. Also this aspect of the invention is based on the advantage that the set of polypeptides P1 and P2 with the disrupted F domain displays no off target effects (for example no pre-activation of CD3-displaying T cells and, hence, less toxic properties and/or side effects, for example as compared to conventional bispecific antibodies).

In one embodiment, said fragment F1 and said fragment F2 together are said functional domain F.

In one embodiment, said polypeptide P1 and said polypeptide P2 are not covalently linked to each other in the absence of a substrate that has both antigens A1 and A2 at its surface, more specifically a cell that carries both antigens A1 and A2 at its cell surface.

In one embodiment, said polypeptide P1 and said polypeptide P2 are not covalently linked to each other.

Said polypeptide P1 and polypeptide P2 and/or, in particular, said fragment F1 and fragment F2 as comprised therein, more particular the $V_H$ and $V_L$ which may be comprised therein, are not associated with each other, in particular when administered to a subject in need of medical intervention. i.e. in need of therapy and/or diagnosis. Accordingly, the pharmaceutical or diagnostic means provided herein comprise the two polypeptides P1 and P2 as comprised in the herein defined "set of polypeptides" in non-associated form. The association of said two polypeptides take place in vivo under the presence of said substrate or cell. Under the presence of said substrate or cell, the association of said two polypeptides may be (further) stabilized by a stabilizing agent (for example an antigen, like, for example, CD3, HIS or DIG as described herein). Preferably, they are not associated with each other in the absence of said substrate or cell and/or do not dimerizise in the absence of said substrate or cell. More preferably, they are not associated with each other in the absence of said substrate or cell and/or do not dimerizise in the absence of said substrate or cell even if an agent is present which stabilizes association and/or dimerization of polypeptide P1 and polypeptide P2 and/or, in particular, fragment F1 and fragment F2, i.e. even if said polypeptide P1 and polypeptide P2 and/or, in particular, said fragment F1 and fragment F2 is present in an stabilizing agent/P1(F1)/P2(F2)-trimeric complex (for example in an antigen/VH/VL-trimeric complex).

In one specific embodiment, said polypeptide P1 and polypeptide P2 and/or, in particular, said fragment F1 and fragment F2 as comprised therein, more particular the $V_H$ and $V_L$ which may be comprised therein, are associated with each other and/or dimerizise into a three-part-complex-formation, preferably by an interaction mediated by an agent which stabilizes association and/or dimerization of polypeptide P1 and polypeptide P2 and/or, in particular, fragment F1 and fragment F2 (for example by an antigen-mediated interaction). Most preferably, however, this association and/or dimerization only occurs in the presence of said substrate or cell.

The affinity strength with which, for example, leucine-zippers and/or constant domains, like immunoglobulin CH3 or Fc fragments, hetero- and homodimerize is estimated to be at a dissociation constant $K_D$ in the range of ~$10^{-8}$ to $10^{-11}$ M (see, for example, Zhu (1997) Protein Sci. 6, 781-8; Plückthun (1997) Immunotech. 3, 83-105). This $K_D$ range is clearly below the $K_D$ with which, in the absence of said substrate or cell, association and/or dimerization of said polypeptides P1 and P2, in particular of said fragments F1 and F2, of this invention might occur. Hence, in one embodiment, polypeptide P1 and polypeptide P2 and/or, in particular, fragment F1 and fragment F2 as comprised therein, more particular the $V_H$ and $V_L$ which may be comprised therein, associate with each other and/or dimerizise in the absence of said substrate or cell only with a $K_D$ which is above the $K_D$ of, for example, hetero- and homodimerization of leucine-zippers and/or constant domains, like immunoglobulin CH3 or Fc fragments. In the presence of said substrate or cell, it is envisaged that polypeptide P1 and polypeptide P2 and/or, in particular, fragment F1 and fragment F2 as comprised therein, more particular the $V_H$ and $V_L$ which may be comprised therein, associate with each other and/or dimerizise with a $K_D$ which is in the range of the $K_D$ of, for example, hetero- and homodimerization of leucine-zippers and/or constant domains, like immunoglobulin CH3 or Fc fragments, or even below this range.

The interaction strength of, for example, isolated VH and VL domains in general is of low affinity. Using calorimetric, fluorometric or ultraviolet difference spectroscopy and/or circular dichroisma techniques, dissociation constants $K_D$ of $10^{-9}$ to $10^{-6}$ M have been determined (see, for example, Wörn J M B (2001) 305, 989-1010; Plückthun (1992) Immunological Reviews No 130). Using surface plasmon resonance techniques (SPR biosensor BIAcore or BIAcore 2000, Pharmacia) and an anti HEL-Antibody system (anti-hen egg lysozyme antibody HyHEL-10), Ueda (loc. cit.) and Ohmuro-Matsuyama (loc. cit.) found that isolated VH and VL domains do not dimerize at all ($K_a < 10^5$/M, below detection limit). However, association of the VH and VL peptides was significantly enhanced in the presence of cognate antigens ($K_a$~$10^9$/M) with a remarkable reduction of the dissociation rate of the antigen/VH/VL-trimeric complex with a calculated $K_d$~$2.73 \times 10^{-5} \pm 1.43 \times 10^{-6}$/s at 1.4 µM of the antigen. Hence, it is particularly envisaged in the context of this invention that the $K_D$ with which, in the absence of said substrate or cell, association and/or dimerization of said polypeptides P1 and P2, in particular of said fragments F1 and F2, of this invention might occur is only at, or even above, the $K_D$ or range of $K_D$ of isolated VH and VL domains, for example as has been estimated in the context of Wörn (loc. cit.), Plückthun (1992; loc. cit.), Ueda (loc. cit.) and Ohmuro-Matsuyama (loc. cit.), in particular above the $K_D$ or range of $K_D$ of the antigen/VH/VL-trimeric complex as has been estimated in the context of Wörn (loc. cit.), Plückthun (1992; loc. cit.), Ueda (loc. cit.) and Ohmuro-Matsuyama (loc. cit.). In the presence of said substrate or cell, it is envisaged that polypeptide P1 and polypeptide P2 and/or, in particular, fragment F1 and fragment F2 as comprised therein, more particular the $V_H$ and $V_L$ which may be comprised therein, associate with each other and/or dimerizise with a $K_D$ which is (far) below the $K_D$ or range of $K_D$ of isolated VH and VL domains, for example as has been estimated in the context of Wörn (loc. cit.), Plückthun (1992; loc. cit.), Ueda (loc. cit.) and Ohmuro-Matsuyama (loc. cit.), preferably at, or even below, the $K_D$ or range of $K_D$ of the antigen/VH/VL-trimeric complex as has been estimated in the context of Plückthun (loc. cit.), Ueda (loc. cit.) and Ohmuro-Matsuyama (loc. cit.)

In one aspect, polypeptide P1 and polypeptide P2 and/or, in particular, fragment F1 and fragment F2 as comprised therein, more particular the $V_H$ and $V_L$ which may be comprised therein, are not associated in the absence of said substrate or cell and/or do not dimerizise in the absence of said substrate or cell. If at all, they associate with each other and/or dimerizise in the absence of said substrate or cell only with a $K_D$ above $10^{-8}$M, preferably above $10^{-6}$ M, more preferably above $10^{-5}$ M and more preferably above $10^{-4}$M. In another aspect, if at all, they associate with each other and/or dimerizise in the absence of said substrate or cell only with a $K_D$ in the range of $10^{-8}$ M to $10^{-2}$ M, preferably $10^{-7}$ M to $10^{-3}$ M, more preferably $10^{-6}$ M to $10^{-3}$ M and even more preferably $10^{-5}$ M to $10^{-3}$ M. In another aspect, polypeptide P1 and polypeptide P2 and/or, in particular, fragment F1 and fragment F2 as comprised therein, more particular the $V_H$ and $V_L$ which may be comprised therein, are associated in the presence of said substrate or cell and/or dimerizise in the presence of said substrate or cell. In particular, they associate with each other and/or dimerizise in the presence of said substrate or cell with a $K_D$ below $10^{-6}$ M, preferably below $10^{-7}$ M, more preferably below $10^{-8}$ M and more preferably below $10^{-9}$M. They may also associate with each other and/or may dimerizise in the presence of said substrate or cell with a $K_D$ in the range of $10^{-11}$ M to $10^{-6}$ M, more preferably $10^{-11}$ M to $10^{-7}$ M and even more preferably $10^{-11}$ M to $10^{-8}$M.

In a preferred embodiment, the above even applies in case an agent is present which stabilizes association and/or dimerization of polypeptide P1 and polypeptide P2 and/or, in particular, fragment F1 and fragment F2. For example, such an stabilizing agent in accordance with this invention may be an antigen, like, for example, CD3, HIS or DIG as described herein, capable to bind to the domain F which, for example, may comprise a $V_H$ and a $V_L$ of an antibody (F1 and F2, respectively, or F2 and F3, respectively).

Being "present", in the context of this invention and, in particular, in the context of the above (i.e. with respect to said agent and/or said substrate or cell and/or said antigens A1 and A2), particularly means being present at a concentration in a range of 0.01 μM to 1 mM, in a range of 0.1 to 500 μM, in a range of 0.1 to 300 μM, in a range of 0.1 to 100 μM, in a range of 1 to 500 μM, in a range of 10 to 500 μM. Being "absent", in the context of this invention and, in particular, in the context of above (i.e. with respect to said agent and/or said substrate or cell and/or said antigens A1 and A2), particularly means being present at a concentration below the above ranges or below 1 mM, 500 μM, 300 μM, 100 μM, 10 μM, 1 μM, 0.1 μM, 0.01 μM, 0.001 μM or 1 nM wherein the lower values are preferred.

The person skilled in the art is readily in the position to measure the $K_D$ of dimerization, in particular, of P1 and P2, more particular of F1 and F2 as comprised therein, more particular of the $V_H$ and $V_L$ which may be comprised therein. Examples of respective measuring methods are x-ray crystallography; nuclear magnet resonance (NMR); isothermal calorimetry (ITC); cryo-electro microscopy (CEM); mass spectrometry (MS); surface Plasmon resonance (SPR). Such methods are, for example, described in Protein Surface Recognition: Approaches for Drug Discovery: Approaches for the Inhibition of Protein-Protein Interactions for Drug Discovery (Eds: Ernest Giralt, Mark Peczuh, Xavier Salvatella John Wiley & Sons; 12. November 2010). Further examples of respective measuring methods are circular Dichroism Analysis; small Zone Gel Filtratoion Chromatography; Fluorescence Gel Retardation; Sedimentation Equilibrium; Fluorescence Polarization Assay; Blot Overlay or Far Western Blot Analysis; Affinity Capillary Electrophoresis Analysis; Fluorescence Resonance Energy Transfer (FRET); such methods are, for example described in Protein'Protein Interactions: Methods and Applications: 261 (Methods in Molecular Biology); Haian Fu (Editor); Humana Press; 1 (23. März 2004). A preferred method to measure the $K_D$ in accordance with this invention is Fluorescence Correlation Spectroscopy (FCS). This method is, for example, described in Douglas Magde (Physical Review Letters 29, 11, 1972, S. 705-708).

In one particular aspect, the $K_{DS}$ referred to herein (i) apply to, (ii) are at or (iii) are to be measured at a temperature of 4 to 38° C., preferably 4 to 20° C. (for example 10° C.) or 20 to 38° C. (for example 30° C.), and/or a pH of 4.5 to 8 (for example a pH of 7), "Not associated" in the context of the present invention particularly means not functionally associated with respect of the function of the domain F, i.e. not allowing F1 and F2 to form a functional F. Hence, in one aspect of the invention, P1 and P2 may be bound to each other (for example covalently) as far as no functional domain F is formed by F1 and F2. It is, however, preferred that P1 and P2 are separated.

In one embodiment, said antigen A1 and/or said antigen A2 is a molecule.

In one embodiment, said antigen A1 and/or said antigen A2 is proteinaceous.

In one embodiment, said antigen A1 and/or said antigen A2 is non-proteinaceous.

In one embodiment, said targeting moiety T1 binds non-covalently to said antigen A1.

In one embodiment, said targeting moiety T2 binds non-covalently to said antigen A2.

In one embodiment, a substrate having both antigens A1 and A2 at its surface induces dimerization of the fragment F1 of said polypeptide P1 with the fragment F2 of said polypeptide P2, whereas a substrate which does not have both antigens A1 and A2 at its cell surface does not induce dimerization of the fragment F1 of said polypeptide P1 with the fragment F2 of said polypeptide P2.

In one embodiment, a cell carrying both antigens A1 and A2 at its cell surface induces dimerization of the fragment F1 of said polypeptide P1 with the fragment F2 of said polypeptide P2, whereas a cell which does not carry both antigens A1 and A2 at its cell surface does not induce dimerization of the fragment F1 of said polypeptide P1 with the fragment F2 of said polypeptide P2. In this context "induces dimerization" particularly means "allows juxtaposition and subsequent dimerization".

In one embodiment, said targeting moiety T1 comprises an immunoglobulin module and/or said targeting moiety T2 comprises an immunoglobulin module.

In one embodiment, said targeting moiety T1 comprises an immunoglobulin module I1 which comprises a $V_L$ domain linked to a $V_H$ domain, preferably an immunoglobulin module I1 that comprises a scFv (single-chain variant fragment) of an antibody, a Fab or a F(ab')$_2$ (for example with additional parts of, for example, an Fc domain) of an antibody or a complete antibody.

and/or said targeting moiety T2 comprises an immunoglobulin module I2 which comprises a $V_L$ domain linked to a $V_H$ domain, preferably an immunoglobulin module I2 that comprises a scFv (single-chain variant fragment) of an antibody a Fab or a F(ab')$_2$ (for example with additional parts of, for example, an Fc domain) of an antibody or a complete antibody.

In one embodiment, said targeting moiety T1 and/or said targeting moiety T2 comprises an immunoglobulin module which comprises a variable domain $V_H$H of a llama antibody, a camel antibody, or a shark antibody.

In one embodiment, said targeting moiety T1 and/or said targeting moiety T2 is an aptamer, or a natural ligand of said antigen A1 or antigen A2, respectively.

In one embodiment, said targeting moiety T1 and/or said targeting moiety T2 comprises a Fv or scFv ((single-chain) variant fragment) of an antibody.

In one embodiment, the immunoglobulin module comprised in the targeting moiety T1 and T2 comprises a V domain selected from the group consisting of:
(i) a V domain of an anti-HLA-A2 antibody comprising a $V_L$ domain comprising SEQ ID NOS: 78 and 79 (CDRs 1 and 3) and DAS (CDR 2) and/or a $V_H$ domain comprising SEQ ID NOS: 75-77 (CDRs 1-3);
(ii) a V domain of an anti-HLA-Cw6 antibody comprising a $V_L$ domain comprising SEQ ID NOS: 83 and 84 (CDRs 1 and 3) and DDS (CDR 2) and/or a $V_H$ domain comprising SEQ ID NOS: 80-82 (CDRs 1-3);
(iii) a V domain of an anti-EpCAM antibody comprising a $V_L$ domain comprising SEQ ID NOS: 88 and 89 (CDRs 1 and 3) and WAS (CDR 2) and/or a $V_H$ domain comprising SEQ ID NOS: 85-87 (CDRs 1-3);
(iv) a V domain of an anti-Her2 antibody comprising a $V_L$ domain comprising SEQ ID NOS: 93 and 94 (CDRs 1 and 3) and SAS (CDR 2) and/or a $V_H$ domain comprising SEQ ID NOS: 90-92 (CDRs 1-3);
(v) a V domain of an anti-EGFR1 antibody comprising a $V_L$ domain comprising SEQ ID NOS: 98 and 99 (CDRs 1 and 3) and DAS (CDR 2) and/or a $V_H$ domain comprising SEQ ID NOS: 95-97 (CDRs 1-3);
(vi) a V domain of an anti-CEA antibody comprising a $V_L$ domain comprising SEQ ID NOS: 103 and 104 (CDRs 1 and 3) and SAS (CDR 2) and/or a $V_H$ domain comprising SEQ ID NOS:100-102 (CDRs 1-3);
(vii) a V domain of an anti-CD45 antibody comprising a $V_L$ domain comprising SEQ ID NOS: 107 and 108 (CDRs 1 and 3) and LAS (CDR 2) and/or a $V_H$ domain comprising SEQ ID NOS: 105 and 106 (CDRs 1 and 2) and CDR3 or SEQ ID NOS:132-134 (CDRs 1-3);
(viii) a V domain of an anti-CD138 antibody comprising a $V_L$ domain comprising SEQ ID NOS: 112 and 113 (CDRs and 1 and 3) and YTS (CDR 2) and/or a $V_H$ domain comprising SEQ ID NOS: 109-111 (CDRs 1-3); and
(ix) a V domain of an anti-CD19 antibody comprising a $V_L$ domain comprising SEQ ID NOS: 158 and 159 (CDRs 1 and 3) and DAS (CDR 2) and/or a $V_H$ domain comprising SEQ ID NOS: 155-157 (CDRs 1-3).

In a further, preferred, embodiment, the immunoglobulin module comprised in the targeting moiety T1 and/or T2 comprises a V domain selected from the group consisting of:
(i) a V domain of an anti-HLA-A2 antibody comprising a $V_L$ domain comprising SEQ ID NO: 52 and/or a $V_H$ domain comprising SEQ ID NO: 51;
(ii) a V domain of an anti-HLA-Cw6 antibody comprising a $V_L$ domain comprising SEQ ID NO: 54 and/or a $V_H$ domain comprising SEQ ID NO: 53;
(iii) a V domain of an anti-EpCAM antibody comprising a $V_L$ domain comprising SEQ ID NO: 56 and/or a $V_H$ domain comprising SEQ ID NO: 55;
(iv) a V domain of an anti-Her2 antibody comprising a $V_L$ domain comprising SEQ ID NO: 58 and/or a $V_H$ domain comprising SEQ ID NO: 57;
(v) a V domain of an anti-EGFR1 antibody comprising a $V_L$ domain comprising SEQ ID NO: 60 and/or a $V_H$ domain comprising SEQ ID NO: 59;
(vi) a V domain of an anti-CEA antibody comprising a $V_L$ domain comprising SEQ ID NO: 62 and/or a $V_H$ domain comprising SEQ ID NO: 61;
(vii) a V domain of an anti-CD45 antibody comprising a $V_L$ domain comprising SEQ ID NO: 64 and/or a $V_H$ domain comprising SEQ ID NO: 63; and
(viii) a V domain of an anti-CD138 antibody comprising a $V_L$ domain comprising SEQ ID NO: 66 and/or a $V_H$ domain comprising SEQ ID NOS: 65;
(ix) a V domain of an anti-CD19 antibody comprising a $V_L$ domain comprising SEQ ID NO: 153 and/or a $V_H$ domain comprising SEQ ID NO: 152.

In a further, preferred, embodiment, the immunoglobulin module comprised in the targeting moiety T1 and/or T2 comprises a V domain comprising any one of SEQ ID NOS: 67-74 and 154.

In one embodiment, polypeptide P1 has the general structure F1-T1 and/or polypeptide P2 has the general structure F2-T2. The F fragment and T moieties may be separated by a linker (e.g. F1-linker-T1 and/or F2-linker-T2) and/or flanked by (an) additional amino acid stretche(s) 1 and/or 2 (stretch-F1-(linker)-T1-stretch2 and/or stretch1-F2-(linker)-T2-stretch2). It is preferred that the above general structure is from the N terminus to the C terminus of the polypeptides, i.e. N-F1-T1-C and/or N-F2-T2-C, N-F1-linker-T1-C and/or N-F2-linker-T2-C and N-stretch1-F1-(linker)-T1-stretch2-C and/or N-stretch1-F2-(linker)-T2-stretch2-C. In case the targeting moiety is or comprises an immunoglobulin module I, like an Fv or scFv, polypeptide P1 may have the general structure F1-VH1-VL1 and/or polypeptide P2 may have the general structure F2-VH2-VL2 or polypeptide P1 may have the general structure F1-VL1-VH1 and/or polypeptide P2 may have the general structure F2-VL2-VH2. Also in these cases the F fragment and T moieties may be separated by a linker (e.g. F1-linker-VH/VL1-VL/VH1 and/or F2-linker-VH/VL2-VL/VH2) and/or flanked by (an) additional amino acid stretche(s) 1 and/or 2 (stretch1-F1-(linker)-VH/VL1-VL/VH1-stretch2 and/or stretch1-F2-(linker)-VH/VL2-VL/VH2-stretch2). Also in this case, it is preferred that the above general structure is from the N terminus to the C terminus of the polypeptides, i.e. N-F1-VH/VL1-VL/VH1-C and/or N-F2-VH/VL2-VL/VH2-C, N-F1-linker-VH/VL1-VL/VH1-C and/or N-F2-linker-VH/VL2-VL/VH2-C and N-stretch1-F1-(linker)-VH/VL1-VL/VH1-stretch2-C and/or N-stretch1-F2-(linker)-VH/VL2-VL/VH2-stretch2-C. There may also a linker be present between VH and VL or VL and VH.

The above described linker, in particular the between the V domains, may comprise 1 to 25 amino acids, preferably 12 to 20 amino acids, preferably 12 to 16 or 15 to 20 amino acids. The above described linker may comprise one or more (G$_3$S; SEQ ID NO:199) and/or (G$_4$S; SEQ ID NO:200) motives, in particular 1, 2, 3, 4, 5 or 6 (G$_3$S) and/or (G$_4$S) motives, preferably 3 or 4 (G$_3$S) and/or (G$_4$S) motives, more preferably 3 or 4 (G$_4$S) motives.

In one embodiment, said immunoglobulin module I1 and said fragment F1 are separated by a linker comprising 1 to 12, preferably 3 to 12, amino acids, and/or said immunoglobulin module I2 and said fragment F2 are separated by a linker comprising 1 to 12, preferably 3 to 12, amino acids.

In one embodiment, the $V_L$ domain of I1 is linked to the $V_H$ domain of I1 by a linker comprising 12 to 25 amino acids, preferably a linker with the sequence $(G_3S)_3$ (SEQ ID NO:199) or $(G_3S)_4$ (SEQ ID NO:199) or $(G_4S)_3$ (SEQ ID NO:200) or $(G_4S)_4$ (SEQ ID NO:200) and/or the $V_L$ domain of I2 is linked to the $V_H$ domain of I2 by a linker comprising 12 to 25 amino acids, preferably a linker with the sequence $(G_3S)_3$ or $(G_3S)_4$ or $(G_4S)_3$ or $(G_4S)_4$.

As mentioned, the linker as describe above may comprise $(G_3S$; SEQ ID NO:199) and/or ($G_4S$; SEQ ID NO:200) motives. Alternative linkers may consist of or comprise the GEGTSTGSGGSGGSGGAD (SEQ ID NO:198) motif. The person skilled in the art can without further ado find and use further (peptide) linker known in the art.

The said additional amino acid stretches 1 and/or 2 may consist of or comprise 1 to 200, 1 to 100, 1 to 70, 1 to 65, 1 to 50, 1 to 25 or 1 to 20 amino acids.

In one embodiment, said antigen A1 and/or said antigen A2 is an antigen expressed on the surface of cells of a tumour or on the surface of progenitor/precursor cells of a tumour, preferably an antigen expressed on the surface of cells of a haematologic tumour, more preferably an antigen expressed on the surface of cells selected from the group consisting of acute myeloic leukemia cells, chronic myeloic leukemia cells, acute lymphatic leukemia cells, chronic lymphatic leukemia cells, lymphoma cells, myeloproliferative syndrome cells, myelodysplastic cells, more preferably myeloma cells, or said antigen A1 and/or said antigen A2 is an antigen expressed on the surface of cells of a non-haematologic tumour, preferably a cell selected from the group consisting of renal cell carcinoma cells, bladder cancer cells, lung cancer cells, mesothelioma cells, prostate cancer cells, brain cancer cells, bone cancer cells, sarcoma cells, soft tissue cancer cells, ovarian cancer cells, cervix cancer cells, breast cancer cells, endometrial cancer cells, uterine cancer cells, germ cell tumour cells, anal cancer cells, rectal carcinoma cells, colon carcinoma cells, small intestine carcinoma cells, gastric carcinoma cells, gastrointestinal stroma tumour cells, liver carcinoma cells, pancreas carcinoma cells, bile duct carcinoma cells, gall bladder carcinoma cells, head and neck cancer cells, hypopharyngeal cancer cells, laryngeal cancer cells, cells of a cancer of the esophagus, skin cancer cells, preferably melanoma cells, cells of a childhood cancer, cells of an endocrine tumour, cells of a carcinoid tumour, thymoma cells, thyroid cancer cells, cells of an islet cell tumour, cells of an adrenal cell tumour, cells of a neuroendocrine tumour and cells of a cancer of unknown primary (cancer of unknown primary origin). Detailed information on such cancers can be found in the relevant literature, such as "Cancer Medicine", J F Holland, E Frei (editors), Mcgraw-Hill Professional, 8th edition (2010) and references cited therein.

In one embodiment, the combination of antigen A1 and antigen A2 is only found on blood cells or precursor cells of blood cells, preferably on only one type of blood cells.

In one embodiment, the combination of antigen A1 and antigen A2 is only found on target, in particular, cancerous cells, and not (or only to a negligible extent) on cells that are not target cells, in particular, that are not cancerous. In a preferred embodiment, the combination of antigen A1 and antigen A2 is specific for cancerous cells of a certain type of cancer.

In one embodiment, the combination of antigen A1 and antigen A2 distinguishes a certain kind of cells, preferably a certain type of cancer cells, from any other cells.

"Certain type of cancer" in this context may mean type of cancer characterized by the same organ in which the cancer is formed or, preferred, type cancer characterized by the same pair of (aberrant) antigens A1 and A2.

In one embodiment, the combination of antigen A1 and antigen A2 is found on progenitor/precursor cells that are progenitor/precursor cells of a tumour and not on progenitor/precursor cells that are not progenitor/precursor cells of a tumour.

In one embodiment, said antigen A1 is an antigen that is specific for the malignant state of a cell and said antigen A2 is an antigen that is specific for the cell type or cell lineage of said cell.

In one embodiment,
a) antigen A1 is EpCAM (epithelial cell adhesion molecule) and antigen A2 is CD10 (cluster of differentiation 10), HER2/neu (human epidermal growth factor receptor 2), VEGF-R (vascular endothelial growth factor receptor), EGFR (epidermal growth factor receptor; also called HER1 (human epidermal growth factor receptor 1) or ErbB1) or MDR (multidrug resistance protein), or
b) antigen A1 is MCSP (melanoma-associated chondroitin sulfate proteoglycan) and antigen A2 is melanoferrin or EpCAM, or
c) antigen A1 is CA125 (cancer antigen 125/carbohydrate antigen 125) and antigen A2 is CD227 (PEM (polymorphic epithelial mucin) or MUC1 (mucin-1)), or
d) antigen A1 is CD56 and antigen A2 is CD140b (PDGFRβ (platelet-derived growth factor receptor beta)) or GD3 ganglioside, or
e) antigen A1 is EGFR and antigen 2 is HER2, or
f) antigen A1 is PSMA (prostate-specific membrane antigen) and antigen 2 is HER2, or
g) antigen 1 is Sialyl Lewis and antigen 2 is EGFR, or
h) antigen 1 is CD44 and antigen 2 is ESA (epithelial surface antigen) (CD326, EpCAM), CD24, CD133, MDR (multidrug resistance protein) or CD117, or
i) antigen 1 is CD34 and antigen 2 is CD19, CD79a, CD2, CD7, HLA-DR (human leukocyte antigen DR), CD13, CD117, CD33 or CD15, or
j) antigen 1 is CD33 and antigen 2 is CD19, CD79a, CD2, CD7, HLA-DR (human leukocyte antigen DR), CD13, CD117 or CD15, or
k) antigen 1 is MUC1 and antigen 2 is CD10, CEA or CD57, or
l) antigen 1 is CD38 and antigen 2 is CD138, or
m) antigen 1 is CD24 and antigen 2 is CD29 or CD49f, or
n) antigen 1 is carbonic anhydrase IX and antigen 2 is aquaporin, preferably aquaporin-2.

In one embodiment, said antigen A1 and/or said antigen A2 is selected from the group consisting of HLA-A (HLA-A major histocompatibility complex, class I, A [*Homo sapiens*]; Gene ID: 3105 updated on 13 Jan. 2013; DAQB-90C11.16-002; Chromosome: 6; NC_000006.11 (29910247 . . . 29913661); for HLA-A2: 1. mRNA=LOCUS NM_001242758=Version NM_001242758.1 GI:337752169=GenBank: AY191309.1 PRI 13 Jan. 2013; 2. Protein=P79495 [UniParc]. Last modified May 1, 1997. Version 1; for HLA-Cw6: mRNA=LOCUS HUMMHCCW6A=GenBank: VERSION M28160.1 GI:531197PRI (18 Aug. 1994); Protein=Q29963 [UniParc]. Last modified Aug. 22, 2003. Version 2); EpCAM (EPCAM epithelial cell adhesion molecule [*Homo sapiens*]; also known as ESA; KSA; M4S1; MK-1; DIAR5; EGP-2; EGP40; KS1/4; MIC18; TROP1; EGP314; HNPCC8; TAC-STD1; Gene ID: 4072, updated on 6 Jan. 2013; mRNA=VERSION NM_002354.2 GI:218505669PRI 6 Jan.

2013; Protein=P16422 [UniParc]. last modified Nov. 13, 2007. Version 2); CD45 (PTPRC protein tyrosine phosphatase, receptor type, C [Homo sapiens]; also known as LCA; LY5; B220; CD45; L-CA; T200; CD45R; GP180; Gene ID: 5788, updated on 13 Jan. 2013; mRNA=VERSION NM_002838.4 GI:392307006 PRI 13 Jan. 2013; Protein=P08575-1=Isoform 1, Last modified Jul. 19, 2003. Version 2; Protein=P08575-2=Isoform 2); Her2 (ERBB2 v-erb-b2 erythroblastic leukemia viral oncogene homolog 2, neuro/glioblastoma derived oncogene homolog (avian) [Homo sapiens]; also known as NEU; NGL; HER2; TKR1; CD340; HER-2; MLN 19; HER-2/neu; gene ID: 2064, updated on 13 Jan. 2013; mRNA transcript variant 1=VERSION NM_004448.2 GI:54792095, PRI 6 Jan. 2013; mRNA transcript variant 2=VERSION NM_001005862.1 GI:54792097, PRI 6 Jan. 2013; Protein=P04626-1=Isoform 1, Last modified Aug. 13, 1987. Version 1; Protein=P04626-2=Isoform 2; Protein=P04626-3=Isoform 3; Protein=P04626-4=Isoform 4); EGFR (EGFR epidermal growth factor receptor [Homo sapiens]; also known as ERBB; HER1; mENA; ERBB1; PIG61; Gene ID: 1956, updated on 13 Jan. 2013; mRNA transcript variant 1=VERSION NM_005228.3 GI:41327737, PRI 13 Jan. 2013; mRNA transcript variant 2=VERSION NM_201282.1 GI:41327731, PRI 13 Jan. 2013; mRNA transcript variant 3=VERSION NM_201283.1 GI:41327733, PRI 13 Jan. 2013; mRNA transcript variant 4=VERSION NM_201284.1 GI:41327735, PRI 13 Jan. 2013; Protein=P00533-1=Isoform 1, Last modified Nov. 1, 1997. Version 2; Protein=P00533-2=Isoform 2; Protein=P00533-3=Isoform 3; Protein=P00533-4=Isoform 4); CD138 (SDC1 syndecan 1 [Homo sapiens]; Gene ID: 6382, updated on 6 Jan. 2013; mRNA transcript variant 1=VERSION NM_001006946.1 GI:55749479, PRI 6 Jan. 2013; mRNA transcript variant 2=VERSION NM_002997.4 GI:55925657, PRI 6 Jan. 2013; Protein=P18827 [UniParc]. Last modified May 5, 2009. Version 3); CEA (CEACAM5 carcinoembryonic antigen-related cell adhesion molecule 5 [Homo sapiens]; also known as CEA; CD66e; Gene ID: 1048, updated on 13 Jan. 2013; mRNA=VERSION NM_004363.2 GI:98986444, PRI 13 Jan. 2013; P06731, Last modified Jan. 11, 2011. Version 3); and CD19 (CD19 CD19 molecule [Homo sapiens]; also known as B4; CVID3; Gene ID: 930, updated on 5 Jan. 2013; mRNA transcript 1=VERSION NM_001178098.1 GI:296010920, PRI 6 Jan. 2013; mRNA transcript 2=VERSION NM_001770.5 GI:296010919, PRI 6 Jan. 2013; Protein=P15391 [UniParc]. Last modified Nov. 13, 2007. Version 6).

In one embodiment, said antigen A1 and/or said antigen A2 is an MHC antigen, preferably an allelic variant of any of HLA-A, HLA-B, HLA-C, HLA-DQ, HLA-DR, or HLA-DM, more preferably an allelic variant of an MHC class I molecule, more preferably an allelic variant selected from the group consisting of HLA-A1, HLA-A2, HLA-A3, HLA-A25, HLA-B7, HLA-B8, HLA-B35, HLA-B44, HLA-Cw3, HLA-Cw4, HLA-Cw6, and HLA-Cw7.

In one embodiment, said antigen A1 is HLA-A2.

In one embodiment, said antigen A1 and/or said antigen A2 is selected from the group consisting of CD45, aquaporin, preferably aquaporin-2, scavenger receptor class B member 1 (SCARB1), CD34, CD33, CD138, CD15, CD1a, CD2, CD3, CD4, CD5, CD8, CD20, CD23, CD31, CD43, CD56, CD57, CD68, CD79a, CD146, synaptophysin, CD56, CD57, nicotinic acetylcholine receptor, muscle-specific kinase (MUSK), voltage-gated calcium channel (P/Q-type), voltage-gated potassium channel (VGKC), N-methyl-D-aspartate receptor (NMDA), TSH (thyroid stimulating hormone) receptor, amphiphysin, HepPar-1, ganglioside GQ1B, ganglioside GD3, ganglioside GM1 and glycophorin-A.

In a preferred embodiment, said antigen A1 is an MHC antigen and said antigen A2 is an antigen that is specific for a certain cell type or cell lineage.

In one embodiment, said functional domain F is an immunoglobulin module, preferably a scFv (single-chain variant fragment) of an antibody more preferably a Fv (variant fragment) of an antibody, or a fluorescent molecule, preferably a bimolecular fluorescence complementation molecule, more preferably GFP or a GFP variant, or a molecule capable of mediating bioluminescence, preferably a *luciferase* molecule, more preferably *Gaussia luciferase.*

In one embodiment, said functional domain F is a Fv (variant fragment) of an antibody.

In one embodiment, said functional domain F specifically binds or is capable of specifically binding to an antigen. In a specific aspect, said antigen may be an antigen that is present on cells of the human immune system. In a preferred embodiment, said binding activates said cells of the human immune system.

In one embodiment, said functional domain F is a T cell engaging domain, preferably a T cell engaging domain specifically binding to CD2, CD3, CD5, T cell receptor or CD28, more preferably a T cell engaging domain specifically binding to CD3ε, an NK cell (natural killer cell) engaging domain, preferably a NK cell engaging domain specifically binding to CD1a, CD16a or CD56, a domain engaging macrophage cells, preferably a domain engaging macrophage cells specifically binding to CD16a, CD32a, CD32b, CD89 or CD64, a monocyte engaging domain, preferably a monocyte engaging domain specifically binding to CD32a, CD32b, CD64 or CD89, a granulocyte engaging domain, preferably a granulocyte engaging domain specifically binding to CD16b, CD32a, CD32b, CD64, or CD89, a domain engaging neutrophil granulocytes, preferably a domain engaging neutrophil granulocytes that specifically binds to CD89 (FcαRI), or a domain engaging activated neutrophil granulocytes, monocytes and/or macrophages, preferably a domain engaging activated neutrophil granulocytes, monocytes and/or macrophages that specifically binds to CD64 (FcγRI).

In one embodiment, said functional domain F is a domain that specifically binds to an antigen linked to a diagnostic or therapeutic compound.

In one embodiment, said functional domain F is a domain that specifically binds to a carrier molecule or an affinity tag. Preferably, said carrier molecule is linked to a diagnostic or therapeutic compound. Preferably, said affinity tag is linked to a diagnostic or therapeutic compound.

Preferably, said affinity tag is selected from the group consisting of a FLAG-tag, a myc-tag, a glutathione-S-transferase (GST)-tag, a hemagglutinin (HA)-tag, a polyhistidine (His)-tag, a digoxigenin (DIG)-tag and a maltose binding protein (MBP)-tag.

Preferably, said carrier molecule is a peptide or a carbohydrate molecule. In a preferred embodiment, said functional domain F is a domain that specifically binds to a carrier molecule, preferably a carrier molecule linked to a diagnostic or therapeutic compound, wherein said carrier molecule is selected from the group consisting of gelatine, inulin, dextrane and hydroxyethyl starch.

In one embodiment, said therapeutic compound is a radioactive compound, preferably a radioactive compound comprising $^{90}Y$, $^{177}Lu$, $^{131}I$, $^{32}P$, $^{10}B$, or $^{213}Bi$. In one embodiment, said therapeutic compound is a toxin. Preferably, said toxin is selected from the group consisting of *B. anthracis* edema factor, *B. anthracis* lethal factor, *C. perfringens* iota toxin, *C. botulinum* C2 toxin, *C. difficile* ADP-ribosyltransferase, *C. diphtherias* diphteria toxin fragment A, *Burgholderia* sp. shiga toxin (subunit A), *Clostridium perfringens* str. 13 toxin pfoA perfringolysin O, Ricin A chain, plant RIP bouganin, Human RNASE3 ribonuclease (RNase A family, 3) and anthrax lethal factor endopeptidase. A further non-limiting example of a toxin in accordance with this invention is a toxin being or comprising an amino acid sequence selected from the group consisting of SEQ ID NOS 160 to 168.

In one embodiment, said diagnostic compound is a radioactive compound, preferably a radioactive compound comprising $^{99m}$Tc, $^{111}$In, $^{82}$Rb or $^{201}$Tl. In one embodiment, said diagnostic compound is a fluorescent compound, preferably GFP, a GFP variant, or a fluorescent small-molecule compound such as FITC (fluorescein isothiocyanate), PE (phycoerythrin), an alexa fluor dye (such as AlexaFluor488 or related dyes) or a cyanine dye (such as Cy3 (Indocarbocyanine) or Cy5 (Indodicarbocyanine) or related dyes), In one embodiment, said diagnostic compound is a molecule capable of mediating bioluminescence, preferably a *luciferase* molecule, more preferably *Gaussia luciferase*.

In one embodiment, said fragment F1 comprises a $V_L$ domain of an antibody and said fragment F2 comprises a $V_H$ domain of the same antibody, wherein, preferably, said antibody is an anti-CD3 antibody, more preferably an anti-CD3ε antibody, or an anti-His or anti-DIG antibody or said fragment F1 comprises a $V_H$ domain of an antibody and said fragment F2 comprises a $V_L$ domain of the same antibody, wherein, preferably, said antibody is an anti-CD3 antibody, more preferably an anti-CD3ε antibody, or an anti-His or anti-DIG antibody.

In another embodiment, the $V_L$ and $V_H$ domains as comprised in the F1 and F2 fragment, respectively, or in the F2 and F1 fragment, respectively may also of two different antibodies, either specific for the same Antigen (and for the same or a different epitope) or for different Antigen. This is, for example, envisaged to be employed where new specifications are to be created (for example in phage-display approaches).

In another embodiment, the immunoglobulin module comprised in the F domain comprises a V domain selected from the group consisting of:
(i) a V domain of an anti-CD3 antibody comprising a $V_L$ domain comprising SEQ ID NOS: 18-20 (CDRs 1-3) and/or a $V_H$ domain comprising SEQ ID NOS: 15-17 (CDRs 1-3);
(ii) a V domain of an anti-CD3 antibody comprising a $V_L$ domain comprising SEQ ID NOS: 24-26 (CDRs 1-3) and/or a $V_H$ domain comprising SEQ ID NOS: 21-23 (CDRs 1-3);
(iii) a V domain of an anti-CD3 antibody comprising a $V_L$ domain comprising SEQ ID NOS: 30-32 (CDRs 1-3) and/or a $V_H$ domain comprising SEQ ID NOS: 27-29 (CDRs 1-3);
(iv) a V domain of an anti-CD3 antibody comprising a $V_L$ domain comprising SEQ ID NOS: 36 and 37 (CDRs 1 and 3) and DTS (CDR 2) and/or a $V_H$ domain comprising SEQ ID NOS: 33-35 (CDRs 1-3);
(v) a V domain of an anti-CD3 antibody comprising a $V_L$ domain comprising SEQ ID NOS: 41 and 42 (CDRs 1 and 3) and YTN (CDR 2) and/or a $V_H$ domain comprising SEQ ID NOS: 38-40 (CDRs1-3); and
(vi) a V domain of an anti-His antibody comprising a $V_L$ domain comprising SEQ ID NOS: 46 and 47 (CDRs 1 and 3) and KVS (CDR 2) and/or a $V_H$ domain comprising SEQ ID NOS: 43-45 (CDRs 1-3);
(vii) a V domain of an anti-DIG antibody comprising a $V_L$ domain comprising SEQ ID NOS: 50 and 131 (CDRs 1 and 3) and YSS (CDR 2) and/or a $V_H$ domain comprising SEQ ID NOS: 48 and 49 (CDRs 1 and 2) and A (CDR 3).

In another, preferred embodiment, the immunoglobulin module comprised in the F domain comprises a V domain selected from the group consisting of:
(i) a V domain of an anti-CD3 antibody comprising a $V_L$ domain comprising SEQ ID NO: 2 and/or a $V_H$ domain comprising SEQ ID NO: 1;
(ii) a V domain of an anti-CD3 antibody comprising a $V_L$ domain comprising SEQ ID NO: 4 and/or a $V_H$ domain comprising SEQ ID NO: 3;
(iii) a V domain of an anti-CD3 antibody comprising a $V_L$ domain comprising SEQ ID NO: 6 and/or a $V_H$ domain comprising SEQ ID NO: 5;
(iv) a V domain of an anti-CD3 antibody comprising a $V_L$ domain comprising SEQ ID NO: 8 and/or a $V_H$ domain comprising SEQ ID NO: 7;
(v) a V domain of an anti-CD3 antibody comprising a $V_L$ domain comprising SEQ ID NO: 10 and/or a $V_H$ domain comprising SEQ ID NO: 9; and
(vi) a V domain of an anti-His antibody comprising a $V_L$ domain comprising SEQ ID NO: 12 and/or a $V_H$ domain comprising SEQ ID NO: 11;
(vii) a V domain of an anti-DIG antibody comprising a $V_L$ domain comprising SEQ ID NO: 14 and/or a $V_H$ domain comprising SEQ ID NO: 30.

In one embodiment, said functional domain F is a domain that specifically binds to a toxin molecule, preferably a toxin molecule that by itself is not capable of penetrating through the cell membrane of a human cell and that, preferably, is internalized into a human cell upon association with the cell membrane of said cell, wherein, preferably, said association with the cell membrane of said cell is mediated by specifically binding to a heterodimer formed from two molecules, preferably two molecules associated with said cell membrane, wherein, preferably, said two molecules are the polypeptides P1 and P2 as described herein. In one embodiment, said functional domain F is a domain that specifically binds to the A-component (active component) of a bacterial two-component A-B toxin. In one embodiment said functional domain F is a domain that specifically binds to a toxin selected from the group consisting of *B. anthracis* edema factor, *B. anthracis* lethal factor, *C. perfringens* iota toxin, *C. botulinum* C2 toxin, *C. difficile* ADP-ribosyltransferase, *C. diphtherias* diphteria toxin fragment A, *Burgholderia* sp. shiga toxin (subunit A), *Clostridium perfringens* str. 13 toxin pfoA perfringolysin O, Ricin A chain, plant RIP bouganin, Human RNASE3 ribonuclease (RNase A family, 3) and anthrax lethal factor endopeptidase. A further non-limiting example of a toxin in accordance with this invention is a toxin being or comprising an amino acid sequence selected from the group consisting of SEQ ID NOS 160 to 168.

In one embodiment, said functional domain F is a domain that specifically binds to a fluorescent molecule, preferably a fluorescent molecule that by itself is not capable of penetrating through the cell membrane of a human cell. Preferably, said fluorescent molecule is GFP or a GFP variant or a molecule that is or comprises a fluorescent small-molecule compound such as FITC (fluorescein isothiocyanate), PE (phycoerythrin), an alexa fluor dye (such as AlexaFluor488 or related dyes) or a cyanine dye (such as Cy3 (Indocarbocyanine) or Cy5 (Indodicarbocyanine) or related dyes).

In one embodiment, said functional domain F is a domain that specifically binds to a molecule capable of mediating bioluminescence, preferably to a *luciferase* molecule, more preferably to *Gaussia luciferase*.

In one embodiment, said functional domain F is a fluorescent molecule, preferably a bimolecular fluorescence complementation molecule, more preferably GFP or a GFP variant, such as YFP, CFP, Venus, or Cerulean.

Examples of particular polypeptides P1 or P2 comprised in the set of polypeptides according to this invention are polypeptides comprising an amino acid sequence selected from the group consisting of SEQ ID NOS: 114-129 and 197.

In general, the present invention relates to the treatment or elimination of any undesired cell population and the treatment or prevention of any disorder or disease which comes along with this undesired cell population. For this purpose, the set of polypeptides of this invention is to be used.

In one embodiment, said set of polypeptides is a set of polypeptides for use in the treatment of a patient who is suffering from a tumour or cancer or for diagnostic use in a patient who is suffering from a tumour or cancer, preferably for use in the treatment of a patient who is suffering from a tumour or cancer and undergoing allogeneic tissue or cell transplantation or meant to undergo such transplantation, or for diagnostic use in a patient who is suffering from a tumour or cancer and undergoing or meant to undergo allogeneic tissue or cell transplantation, wherein, preferably, said set of polypeptides is administered to said patient.

Examples of tumours to be treated or diagnosed are those for which the tumour or cancer cells are described herein above with respect to the antigens A1 and/or A2.

In one embodiment, said treatment involves the elimination of recipient tissue/cells of a certain cell type, preferably a cancerous cell type, or recipient precursor cells giving rise to a certain cell type, preferably to a cancerous cell type, optionally after or in parallel to transplantation to the recipient of donor tissue/cells of said same cell type or donor precursor cells giving rise to said same cell type.

In one embodiment, the set of polypeptides of the invention is for use in an allogeneic transplantation setting for haematopoietic neoplasias, for example, with mismatched HLA antigens, in particular for use in therapeutically exploiting this mismatch situation. In this exemplary situation, the dual information of recipient HLA haplotype (HLA$_{patient}$) and haematopoietic lineage origin (CD45) is displayed exclusively on leukemic blasts and other haematopoietic cells of the patient. All other cells of recipient origine express the recipient haplotype but not the hematopoietic lineage antigen CD45 (e.g. recipient non-hematopoietic cells are positive for HLA-A2 but negative for CD45). Likewise, all donor hematopoietic cells express donor HLA haplotype molecules that means that they are CD45 positive but HLA-A2 negative in the situation a mismatch transplantation where the patient but not the donor is positive for HLA-A2. Consequently, the present invention also relates to bimolecular and complementing single-chain antibody constructs directed against HLA-A2, in cases where the patient but not the donor is HLA-A2 positive, and a second construct specific for the haematopoietic lineage marker CD45 to specifically target all hematopoietic cells of the patient including all hematologic neoplasms. Hence, the first polypeptide P1 may comprise a single-chain variable fragment antibody construct directed against the HLA of the patient (targeting moiety T1) fused to the V$_L$ fragment of F1 antiCD3 (for example, fragment F1). The second polypeptide P2 may comprise a single-chain variable fragment construct specific for a haematopoietic lineage marker (for example, CD45; targeting moiety T2), fused to the V$_H$ split-fragment of F2 anti CD3-Fv (fragment F2).

In one embodiment, said elimination involves the destroying of said recipient tissue/cells or said recipient precursor cells by cells of the immune system, by a toxin or by a radioactive compound.

In one embodiment, said set of polypeptides is a set of polypeptides for diagnostic use in a patient undergoing allogeneic tissue or cell transplantation, wherein, preferably, said patient is a patient suffering from a tumour.

In one embodiment, said diagnostic use involves the specific detection of recipient cells of a certain cell type or cell lineage among recipient cells of different cell type or cell lineage and donor cells of the same or different type or cell lineage.

In one embodiment, said diagnostic use involves the specific detection of recipient cells that are malignant cells among recipient cells that are not malignant and among donor cells. In one embodiment, said set of polypeptides is administered to a patient.

Preferably, said patient is a mammal, more preferably a human being.

In one embodiment, said administration occurs by bolus administration or by continuous administration.

In one embodiment, the polypeptides P1 and P2 of said set of polypeptides are administered in parallel. In another embodiment, the polypeptides P1 and P2 of said set of polypeptides are administered sequentially.

In one embodiment, one of the polypeptides P1 or P2 of said set of polypeptides is administered by bolus administration, whereas the other one is administered by continuous administration.

In one embodiment, the amount of polypeptide administered is in the range of from 0.5 μg/m$^2$ per day to 500 μg/m$^2$ per day for the polypeptide P1 or for the polypeptide P2 or for each of the polypeptides P1 and P2, preferably in the range of from 5 μg/m$^2$ per day to 200 μg/m$^2$ per day for the polypeptide P1 or for the polypeptide P2 or for each of the polypeptides P1 and P2, more preferably in the range of from 10 μg/m$^2$ per day to 80 μg/m$^2$ per day for the polypeptide P1 or for the polypeptide P2 or for each of the polypeptides P1 and P2.

In one embodiment, the amount of polypeptide administered is in the range of from 0.05 μg/m$^2$ per day to 0.5 μg/m$^2$ per day for the polypeptide P1 or for the polypeptide P2 or for each of the polypeptides P1 and P2.

In one embodiment, the amount of polypeptide P1 administered is different from the amount of polypeptide P2 administered.

In one embodiment, the amount of polypeptide administered is in the range of from 0.5 μg/m$^2$ per day to 50 μg/m$^2$ per day for the polypeptide P1 or for the polypeptide P2 or for each of the polypeptides P1 and P2. In one embodiment, the amount of polypeptide administered is in the range of from 50 μg/m$^2$ per day to 100 μg/m$^2$ per day for the polypeptide P1 or for the polypeptide P2 or for each of the polypeptides P1 and P2. In one embodiment, the amount of polypeptide administered is in the range of from 100 μg/m$^2$ per day to 200 μg/m$^2$ per day for the polypeptide P1 or for the polypeptide P2 or for each of the polypeptides P1 and P2. In one embodiment, the amount of polypeptide administered is in the range of from 200 μg/m$^2$ per day to 300 μg/m$^2$ per day for the polypeptide P1 or for the polypeptide P2 or for each of the polypeptides P1 and P2. In one embodiment, the amount of polypeptide administered is in the range of from 300 μg/m$^2$ per day to 400 μg/m$^2$ per day for the polypeptide P1 or for the polypeptide P2 or for each of the polypeptides P1 and P2. In one embodiment, the amount of polypeptide administered is in the range of from 400 µg/m² per day to 500 µg/m² per day for the polypeptide P1 or for the polypeptide P2 or for each of the polypeptides P1 and P2. In one embodiment, the amount of polypeptide administered is in the range of from 500 µg/m² per day to 1 mg/m² per day for the polypeptide P1 or for the polypeptide P2 or for each of the polypeptides P1 and P2.

Further reference points for deriving the amounts of the polypeptides P1 and P2 to be administered can also be obtained by consulting studies carried out with bispecific antibody constructs (e.g. Bargou R et al., Tumor regression in cancer patients by very low doses of a T cell-engaging antibody. Science. 2008; 321(5891):974-7; and Topp M S et al. Targeted therapy with the T-cell-engaging antibody blinatumomab of chemotherapy-refractory minimal residual disease in B-lineage acute lymphoblastic leukemia patients results in high response rate and prolonged leukemia-free survival. J Clin Oncol. 2011, 29:2493-8).

In one embodiment, said administration occurs continuously for at least 12 hours or for at least 1 day or for at least 2 days or for at least 3 days or for at least 4 days or for at least 5 days or for at least 6 days or for at least 7 days or for at least 8 days or for at least 9 days or for at least 10 days or for at least 11 days or for at least 12 days or for at least 13 days or for at least 14 days or for at least 15 days or for at least 16 days or for at least 17 days or for at least 18 days or for at least 19 days or for at least 20 days or for at least 21 days or for at least 22 days or for at least 23 days or for at least 24 days or for at least 25 days or for at least 26 days or for at least 27 days or for at least 28 days or for at least 29 days or for at least 30 days or for at least 5 weeks or for at least 6 weeks.

In one embodiment, said administration of said set of polypeptides or of one of the polypeptides of said set of polypeptides occurs intravenously, preferably by intravenous injection.

In one embodiment, said administration of said set of polypeptides or of one of the polypeptides of said set of polypeptides occurs subcutaneously, preferably by subcutaneous injection.

In one embodiment, said set of polypeptides is administered in combination with one or more drugs selected from the group consisting of an immunomodulatory drug, and/or a steroid, preferably prednisolone or prednisone.

In one embodiment, said set of polypeptides is administered in combination with a radioactive compound, preferably a radioactive compound linked to an antigen, a carrier molecule or an affinity tag, wherein said radioactive compound, said antigen, said carrier molecule or said affinity tag is specifically bound by said functional domain F.

In one embodiment, said set of polypeptides is administered in combination with a toxin, preferably a toxin linked to an antigen, a carrier molecule or an affinity tag, wherein said toxin, said antigen, said carrier molecule or said affinity tag is specifically bound by said functional domain F.

In one embodiment, said set of polypeptides is administered in combination with a fluorescent molecule, preferably a fluorescent molecule linked to an antigen, a carrier molecule or an affinity tag, wherein said fluorophore, said antigen, said carrier molecule or said affinity tag is specifically bound by said functional domain F.

In one embodiment, said functional domain F is a domain that specifically binds to an antigen which is not recognized as foreign by the immune system of said patient to whom said set of polypeptides is administered.

In one embodiment two sets of polypeptides as described above (a first set of polypeptides and a second set of polypeptides) are administered simultaneously or sequentially. In one preferred embodiment, said first set of polypeptides has different fragments F1 and F2 than said second set of polypeptides. In one preferred embodiment, said first set of polypeptides has the same fragments F1 and F2 as said second set of polypeptides. In one preferred embodiment, the targeting moieties T1 and T2 of said first set of polypeptides bind to the same antigens as the targeting moieties T1 and T2, respectively, of said second set of polypeptides. In one preferred embodiment, the targeting moieties T1 and T2 of said first set of polypeptides bind to different antigens than the targeting moieties T1 and T2 of said second set of polypeptides.

In one embodiment, said patient has undergone cancer treatment before treatment with said set of polypeptides, said cancer treatment preferably being chemotherapy, radiation therapy or operative removal of the tumour, or undergoes cancer treatment parallel to treatment with said set of polypeptides, said cancer treatment preferably being chemotherapy, radiation therapy or operative removal of the tumour.

In one embodiment, said set of polypeptides or one of the polypeptides of said set of polypeptides has been produced by means of a prokaryotic or eukaryotic expression system or by de novo peptide synthesis.

In one embodiment, said set of polypeptides or one of the polypeptides of said set of polypeptides is generated inside said patient by protein expression from a nucleic acid introduced into said patient.

Many patients suffer from allergic or auto-immune diseases. In many of these cases, a clonal B cell population produce an errant antibody that reacts with antigens expressed by the patients' tissues or complex with an allergen, causing anaphylactic reactions. In both cases, it is desirable to specifically eliminate the errant B cell clone.

To this end, one may modify the combinatorial system in a way so that one arm (P1 or P2, in particular T1 or T2) recognizes a B cell associated antigen (e.g. CD19, CD20, CD38 or CD138) and the other arm (P2 or P1, in particular T2 or T1, respectively) is the allergen or the substrate bound by the antibody that causes the autoimmune disease. When these two constructs bind to a B cell that is CD19 (CD20, CD38 or CD138) positive and simultaneously displays the clonotypic antibody on the surface, the attached anti-CD3 VH and VL can interact and reconstitute the CD3 binding site exactly on the B cell. This allergen-specific or antigen-specific assembly will ultimately result in the clonal depletion of the Target B cells.

Hence, in accordance with this invention, any of said antigens A1 and A2 may also be a clonotypic antibody on the surface of a B cell, in particular a B cell that causes an autoimmune disorder.

In this context, for example, one of said antigens A1 and A2 may be CD19 and the other one may be a clonotypic antibody on the surface of a B cell, in particular a B cell that causes an autoimmune disorder.

In accordance with this aspect of the invention, any one of said targeting moiety T1 and T2 may comprise an allergen or substrate which binds to the clonotypic antibody on the surface of the B cell and/or which is, upon binding to the clonotypic antibody, capable to cause an autoimmune disorder. Non-limiting examples of an allergen comprised in any one of said targeting moiety T1 and T2 are hair allergens, like, for example, dog-hair, cat-hair (e.g. Fel d 1, Feld d1A, Feld d1B) or guinea-pig-hair allergens, or pollen allergens, like, for example, birch, grass, pollen allergens. Further non-limiting examples are mite allergens (for example Tyr p 2, Der P1, Der f 2), cat allergens (for example Fel d 1, Feld d1A, Feld d1B), peanut allergens (for example Conglutin-7), rot fungus allergens (for example Alt a 1), dog allergens (for example Can f 1), sprue wheat allergens (for example Alpha/beta-gliadin), german cockroach allergens (for example Bla g 1.02 variant allergen), birch tree or (major) pollen allergens (for example Cyn d 1, Pha a 1, Dac g 3, Phl p 2, Phl p 1, Profilin, Bet v 1-L, Bet v 1-A), major apple allergens (for example Mal d 1), cow's milk allergens (for example alpha-lactalbumin, alpha-S1-casein), chicken egg allergens (for example lysozyme C, ovalbumin) and Horse allergens (for example latherin, Equ c 1), and the like. A further non-limiting and preferred example of an allergen comprised in any one of said targeting moiety T1 and T2 is the antigen for human myeloma cell line U266 antibody IgE-ND. A further non-limiting and preferred example of an allergen comprised in any one of said targeting moiety T1 and T2 is an allergen being or comprising an amino acid sequence selected from the group consisting of SEQ ID NOS 169 to 195.

In this context, the inventions also relates to the set of polypeptides as described herein, and, in particular in the above aspect, for use in treating or preventing a disorder selected from the group consisting of
  (i) an autoimmune disorder; and
  (ii) a hypersensitivity disorder.

Non-limiting examples of an autoimmune disorder to be treated or prevented in accordance with this invention are selected from the group consisting of
  (i) allergic disorders;
  (ii) Multiple Sclerosis;
  (iii) Psoriasis;
  (iv) Systemic Lupus Erythematosus;
  (v) Sjögren's syndrome;
  (vi) Rheumatoid Arthritis;
  (vii) Idiopathic Thrombocytopenic Purpura;
  (viii) Diabetes;
  (xi) Vasculitis;
  (x) Crohn's disease; and
  (xi) Amyloidosis.

Non-limiting examples of a hypersensitivity disorder to be treated or prevented in accordance with this invention are selected from the group consisting of allergies (type I hypersensitivity reaction according to Coombs and Gell classification), an antibody dependent cytotoxic reaction (type II hypersensitivity reaction), a immune complex disease (type III hypersensitivity reaction), delayed type hypersensitivity (type IV hypersensitivity reaction) and a receptor mediated autoimmune disease (type V hypersensitivity reaction).

In a preferred embodiment, said autoimmune or hypersensitivity disorder comes along with or is triggered by allogenic stem cell transplantation (i.e. any of type I to type V hypersensitivity disorder according to the Coombs and Gell classification).

Many cells which are infected by a pathogen (for example a virus, like, for example, HIV, EBV, CMV) express pathogen-encoded proteins on their cell surface. Hence, in accordance with this invention, any of said antigens A1 and A2 may also be such a pathogen-encoded protein, like, for example, a HIV, EBV or CMV protein on the surface of a cell. In this context, the inventions also relates to the set of polypeptides as described herein for use in treating or preventing an infectious disease, for example a viral infectious disease. Particular examples of pathogen-encoded proteins can be derived from uniprot.org/uniprot/ on the worldwide web and are HIV gp120 (Q78706); EBV LMP-2 (P13285); CMV gB (P06473); HBV HBS (Q9JG36); HCV E1 (C4B751); HCV E2 (Q6TRB1); Human adenovirus C serotype 2 HAdV-2 (P03276).

The objects of the present invention are also solved by a nucleic acid molecule or a set of nucleic acid molecules encoding the set of polypeptides or one of the polypeptides of the set of polypeptides as defined in the embodiments above, wherein, preferably, said nucleic acid molecule or the nucleic acid molecules of said set of nucleic acid molecules comprises an export signal that mediates secretion of the encoded polypeptide(s) by a bacterial or eukaryotic cell.

A non-limiting example of the nucleic acid molecule or set of nucleic acid molecules according to this invention comprises one or more of the nucleotide sequences as depicted in any one of SEQ ID NOS: 135-150 and 196.

The objects of the present invention are also solved by a vector comprising the nucleotide sequence of the nucleic acid molecule as defined above or the sequence of one of the nucleic acid molecules of the set of nucleic acid molecules as defined above.

The objects of the present invention are also solved by a cell comprising said nucleic acid/set of nucleic acids or said vector.

The objects of the present invention are also solved by a pharmaceutical composition comprising either the set of polypeptides as defined above or the nucleic acid molecule/set of nucleic acid molecules as defined above or the vector as defined above, wherein, preferably, said pharmaceutical composition further comprises a pharmaceutically acceptable carrier.

The objects of the present invention are also solved by a kit comprising the set of polypeptides as defined above and/or the nucleic acid molecule or the set of nucleic acid molecules according the invention and/or the vector according the invention.

In one embodiment, the polypeptides of said set of polypeptides comprised by said kit are contained in a single vial.

In one preferred embodiment, the polypeptides of said set of polypeptides comprised by said kit are contained in separate vials.

In one embodiment, one or more of the polypeptides of said set of polypeptides comprised by said kit are freeze-dried.

In one embodiment, one or more of the polypeptides of said set of polypeptides comprised by said kit are in solution.

The objects of the present invention are also solved by a method for treatment of a patient who is suffering from a
  (i) tumour or cancer and/or who is undergoing allogeneic cell or tissue transplantation;
  (ii) an autoimmune disorder; or
  (iii) a hypersensitivity disorder.

Said method may comprise the steps:
  obtaining a set of polypeptides, said set of polypeptides comprising
    a first polypeptide P1 comprising
      (i) a targeting moiety T1,
        wherein said targeting moiety T1 specifically binds to an antigen A1, and
      (ii) a fragment F1 of a functional domain F,
    wherein neither said fragment F1 by itself nor said polypeptide P1 by itself is functional with respect to the function of said domain F,
  and a second polypeptide P2 comprising
(i) a targeting moiety T2,
wherein said targeting moiety T2 specifically binds to an antigen A2, said antigen A2 being a cell surface molecule that is specific for a certain cell type or cell lineage, and
(ii) a fragment F2 of said functional domain F,
wherein neither said fragment F2 by itself nor said polypeptide P2 by itself is functional with respect to the function of said domain F,
wherein said antigen A1 is different from said antigen A2,
wherein said polypeptide P1 and said polypeptide P2 are not associated with each other in the absence of a substrate that has both antigens A1 and A2 at its surface, more specifically a cell that carries both antigens A1 and A2 at its cell surface, and
wherein, upon dimerization of said fragment F1 of said polypeptide P1 with said fragment F2 of said polypeptide P2, the resulting dimer is functional with respect to the function of said domain F,
administering said set of polypeptides to said patient.

In such method of treatment, said set of polypeptides is as defined in the embodiments above.

The objects of the present invention are also solved by a method of using the set of polypeptides as described above for treatment of a patient undergoing cell or tissue transplantation.

The objects of the present invention are also solved by the use of a set of proteins as defined in the embodiments above for the manufacture of a medicament for the treatment of a patient suffering from the above defined and described diseases a disorder or, for example, a patient suffering from cancer and/or undergoing cell or tissue transplantation.

As used herein, the term "polypeptide" refers to a linear molecular chain of amino acids containing more than 30 amino acids. Optionally, a polypeptide may include one or more disulfide bonds or be chemically modified. Moreover, optionally a non-proteinaceous element (such as a fluorophore, RNA-aptamer, DNA-aptamer, or small molecule) may be attached to said linear molecular chain of amino acids. Such polypeptides can be produced by any known method. The polypeptide can for example be generated by expression from a nucleic acid coding for said polypeptide, or can be synthesized by solid phase synthesis methods, or be produced by conjugation or linkage of existing molecules, e.g., by chemical linkage.

The term "polypeptide P1" is used to refer to a polypeptide comprising (i) a targeting moiety, wherein said targeting moiety specifically binds to an antigen, and (ii) a fragment of a functional domain, wherein neither said fragment by itself nor said polypeptide P1 by itself is functional with respect to the function of said functional domain. The term "polypeptide P2" is used to refer to a polypeptide comprising (i) a targeting moiety, wherein said targeting moiety specifically binds to an antigen, and (ii) a fragment of a functional domain, wherein neither said fragment by itself nor said polypeptide P2 by itself is functional with respect to the function of said functional domain.

The term "domain", as used herein, refers to a linear molecular chain of amino acids that includes the amino acid sequence of an entire polypeptide or a portion of a polypeptide. Optionally, a domain may include one or more disulfide bonds or be chemically modified. Moreover, optionally a domain may comprise a non-proteinaceous element (such as a fluorophore). In one embodiment, however, the term "domain" does not comprise compounds that are chemically modified or comprise non-proteinaceous element(s).

A "functional domain", as used herein, is a domain that is capable of fulfilling a certain function, such as specific binding to a certain binding partner or antigen, specific activation of a certain receptor, mediation of toxic effects, or fluorescence upon excitation with light of an appropriate wavelength.

The term "functional domain F" is preferably meant to also include compounds that are non-proteinaceous. In one embodiment, however, it refers to a proteinaceous compound or a functional part thereof.

The term "a fragment of a domain", as used herein, refers to a linear molecular chain of amino acids that corresponds to a part of a domain, but not the entire domain. Optionally, a fragment of a domain may include one or more disulfide bonds or be chemically modified. Moreover, optionally a domain may comprise a non-proteinaceous element or part of such a non-proteinaceous element.

The term "fragment F1" is used to refer to a fragment of a functional domain. The term "fragment F2" is used to refer to a fragment of a functional domain.

The pairwise abbreviations P1, P2; T1, T2; F1, F2; A1, A2; and I1, I2, as used herein, are meant to designate different polypeptides, targeting moieties, fragments, antigens, and immunoglobulin modules, respectively. They are synonymous to first polypeptide, second polypeptide; first targeting moiety, second targeting moiety; first fragment, second fragment; first antigen, second antigen; and first immunoglobulin module, second immunoglobulin module, respectively.

The term "moiety", as used herein, refers to a linear molecular chain of amino acids that includes the amino acid sequence of an entire polypeptide or a portion of a polypeptide. Optionally, a moiety may include one or more disulfide bonds or be chemically modified. Moreover, optionally a moiety may comprise a non-proteinaceous element (such as an oligonucleotide). In one embodiment, however, the term "moiety" does not comprise compounds that are chemically modified or comprise non-proteinaceous element(s).

The term "targeting moiety T1" is used to refer to a moiety that specifically binds to an antigen, for example antigen A1. The term "targeting moiety T2" is used to refer to a moiety that specifically binds to an antigen, for example antigen A2.

As used herein, a "linker" is a sequence of amino acids within a polypeptide that connects two parts of said polypeptide or two domains comprised by said polypeptide.

The term "nucleic acid molecule", as used by the present invention, defines a linear molecular chain consisting of more than 30 nucleotides. The term includes DNA, such as cDNA or genomic DNA, and RNA.

The term "construct", as used herein, refers to a nucleic acid molecule comprising one or more recombinant nucleotide sequences. The term also includes polypeptides that are expressed from a recombinant nucleotide sequence or that are artificially made or recombinant molecules that comprise two or more amino acid sequences that are not naturally found within the same protein.

The term "specifically binds to" or "specifically binds", as used by the present invention in the context of a molecule or domain that specifically binds to an interaction partner or antigen or that specifically binds an interaction partner or antigen, means that a molecule or domain binds to said interaction partner or antigen, preferably by non-covalent binding, or is capable of binding said interaction partner or antigen, preferably by non-covalent binding, and does not or essentially not cross-react with any other interaction partner or antigen with a structure similar to that of the interaction partner or antigen.

In the context of a targeting moiety (such as targeting moiety T1 or T2) specifically binding to an antigen (such as antigen A1 or A2), the term "specifically binds to" is meant to refer to a situation where either said targeting moiety is capable of specifically binding to said antigen, or where it actually binds thereto.

In the context of a T cell engaging domain, an NK cell engaging domain, domain engaging macrophage cells, a monocyte engaging domain, a granulocyte engaging domain, a domain engaging neutrophil granulocytes, or a domain engaging activated neutrophil granulocytes, monocytes and/or macrophages, the term "specifically binding to" an antigen or molecule or "specifically binds to" an antigen or molecule is meant to refer to a situation where either the respective domain is capable of specifically binding to said antigen or molecule, or where it actually binds thereto.

In the context of a functional domain being a domain that "specifically binds to" an antigen, a molecule, a compound, a carrier molecule or an affinity tag, the term "specifically binds to" is meant to refer to a situation where either said functional domain is capable of specifically binding to said antigen, molecule, compound, carrier molecule or affinity tag, or where it actually binds thereto.

In the context of a toxin, fluorophore, antigen, carrier molecule or affinity tag being "specifically bound by" a functional domain, this is meant to refer to a situation where either said functional domain is capable of specifically binding to said toxin, fluorophore, antigen, carrier molecule or affinity tag, or where it actually binds thereto.

As used in the present application, a molecule or antigen is "specific for a certain cell type or cell lineage" if it is expressed by said cell type/cells of said cell lineage, but not (or only to a negligible extent) by other cell types or cells of other cell lineage. In some embodiments, a molecule or antigen is "specific for a certain cell type or cell lineage" if it is expressed by said cell type/cells of said cell lineage, and not more than a few other cell types or cells of other cell lineage besides said cell type/cells of said cell lineage express said antigen as well, while most other cell types or cells of other cell lineage besides said cell type/cells of said cell lineage do not express said antigen (or only to a negligible extent). The term "specific for a certain cell type or cell lineage" may also mean that said molecule or antigen is expressed by said cell type/cells of said cell lineage at a higher rate or at a higher proportion or amount than by other cell types/cells of other cell lineages, in the sense that there may be a small but detectable expression of said molecule also in other cell types/cells of other cell lineages. The term "marker", as used herein in the context of a marker for a certain cell type or cell lineage, can refer to a molecule or antigen that is specific for a cell type or cells of a cell lineage, respectively, as described above.

As used herein, the term "aptamer" refers to a small compound composed of oligonucleic acid (such as RNA or DNA) or peptidic or non-peptidic molecule that binds to a specific target molecule with high affinity.

As used herein, the term "carrier molecule" refers to a molecule or part of a molecule that is not recognized as foreign by the immune system of a patient to whom the set of polypeptides according to the invention is administered or that causes no or only a weak immune reaction by a patient to whom the set of polypeptides according to the invention is administered. Preferably, such a "carrier molecule" is being bound by or capable of being bound by another molecule, such as an antibody. In some embodiments, a "carrier molecule" is a molecule or part of a molecule that In certain embodiments, the carrier molecule is attached covalently or non-covalently to a second molecule or part of a second molecule, for example a fluorophore or toxin.

The term "MHC" refers to the Major Histocompatibility Complex, which is a set of genes encoding a group of molecules comprising cell-surface molecules that are required for antigen presentation to T-cells and that are also responsible for rapid graft rejections. In humans, the MHC includes the genes HLA-A, HLA-B, HLA-C, HLA-DP, HLA-HQ, and HLA-DR. In the present application, the term is used to refer to the genes of the Major Histocompatibility Complex as well to the gene products encoded by these genes. The term "HLA" refers to Human Leukocyte Antigens. As used herein, "HLA" is the human form of "MHC".

The term "allelic variant", as used herein, denotes any of two or more alternative forms of a gene occupying the same chromosomal locus. For example, HLA-A1, HLA-A2, and HLA-A3 are three of the allelic variants of HLA-A. The term allelic variant is also used herein to denote a protein encoded by an allelic variant of a gene.

The term "antigen", as used herein, refers to a molecule known to be specifically bound by or capable of being specifically bound by an antibody or the antigen-binding part of an antibody. In its broadest meaning, "antigen A1" refers to an antigen as defined above. In its broadest meaning "antigen A2" refers to an antigen as defined above. The designations "antigen A1" and "antigen A2" have been chosen in order to allow for distinction between "antigen A1" and "antigen A2". An "MHC antigen" is an antigen that is also a molecule belonging to the major histocompatibility complex. MHC antigens include MHC class I antigens (in humans, the antigens HLA-A, -B, and -C) and MHC class II antigens (in humans, the antigens HLA-DP, -DQ, and -DR). The phrase that a cell "carries an antigen" or "carries an antigen at its cell surface" is meant to refer to a situation where a cell expresses an antigen that is present at the cell surface of said cell and accessible for an antibody from outside said cell. The phrase that a substrate "has an antigen at its surface" is meant to refer to a situation where said antigen is present at the surface of said substrate and accessible for an antibody applied to said substrate.

The term "an antigen that is specific for the malignant state of a cell", as used herein, refers to an antigen that a malignant cell of a certain cell type (such as a malignant B-cell tumour cell) carries at its cell surface, but that a cell of the same cell type that is not malignant (such as a non malignant B-cell) does not (or only to a negligible extent) carry at its cell surface.

The term "an antigen/molecule that is specific for a malignant cell type", as used herein, refers to an antigen/molecule that a malignant cell of a certain cell type (such as malignant B-cell tumour cell) carries at its cell surface, but that a cell of the same cell type that is not malignant (such as a non malignant B-cell) or cells of other cell types (such as T-cells or hepatocytes) do not (or only to a negligible extent) carry at their cell surface. In some embodiments, the term "an antigen/molecule that is specific for a malignant cell type" refers to an antigen/molecule that a malignant cell of a certain cell type (such as malignant B-cell tumour cell) carries at its cell surface, but that a cell of the same cell type that is not malignant (such as a non malignant B-cell) does not (or only to a negligible extent) carry at its cell surface, and that only cells of a few other cell types besides that certain cell type carry at their cell surface, while cells of most other cell types do not (or only to a negligible extent). The term "an antigen/molecule that is specific for a malignant cell type" may also mean that said antigen/molecule is expressed by said malignant cell of a certain cell type at a higher rate or at a higher proportion or amount than by a cell of the same cell type that is not malignant, in the sense that there may be a small but detectable expression of said molecule also in a cell of the same cell type that is not malignant. The term "marker", as used herein in the context of a marker for the malignant state of a certain cell or for a malignant cell type, can refer to a molecule or antigen that is specific for the malignant state of a certain cell or for a malignant cell type, respectively, as described above.

The term "immunoglobulin domain", as used herein, refers to a domain that essentially consists of a globular region of an antibody chain. Immunoglobulin domains are characterized in that they retain the immunoglobulin fold characteristic of antibody molecules. Immunoglobulins, such as IgG, IgE, or IgM, are composed of a varying number of heavy and light chains. Each heavy and light chain contains a constant region and a variable region. Each light chain variable region ($V_L$) and each heavy chain variable region ($V_H$) contains three hypervariable regions, also called "complementarity-determining regions" or "CDRs". The CDRs are primarily responsible for binding of the immunoglobulin to an antigen.

The terms "$V_H$" or "$V_H$ domain" are used interchangeably and refer to the variable region of an immunoglobulin heavy chain of an antibody. The terms "$V_L$" or "$V_L$ domain" are used interchangeably and refer to the variable region of an immunoglobulin light chain of an antibody.

The term "immunoglobulin module", as used herein, refers to a molecule, part of a molecule or molecular assembly which comprises one or more, preferably two or more, immunoglobulin domains and which is capable of binding to an antigen. Preferably, an "immunoglobulin module" comprises a linear molecular chain of amino acids that includes the amino acid sequence of one or more, preferably two or more, immunoglobulin domains. Optionally, an "immunoglobulin module" comprises one ore more, preferably two or more, disulfide bonds. Included in the term "immunoglobulin module" are molecules or parts of a molecule that comprise or consist of a "single-chain variant fragment" of an antibody. Included in the term "immunoglobulin module" are also molecules or parts of a molecule that comprise or consist of a $V_H H$ domain of a llama antibody, a camel antibody, or a shark antibody.

The term "immunoglobulin module I1" is used to refer to an immunoglobulin module comprising a $V_L$ domain linked to a $V_H$ domain. Preferably, said $V_L$ domain and said $V_H$ domain of said immunoglobulin module I1 are derived from the same antibody. Preferably, said $V_L$ domain and said $V_H$ domain of said immunoglobulin module I1 form a dimer. Preferably, said dimer is capable of specifically binding to an antigen. Said antigen may be, for example, the antigen A1. In one embodiment, said "immunoglobulin module I1" comprises a "single-chain variant fragment" of an antibody that is capable of specifically binding to an antigen, for example the antigen A1.

The term "immunoglobulin module I2" is used to refer to an immunoglobulin module comprising a $V_L$ domain linked to a $V_H$ domain. Preferably, said $V_L$ domain and said $V_H$ domain of said immunoglobulin module I2 are derived from the same antibody. Preferably, said $V_L$ domain and said $V_H$ domain of said immunoglobulin module I2 form a dimer. Preferably, said dimer is capable of specifically binding to an antigen. Said antigen may be, for example, the antigen A2. In one embodiment, said "immunoglobulin module I2" comprises a "single-chain variant fragment" of an antibody that is capable of specifically binding to an antigen, for example the antigen A2.

Within a construct of an immunoglobulin module comprising a $V_L$ domain linked to a $V_H$ domain, the $V_L$ domain may be positioned N- or C-terminally of the corresponding $V_H$ domain. The skilled person is able to determine which arrangement of the $V_H$ and $V_L$ domains is more suitable for a specific single-chain variant fragment domain.

The terms "Fv" and "variant fragment", as used herein, refers to a fragment of an antibody that is the minimum antibody fragment which contains a complete antigen recognition and binding site. This region consists of a dimer of one heavy and one light chain variable region in a tight, non-covalent association ($V_H$–$V_L$ dimer). In this configuration, the $V_H$ and $V_L$ domain together define an antigen binding site with antigen binding specificity on the surface of the $V_H$–$V_L$ dimer.

The terms "scFv", "single chain Fv", and "single-chain variant fragment" are used interchangeably and are meant to designate an antibody or portion of an antibody in which the variable region of the heavy chain ($V_H$) and the variable region of the light chain ($V_L$) of a traditional two chain antibody have been joined to form one chain. Typically, a linker is inserted between the two chains to allow for proper folding and creation of an active binding site.

The term "llama antibody", as used herein, refers to an antibody or part of an antibody derived from llama. The term "camel antibody", as used herein, refers to an antibody or part of an antibody derived from camel. The term "shark antibody", as used herein, refers to an antibody or part of an antibody derived from shark. Llama, camel and shark antibodies have an antigen binding moiety that is built up by one single domain, $V_H H$, (rather than a $V_H$ and a $V_L$ chain).

The expression "T cell engaging domain", as used herein, is meant to refer to a domain that specifically binds to an antigen that is present on the cell surface of T cells. Preferably, binding of said T cell engaging domain to said antigen activates said T cell. Similarly, the expression "NK cell engaging domain" refers to a domain that specifically binds to an antigen that is present on the cell surface of Natural Killer cells. Preferably, binding of said NK cell engaging domain to said antigen activates said Natural Killer cells. The expression "domain engaging macrophage cells" refers to a domain that specifically binds to an antigen that is present on the cell surface of macrophage cells. Preferably, binding of said domain engaging macrophage cells to said antigen activates said macrophage cells. The expression "monocyte engaging domain" refers to a domain that specifically binds to an antigen that is present on the cell surface of monocytes. Preferably, binding of said monocyte engaging domain to said antigen activates said monocytes. The expression "granulocyte engaging domain" refers to a domain that specifically binds to an antigen that is present on the cell surface of granulocytes. Preferably, binding of said granulocyte engaging domain to said antigen activates said granuloctyes. The expression "domain engaging neutrophil granulocytes" refers to a domain that specifically binds to an antigen that is present on the cell surface of neutrophil granulocytes. Preferably, binding of said domain engaging neutrophil granulocytes to said antigen activates said neutrophil granuloctyes. The expression "domain engaging activated neutrophil granulocytes, monocytes and/or macrophages" refers to a domain that specifically binds to an antigen that is present on the cell surface of activated neutrophil granulocytes, monocytes and/or macrophages. Preferably, binding of said domain engaging activated neutrophil granulocytes, monocytes and/or macrophages to said antigen activates said monocytes and/or macrophages.

The term "molecule capable of mediating bioluminescence", as used herein, refers to a molecule (or functional part of a molecule) that has an enzymatic activity which in the presence of the appropriate substrate(s) catalyzes a reaction that causes bioluminescence. The term includes luciferases, such as the luciferases of firefly or *Gaussia*.

The term "GFP variant", as used herein, refers to a molecule that has an amino acid sequence derived from the amino acid sequence of green fluorescent protein from *Aequorea victoria* by introducing alterations resulting in greater fluorescence or fluoresce in different colors. The term is meant to include, among others, YFP (yellow fluorescent protein), CFP (cyan fluorescent protein), Venus (Nagai T et al., A variant of yellow fluorescent protein with fast and efficient maturation for cell-biological applications. Nat Biotechnol. 2002 January; 20(1):87-90), Cerulean (Enhanced CFP with S72A, Y145A and H148D substitutions).

"Enhanced GFP" (and, analogously, "enhanced YFP", "enhanced CFP") refers to a GFP (YFP, CFP) which has been "humanized", as reported in Kain et al. (1995) Biotechniques 19(4):650-55. "Humanized" refers to changes made to the GFP (YFP, CFP) nucleic acid sequence to optimize the codons for expression of the protein in human cells.

The term "bimolecular fluorescence complementation molecule", as used herein, refers to a fluorescent molecule that can be provided as two fragments which by themselves are not fluorescent, but which upon heterodimerization between the two fragments form a dimer that is capable of fluorescence.

The term "therapeutic compound", as used herein, refers to a compound suited for preventing, treating, alleviating or curing a disease or disease state. Preferably, a "therapeutic compound" is a compound that, upon entry into a cell, is capable of causing the death of that cell. In some embodiments, a therapeutic compound can be a chemical or radioactive compound that damages vital cellular structures or interrupts vital cellular processes.

The term "diagnostic compound", as used herein, refers to a compound that can be detected by common detection methods, such as methods used in the clinic or in biochemical or medical diagnostic laboratories, for example a fluorescent compound, a radioactive compound, or a molecule mediating bioluminescence.

The term "progenitor/precursor cells" is meant to refer to immature, undifferentiated or partially differentiated cells that are typically found in post-natal animals/humans and have the potential to differentiate into a specific cell type or into specific cell types. The term "progenitor/precursor cells of a tumour" designates progenitor/precursor cells with altered properties (e.g. regarding their proliferation behaviour or gene expression pattern) that give rise to tumour cells. Examples for such progenitor/precursor cells of a tumour are e.g. leukemic precursor or progenitor cells.

The term "cancer", as used herein, refers to a malignant cell, group of cells, or malignant neoplasia. The term is meant to comprise carcinomas, sarcomas, lymphomas, leukemias, germ cell tumours, and blastomas. A "cancerous cell" is a cell that is part of or derived from a cancer. The term "tumour" is used interchangeably with the term "cancer".

As used herein, the term "haematologic tumour" refers to a cancer of the blood or blood building system (such as bone marrow cells, blood-building cells, and precursor cells of mature blood cells). In some embodiments, the term "haematologic tumour" refers to a haematologic neoplasia. As used herein, the term "non-haematologic tumour" refers to a tumour that is not a haematologic tumour.

The term "a patient who is undergoing allogeneic tissue or cell transplantation", as used herein, refers to a situation where a patient receives or has received transplanted cells or transplanted tissue that has/have been obtained from another person. A preferred situation as to this aspect is the situation with mismatched HLA antigens. The unit "$\mu g/m^2$", as used herein in the context of an amount of a polypeptide administered, refers to a certain amount of polypeptide per square meter of body surface of the patient to whom said polypeptide is administered (the peptide may be administered by any adequate route of administration, such as by intravenous or subcutaneous injection). For example, the expression "The amount of polypeptide administered is 50 $\mu g/m^2$ per day for the polypeptide P1." is meant to refer to a situation where the amount of polypeptide P1 administered per day is 50 µg per square meter of body surface of the patient to whom the polypeptide P1 is administered. In the case of a patient having a body surface of 2 $m^2$ this would mean that 100 µg of polypeptide P1 are administered per day.

The present inventors have surprisingly found that with a set of polypeptides according to the invention the above-indicated problems of the prior art can be overcome and the above-described objects can be accomplished. Moreover, the present inventors have surprisingly found that with a set of polypeptides according to the invention, cells with a specific combination of two antigens can be identified and/or eliminated with high specificity and reduced side-effects.

It is one advantage of the combinatorial strategy of the invention that no preformed F units (for example anti-CD3 units) are used. The F1 and CD3 $V_H$ and $V_L$) do not heterodimerize per se, not even in the presence of an agent which stabilizes their dimerization (for example an antigen capable to bind to the domain F, like for example, CD3, HIS or DIG), and thus do not result in a functional F domain (for example do not stimulate T cells). Exclusively in situations where both complementary constructs P1 and P2 simultaneously bind on the surface of a given cell, the two components F1 and F2 reconstitute the F domain (for example, the CD3 binding site). Thus, function of the F domain (for example T cell activation) takes place precisely where needed but not systemically. Hence, it can be assumed that the combinatorial strategy of the invention has less toxic effects, for example as compared to normal bispecific antibody strategies. This is also evidenced by the appended examples, in particular by the in vivo model for allogeneic transplantation, where HLA-A2 positive mice did not suffer any clinical effects after infusion of HLA-A2 reactive constructs.

In particular, to tag cells that express a predefined antigen signature, two single-chain polypeptides were designed as parts of the final bipartite (bi-molecular) construct (bi-molecular/trispecific antibody construct), each composed of an antigen-binding single-chain variable fragment (scFv) and either the variable light (VL) or variable heavy chain (VH) domain of an antibody. When these two hybrid fragments bind their respective antigens on the surface of a single cell, the VL and VH domains interact with each other to reconstitute the original antigen binding site and thus fulfill the desired requirements.

As mentioned, it is one advantage of the set of polypeptides of the invention that binding of both target antigens on the cell surface is requisite for functional heterodimerization. Self-assembly of the two complementary parts and subsequent T cell stimulation after binding of only one arm to its antigen can be ruled out, thus corroborating published data showing that $V_H$ or $V_L$ binding by itself is of low affinity and that $V_H/V_L$ heterodimers tend to dissociate rapidly in the absence of antigen (Colman, 1987, Nature 326, 358-363; Amit, 1986, Science 233, 747-753; Law, 2002, Int Immunol 14, 389-400; Ueda, 1996, Nat Biotechnol 14, 1714-1718).

In contrast to the homo- or hetero-dimerization domains well known in the art (leucine-zipper, Fc-domains, knob in the hole etc), VH and HL interactions are of low affinity. However, it has been shown that VH/VL interaction can be stabilized after binding to the specific antigen. Without being bound by theory, VH/VL interaction in accordance with this invention takes place only in situations after both fragments have previously bound to their cognate target antigens, for example on the surface of a target cell. Also without being bound by theory, after simultaneous on-target binding, the constructs are brought into close proximity so that they can form a trimeric complex with the antigen. The thus on-target complemented trispecific heterodimer of the invention is functional with respect to the function of the domain F, for example, engages and stimulates T cells for tumor cell destruction if anti CD3 is reconstituted.

Beside one advantage of the constructs of the invention P1 and P2, e.g. the combinatorial nature of the immune response elicited, it was surprisingly found in the context of this invention that the bi-molecular construct with the disrupted F domain, for example scFv-anti CD3, displays no off target effects.

The set of polypeptides according to this invention, in particular the polypeptides P1 and P2 comprised therein, have the further advantage to be more stable and/or have an improved shelf life (in particular at 4° C.) as compared to conventional bispecific constructs like BiTE constructs. These conventional bispecific constructs tend to aggregate (in particular at 4° C.).

It is envisaged that the polypeptides of this invention P1 and P2, more particular of F1 and F2 as comprised therein, more particular of the $V_H$ and $V_L$ which may be comprised therein, due to their hydrophobic interface, are capable to bind albumin. This leads to an improved retention time; i.e. longer bioavailability in vivo but also in vitro, like, for example, in serum or blood samples.

The set of polypeptides according to the present invention comprises a first polypeptide P1 and a second polypeptide P2. The first polypeptide P1 comprises a first targeting moiety T1 (which is capable of specifically binding to an antigen A1) fused to a first fragment F1 of a functional domain F (see FIG. 1A, top). The second polypeptide P2 comprises a second targeting moiety T2 (which is capable of specifically binding to an antigen A2) linked to a second fragment F2 of the functional domain F (see FIG. 1A, bottom). Importantly, the fragments F1 resp. F2 of the functional domain are non-toxic by their own and unable to exert any biological function unless there is partnering between the two polypeptides P1 and P2. When both polypeptides P1 and P2 simultaneously bind to their antigens on the surface of a single cell that expresses both antigens A1 and A2, the fragments F1 and F2 of the functional domain F are brought together in close proximity, they hetero-dimerize and thus complement the desired biological function (see FIG. 1B). On the other hand, a cell that expresses either only antigen A1 (FIG. 1C) or only antigen A2 (FIG. 1D) or none of the antigens does not cause complementation of the biological function. Thus, the biological function is achieved with high specificity only in the presence of cells having both antigens A1 and A2 at their cell surface upon simultaneous binding of both polypeptides P1 and P2 to such a cell. Depending on the nature of the functional domain F, different objects, such as specific identification/detection or elimination of cells that express both antigens A1 and A2, can be accomplished.

In one exemplary embodiment, this inventive principle is applied for the specific elimination of tumour cells:

Novel histopathological and flow cytometry analyses have revealed that tumour cells can be detected and distinguished from their non-transformed counterparts not by single surface markers but by the expression of aberrant antigen combinations/profiles, as is known for haematopoietic neoplasias and cancer and cancer stem cells of various other provenience. Thus, while a single antigen may not be sufficient to specifically identify a certain tumour cell, a specific combination of two antigens may allow discriminating the tumour cell from any other type of cell.

For example, the set of polypeptides according to the invention may be used to specifically eliminate cancer cells characterized by the simultaneous expression of the antigens CD33 and CD19 at their cell surface. This combination of antigens is found on certain types of acute leukemia cells and distinguishes these cells from any other cells (such as non-malignant cells), which may carry either CD33 or CD19 at their cell surface, but do not carry both CD33 and CD19 at their cell surface (Ossenkoppele et al., Review of the relevance of aberrant antigen expression by flow cytometry in myeloid neoplasms. Br J Haematol 2011, 153(4):421-36).

To specifically eliminate these leukemic cells carrying both CD33 and CD19 at their cell surface, the first targeting moiety T1 of the first polypeptide P1 may be a single chain variable Fragment (scFv) specific for CD33. As fragment F1 of the functional domain F, the light chain variable domain $V_L$ of an anti CD3 antibody may be chosen. The second targeting moiety T2 of the second polypeptide P2 may be a scFv specific for CD19. As the fragment F2 of the functional domain F the heavy chain variable domain $V_H$ of that anti CD3 antibody may be chosen. The light chain variable domain $V_L$ and the heavy chain variable domain $V_H$ of the anti CD3 antibody are each non-toxic by their own. They are also unable to exert their biological function (i.e. to effectively bind the CD3 antigen) unless there is partnering between the polypeptides P1 and P2.

In the presence of a leukemic cell having both CD33 and CD19 at its cell surface, both polypeptides P1 and P2 simultaneously bind to that cell. As a consequence, the fragments F1 and F2 of the functional group F (i.e. the heavy and light chain of the Fv anti CD3 variable domain of that anti-CD3 antibody) are brought together in close proximity, they hetero-dimerize and thus complement the desired biological function, enabling the dimer of P1 and P2 to specifically bind to CD3.

CD3 is a cell surface molecule that is present on the surface of T cells. The molecule is part of the T cell signaling complex, and cross-linking of CD3 molecules on the surface of a T cell after binding of a CD3-specific antibody leads to activation of the T cell. By engaging CD3 antigens on the surface of T cells, heterodimers of polypeptides P1 and P2 are capable of recruiting T cells and activating them. As a result, typical effector mechanisms of a cytotoxic T cell response are elicited, leading to cell lysis: release of lytic granules containing the cytotoxic proteins perforin, granzymes, and granulysin. Perforin forms pores into the membrane of the target cell through which the granzymes can enter and induce apoptosis. These effects lead to specific destruction of leukemic cells that carry both CD33 and the CD19 antigen at their cell surface.

Other cells than the leukemic cells do not have both the CD33 and CD19 antigen at their cell surface. Therefore, they cannot recruit both polypeptides P1 and P2, and no complementation of the CD3 binding capability and engagement of CD3 positive T lymphocytes is achieved. Consequently, other cells besides the leukemic cells are unaffected, and destruction of the malignant cells with exquisite specificity is achieved.

This is in stark contrast to conventional bispecific antibodies. A conventional bispecific construct that engages T cells and has specificity for cells expressing CD33 would mediate the destruction of all CD33 positive cells. Since CD33 is myeloid lineage marker which is expressed on many myeloid cells and myeloid progenitor cells, the destruction of these cells would result in long lasting aplasia and probably death of the patient. A conventional bispecific construct that engages T cells and has specificity for CD19 positive cells would lead to the elimination of all cells carrying the CD19 antigen at their cell surface. CD19 is expressed on a significant subset of B-lymphocytes. Destruction of these cells would lead to a severe defect of the immune system. Thus, besides eliminating leukemic cells that simultaneously express CD33 and CD19 on the surface, the application of conventional bispecific antibodies with specificity for CD33 and CD19 would lead to elimination of myeloid cells and a substantial subset of B-lymphocytes.

Thus, while conventional bispecific antibodies recognize only one antigen on the cell to be eliminated, effector activation according to the present invention requires the simultaneous recognition of two specific antigens on the surface of the cell to be identified/eliminated. In consequence, the present invention achieves significantly improved specificity and reduced side effects.

It is clear to a person of skill in the art that, within the principle of the present invention, diverse variations to the exemplary embodiment described above are possible.

For example, the approach described in the above exemplary embodiment can easily be adapted for the identification/elimination of other types of tumour cells besides CD33 and CD19 positive acute leukemia cells simply by choosing appropriate targeting moieties T1 and T2 that specifically bind to antigens A1 and A2, respectively, that are present simultaneously on the cells to be identified/eliminated, but not present simultaneously on other cell types. As quoted above, many if not all cancer cells (but also progenitor/precursor cells of cancer cells) express a number of cell surface molecules which per se are widely expressed on normal tissues, but are indicative for the malignant phenotype if expressed in a non-physiological combination. For example, CD34 is a marker for haematopoietic stem cells and CD7 can be detected on a subset of lymphoid cells. The combination of CD34 and CD7, however, is strongly associated with malignancy, and aberrant co-expression of the two antigens can be detected on a substantial proportion of acute myelogenous leukemias (Ossenkoppele et al., Review of the relevance of aberrant antigen expression by flow cytometry in myeloid neoplasms. Br J Haematol 2011, 153(4):421-36). Similarly, aberrant co-expression of CD44 and CD117 has been described for ovarian cancer stem cells, CD44 and CD24 for pancreas cancer initiating cells and the combination of EpCAM and CD44 in colon and breast cancer stem cells (Natasha Y. Frank, Tobias Schatton, Markus H. Frank; The therapeutic promise of the cancer stem cell concept. J Clin Invest. 2010; 120:41-50). Expression of CD24 and CD29, as well as CD24 and CD49f has been found to be specific for breast carcinoma (Vassilopoulos A et al. Identification and characterization of cancer initiating cells from BRCA1 related mammary tumours using markers for normal mammary stem cells. *Int J Biol Sci* 2008; 4:133-142). Moreover, combinations with highly expressed antigen levels are indicative for a number of malignancies, like CD38 and CD138 for myeloma.

In addition to the cancer-specific antigen combinations listed above and those known from the scientific literature, additional combinations of two antigens that are expressed simultaneously on specific tumour cells but not on other cells can be derived in a straight-forward manner by the person of skill in the art.

Firstly, the skilled person may arrive at an antigen combination that is specific for a certain cancer by combining an antigen that is specific for the malignant state of the respective cell type with an appropriate cell type marker or cell lineage marker. For example, carbonic anhydrase IX is a marker strongly associated with renal cell carcinoma and metastases of renal cell carcinoma and thus represents a marker for the malignant state of renal cells. This membrane located marker, however, is also expressed on normal cells of the intestinal tract. By selecting as second antigen a renal lineage marker like aquaporin, the resulting combination of two antigens is specific for renal cell carcinoma cells and cells resulting from metastasis of renal cell carcinoma, while neither non-malignant kidney cells (which do not express carbonic anhydrase IX) nor cells from the intestinal tract (which do not express aquaporins) are characterized by the selected pair of antigens.

Detailed information on markers for the malignant state of various cell types and on markers for numerous cell types or cell lineages is available from the literature and web-based resources (see below for details) or can be obtained by straight-forward experimentation (see below).

Examples for markers for the malignant state of a cell include: E-cadherin for epithelial cells and ductal-type breast carcinoma cells; Ca-125 for Epitheloid malignancies and ovary cancer cells, adenocarcinoma cells and breast cancer cells; Her-2/neu for breast cancer cells; gross cystic disease fluid protein (BRST-2 protein) for breast cancer cells; BCA-225 (breast carcinoma associated glycoprotein) for lung and breast cancer cells; CA 19-9 (carbohydrate antigen 19-9) for pancreas, bile duct and intestinal tract cancer cells; CEA for colorectal cancer cells; CD117 (c-kit) for gist (gastrointestinal stromal tumour) cells (and myeloid and mast cells); CD30 for Reed-Sternberg cells (and Ki-1 activated T-cells and B-cells); Epithelial antigen (BER-EP4), Epithelial membrane antigen, and Epithelial Related Antigen (MOC-31) for epithelial cancer cells; Epidermal growth factor receptor (HER1) for cells of various cancers; Platelet derived growth factor receptor (PDGFR) alpha for cells of various cancers; Melanoma associated marker/Mart 1/Melan-A for melanoma cells; CD133 for cancer stem cell populations and others; TAG 72 (tumour associated gp 72) for adenocarcinoma cells.

Further examples for markers for a malignant state of a cell/cells include: EpCAM, CD19, HER-2, HER-3, HER-4, PSMA, MUC-1 (mucin), MUC2, MUC3, MUC4, MUC5AC, MUC5B, MUC7, Lewis-Y, CD20, CD33, CD44v6, Wue-1, Plasma Cell Antigen, (membrane-bound) IgE, Melanoma Chondroitin Sulfate Proteoglycan (MCSP), STEAP, mesothelin, Prostate Stem Cell Antigen (PSCA), sTn (sialylated Tn antigen), FAP (fibroblast activation antigen), EGFRvIII, Igα, Igβ, MT-MMPs, Cora antigen, EphA2, L6 and CO-29, CCR5, βHCG, ganglioside GD3, 9-O-Acetyl-GD3, GM2, Globo H, fucosyl GM1, Poly SA, GD2, Carboanhydrase IX (MN/CA IX), Sonic Hedgehog (Shh), CCR8, TNF-alpha precursor, A33 Antigen, Ly-6, desmoglein 4, E-cadherin neoepitope, Fetal Acetylcholine Receptor, CD25, Muellerian inhibitor Substance (MIS) Receptor type II, endosialin, SAS, CD63, TF-antigen, CD7, CD22, Igα (CD79a), Igβ (CD79b), G250, gp100, F19-antigen and EphA2.

Examples for antigens that are specific for a certain cell type/cell lineage or for a few cell types/cell lineages (cell type markers/cell lineage markers) include: CD45 for hematopoietic cells; CD34 for endothelial cells, stem cells, and stromal cells; CD33 for myeloid cells; CD138 for plasma cells and a subset of epithelial cells; CD15 for epithelial, myeloid, and Reed-Sternberg cells; CD1a for cortical thymocytes and Langerhans cells; CD2 for thymic cells, T-cells, and Natural Killer (NK) cells; CD3 for T-cells; CD4 for helper T-cells; CD5 for T-cells, a subset of B-cells, and thymic carcinoma cells; CD8 for cytotoxic T-cells; CD20 for B-cells; CD23 for activated B-cells; CD31 for endothelial cells; CD43 for T-cells, myeloid cells, a subset of B-cells, histiocytes, and plasma cells; CD56 for NK cells; CD57 for neuroendocrine cells, and NK cells; CD68 for macrophages; CD79a for B-cells and plasma cells; CD146 for the endothelial cell lineage; surfactant proteins for lung cells; synaptophysin, CD56 or CD57 for neuroendocrine cells; nicotinic acetylcholine receptor or muscle-specific kinase (MUSK) for muscle cells; voltage-gated calcium channel (P/Q-type) or voltage-gated potassium channel (VGKC) or N-methyl-D-aspartate receptor (NMDA) for muscle cells and neurons; TSH (thyroid stimulating hormone) receptor for thyroid gland; amphiphysin for muscle cells; HepPar-1 for hepatocytes; ganglioside GQ1B, GD3 or GM1 for neuronal cells; and glycophorin-A for cells of the erythropoietic cell lineage.

It should be noted that there are situations where it may be advantageous to rely for the purposes of the present invention on an antigen with a less than perfect specificity for the cell type or cell lineage of interest. For example in situations where no antigen is known that is found exclusively on the cell type/cell lineage of interest and not on any other cell types/lineages or in situations where it is not possible to confirm the exclusive specificity of an antigen, also antigens that are present on one or more other cell types/cell lineages besides the cell type/cell lineage of interest may be considered. Similar consideration apply for markers for the malignant state of a cell, or even for the specificity of the combination of two antigens. Thus, there are for example situations where for the purposes of the present invention a combination of two antigens is selected that is specific not only for the cells of interest, but also for one or more (a few) other cell types/cell lineages/kinds of malignant cells.

Secondly, the skilled person may arrive at an antigen combination that is specific for a certain cancer by straightforward experimentation. This may comprise the steps of (1) determining the surface antigens on the tumour cells to be eliminated and (2) identifying among these tumour cell surface antigens two antigens that are not present simultaneously on other cell types (or, in some embodiments, present on only a few other cell types).

Often, experimentation may not be necessary to determine the surface antigens on tumour cells to be eliminated, because such information may already be available for the respective type of cancer from the printed literature (see, e.g. David J. Dabbs, Diagnostic immunohistochemistry, Churchill Livingstone, 3rd edition (2010); or F Lin and J Prichard, Handbook of Practical Immunohistochemistry: Frequently Asked Questions, Springer, New York, 1st edition (2011)). Even more extensive information is available through web-based resources. For example, the Cancer Genome Anatomy Project (CGAP) of the U.S. National Cancer Institute (NCI) has systematically determined the gene expression profiles of various normal, precancer, and cancer cells (Strausberg RL. The Cancer Genome Anatomy Project: building a new information and technology platform for cancer research. In: Molecular Pathology of Early Cancer, 1999, (Srivastava, S., Henson, D.E., Gazdar, A., eds. IOS Press), pp. 365-370). The resources generated by the CGAP initiative are freely available (cgap.nci.nih.gov/ on the worldwide web) and include access to all CGAP data and the necessary analysis tools. Similarly, the Cancer Genome Characterization Initiative (CGCI) of the National Cancer Institute focuses on tools for characterizing the genomic changes involved in different tumours, for example genomic characterization methods including exome and transcriptome analysis using second generation sequencing. The data generated by CGCI is available through a publicly accessible database (cgap.nci.nih.gov/cgci on the worldwide web). Thus, in many cases information about the presence or absence of various known cell surface proteins on the tumour cells of interest can be derived by simply checking these publicly accessible databases. If desired, this information may then be verified in a second step by immunocytochemical/immunohistochemical analysis of tumour cells/tissue according to the methods described below.

If there is no information available on the proteins expressed by the tumour cells/tissue of interest, the skilled person can carry out a characterization of the antigens on the tumour cells/tissue by immunocytochemical/immunohistochemical methods with a panel of antibodies (see, e.g., "Handbook of Practical Immunohistochemistry: Frequently Asked Questions" by F Lin and J Prichard, Springer New York, 1st edition (2011); or "Using Antibodies: A Laboratory Manual" by E Harlow and D Lane, Cold Spring Harbor Laboratory Press (1998)). In brief, a histological preparation or cells isolated from the tumour are incubated with a first antibody directed at a potential surface antigen and, after a washing step, incubation of a second antibody directed against the Fc domain of the first antibody. This second antibody is labelled with a fluorophore or an enzyme like HRP (horse radish peroxidase), in order to visualize expression of the targeted antigen. Panels of antibodies that can be used for high throughput antigen profiling purposes of cell surface antigens are commercially available from numerous manufacturers.

In addition, tools specifically dedicated to high throughput proteomic cell characterization to identify and analyze cell surface protein expression are commercially available, such as the FACS (Fluorescence-activated cell sorting)-based high throughput array technology BD FACS™ CAP (Combinational Antibody Profile) of Becton, Dickinson & Company.

The immunocytochemical/immunohistochemical/proteomic analysis described above may be preceded (or, in some cases, replaced) by genome-wide gene expression profiling of tumour cells or by mass spectrometric analysis of the proteins expressed by the tumour cells/tissue of interest. For example, genome-wide gene expression profiling of tumour cells can be carried out to check for the expression of various cell surface molecules, and the presence of such antigens on the cell surface of the tumour cells may then be confirmed through antibody-based staining methods as described above.

Further information about approaches to characterize the surface antigens of (cancer) cells is available in the relevant scientific literature (e.g. Zhou J, Belov L, Huang P Y, Shin J S, Solomon M J, Chapuis P H, Bokey L, Chan C, Clarke C, Clarke S J, Christopherson R I. Surface antigen profiling of colorectal cancer using antibody microarrays with fluorescence multiplexing. J Immunol Methods. 2010; 355:40-51; or Carter P, Smith L, Ryan M. Identification and validation of cell surface antigens for antibody targeting in oncology. Endocr Relat Cancer. 2004; 11:659-87).

In a next step, the skilled person may identify among the cell surface antigens of the tumour cells a combination of two antigens which is not expressed simultaneously on other cell types.

Often, already the literature or publicly available databases may provide detailed information about the presence or absence of antigens from other cell types:

The expression of various cell surface molecules on diverse cell types has been studied systematically by researchers in the past decades by immunophenotyping and gene expression profiling of almost any cell type of the body. For example, detailed information on the expression of more than 360 "cluster of differentiation" antigens (or CD antigens) is available in print (e.g. "Leukocyte and Stromal Cell Molecules: The CD Markers" by Zola H, Swart B, Nicholson I, and Voss E; John Wiley & Sons, 1st ed. (2007)) and in online depositories (e.g. hcdm.org/MoleculeInformation/tabid/54/Default.aspx), and includes information on tissue distribution and expression levels of antigens, as well as information about antigen reactive antibodies and the epitopes these antibodies bind to. Moreover, there are publicly available databases which provide access to a large amount of genomic data generated by the scientific community. For example, the Gene Expression Omnibus (GEO) platform of the National Center for Biotechnology Information (NCBI) of the United States (Barrett T et al., NCBI GEO: archive for functional genomics data sets—10 years on. Nucleic Acids Res. 2011;39(Database issue):D1005-10) archives and gives access to an enormous collection of microarray, next-generation sequencing, and other forms of high-throughput functional genomic data, and further provides web-based interfaces and applications for easy access to this information (ncbi.nlm.nih.gov/geo/on the worldwide web).

Once a pair of two antigens has been identified through these resources that appears to be absent from other cell types besides the tumour cells of interest, a person skilled in the art can easily validate the suitability of the antigen combination for further development of P1 and P2-polypeptide constructs. Such validation that the identified combination of two antigens is indeed not expressed simultaneously on other cell types besides the tumour cells can be carried out by immunohistochemical/immunocytochemical analysis of a (optimally large) collection of assorted cell types and/or tissues with antibodies against the two antigens. Cells and tissues of any kind can be obtained from ATCC (American Type Culture Collection), from pathology departments and from tissue banks associated with universities and research institutions. A suitable antigen combination is defined as a pair of antibodies that stains exclusively the tumour cells, but not healthy tissues or healthy cells (i.e. both antibodies of the pair stain the tumour cells, but no other tissues/cells are stained by both antibodies).

It should be noted that, while in many situations the highest degree of specificity (preferably absolute specificity) is of course desirable, there are situations where a lower degree of specificity is acceptable. For example, if the set of polypeptides is used for diagnostic purposes, some degree of crossreactivity with other cell types or tissues may be acceptable (especially in the case of solid tumours, since the additional positional information helps to distinguish tumour cells from crossreacting cells). Moreover, if the set of polypeptides is used for therapeutic purposes, some degree of crossreactivity with other cell types or tissues may also be acceptable, depending on the severity the disease in a treated patient and on the cell types/tissues affected by the crossreactivity. Other situations where a lower degree of specificity may be acceptable may arise in the context of a transplantation setting (see below).

In cases where no hint about a suitable antigen combination can be derived from the literature or public databases, the presence/absence of the cell surface antigens of the tumour cells from other cell types can be checked by straightforward experimentation. To this end, a variety of cell types and/or tissues obtainable from the sources indicated above may be subjected to proteomic cell characterization, immunocytochemical/immunohistochemical analysis and/or gene expression profiling. (It should be noted that such analysis of non-tumour cells/tissues has to be carried out only once in order to obtain data that can be used for the design of various constructs according to the invention that may be adapted to diverse different therapeutic or diagnostic situations.) Upon comparison of the obtained results with the information about cell surface antigens of the tumour cells of interest, a combination of two antigens that is not present on any other cells besides the tumour cells of interest can be easily identified.

A similar systematic approach to identify a pair of two antigens that is specific for tumour cells is also described in a recent publication by Balagurunathan, which relies on genome-wide gene expression profiling followed by immunohistochemistry (Yoganand Balagurunathan, Gene expression profiling-based identification of cell-surface targets for developing multimeric ligands in pancreatic cancer. Mol Cancer Ther 2008; 7. 3071-3080). Using DNA microarrays, the authors of that manuscript generated databases of mRNA gene expression profiles for a substantial number of pancreatic cancer specimens and normal tissue samples. The expression data for genes encoding cell-surface molecules were analyzed by a multivariate rule-based computational approach in order to identify gene combinations that are preferentially expressed on tumour cells but not in normal tissues. Aberrant co-expression of antigens constituting a tumour-specific antigen combination was then confirmed using standard immunohistochemistry techniques on pancreatic tumour tissue and normal tissue microarrays.

Having identified and validated such a combination of antigens that is specific for the tumour cells of interest, the constructs of polypeptide P1 and polypeptide P2 can be engineered by standard protein engineering techniques and methods of molecular biology (see, e.g. G Howard and M Kaser, Making and Using Antibodies: A Practical Handbook, CRC Press, 1st edition (2006); Sambrook et al., Molecular Cloning: A Laboratory Manual, Cold Spring Harbor Laboratory Press, New York (2001)).

For many cell surface molecules, specific monoclonal antibodies are characterized and therefore readily available. Thus, in many cases the skilled person may have access to hybridoma cells of monoclonal antibodies that are specific for the antigens of the identified combination of antigens. Having the option to choose from a panel of antibodies specific for a given antigen, a person skilled in the art may choose a reactive antibody which binds an epitope close to the membrane, in order to minimize the distance of the antigen expressing cell from the effector cell (Bluemel C, Hausmann S, Fluhr P, Sriskandarajah M, Stallcup W B, Baeuerle P A, Kufer P. Epitope distance to the target cell membrane and antigen size determine the potency of T cell-mediated lysis by BiTE antibodies specific for a large melanoma surface antigen. Cancer Immunol Immunother. 2010 August; 59(8):1197-209). If no such antibody is available against one or both antigens of the identified combination of antigens, monoclonal antibodies against the antigens can be generated by standard techniques (e.g. G Howard and M Kaser, Making and Using Antibodies: A Practical Handbook, CRC Press, 1st edition (2006)). Moreover, various companies offer full services for the generation of custom-made monoclonal antibodies and hybridoma cells.

DNA or mRNA coding for the variable domains of the monoclonal antibodies of interest can be obtained from hybridomas by PCR amplification or cloning (Orlandi R, Gussow P T, Jones: Cloning immunoglobulin variable domains for expression by the polymerase chain reaction. Proc Natl Acad Sci USA 1989, 86(10):3833-3837; Wang Z, Raifu M, Howard M, Smith L, Hansen D, Goldsby R, Ratner D: Universal PCR amplification of mouse immunoglobulin gene variable regions: the design of degenerate primers and an assessment of the effect of DNA polymerase 3' to 5'exonuclease activity. J Immunol Methods 2000, 233(1-2): 167-177; Essono S, Frobert Y, Grassi J, Cremino C, Boquet D: A general method allowing the design of oligonucleotide primers to amplify the variable regions from immunoglobulin cDNA. J Immunol Methods 2003, 279:251-266; G Howard and M Kaser, Making and Using Antibodies: A Practical Handbook, CRC Press, 1st edition (2006)) or from already established vectors comprising the DNA sequence of the variable fragment of the respective antibody. Often, the sequence can be extracted from public databases, where many sequences are deposited, and then the construct may even be generated by gene synthesis as it is offered by various commercial service providers (e.g. Creative Biolabs, Shirley, USA).

To form the construct of polypeptide P1, the sequence coding for the variable fragment Fv of an antibody specific for the first antigen of the identified pair of antigens (or, optionally, the sequence of a single chain variable fragment derived from that sequence) is used for the first targeting moiety (T1) and linked via a suitable linker (coding, e.g., for less than 12 aa) to a sequence coding for the first fragment F1 of a functional domain (e.g. the $V_L$ domain of an anti CD3 antibody). Likewise, to form the construct of polypeptide P2 the sequence coding for the variable fragment Fv of an antibody specific for the second antigen of the identified pair of antigens (or, optionally, the sequence of a single chain variable fragment derived from that sequence) is used for the second targeting moiety (T2) and linked via a suitable linker to a sequence coding for the second fragment F2 of that functional domain (e.g. the $V_H$ domain of an anti CD3 antibody).

For any construct of a polypeptide P1 or P2 according to the invention, modifications to the construct or to the sequences used for forming the construct are considered in order to adapt the construct to specific needs. For example, a construct can be modified in a way that reduces or abolishes its immunogenicity in humans. In case a sequence is derived from a non-human parent antibody, such as a murine antibody, modifications to the sequence can be carried out that result in a reduced immunogenicity in humans while retaining or substantially retaining the antigen-binding properties of the parent antibody (known to the skilled person as "humanizing" an antibody/construct).

Various modifications of the above-described procedure and adaptions in order to accommodate the embodiments and variations described in this application are evident to the person of skill in the art.

In addition to variations with respect to the antigens that the targeting moieties T1 and T2 specifically bind to, various other modifications are possible. For example, instead of single chain variant fragments (scFv) as targeting moiety T1 and/or T2 other types of monovalent antibodies or antibody-like structures can be employed. For example, an antibody/antibody-like structure derived from a llama, camel or shark antibody can be used. Since llama, camel and shark antibodies have an antigen binding moiety that is built up by one single domain (rather than a $V_H$ and a $V_L$ chain), the resulting polypeptide P1 or P2 is much smaller and may thus better penetrate into tumour tissues.

Furthermore, since many tumour-relevant antigens are cell surface-bound receptors, the single chain Fv of targeting moiety T1 and/or T2 can be replaced by the natural or artificial ligand of such a cell surface-bound receptor. Like antibodies, these natural or artificial ligands confer excellent specificity towards the target receptor. Alternatively, the targeting moiety T1 and/or T2 can be an aptamer.

Moreover, in order to enhance binding affinity of a targeting moiety towards the antigen, the targeting moiety can be multimerized and/or altered by glycosylation or other types of posttranslational or chemical modification or be optimized through site directed mutagenesis or a phage display selection process.

Moreover, the fragments F1 and F2 (i.e. the $V_L$ and $V_H$ fragments of anti CD3 Fv in the above-described exemplary embodiment) can be replaced by fragments of a different functional domain F, resulting in a different biological effect upon complementation of the two fragments. By using fragments of anti CD56, anti CD1a, or anti CD16a, natural killer cells can be recruited and activated. By using fragments of anti CD16, natural killer cells, neutrophil polymorphonuclear leukocytes, monocytes and macrophages can be recruited and activated. By using fragments of anti CD32a, anti CD32b, anti CD89, anti CD16a, or anti CD64, macrophages can be recruited and activated. By using fragments of anti CD32a, anti CD32b, anti CD64, or anti CD89, monocytes can be recruited and activated. By using fragments of anti CD16b, anti CD89, anti CD32a, anti CD32b, or anti CD64, granulocytes can be recruited and activated. Moreover, alternatively to anti CD3, T cells can also be recruited and activated by using fragments of anti CD2, anti CD5, anti CD28, or anti TCR (T cell receptor). Further information or additional options regarding the recruitment and activation of effector cells through antibody binding are available from the published literature, e.g. "Bispecific Antibodies" by Roland E. Kontermann (editor), Springer Berlin Heidelberg; 1st Edition. (2011).

An additional option is to use a set of polypeptides P1 and P2 with fragments F1 and F2 of a functional domain F that binds an antigen on an effector cell upon complementation of the two fragments, but wherein binding to this antigen of the effector cell does not cause activation of said effector cell. This set of polypeptides ("first set of polypeptides") is then used (e.g. administered to a patient) in combination with a second set of polypeptides with fragments of a functional domain F that upon complementation binds to a second, different antigen on the same effector cell, but wherein again binding to this antigen of the effector cell does not cause activation of the effector cell. The antigens to which the first and the second sets of polypeptides bind are chosen in a way that, while binding of only one of the two antigens on the effector cells does not result in activation of the effector cell, binding of both antigens on the effector cell simultaneously leads to activation of the effector cell. This has the advantages that (1) antigens on effector cells can be used that do not function individually, but require costimulation of a second antigen, and (2) the number of different antigens that dictates the specificity with which a certain cell (such as a cancer cell) is differentiated from other cells can be increased from two (if the first and second set of polypeptides have the same targeting moieties T1 and T2, respectively) to up to four different antigens (if the first and second set of polypeptides have no targeting moiety in common).

Similar effects may be achieved with two sets of polypeptides with different targeting moieties, but the same functional domain: These sets of polypeptides are designed to have a functional domain directed against an effector cell antigen that normally allows each set of polypeptides by itself to activate the effector cell. However, both sets of polypeptides are used in a concentration that is just too low to cause efficient effector cell activation. If both sets of polypeptides are present simultaneously (e.g. upon simultaneous administration to a patient) each set of polypeptides by itself is not capable of activating the effector cell (due to its low concentration), while the combination of both sets of polypeptides is (because the effects of the two sets of polypeptides act synergistically and thus the sum of the effects caused by the two sets of polypeptides is sufficient to activate the effector cell).

As another alternative to recruitment/activation of effector cells, a "pretargeting" approach can be pursued, as it is well established for bispecific antibody constructs (Cancer Imaging and Therapy with Bispecific Antibody Pretargeting. Goldenberg D M, Chatal J F, Barbet J, Boerman O, Sharkey R M. Update Cancer Ther. 2007 March; 2(1):19-31). To this end, F1 and F2 are substituted by $V_H$ and $V_L$ fragments of an antibody specific for an antigen, a carrier molecule (i.e. a molecule/part of a molecule that is not recognized as foreign by the immune system of the patient to whom said set of polypeptides is administered or a molecule that causes no or only a weak immune reaction by a patient to whom it is administered) or an affinity tag. Subsequently (or simultaneously) to administering the polypeptides P1 and P2, a therapeutic or diagnostic compound coupled to said antigen, carrier molecule or affinity tag is administered. Only cells which carry both the antigens A1 and A2 at their surface are bound by both polypeptide P1 and polypeptide P2. Consequently, only at these cells functional complementation leads to generation of a binding site capable of recruiting the therapeutic or diagnostic compound through said antigen, carrier molecule or affinity tag. This approach allows exclusive addressing of target cells combined with the possibility of precise administration and dosing of therapeutic compounds like toxins or radioactive substances or diagnostic compounds, while cells that do not express the antigens or do express only one of the antigens are not affected.

A suitable carrier molecule may for example be a peptide or a carbohydrate molecule. Preferably, the carrier molecule may be gelatine, dextrane, or hydroxyethyl starch, which are common plasma expanders that are metabolically inert, remain in the blood and are, if they are small enough, renally eliminated. Alternatively, the carrier molecule may be inulin, a metabolically inert molecule that is used routinely in the clinic for determination of glomerular clearance (and, in addition, antibodies exist that specifically recognize inulin).

A suitable affinity tag may be, for example, a Flag-tag, a myc-tag, a glutathione-S-transferase (GST)-tag, a hemagglutinin (HA)-Tag, a polyhistidine (His)-tag, or a maltose binding protein (MBP)-tag, a digoxigenin (DIG)-tag.

The therapeutic compound coupled to the antigen, carrier molecule or affinity tag may for example be a radioactive compound or a toxin.

Suitable radioactive compounds are for example compounds comprising $^{90}Y$, $^{177}Lu$, $^{131}I$, $^{32}P$, $^{10}B$, or $^{213}Bi$. Recruitment of the antigen, carrier molecule or affinity tag linked to the radioactive compound to cells that express both the first and the second antigen leads to accumulation of radioactivity onto the tumour site, resulting in specific destruction of tumour cells/tissue.

Alternatively, the therapeutic compound coupled to the antigen, carrier molecule or affinity tag may for example be a toxic compound that is not able to cross the cell membrane without prior binding to the cell surface.

This prerequisite is fulfilled by the A components of classical AB-toxins derived from a number of pathogenic bacteria like *Clostridium perfringens, C. botulinum, C. difficile, B. anthracis* and others. AB-toxins are two-component protein complexes that interfere with internal cell functions. The A component is the "active" component (i.e. it kills a cell upon membrane penetration), but is not able to cross the cell membrane on its own. The B component is the "binding" component that by itself is non-toxic, but is essential for uptake and membrane penetration of component A.

For example, *Bacillus anthracis* protective antigen (PA) is a classical toxin B component which mediates the uptake of the actual anthrax exotoxins edema factor and lethal factor (LF). LF without the PA-component is non-toxic since LF by its own does not penetrate membranes and thus cannot execute its pathogenic capabilities (Pezard C, Berche P, Mock M. "Contribution of individual toxin components to virulence of *Bacillus anthracis*" 1991 Infect. Immun. 59 (10): 3472). However, when bound to cell surface molecules, LF is internalised and highly toxic to the cell.

Upon dimerization of the polypeptides P1 and P2, the function of the functional domain F is reconstituted. Through interaction of the reconstituted functional domain with the antigen, carrier molecule or affinity tag coupled to the toxin, the toxin is recruited to the cell membrane of the target cells, incorporated into the cells and kills the cells.

This principle is easily adapted to the purposes of the invention by the skilled person, since it is already widely used in so called immunotoxins, where a targeting moiety, mostly an antibody-like domain or natural ligand, is coupled to the toxin component (see, e.g., Immunotoxins for targeted cancer therapy. Kreitman R J, AAPS J. 2006 Aug. 18; 8(3):E532-51). Examples include immunotoxins based on diphtheria toxin (such as Denileukin diftitox (U.S. trade name Ontak) which has been approved by FDA for the treatment of some T cell lymphomas) or based on *B. anthracis* Lethal Factor (Pastan I, Hassan R, FitzGerald D J, Kreitman R J (2007). "Immunotoxin treatment of cancer". Annu. Rev. Med. 58: 221-37). Suitable A components of AB-toxins may for example be *B. anthracis* edema factor, *B. anthracis* lethal factor, *C. perfringens* iota toxin, *C. botulinum* C2 toxin, *C. difficile* ADP-ribosyltransferase *C. diphtheriae* diphteria toxin fragment A.

Alternatively, the therapeutic compound may for example be a cytotoxic compound that is toxic upon entry into a cell and that is capable of crossing the cell membrane by itself without prior binding to the cell surface. In this case, the antigen, carrier molecule or affinity tag that the therapeutic compound is coupled to is selected such that it prevents the resulting conjugate (i.e. the therapeutic compound linked to the antigen/carrier molecule/affinity tag) from crossing cell membranes and entering cells without prior binding of the conjugate to the cell surface (a suitable carrier molecule may for example be a hydroxyethyl starch carrier). Thus, such a conjugate does not enter cells without prior binding to their cell surface; once such a conjugate binds to the cell surface, however, it is internalized into the cell and the toxic compound kills the cell. The conjugate does not bind to cells, unless it is recruited in the presence of the inventive set of polypeptides to cells that simultaneously express both antigens A1 and A2 at their cell surface. Such cells bind and recruit both polypeptides P1 and P2, and the reconstituted functional domain specifically binds to and recruits the antigen/carrier molecule/affinity tag which, in turn, results in internalization of the therapeutic compound. In consequence, a specific killing of cells that carry both antigens A1 and A2 at their cell surface is accomplished. Cytotoxic compounds that may be used in this context include e.g. auristatin, ricin, saponin, bryodin 1, bouganin, gelonin, pokeweed antiviral protein (PAP), antifolates, vinca alkaloides, anthracyclines, calicheamicin, ribonuclease, abrin, modeccin, or Listeriolysin O.

The diagnostic compound coupled to the antigen, carrier molecule or affinity tag may for example be a radioactive compound, a fluorophore, or a compound capable of mediating bioluminescence.

Suitable radioactive compounds are for example compounds comprising $^{99m}Tc$, $^{82}Rb$ or $^{201}Tl$. Such compounds are detected by well-known medical imaging procedures in the clinic.

Alternatively, a fluorescent compound may be used as diagnostic compound, such as GFP (green fluorescent protein) or a GFP variant (e.g. BFP (blue fluorescent protein), CFP (cyan fluorescent protein), or YFP (yellow fluorescent protein)), or a fluorescent small-molecule compound like FITC (fluorescein isothiocyanate) or PE (phycoerythrin), alexa fluor dyes (such as AlexaFluor488 and related dyes sold by Molecular Probes, e.g.) or cyanine dyes (such as Cy3 (Indocarbocyanine) or Cy5 (Indodicarbocyanine) or related dyes).

Alternatively, a compound capable of mediating bioluminescence may be used as diagnostic compound, such as a luciferase, for example *Gaussia* luciferase (Chopra A. *Gaussia princeps* luciferase. In: Molecular Imaging and Contrast Agent Database (MICAD) [database online]. Bethesda (Md.): National Library of Medicine (US), NCBI; 2004-2012. Available from on the worldwide web at: micad-.nih.gov.). The employment of *Gaussia* luciferase for in vivo imaging is well established (see, e.g., Santos EB et al. Sensitive in vivo imaging of T cells using a membrane-bound *Gaussia princeps* luciferase. Nat Med. 2009 March; 15(3):338-44. Epub 2009 Feb 15; or Inoue Y et al. *Gaussia luciferase* for bioluminescence tumor monitoring in comparison with firefly luciferase. Mol Imaging. 2011 Oct 1;10(5):377-85. doi: 10.2310/7290.2010.00057. Epub Apr 26, 2011; see also below for additional details).

Moreover, the fragments F1 and F2 (i.e. the $V_L$ and $V_H$ fragments of anti CD3 Fv in the above-described exemplary embodiment) can be replaced by $V_L$ and $V_H$ fragments of an antibody that is specific for a therapeutic or diagnostic compound (i.e. in this case the functional domain F is capable of directly binding to the therapeutic or diagnostic compound). Here, the same therapeutic and diagnostic compounds as described above in the context of the "pretargeting" approach may be considered.

Furthermore, the fragments F1 and F2 (i.e. the $V_L$ and $V_H$ fragments of anti CD3 Fv in the above-described exemplary embodiment) can be replaced by fragments of a fluorescent or bioluminescent compound that are biologically inactive on their own, but regain their function (i.e. their ability to mediate fluorescence or bioluminescence) upon association of the two fragments and functional complementation, thus allowing for specific identification of cells that carry both the antigens A1 and A2.

A number of fluorescent molecules that may be used in this context are well known and characterized in the art including, but are not limited to, GFP (green fluorescent protein), GFP derivatives (like YFP (yellow fluorescent protein) and CFP (cyan fluorescent protein), Venus (Nagai T et al., A variant of yellow fluorescent protein with fast and efficient maturation for cell-biological applications. Nat Biotechnol. 2002 January; 20(1):87-90), or Cerulean (Enhanced CFP with S72A, Y145A and H148D substitutions)). For these molecules, split fragments are described that self-assemble in the situation of close proximity in a process called bimolecular fluorescence complementation (BiFC).

For example, GFP, CFP, Venus, Venus with a M153T substitution, or Cerulean may be split after amino acid 155 (i.e., for example, fragment F1 may comprise amino acids 1-155 of GFP, while fragment F2 may comprise amino acids 156-245 of GFP, or vice versa). Alternatively, YFP or Venus may be split after amino acid 173. Further details on split GFP and split GFP variants can be found in Kerppola T K., Visualization of molecular interactions using bimolecular fluorescence complementation analysis: characteristics of protein fragment complementation. Chem Soc Rev. 2009; 38:2876-86.

An example for a molecule that mediates bioluminescence and that can be used in this context is split *luciferase*. Particularly suited is the *luciferase* of *Gaussia princeps*, which requires no cofactors to be active and catalyzes the oxidation of the substrate coelenterate luciferin (coelenterazine) in a reaction that emits blue light, or derivatives of *Gaussia luciferase* (Remy I and Michnick S, A highly sensitive protein-protein interaction assay based on *Gaussia luciferase*. Nature Methods—3, 977-979 (2006)). For example, fragment F1 may comprise a fragment from the N-terminus of *Gaussia luciferase* to Gly-93, while fragment F2 may comprise a fragment from Glu-94 to the C-terminus of *Gaussia luciferase*, or vice versa (see Remy I and Michnick S, Nature Methods, 2006 for details). Application of the *Gaussia* split *luciferase* system in vivo has been established (Luker et al., In vivo imaging of ligand receptor binding with *Gaussia luciferase* complementation. Nature Medicine 2011, doi:10.1038/nm.2590), allowing for straightforward adaptation to the purposes of the present invention by a skilled person.

Intravital imaging of tumour lesions is of eminent importance in cases, where cancer cells infiltrate tissues and the complete elimination of all transformed cells is prerequisite for cure. A surgeon searching for disseminated cancer cells in the operation site may use split GFP or split GFP derivatives fused to the targeting moieties and a laser assisted Multispectral fluorescence camera system for detection of cells aberrantly expressing an addressed antigen profile, similar to the intraoperative use of fluorescence or bioluminescence that is already exploited in some clinical settings (van Dam G M et al., Intraoperative tumor-specific fluorescence imaging in ovarian cancer by folate receptor-α targeting: first in-human results. Nat Med. 2011 Sep. 18; 17(10):1315-9; Luker et al., In vivo imaging of ligand receptor binding with *Gaussia luciferase* complementation. Nature Medicine 2011, doi:10.1038/nm.2590).

For detection of complemented split *luciferase*, the application of a substrate for *luciferase*, which can be luciferin or coelenterazine, is mandatory. Coelenterazine is preferred because coelenterazine emits light independent of ATP and is well established for in vivo imaging and in vivo applications. A surgeon will be able to visualize cancer cells after having tagged the tumor with polypeptide P1 and P2 and injected a non-toxic amount of coelenterazine intravenously.

In another exemplary embodiment, the inventive principle is applied in the context of a patient who suffers from a haematopoietic tumour and who received a transplantation of healthy haematopoietic cells from another person (the donor). Here, the set of polypeptides according to the invention can be used for the specific elimination (or detection) of remaining malignant haematopoietic cells of the recipient after transplantation of healthy haematopoietic cells from the donor.

To destroy the malignant haematopoietic cells in a patient suffering from a haematopoietic tumour, the patient may be subjected to chemotherapy and/or radiation therapy. Subsequently, the patient receives a transplantation of healthy haematopoietic cells from a donor.

To minimize the risk of transplant rejection or graft versus host disease, transplantation of tissue/cells (e.g. bone marrow) from a donor who has the same set of MHC (major histocompatibility complex) molecules is usually preferred. However, often no donor with the same set of MHC molecules ("HLA-identical donor") can be identified. Therefore, transplant grafts with one or two mismatches in the set of MHC variants, unrelated cord blood with up to three mismatches, or haploidentical transplantations are increasingly employed. Accordingly, it is common that there is at least one distinctive difference between the set of MHC molecules expressed by the cells of the recipient and the cells of the donor.

In the transplantation according to this exemplary embodiment of the invention, donor cells are used that are distinct from the recipient cells with respect to at least one of their HLA variants. This means that there is at least one "distinguishing antigen" that is present at the cell surface of the recipient cells, but not at the cell surface of the donor cells. For example, the distinguishing antigen may be HLA-A2, if the patient (i.e. the recipient) is HLA-A2 positive, while the donor is HLA-A2 negative.

Despite chemotherapy/radiation therapy, individual malignant haematopoietic cells of the recipient may have escaped eradication. Since the surviving malignant haematopoietic cells are recipient cells, they carry the distinguishing antigen that differentiates recipient cells from donor cells. At the same time, they are cells of haematopoietic lineage origin and thus have markers of this cell lineage, such as CD45, at their cell surface. Leukemic blasts and other haematopoietic cells of the patient are the only cells that simultaneously display the distinguishing antigen (here HLA-A2) and markers of haematopoietic cell lineage (here CD45). The set of polypeptides according to the invention exploits this fact to specifically eliminate these cells.

To this end, the first targeting moiety T1 of the first polypeptide P1 may be a scFv specific for the distinguishing antigen which is present only on recipient cells (here HLA-A2). As fragment F1 of the functional domain F, the variable region of the light chain ($V_L$) of a CD3ε-specific antibody may be chosen. The second targeting moiety T2 of the second polypeptide P2 may be a single chain variable Fragment (scFv) specific for CD45. As fragment F2 of the functional domain F, the variable region of the heavy chain ($V_H$) of said CD3ε-specific antibody may be chosen. (Naturally, it is equally possible to use the variable region of the heavy chain ($V_H$) of a CD3ε-specific antibody as fragment F1 and the variable region of the light chain ($V_L$) of said CD3ε-specific antibody as fragment F2. As is evident for a person of skill in the art, this is a general principle, and it is generally possible to switch the fragments used for fragment F1 and fragment F2.) Neither is $V_L$ of the CDR3ε-specific antibody capable of engaging CD3ε in the absence of $V_H$, nor is $V_H$ of the CDR3ε-specific antibody capable of engaging CD3ε in the absence of $V_L$. Accordingly, neither P1 nor P2 is by itself capable of binding to CD3ε.

However, if both the distinguishing antigen (e.g. HLA-A2) and the CD45 antigen are present on one single cell, binding to their respective antigens brings the two polypeptides P1 and P2 into close proximity. As a consequence, the unpaired $V_H$ and $V_L$ domains assemble, resulting in heterodimerization of the polypeptides P1 and P2 and in the formation of a functional variable antibody fragment Fv from the $V_H$ and $V_L$ domains that is capable of binding to CD3ε (see FIG. 2).

As a result, T cells are recruited and activated through CDR3ε, and the cell carrying both HLA-A2 and CD45 at its cell surface is specifically eliminated by a cytotoxic T cell response.

A person of skill in the art understands that, within the principle of the present invention, diverse variations to this exemplary embodiment are possible.

For example, in polypeptide P2 the scFv fragment recognising the haematopoietic cell lineage marker CD45 can be replaced by a scFv fragment recognising a marker of a different cell lineage or cell type, i.e. the targeting moiety T2 may be a domain that specifically binds an antigen that is specific for a cell lineage other than the haematopoietic cell lineage or for a certain cell type (for a detailed list of various cell lineage markers and cell type markers that may be used in this context see David J. Dabbs, Diagnostic immunohistochemistry, Churchill Livingstone, 3rd edition (2010); or F Lin and J Prichard, Handbook of Practical Immunohistochemistry: Frequently Asked Questions, Springer, New York, 1st edition (2011)). To adapt the set of polypeptides to an alternative cell lineage marker/cell type marker, it is sufficient to replace the targeting moiety T2 of polypeptide P2 with a targeting moiety that has binding specificity for the desired alternative cell lineage marker/cell type marker.

For example, in the situation of metastatic renal cell carcinoma (RCC), a person skilled in the art might consult the above-cited databases for information on cell surface proteins with restricted expression to kidney cells. Among many other molecules, he will learn that expression of certain members of the aquaporin family is confined to kidney cells and erythrocytes. Having obtained this information, a person skilled in the art will construct a polypeptide P2 recognising an aquaporin family member that is confined to kidney cells and erythrocytes fused to the variable region of the heavy chain ($V_H$) of a CD3ε-specific antibody. In case that the patient suffering renal cell carcinoma is HLA A2 positive and a kidney transplant from a healthy donor is HLA A2 negative, the clinician treating the patient may utilise the two constructs (anti-aquaporin fused to anti-CD3($V_H$) and anti-HLA A2 fused to the light chain ($V_L$) of said CDR3ε-specific antibody). In this case, all cells simultaneously expressing said aquaporin and HLA A2 will be tagged for lysis by T cells which are renal cell carcinoma cells and metastatic tissues. Kidney cells donated by the healthy donor are HLA A2 negative and will not be attacked.

Since erythrocytes loose HLA expression along the process of ontogeny and thus do not carry HLA molecules on their surfaces, they will be spared despite expressing large amounts of aquaporins. Again, a conventional, non-complementing bispecific antibody addressing aquaporin would mediate killing of all kidney cells from donor and recipient as well as erythrocytes. A bispecific antibody addressing HLA A2 in a HLA A2 positive patient most likely would be fatal, since every recipient cell except erythrocytes express HLA A2 and can be attacked by the retargeted T cells.

Another example is hepatocellular carcinoma (HCC). Hepatocytes are largely involved in a number of metabolic processes including the trafficking of lipoproteins. To this end, hepatocytes express receptors for high density lipoproteins (HDL) on their surfaces (scavenger receptor class B member 1, SCARB1). Treatment of an HLA A2 positive patient suffering HCC which expresses SCARB1 on the surface of tumor cells and metastases can be accomplished by a Polypeptide P2 construct comprising a scFv domain addressing SCARB1 fused to the variable region of the heavy chain ($V_H$) of said CDR3ε-specific antibody and a Polypeptide P1 (anti-HLA A2 scFv fused to the light chain ($V_L$) of said CD3ε-specific antibody) and transplantation of liver cells from a healthy, HLA A2 negative donor. In this case, all hepatocytes and hepatocyte-derived malignant cells expressing both, SCARB1 and HLA A2 will be tagged for lysis by T lymphocytes. Hepatocytes of the donor lacking HLA A2 will be spared as well as normal SCARB1 negative donor cells expressing HLA A2. Since SCARB1 expression is also reported for cells participating in steroid synthesis in the adrenal gland, these cells most likely will also be destroyed by redirected T cells, resulting in Addison's disease.

Various markers that are specific for certain cell types or cell lineages or a few cell types/lineages are known (for a list of examples, see above). More information on lineage markers, differentiation antigens and tissue markers as well as their tissue distribution are easily accessible from published sources (see, e.g. David J. Dabbs, Diagnostic immunohistochemistry, Churchill Livingstone, 3rd edition (2010); or F Lin and J Prichard, Handbook of Practical Immunohistochemistry: Frequently Asked Questions, Springer, New York, 1st edition (2011)) and public databases (such as the Gene Expression Atlas of the European Bioinformatics Institute (EBI), ebi.ac.uk/gxa/on the worldwide web; or the Gene Expression Omnibus (GEO) platform, see above). Moreover, such markers can be identified and/or verified in a straightforward manner by a skilled person using similar methods as described above for the identification of tumour-specific combinations of antigens.

In certain preferred embodiments, an antigen with less than perfect specificity for a certain cell type or cell lineage is used (i.e. an antigen is used that is present on more than one, but preferably only a few, cell types or cell lineages). In some embodiments, an antigen is used that is expressed by said cell type/cell lineage at a higher rate or at a higher proportion or amount than by other cell types/cell lineages, in the sense that there may be a small but detectable expression of said antigen also in other cell types/cell lineages.

The concept can further be adapted to any other HLA haplotype besides HLA-A2 used in the exemplary embodiment above, as long as the recipient cells are positive for this HLA antigen and the donor cells are negative for it. Possible HLA antigens include, among others, HLA A1, HLA A2, HLA A3, HLA A25, HLA B7, HLA B8, HLA B35, HLA B44 and HLA Cw3, HLA Cw4, HLA Cw6, HLA Cw7. To adapt the set of polypeptides to an alternative HLA antigen, it is sufficient to replace the targeting moiety T1 of polypeptide P1 with a targeting moiety that has binding specificity for the desired alternative HLA antigen. By an appropriate choice of the targeting moiety T1, it is of course also possible to specifically eliminate donor cells.

Moreover, instead of a $V_L$ domain and a $V_H$ domain that upon assembly form a domain capable of binding to CD3ε (i.e. fragment F1 and fragment F2 of polypeptides P1 and P2, respectively), the $V_L$ domain and $V_H$ domain can be replaced with domains/fragments that upon assembly confer a different function to the resulting dimer. In this respect, all the variations described above for the exemplary embodiment relating to the elimination/detection of tumour cells identified by a specific combination of two cell surface antigens are equally applicable. For example, upon assembly the complemented functional domain may mediate binding/activation of other effector cells than T cells, may be adapted to a "pretargeting" approach, may bind a therapeutic or diagnostic compound, or may form a fluorescent molecule/molecule capable of mediating bioluminescence.

The diverse options for the choice of the fragments F1 and F2 and for the choice of the targeting moieties T1 or T2 described above in the exemplary embodiment relating to application of the inventive principle for the specific elimination of tumour cells may of course be considered, as well.

From the described exemplary embodiments and variations, it will be clear to a person of skill in the art that the inventive principle described above can not only be used for the highly specific identification/elimination of tumour cells or of remaining malignant recipient cells after a cell transplantation, but also for the identification/elimination of any other type of cell carrying a specific combination of two antigens that distinguishes it from other types of cells.

Figure 1B:
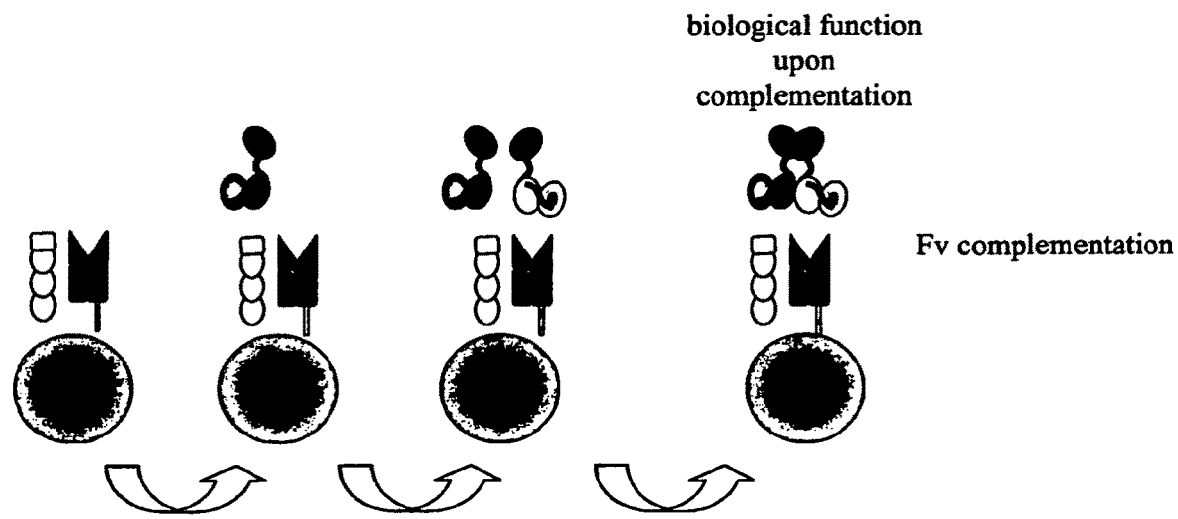
Figure 1C:
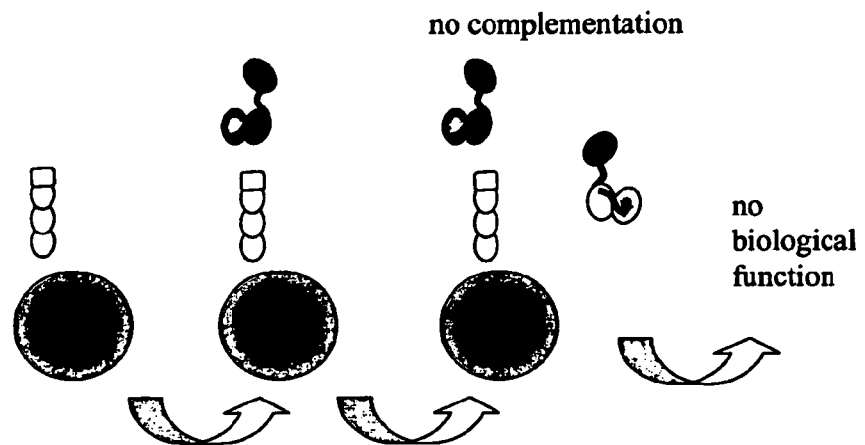
Figure 1D:
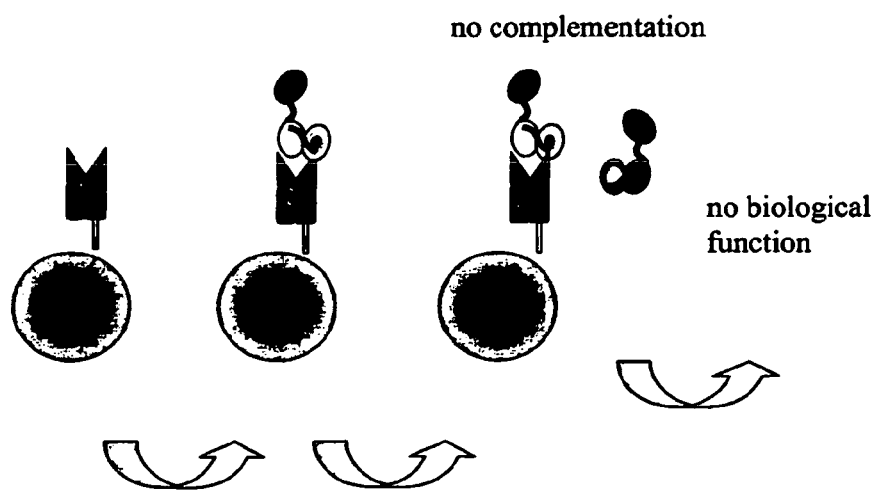

In the following, reference is made to the figures:

FIG. 1A to FIG. 1D show the principle of the invention. FIG. 1A: Antigens and design of polypeptides P1 and P2. FIG. 1B: If a cell expresses both antigens 1 and 2 at its cell surface, simultaneous binding of polypeptide P1 and polypeptide P2 to the surface of this cell brings P1 and P2 in close proximity, causes association of fragments F1 and F2 and restoration of the biological function of domain F by complementation. No restoration of biological function occurs if only antigen A1 (FIG. 1C) or antigen A2 (FIG. 1D) is present on the cell surface.

Figure 2:
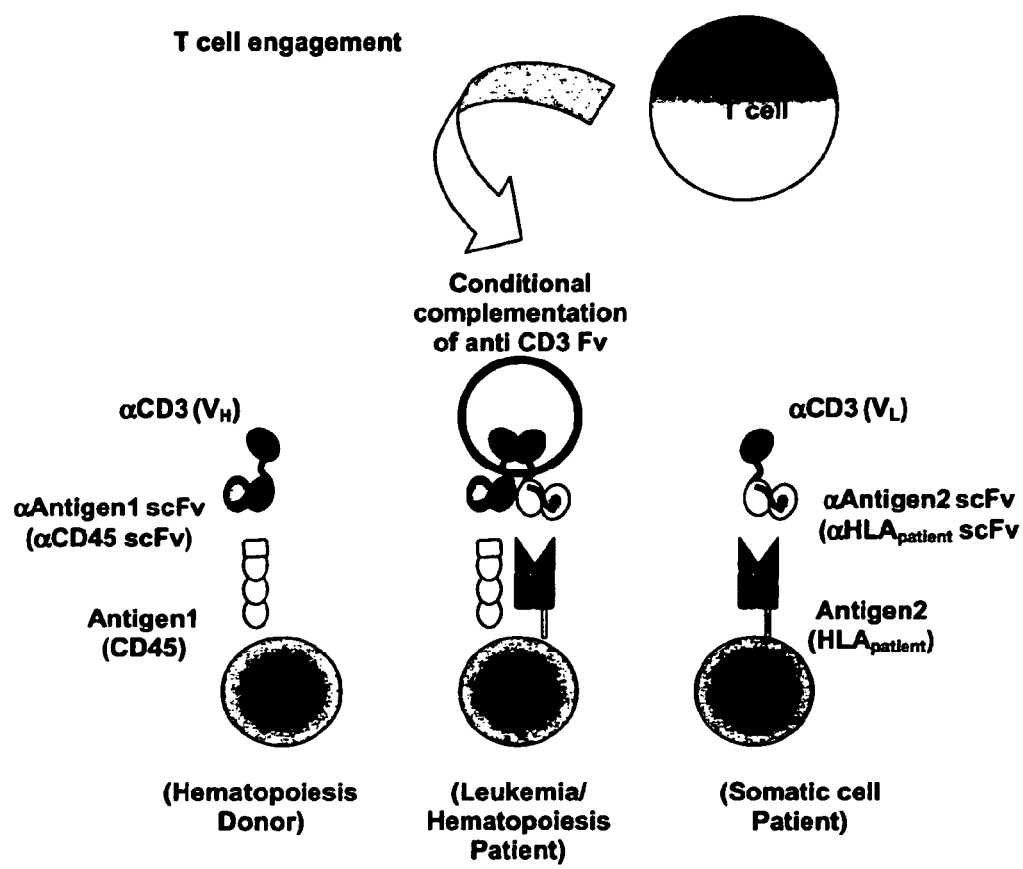

FIG. 2 shows an exemplary embodiment of the invention in an allogeneic transplantation setting for haematopoietic neoplasias with mismatched HLA antigens. In this situation, the dual information of recipient HLA haplotype ($HLA_{patient}$) and haematopoietic lineage origin (CD45) is displayed exclusively on leukemic blasts and other haematopoietic cells of the patient. The first polypeptide P1 comprises a single-chain variable fragment antibody construct directed against the HLA of the patient (targeting moiety T1) fused to the $V_L$ fragment of anti CD3 (fragment F1). The second polypeptide P2 comprises a single-chain variable fragment construct specific for the haematopoietic lineage marker CD45 (targeting moiety T2), fused to the $V_H$ split-fragment of anti CD3 Fv (fragment F2).

CD45: antigen specific for haematopoietic cells. $HLA_{patient}$: HLA-antigen specific for patient cells, i.e. an allelic variant of the human MEW that is present on the surface of patient cells (=cells of the recipient of cell transplantation), but absent from the surface of donor cells. αCD45 scFv: scFv with binding specificity for CD45. α$HLA_{patient}$ scFv: scFV with binding specificity for $HLA_{patient}$. CD3($V_H$): variable region of an immunoglobulin heavy chain of an antibody with binding specificity for CD3. CD3($V_L$): variable region of an immunoglobulin light chain of an antibody with binding specificity for CD3.

Upon binding of the two constructs through their αCD45 scFv and αHLA$_{patient}$ scFv, respectively, to a cell carrying both the CD45 and the HLA$_{patient}$ antigen, assembly of CD3($V_H$) with CD3($V_L$) leads to functional complementation of the antibody with binding specificity for CD3, thus allowing for specific recruitment and activation of T cells through the CD3 molecules at their cell surface.

Figure 3A:
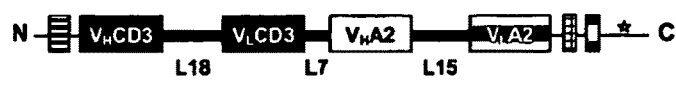
Figure 3A:
Figure 3A:
Figure 3A:
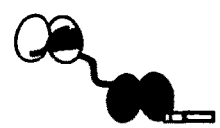
Figure 3A:
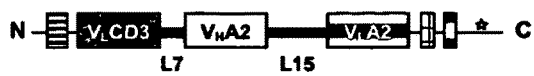
Figure 3A:
Figure 3A:
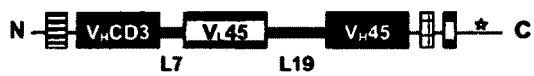
Figure 3A:
Figure 3A:
Figure 3A:
Figure 3A:
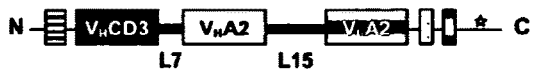
Figure 3A:
Figure 3B:
Figure 3B:
Figure 3B:
Figure 3B:
Figure 3B:
Figure 3B:
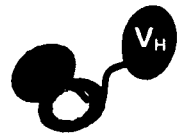

FIG. 3A-FIG. 3B show the constructs used in the experiments depicted in FIG. 4-FIG. 9. (Construct 85 differs from construct 71 by the fact that construct 85 has a Flag tag while construct 71 has a myc tag. Construct 75 differs from construct 82 by the fact that construct 75 has a Flag tag while construct 82 has a myc tag.) $V_H$CD3: variable region of the heavy chain of an anti-CD3 antibody; $V_L$CD3: variable region of the light chain of an anti-CD3 antibody; $V_H$A2: variable region of the heavy chain of an anti-HLA-A2 antibody; $V_L$A2: variable region of the light chain of an anti-HLA-A2 antibody; $V_L$45: variable region of the heavy chain of an anti-CD45 antibody; $V_H$45: variable region of the light chain of an anti-CD45 antibody; L18, L7, L15, L6, L19: linker of 18, 7, 15, 6, 19 amino acids, respectively.

Figure 4:
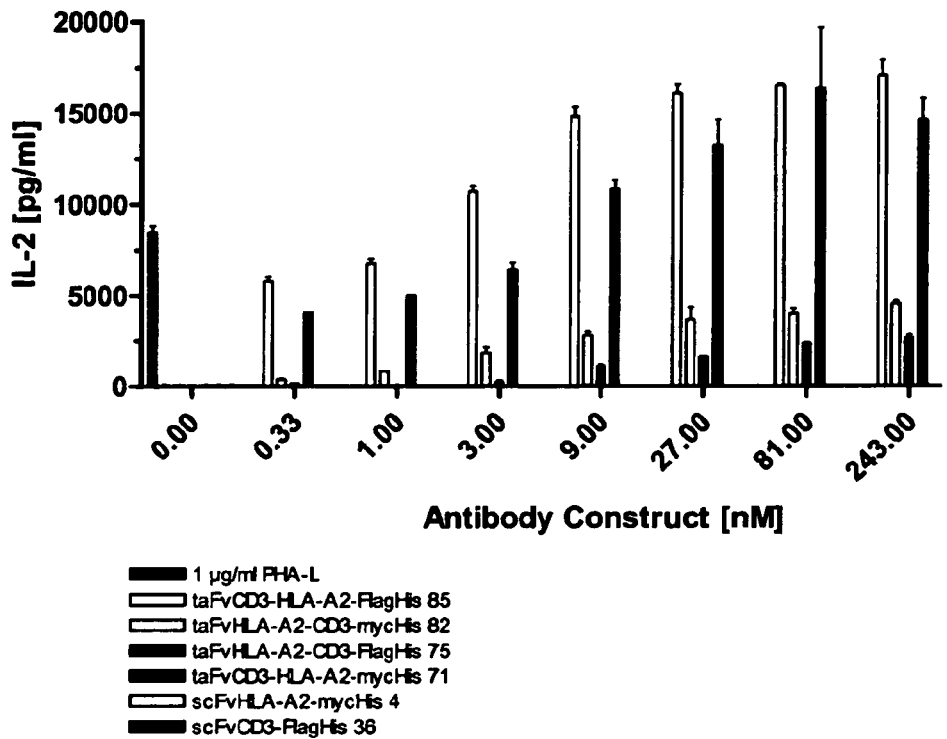

FIG. 4 shows conventional tandem bispecific single chain scFv constructs used to control the assay system. Briefly, bispecific antibody constructs with specificity for CD3 and HLA A2 were titrated as indicated to a co-culture of U266, a HLA A2 positive, CD45 positive myeloma cell line, and HLA A2 negative T cells (monocyte depleted peripheral blood mononuclear cells), and production of interleukin 2 by T cells was determined. Substantial T cell stimulatory capacity was detected for the two FvCD3–HLA-A2 constructs 85 and 71, which differ by their respective Flag or Myc-Tags (For domain structure of constructs see FIG. 3). Bispecific tandem Fv constructs in HLA-A2–CD3 configuration were less efficient and single chain constructs addressing either HLA-A2 or CD3 did not stimulate T cells at all. Positive control is conducted using unspecific PHA-L (phytohemagglutinin) stimulation.

Figure 5:
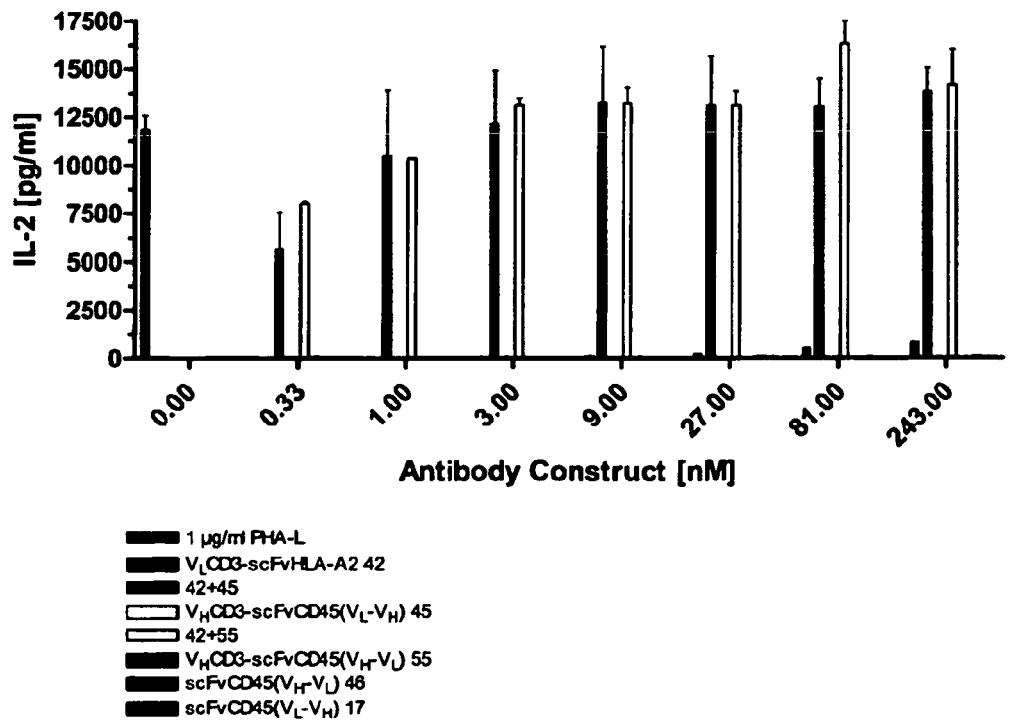

FIG. 5 shows exquisite and highly specific T cell stimulatory capacity if a pair of complementing constructs according to the invention is used, but not if only one of the two constructs of a pair is used individually. Briefly, $V_L$CD3–scFvHLA-A2 (construct 42), $V_H$CD3–scFvCD45($V_L$–$V_H$) (construct 45) and $V_H$CD3–scFvCD45($V_H$–$V_L$) (construct 55) were titrated separately or in the combinations of constructs 42 and 45, or 42 and 55 to co-cultures of U266 and T cells as described. High T cell stimulatory capacity was demonstrated for the combinations of 42/45 or 42/55 with minute activity, if only one of these constructs was given separately. These results show that the $V_L$ and $V_H$ domains of FvCD3 have to cooperate in order to reconstitute or complement T cell engaging function. Importantly, the scFvCD45 targeting moiety could be switched from ($V_L$–$V_H$) to the ($V_H$–$V_L$) configuration, clearly indicating that the modular character of the constructs allows replacement of a targeting moiety by another targeting moiety with desired specificity. The assay system was controlled by the use of single chain constructs CD45($V_L$–$V_H$) and CD45($V_H$–$V_L$) which did not stimulate T cells to produce IL2.

Figure 6:
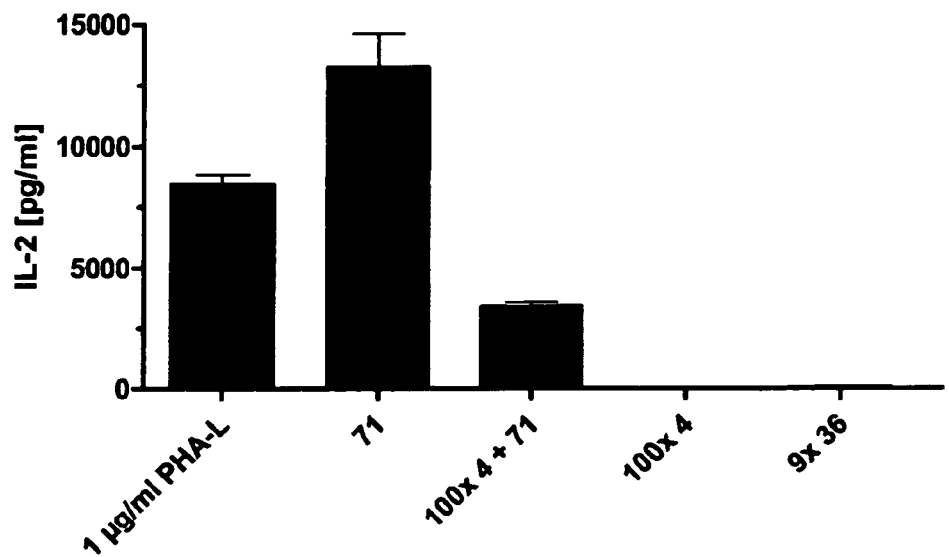

FIG. 6 shows a first of three competitive blocking experiments. The bispecific tandem construct FvCD3–HLA-A2 (construct 71) was given to co-cultures of U266 and T cells as described and stimulatory function was determined through induced IL2 production by T lymphocytes. The T cell stimulating function was blocked by single chain constructs that occupy the targeted epitope on the HLA A2 molecule (construct 4, concentration*100). Intrinsic stimulation of T cells by the HLA A2 or CD3 specific single chain constructs (construct 4 (concentration*100) or construct 36 (concentration*9)) was ruled out. PHA-L was used as positive control.

Figure 7:
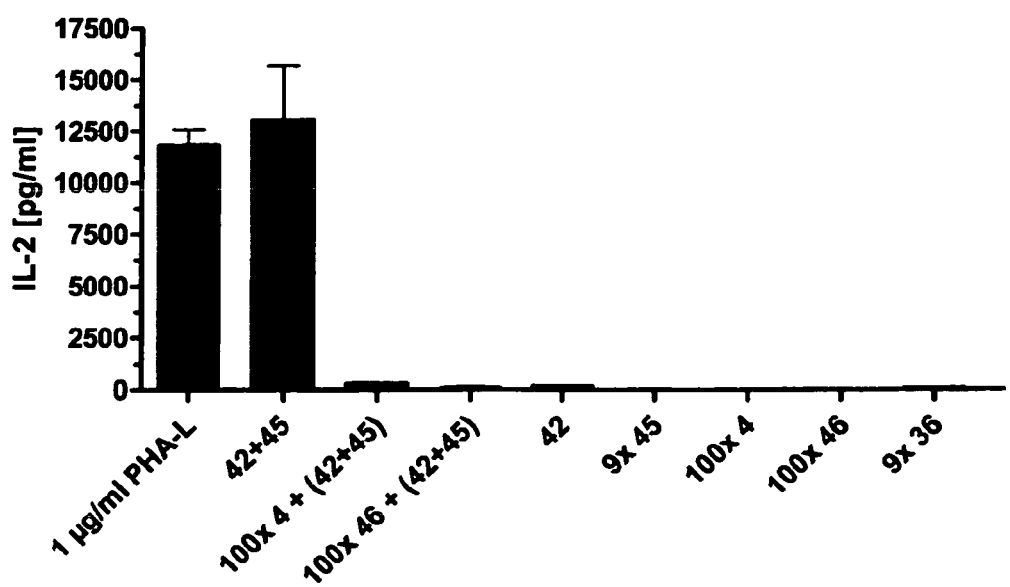

FIG. 7 shows that "tridomain constructs" (i.e. constructs according to the invention) first have to bind on the surface of a single cell to dimerize and complement T cell engaging functions the competitive epitope blocking experiments. Briefly, constructs 42 and 45 were given to co-cultures of U266 cells and HLA-A2 negative T lymphocytes and stimulatory capacity was determined by IL2 production of T cells. In experimental situations where the epitopes on HLA A2 or CD45 molecules were competitively blocked by constructs 4 or 46 (both concentrations*100), T cell stimulatory function was abrogated. These results clearly indicate that the two respective "tridomain constructs" have to bind simultaneously onto the surface of a cell in order to restore or to complement T cell engaging function. Intrinsic stimulatory activity of either construct (42, 45, 4, 46 and 36) was ruled out using different concentrations.

Figure 8:
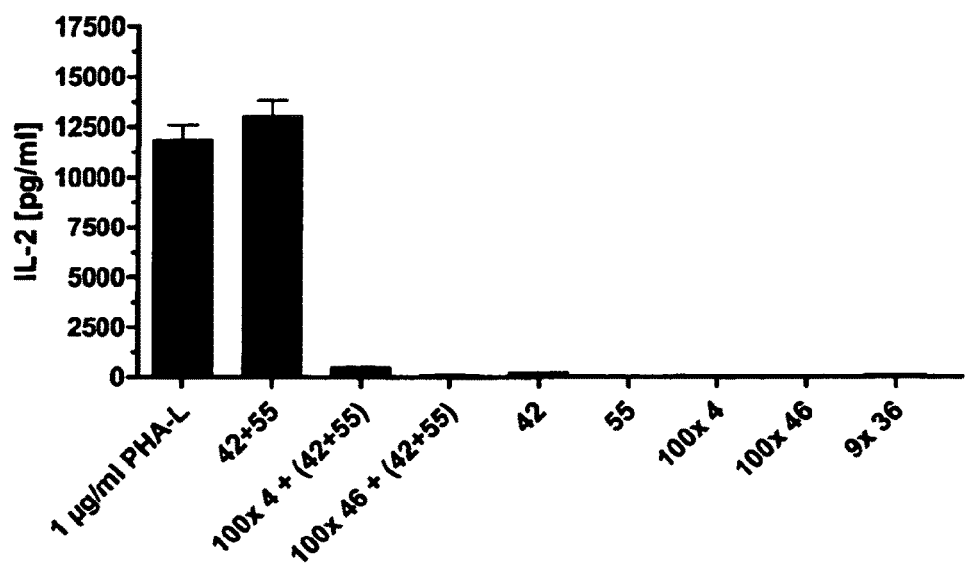

FIG. 8 shows the analogous experiment to FIG. 7 for the combination of constructs 42 and 55. Again, T cell stimulatory capacity of the combination of the two "tridomain constructs" was abrogated by competitive blocking of antigenic epitopes on the HLA A2 or the CD45 molecule. Importantly, these results again show that the targeting module can be easily replaced by another module with appropriate specificity. More importantly, the $V_L$-$V_H$-$V_L$ configuration of construct 42 and the $V_H$-$V_H$-$V_L$ configuration of construct 55 impede homo- or hetero-dimerization or self-assembling of the constructs without prior binding to a substrate expressing both, HLA A2 and CD45 antigens.

Figure 9:
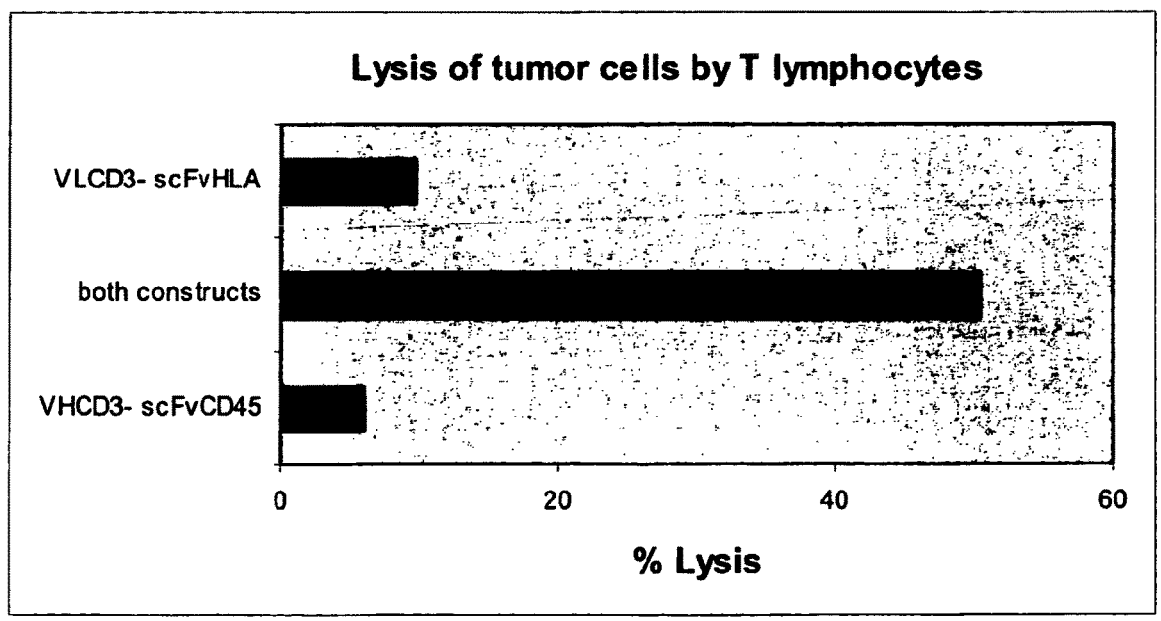

FIG. 9 shows lysis of U266 cells by HLA A2 negative T cells in a sample comprising both $V_L$CD3–scFvHLA-A2 and $V_H$CD3–scFvCD45($V_H$–$V_L$) constructs ("both constructs"). No significant lysis was observed in control samples comprising only one of the two constructs.

Figure 10:
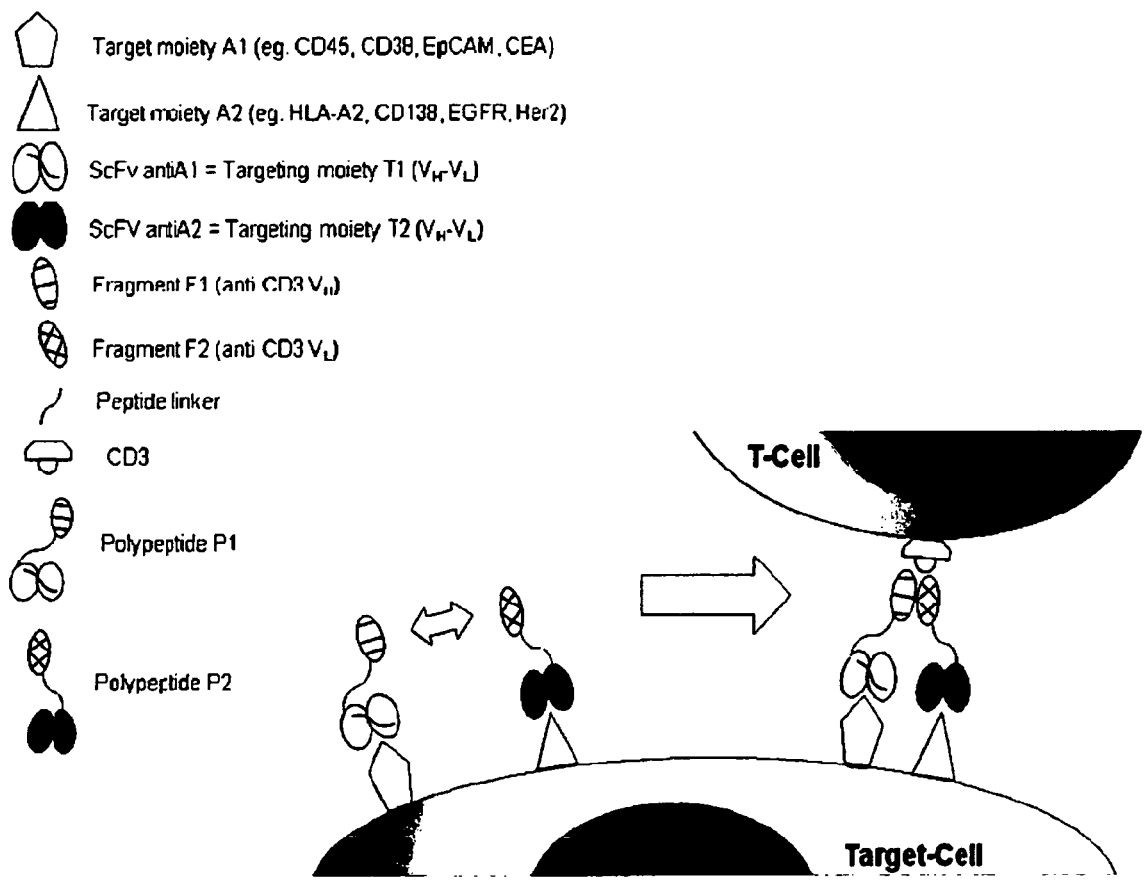

FIG. 10 shows the On-target restoration of the polypeptides. Binding of two separate polypeptides (P1 and P2) to their respective antigens on a target cell, each consisting of a specific single-chain variable antibody fragment (scFv, $V_H$–$V_L$) fused to the variable light ($V_L$) or variable heavy chain domain ($V_H$) of a CD3-specific antibody (Fragment F1 and F2), enables $V_H$/$V_L$ heterodimerization and the formation of a functional CD3 binding site to engage T cells.

Figure 11A:
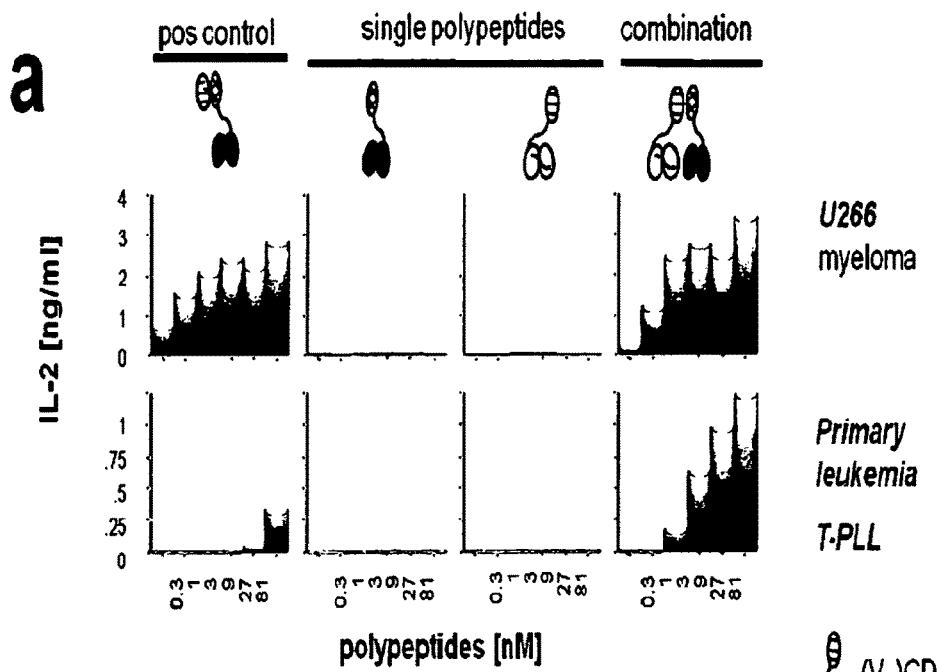
Figure 11B:
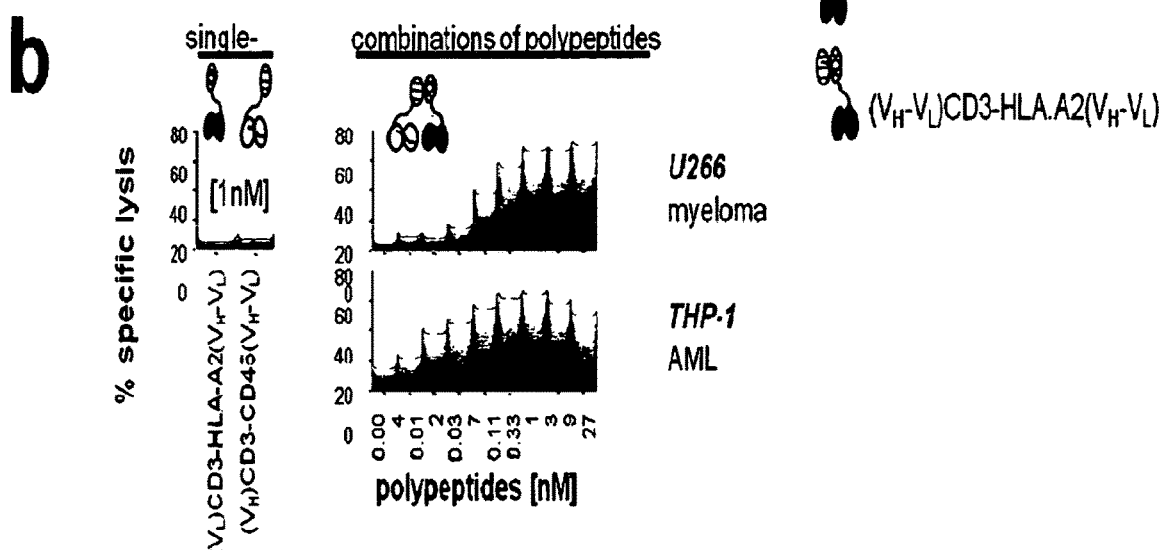

FIG. 11A-FIG. 11D show that CD3 $V_H$/$V_L$ dimerization engages T cells and is dual-antigen-restricted. U266 myeloma, primary T cell pro-lymphocytic leukemia (T-PLL), and THP-1 acute myeloid leukemia cells, all HLA-A2-positive and CD45-positive, were probed with HLA-A2-negative donor peripheral blood mononuclear cells (PBMC) and the polypeptides as indicated. T-cell engagement was assessed by reactive interleukin-2 (IL-2) production (FIG. 11A) and target cell lysis (FIG. 11B). The bispecific tandem scFv (CD3($V_H$–$V_L$)–HLA-A2($V_H$–$V_L$) antibody was used as a positive control. (FIG. 11C), Binding of the polypeptides on THP-1 cells is competitively blocked by an excess of scFvCD45 (left) and scFvHLA-A2 (right) inhibitors (blocking the individual antigen epitopes on the target cell), as indicated, and reactive IL2 production by donor PBMCs was investigated. (FIG. 11D), The single or double antigen negative cell lines RAJI and KMS-12-BM were probed with the polypeptides. PHA-L was used as a nonspecific stimulus control for PBMCs.

Figure 12A:
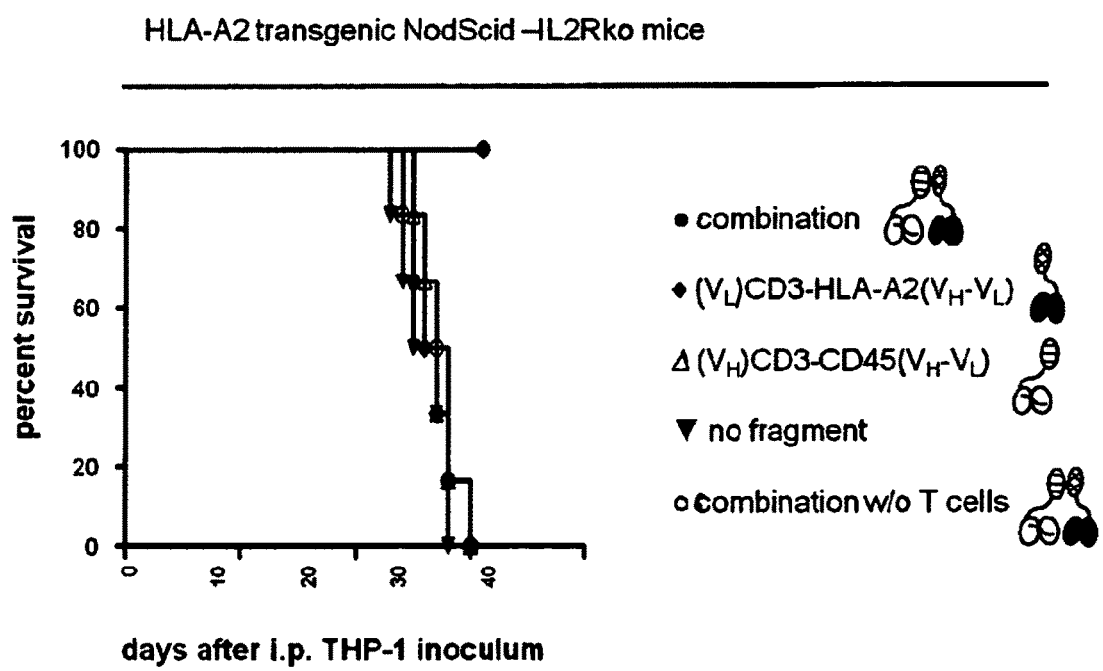
Figure 12B:
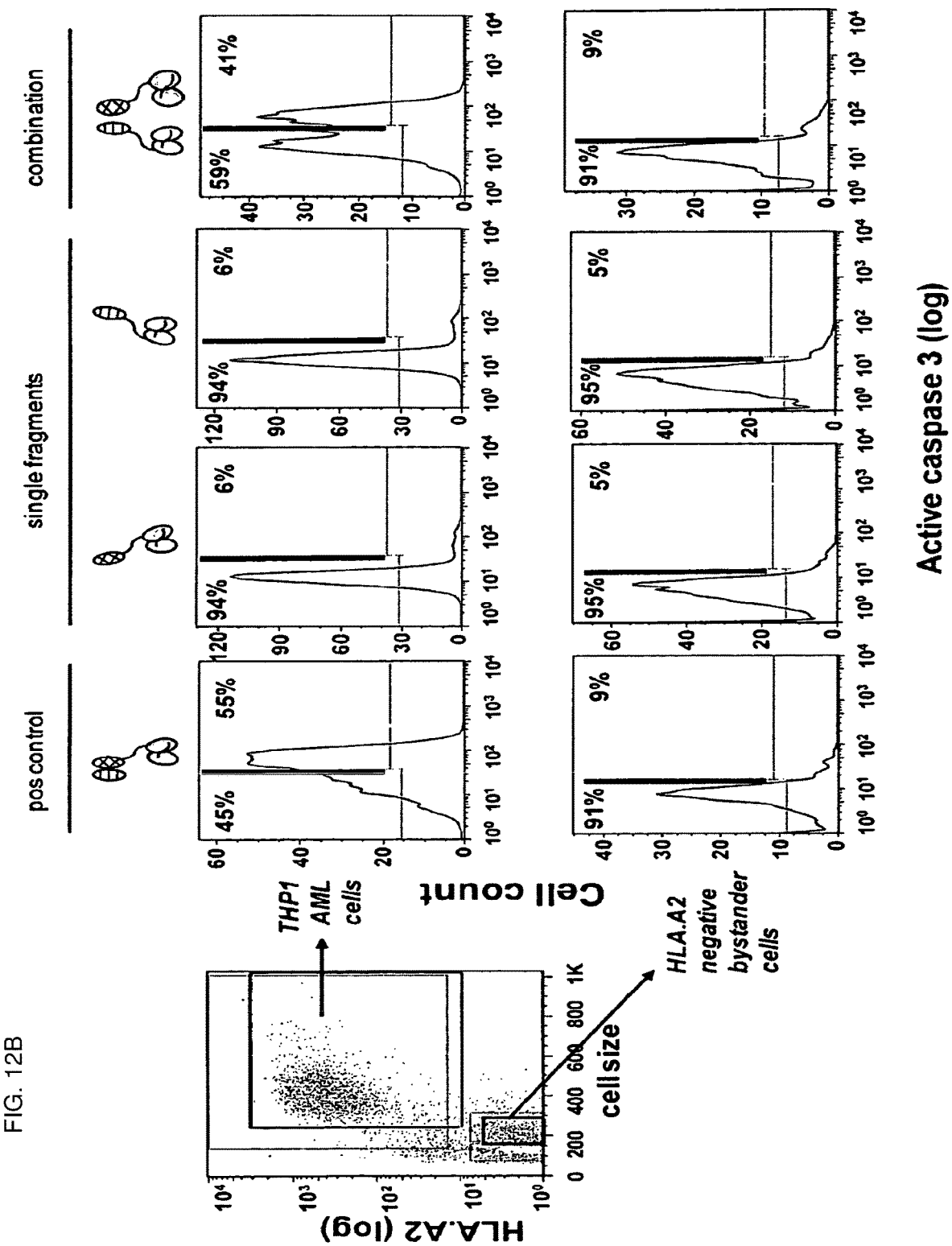

FIG. 12A-FIG. 12B show targeted therapy by conditional CD3$V_H$/$V_L$ complementation in vivo. (FIG. 12A), Survival of mice (n=6 per group) after intraperitoneal injection of 5×10$^6$ THP-1 acute leukemic cells together with 1.25×10$^5$ CMV-specific, HLA-A2-negative donor T cells and the polypeptides (0.5 µg) as indicated (tumor cells: T-cell ratio=40/1). (FIG. 12B), Caspase 3 activation was assessed in vitro by flow cytometry in HLA-A2/CD45 double-positive THP-1 and CD45-positive but HLA-A2-negative bystander cells after co-culture with donor T cells and the polypeptides (3 nM) as indicated. The bispecific tandem scFv (CD3($V_H$–$V_L$)–HLA-A2($V_H$–$V_L$)) antibody was used as a positive control.

Figure 13A:
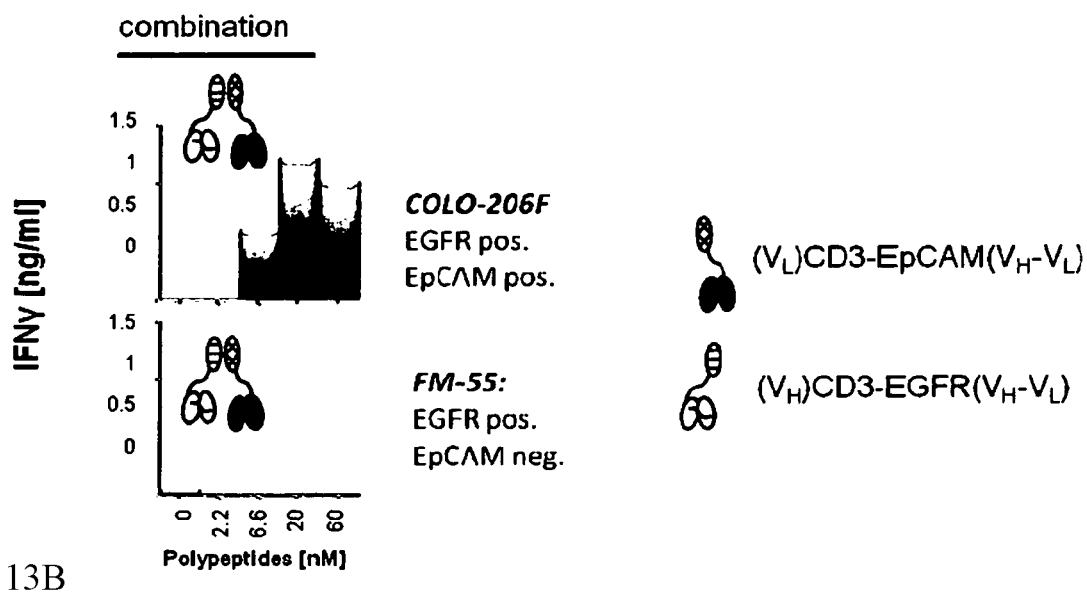
Figure 13B:
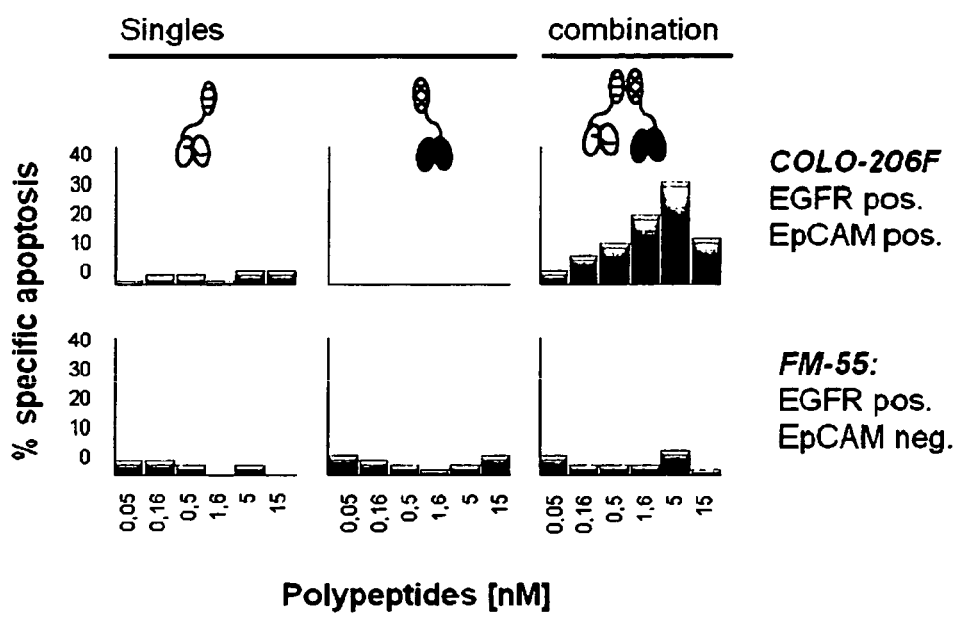

FIG. 13A-FIG. 13B show that EGFR- and EpCAM-directed polypeptides engage T cells for carcinoma cell destruction. EGFR and EpCAM double-positive human colon cancer cell line COLO-206F and melanoma cell line FM-55 (EGFR-positive but EpCAM-negative) were probed with PBMCs in the presence of polypeptides specific for EGFR (CD3($V_H$)-EGFR($V_H$–$V_L$)) and EpCAM (CD3($V_L$)–EpCAM($V_H$–$V_L$)) as indicated. T cell engagement was assessed by reactive interferon-γ (IFNγ) production (FIG. 13A) and activation of caspase 3 in target cells (FIG. 13B).

Figure 14:
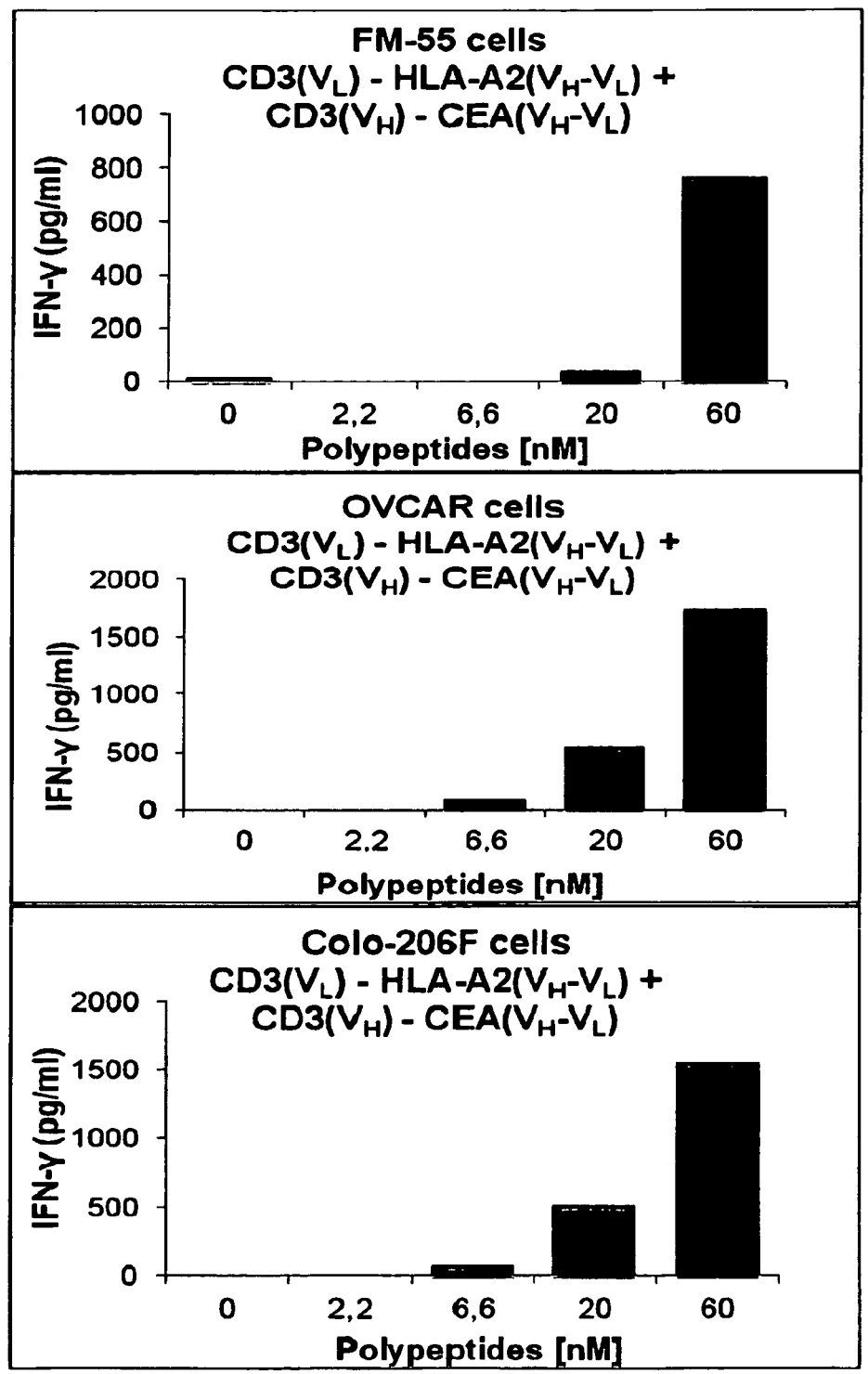

FIG. 14 shows that HLA-A2 and CEA directed polypeptides redirect T cells for tumor cell destruction. Human colon cancer cell line COLO-206F, melanoma cell line FM-55 and ovarian cancer cell line OVCAR were probed with PBMCs in the presence of polypeptides specific for HLA-A2 (CD3($V_L$)–HLA-A2($V_H$–$V_L$)) and CEA (CD3($V_H$)–CEA($V_H$–$V_L$)) as indicated. T cell engagement was assessed by reactive IFNγ production. Samples were run and analyzed as duplicates.

Figure 15:
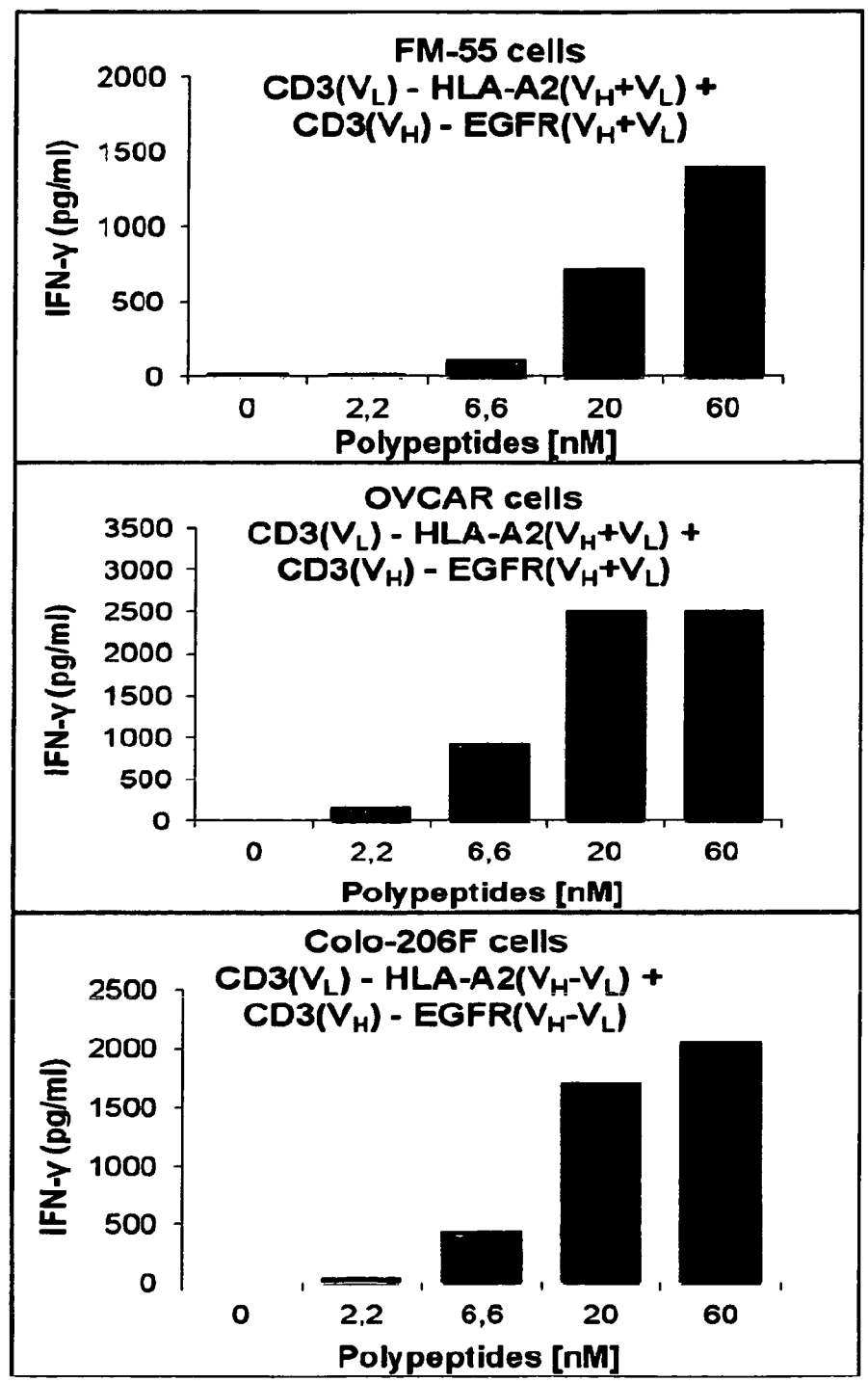

FIG. 15 shows that HLA-A2 and EGFR directed polypeptides redirect T cells for tumor cell destruction. Human cell lines COLO-206F, FM-55 and OVCAR were probed with PBMCs in the presence of polypeptides specific for HLA-A2 (CD3($V_L$)–HLA-A2($V_H$–$V_L$)) and EGFR (CD3($V_H$)–EGFR($V_H$–$V_L$)) as indicated. T cell engagement was assessed by reactive IFNγ production. Samples were run and analyzed as duplicates.

Figure 16:
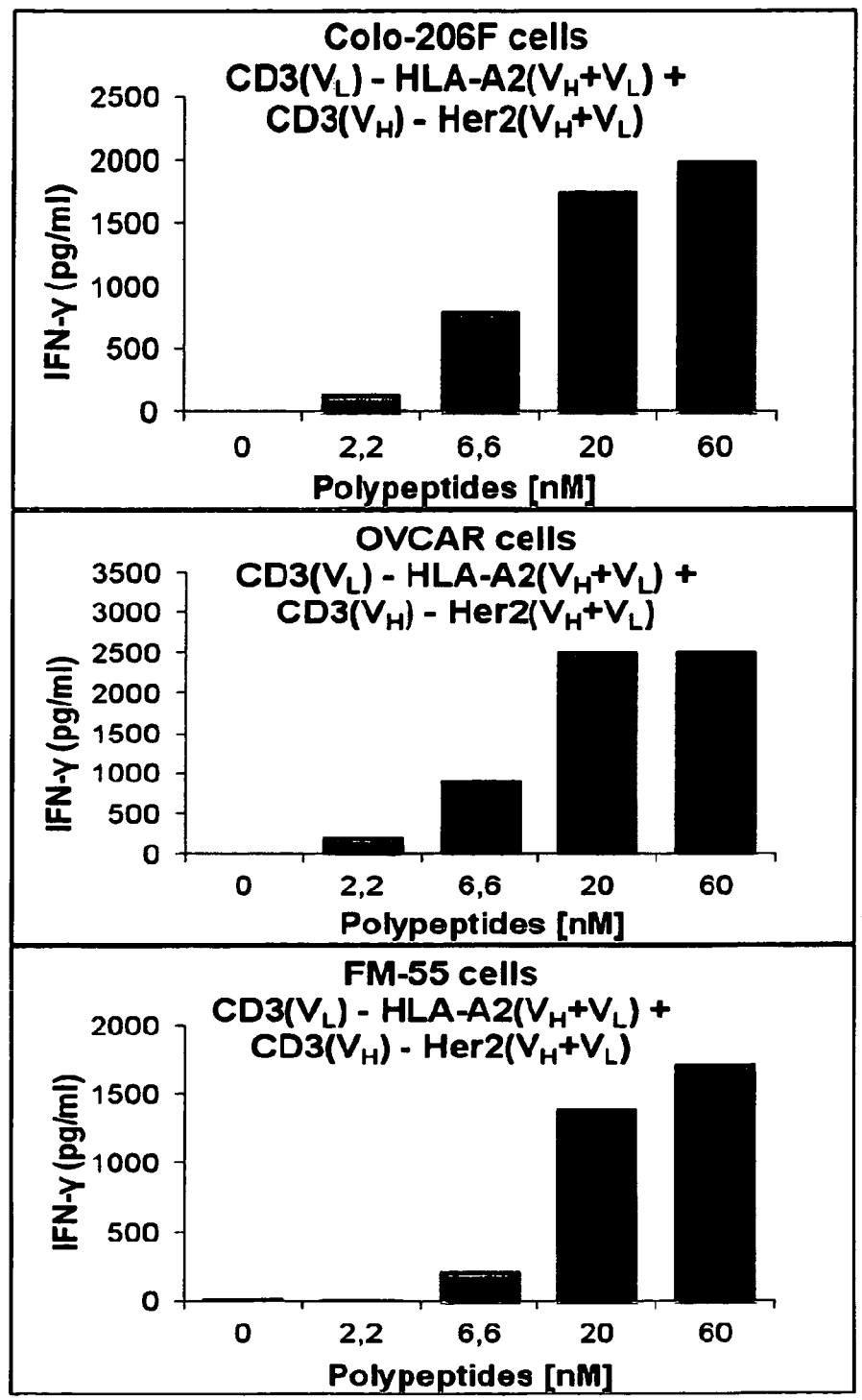

FIG. 16 shows that HLA-A2 and Her2 directed polypeptides redirect T cells for tumor cell destruction. Human cell lines COLO-206F, FM-55 and OVCAR were probed with PBMCs in the presence of polypeptides specific for HLA-A2 (CD3($V_L$)–HLA-A2($V_H$–$V_L$)) and Her2 (CD3($V_H$)–Her2($V_H$–$V_L$)) as indicated. T cell engagement was assessed by reactive IFNγ production. Samples were run and analyzed as duplicates.

Figure 17:
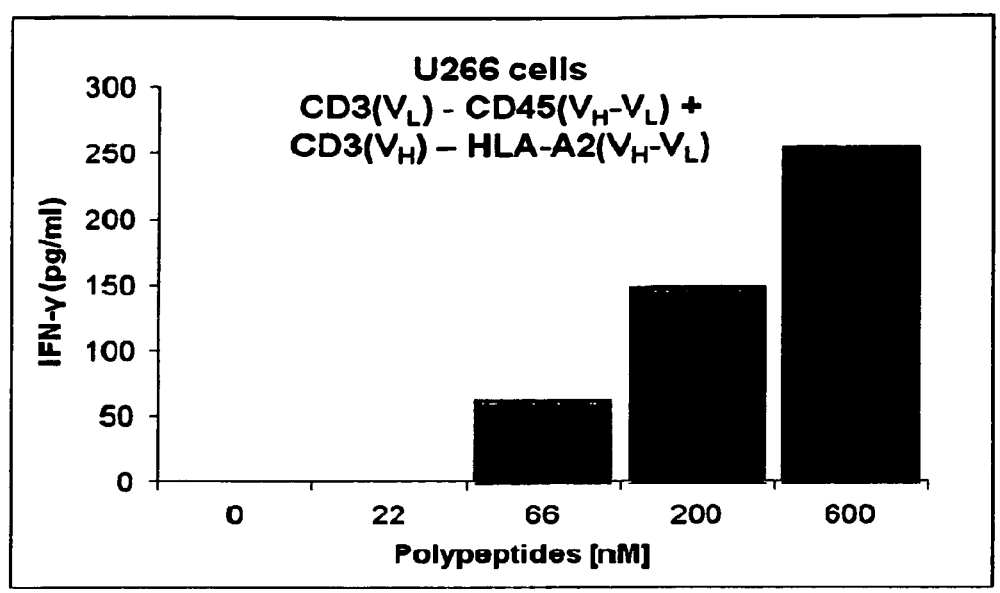

FIG. 17 shows that CD45 and HLA-A2 directed polypeptides redirect T cells for tumor cell destruction. In this experiment the split antiCD3 fragments (CD3($V_H$) and CD3($V_L$)) for the anti-CD45 and anti-HLA-A2 targeting moieties were exchanged, compared to the CD45 and HLA-A2 polypeptides used in FIG. 5,7-9, 11,12, 14-16. Human myeloma cell line U266 was probed with PBMCs in the presence of polypeptides specific for CD45 (CD3($V_L$)–CD45($V_H$–$V_L$)) and HLA-A2 (CD3($V_H$)–HLA-A2($V_H$–$V_L$)) as indicated. T cell engagement was assessed by reactive IFNγ production. Samples were run and analyzed as duplicates.

Figure 18:
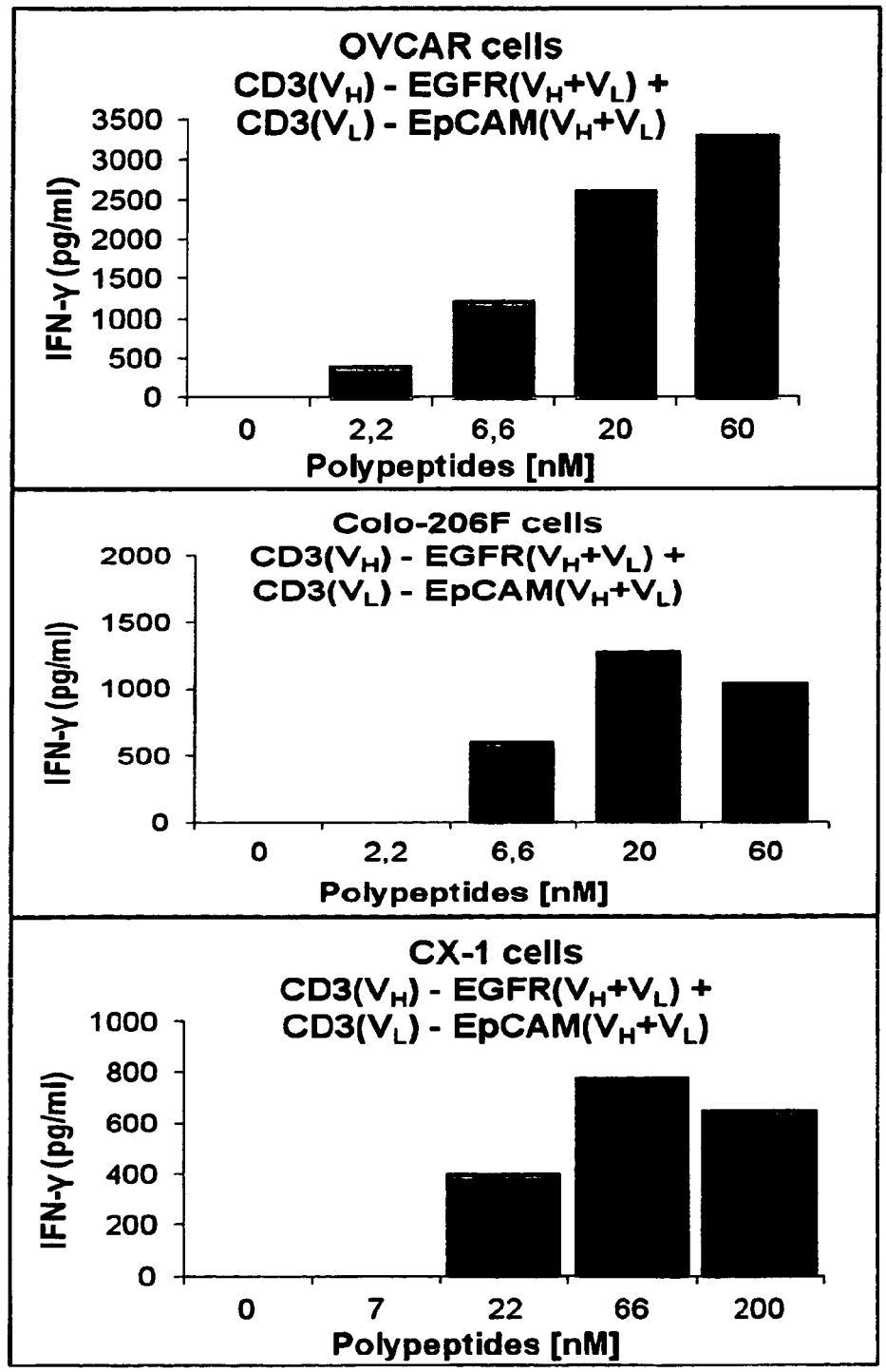

FIG. 18 shows that EGFR and EpCAM directed polypeptides redirect T cells for tumor cell destruction. Human colon cancer cell lines COLO-206F and CX-1 and ovarian cancer cell line OVCAR were probed with PBMCs in the presence of polypeptides specific for EpCAM (CD3($V_L$)–EpCAM($V_H$–$V_L$)) and EGFR (CD3($V_H$)–EGFR($V_H$–$V_L$)) as indicated. T cell engagement was assessed by reactive IFNγ production. Samples were run and analyzed as duplicates.

Figure 19:
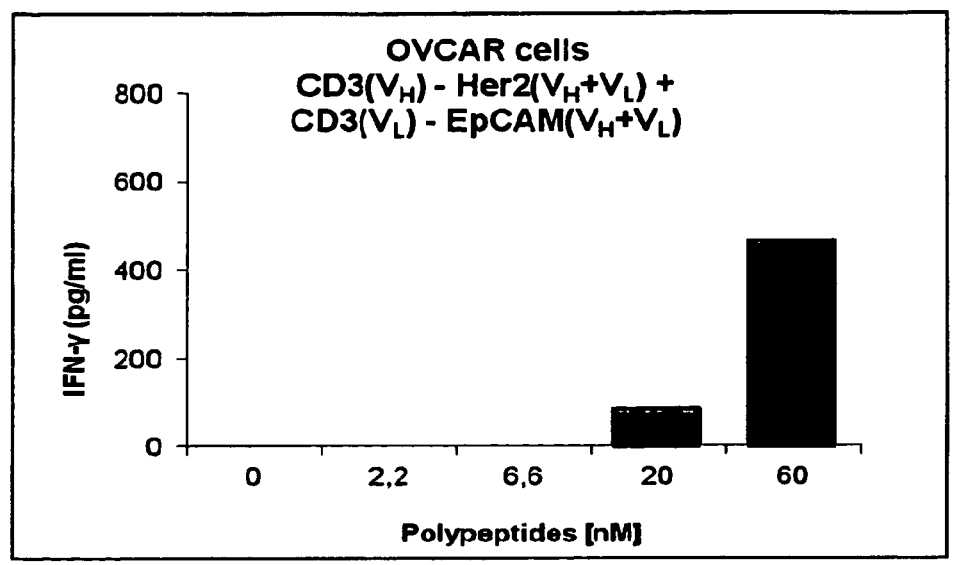

FIG. 19 shows that Her2 and EpCAM directed polypeptides redirect T cells for tumor cell destruction. Human ovarian cancer cell line OVCAR were probed with PBMCs in the presence of polypeptides specific for EpCAM (CD3($V_L$)–EpCAM($V_H$–$V_L$)) and Her2 (CD3($V_H$)–Her2($V_H$–$V_L$)) as indicated. T cell engagement was assessed by reactive IFNγ production. Samples were run and analyzed as duplicates.

Figure 20:
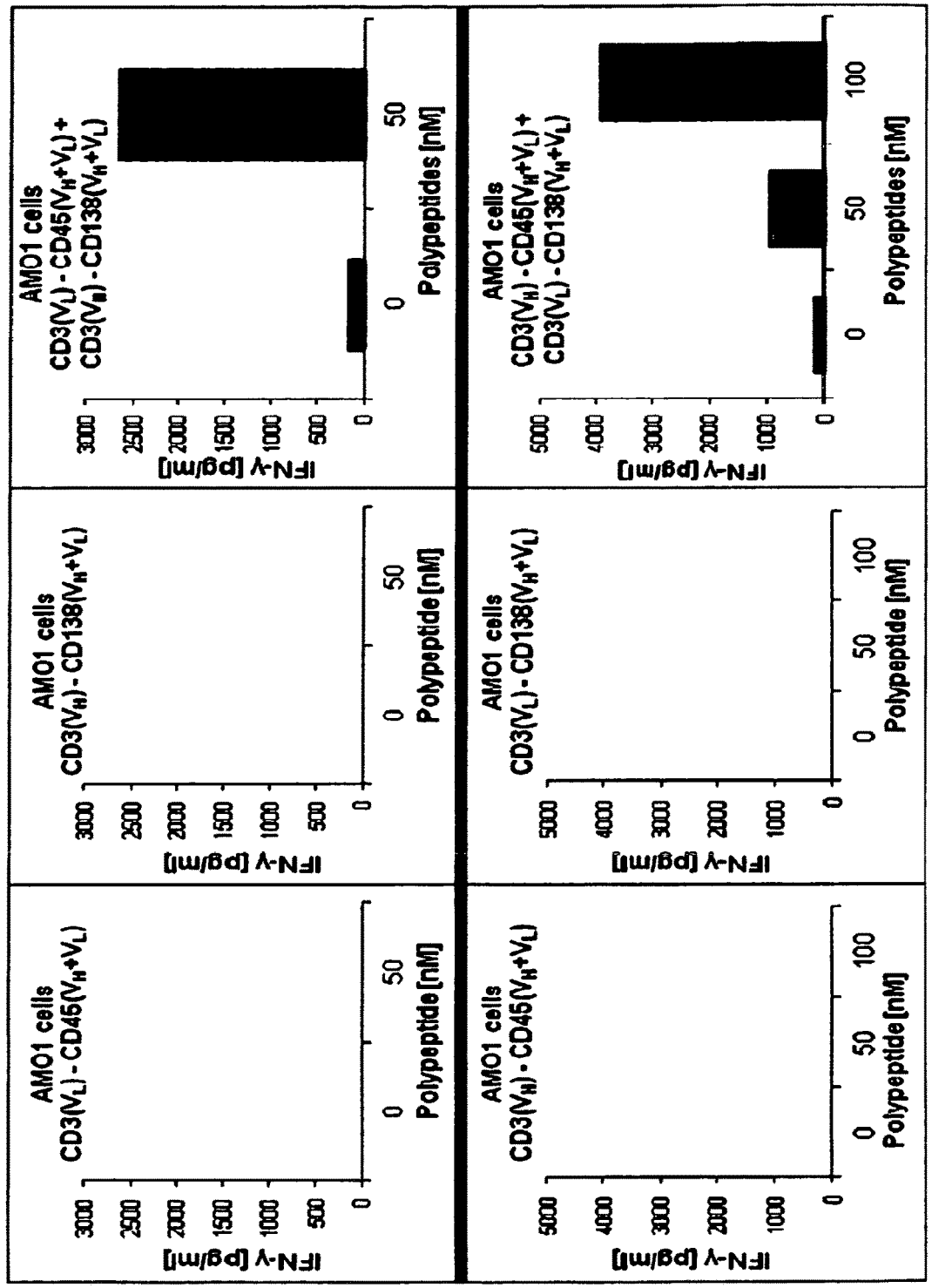

FIG. 20 shows that CD45 and CD138 directed polypeptides redirect T cells for tumor cell destruction. Human myeloma cell line AMO-1 was probed with PBMCs in the presence of polypeptides specific for CD45 (CD3($V_L$)–CD45($V_H$–$V_L$) upper panel, CD3($V_H$)–CD45($V_H$–$V_L$) lower panel) and CD138 (CD3($V_H$)–CD138($V_H$–$V_L$) upper panel, CD3($V_L$)–CD138($V_H$–$V_L$) lower panel) as indicated. T cell engagement was assessed by reactive IFNγ production. Samples were run and analyzed as duplicates.

Figure 21:
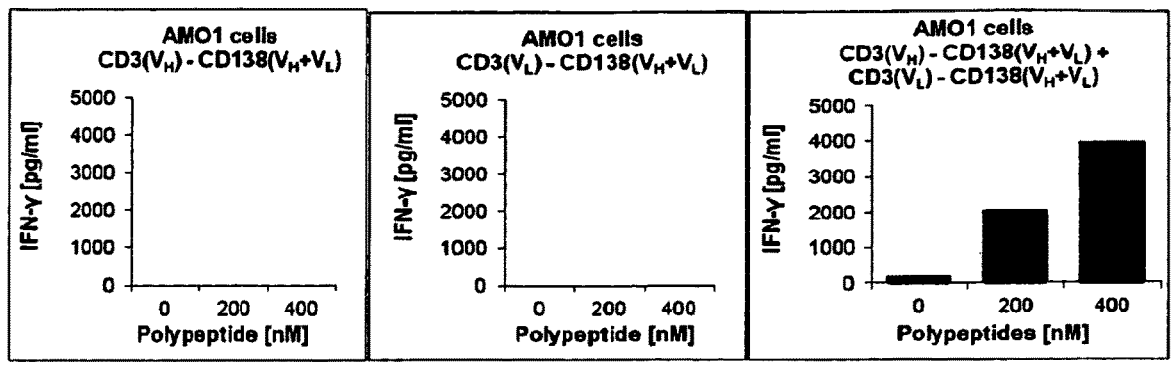

FIG. 21 shows that targeting a single antigen (CD138) with CD138 directed polypeptides redirect T cells for tumor cell destruction. Human myeloma cell line AMO-1 was probed with PBMCs in the presence of polypeptides specific for CD138 (CD3($V_L$)–CD138($V_H$–$V_L$) and (CD3($V_H$)–CD138($V_H$–$V_L$)) as indicated. T cell engagement was assessed by reactive IFNγ production. Samples were run and analyzed as duplicates.

Figure 22:
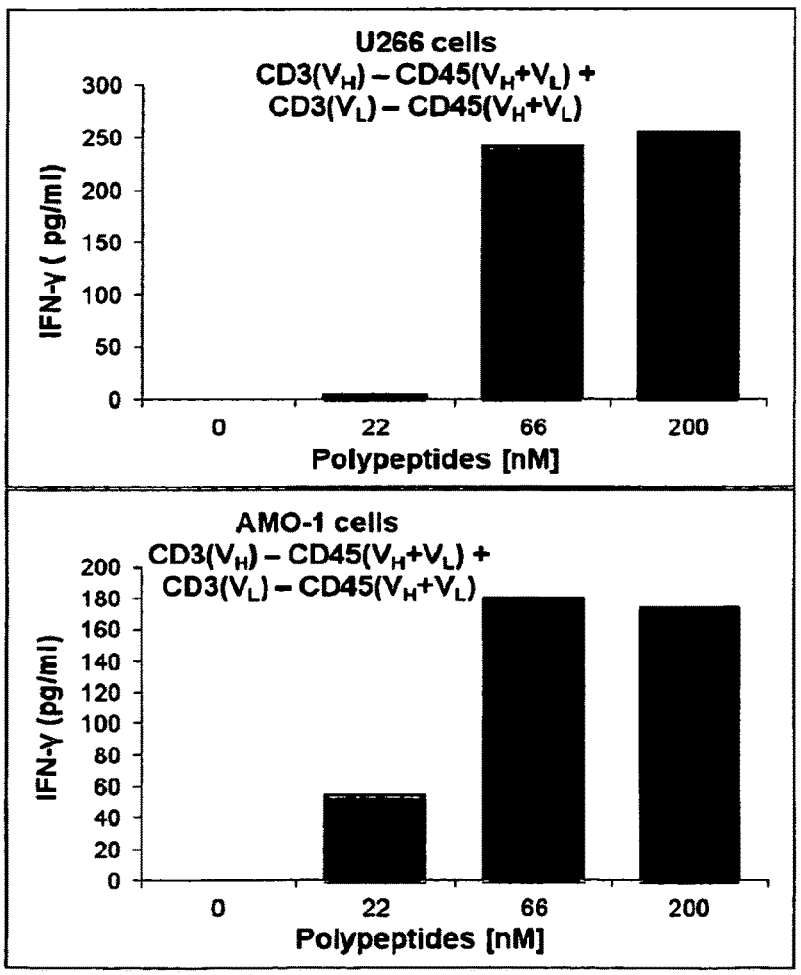

FIG. 22 shows that targeting a single antigen (CD45) with CD45 directed polypeptides redirect T cells for tumor cell destruction. Human myeloma cell lines AMO-1 and U266 were probed with PBMCs in the presence of polypeptides specific for CD45 (CD3($V_L$)–CD45($V_H$–$V_L$) and (CD3($V_H$)–CD45($V_H$–$V_L$)) as indicated. T cell engagement was assessed by reactive IFNγ production. Samples were run and analyzed as duplicates.

Figure 23:
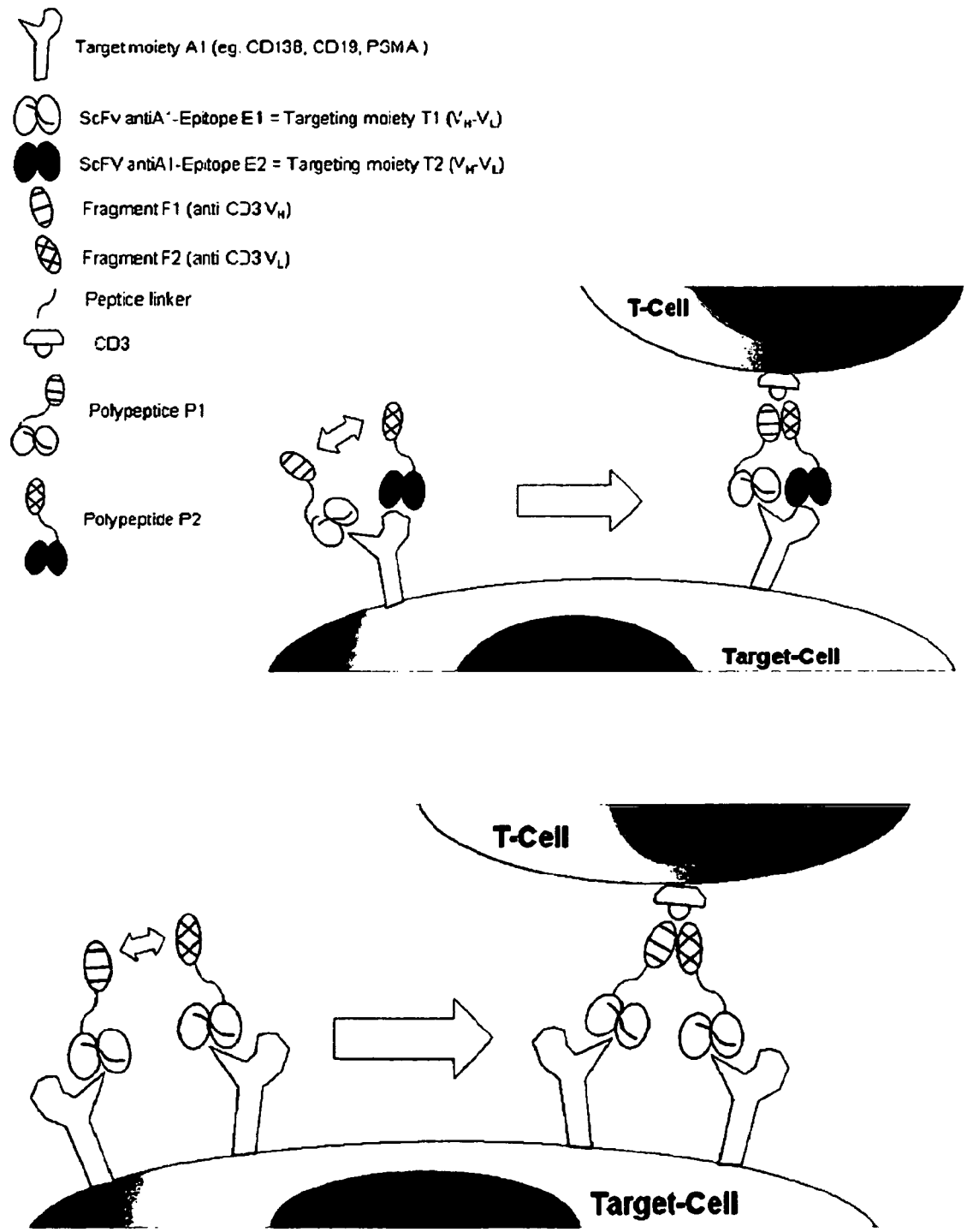

FIG. 23 shows the On-target restoration of two polypeptides directed against a single antigen on the cell surface, targeting two different epitopes (upper part) or the same epitope (lower part) on the antigen. Binding of two separate polypeptides (P1 and P2) to their respective epitope, on the same antigen, on a target cell. For targeting two different epitopes, the targeting moiety of each polypeptide consists of a specific single-chain variable antibody fragment (scFv). For targeting the same epitope, the targeting moiety of each polypeptide consists of the same single-chain variable antibody fragment (scFv). The targeting moieties are fused via peptide linkers to the variable light ($V_L$) or variable heavy chain domain ($V_H$) of a CD3-specific antibody (Fragment F1 and F2), enables $V_H$/$V_L$ heterodimerization and the formation of a functional CD3 binding site (functional domain) to engage T cells.

Figure 24:
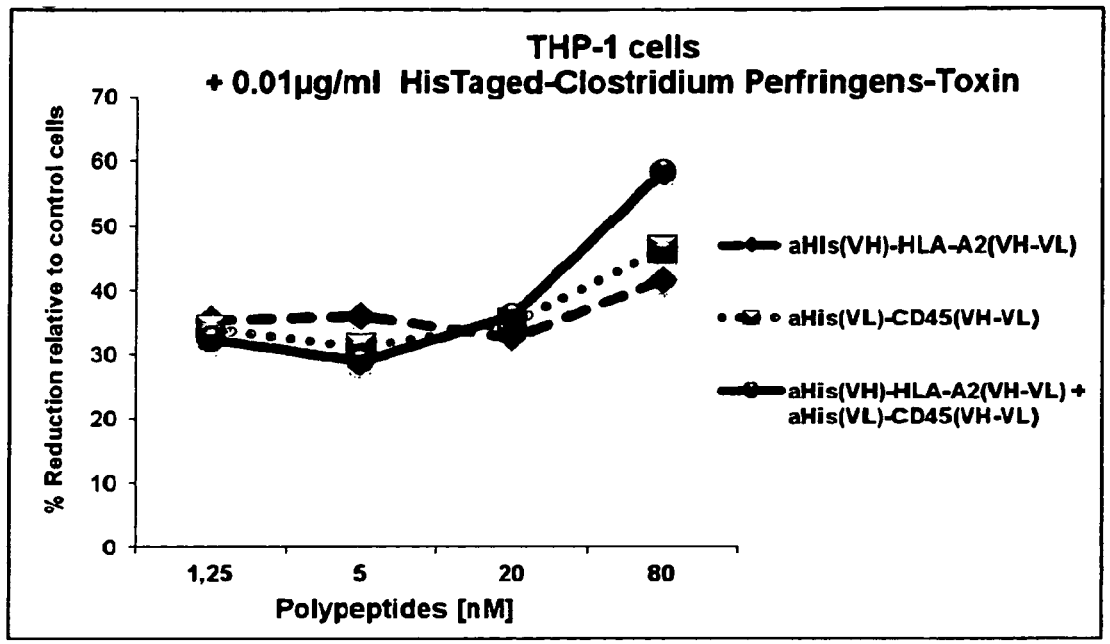

FIG. 24 shows the possibility to use different effector ways to kill a target cell with a kit of polypeptide parts. To this end, the anti-CD3 module (F1 and F2) is replaced by an anti-HIS (hexa-histidine) module which, after simultaneous binding of polypeptide 1 and 2, complements a hexa-histidine binding site and thus binds histidine labeled payloads (eg. a HIS-tagged toxin). The targeting moiety T1 ($V_H$–$V_L$) of polypeptide P1 specifically binds to HLA-A2, the targeting moiety T2 ($V_H$–$V_L$) of polypeptide P2 specifically binds to CD45. The fragment F1 of polypeptide P1 comprises of a $V_H$ domain of an antibody against a hexa-histidine-tag and fragment F2 of polypeptide P2 comprises a $V_L$ domain of the same antibody. Human myeloid leukemia cell line THP-1 was probed with a histidine (His) tagged *Clostridium perfringens* Iota toxin component Ia at 0.01 µg/ml in combination with indicated polypeptides. After 48 hours in culture the cell viability was measured using the ALAMARBLUE® assay. The results show a reduction of viability against the background of the assay for cells probed with the combination, but not with individual polypeptides. Control THP-1 cells were grown simultaneously in culture without toxin. Samples were run and analyzed as duplicates.

Figure 25:
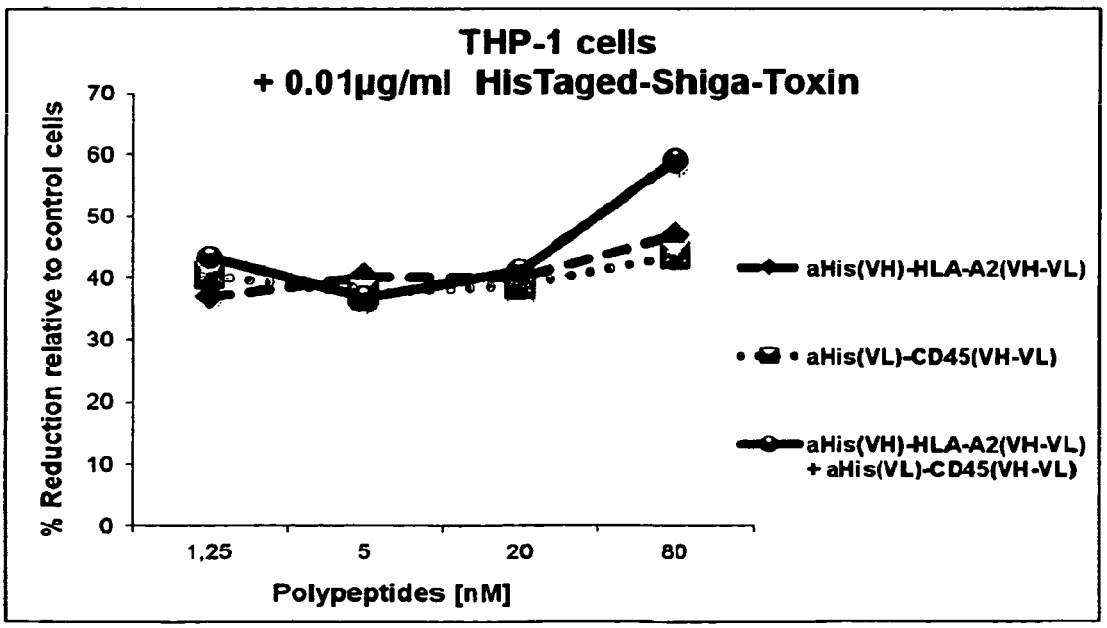
Figure 26:
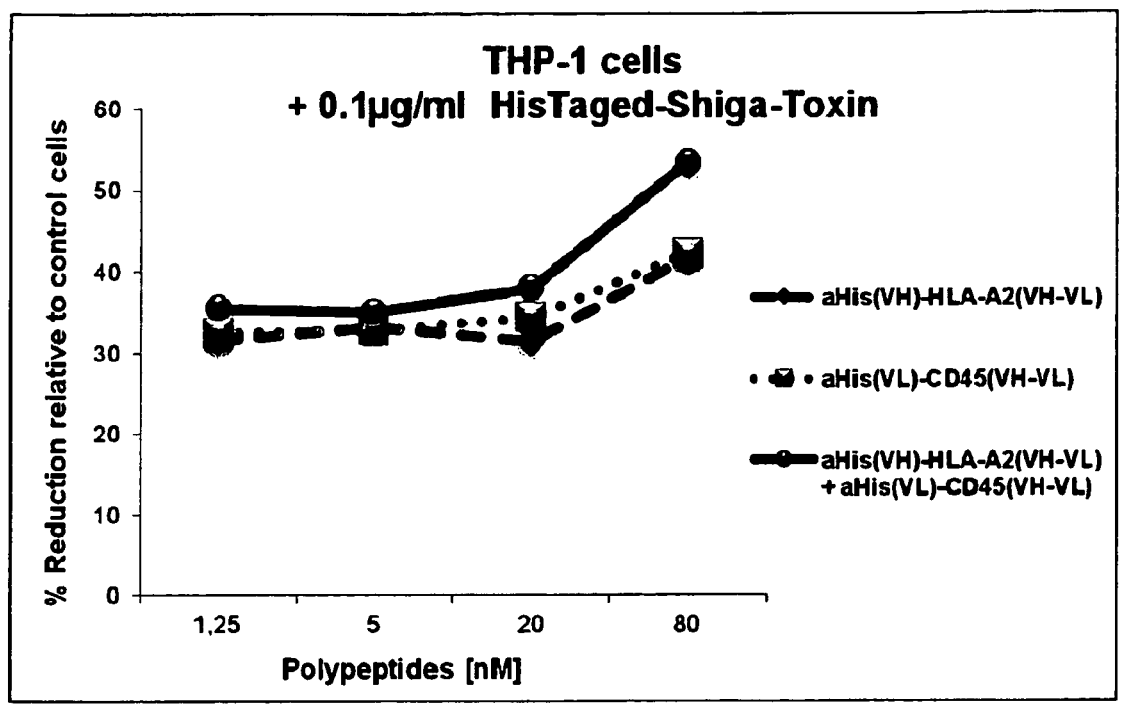
Figure 27:
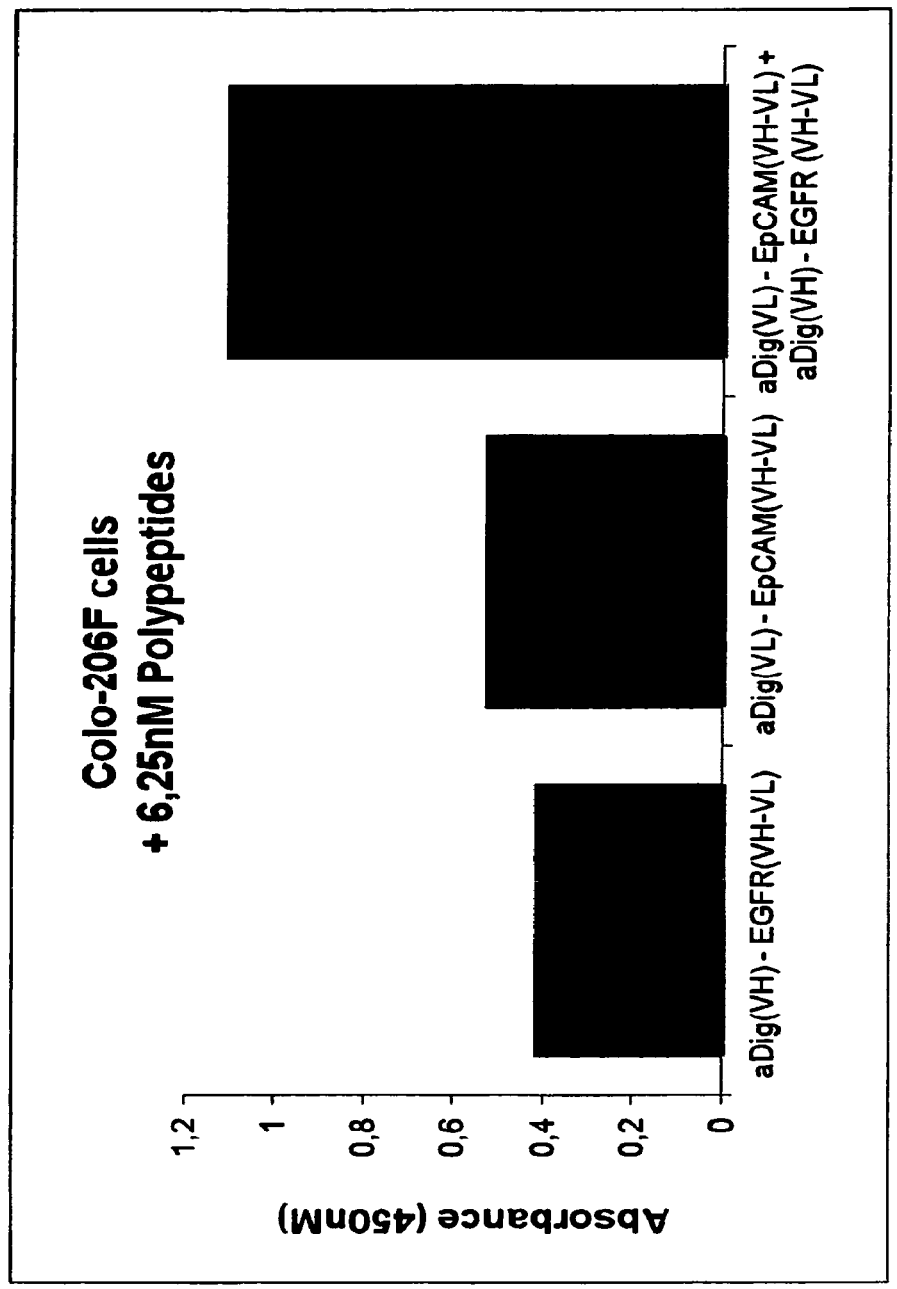
Figure 28:
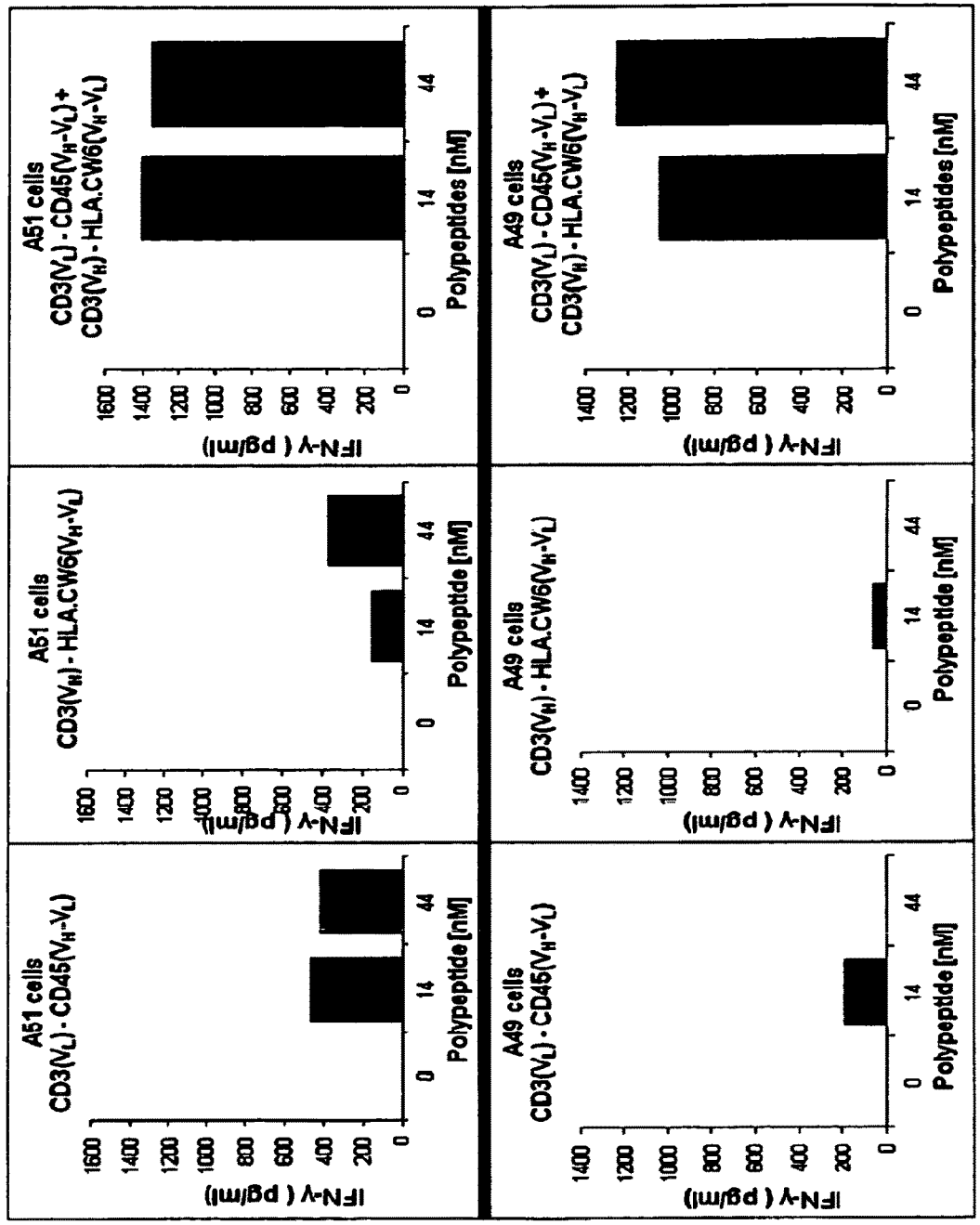

FIG. 25 shows that HLA-A2 and CD45 directed polypeptides, comprising of a split antibody against a His-tag, kill tumor cells using a histidine (His) tagged Shiga toxin subunit A at a concentration of 0.01 μg/ml. The same experimental setup was used as in FIG. 24.

FIG. 26 shows that HLA-A2 and CD45 directed polypeptides, comprising of a split antibody against a His-tag, kill tumor cells using a histidine (His) tagged Shiga toxin subunit A at a concentration of 0.1 μg/ml. The same experimental setup was used as in FIG. 24 and FIG. 25.

FIG. 27 shows that EGFR and EpCAM directed polypeptides, comprising of a functional domain F with F1 and F2 are $V_H$ and $H_L$ of a antibody specific for digoxigenin (aDig), mark tumor cells using a digoxigenin labeled horse radish peroxidase (HRP) molecule. The targeting moiety T1 ($V_H$–$V_L$) of polypeptide P1 specifically binds to EGFR, the targeting moiety T2 ($V_H$–$V_L$) of polypeptide P2 specifically binds to EpCAM. The fragment F1 of polypeptide P1 comprises of a $V_H$ domain of an antibody against digoxigenin and fragment F2 of polypeptide P2 comprises a $V_L$ domain of the same antibody. Human colon cancer cell line Colo-206F was first probed with indicated polypeptides followed by probing with digoxigenin labeled HRP. The samples were analyzed using the (Invitrogen™, ELISA Kit) and the absorbance was read with a BioRAD-micro plate reader. For analysis the chromogen blank sample (no Digoxigenin-HRP) was set to 0. Samples were run and analyzed as duplicates.

FIG. 28 shows that CD45 and HLA-CW6 directed polypeptides redirect T cells for patient cell destruction. Primary patient cells with known HLA-haplotypes were used. A51=cells of a patient with MDS (myelodysplastic syndrom), homozygous for the HLA-Cw6 haplotype. A49=cells of a patient after allogeneic bone marrow transplantation, heterozygous for the HLA-Cw6 haplotype. Patient cells were incubated with healthy PBMCs for 30 hours, in the presence of polypeptides specific for CD45 (CD3($V_L$)–CD45($V_H$–$V_L$) and HLA-Cw6 (CD3($V_H$)–HLA-CW6($V_H$–$V_L$)) as indicated. T cell engagement was assessed by reactive IFNγ production. Samples were run and analyzed as duplicates.

FIG. 29 shows that EGFR and EpCAM directed polypeptides redirect T cells for primary cancer patient cell destruction. A44 tumor cells were collected from the malignant ascites of a 48 years old male patient with metastatic pancreatic cancer. Patient tumor cells were incubated with patients own PBMCs (collected by phlebotomy) for 30 hours, in the presence of polypeptides specific for EpCAM (CD3($V_L$)–EpCAM($V_H$–$V_L$) and EGFR (CD3($V_H$)–EGFR ($V_H$–$V_L$)) as indicated. T cell engagement was assessed by reactive IFNγ production. Samples were run and analyzed as duplicates.

FIG. 30 shows that CD45 and HLA-A2 directed polypeptides redirect CMV restricted CD8+ T cells for tumor cell destruction. Human tumor cells THP-1 and U266 were incubated with CMV restricted T-cells from a HLA-A2 negative healthy donor for 30 hours, in the presence of polypeptides specific for HLA-A2 (CD3($V_L$)–HLA-A2 ($V_H$–$V_L$) and CD45 (CD3($V_H$)–CD45($V_H$–$V_L$)) as indicated. The bispecific tandem scFv (CD3($V_H$–$V_L$)×HLA-A2 ($V_H$–$V_L$)-antibody was used as a positive control. T cell engagement was assessed by reactive IFNγ production. Samples were run and analyzed as duplicates.

FIG. 31 shows the principle idea to eliminate autoimmune or hypersensitivity disorder causing B-cell clones with a kit of polypeptide parts, consisting of an allergen specific polypeptide and a cell type specific polypeptide. The first polypeptide P1 has at its targeting moiety an allergen (eg. Betv-1A, Der-f2, Conglutin-7, Can-f1, Feld-d1). The second polypeptide P2 has at its targeting moiety a specific single-chain variable antibody fragment (scFv, $V_H$–$V_L$) targeting a cell surface protein (eg. CD19, CD138, CD38). Both targeting moieties are fused to either the variable light ($V_L$) or variable heavy chain domain ($V_H$) of a CD3-specific antibody (Fragment F1 and F2).

In the following, reference is made to certain (human) genes or proteins also referred to in the specification, the appended examples and figures as well as (partially) in the claims. Herein below, corresponding (exemplary) gene accession numbers are provided. Further accession numbers are also provided in the specification elsewhere herein as well as the appended examples.

CD45: Gene ID: 5788, updated on 13 Jan. 2013, 3. Protein=P08575-1=Isoform 1, Last modified Jul. 19, 2003. Version 2

CD34: Protein: P28906-1/2 Last modified Jul. 15, 1998. Version 2.

CD33: Gene ID: 945, updated on 30 Dec. 2012: Protein: P20138 [UniParc]. Last modified Oct. 17, 2006. Version 2. Checksum: 1C73E588240FBAD8

CD138: Gene ID: 6382, updated on 6 Jan. 2013, 4. Protein=P18827 [UniParc]. Last modified May 5, 2009. Version 3.

CD15: Gene ID: 2526, updated on 5 Jan. 2013

CD1a: Gene ID: 909, updated on 30 Dec. 2012, P06126 [UniParc]. Last modified Feb. 9, 2010. Version 4. Checksum: C575C3C538F0AA29

CD2: Gene ID: 914, updated on 5 Jan. 2013; P06729 [UniParc]. Last modified Oct. 23, 2007. Version 2. Checksum: A03D853C3B618917

CD3e: Gene ID: 916, updated on 5 Jan. 2013, P07766 [UniParc]. Last modified Feb. 1, 1996. Version 2. Checksum: A1603D010E9957D7

CD4: Gene ID: 920, updated on 13 Jan. 2013; P01730 [UniParc]. Last modified Nov. 1, 1988. Version 1. Checksum: 20ED893F9E56D236

CD5: Gene ID: 921, updated on 30 Dec. 2012; P06127 [UniParc]. Last modified Nov. 30, 2010. Version 2. Checksum: 9131AEC9683EE1D3

CD8a: Gene ID: 925, updated on 30 Dec. 2012; Isoform 1/2 (membrane) P01732-1/2 (mCD8alpha) [UniParc]. Last modified Jul. 21, 1986. Version 1. Checksum: FCCA29BAA73726BB CD20: Gene ID: 931, updated on 6 Jan. 2013; P11836 [UniParc]. Last modified Oct. 1, 1989. Version 1. Checksum: AC5420F8B626BDD1

CD23: Gene ID: 2208, updated on 4 Jan. 2013; P06734 [UniParc]. Last modified Jan. 1, 1988. Version 1. Checksum: F86708C0E6515B87

CD31: Gene ID: 5175, updated on 13 Jan. 2013; Isoform Long [UniParc]. Last modified Apr. 1, 1990. Version 1. Checksum: C57BBFA200A407A6, P16284-1/2/3/4/5/6=Isoforms 1-6

CD43: Gene ID: 6693, updated on 30 Dec. 2012; P16150 [UniParc]. Last modified Apr. 1, 1990. Version 1. Checksum: C9C9AB8435D5E1FE CD56: Gene ID: 4684, updated on 30 Dec. 2012; Isoform 1 [UniParc]. Last modified Jul. 22, 2008. Version 3. Checksum: FD3B9DE80D802554, P13591-2/1/3/4/4/6, Isoforms 1-6

CD57: Gene ID: 27087, updated on 5 Jan. 2013

CD68: Gene ID: 968, updated on 6 Jan. 2013; Isoform Long (CD68.1) [UniParc]. Last modified May 15, 2007. Version 2. Checksum: 69E68D69EDE8EFBO, P34810-1/2, Isoform 1/2

CD79a: Gene ID: 973, updated on 5 Jan. 2013; Isoform 1 (Long) [UniParc].
Last modified Jun. 1, 1994. Version 2., Checksum: 6E5B837409969292, P11912-1/2, Isoform 1/2

CD146: Gene ID: 4162, updated on 30 Dec. 2012; Isoform 1 [UniParc]. Last modified Jan. 10, 2006. Version 2. Checksum: E46CB8AC7BA0738E, P43121-1/2, Isoform 1/2.

surfactant proteins (A and B):
Gene ID: 6440, updated on 30 Dec. 2012 and Gene ID: 6439, updated on 30 Dec. 2012, P07988 [UniParc]. Last modified May 1, 1992. Version 3. Checksum: 9FD7F66678A35153, and Isoform 1 [UniParc]. Last modified Apr. 1, 1990. Version 2. Checksum: C26A21E33C60AA78, P11686-1/2, Isoform 1/2 synaptophysin:
Gene ID: 6855, updated on 30 Dec. 2012, P08247 [UniParc]. Last modified Aug. 1, 1991. Version 3. Checksum: 592289C43B12EFA7 nicotinic acetylcholine receptors:
Gene ID: 1138, updated on 30 Dec. 2012, Gene ID: 1136, updated on 6 Jan. 2013, Gene ID: 1139, updated on 13 Jan. 2013, Gene ID: 1137, updated on 30 Dec. 2012, Gene ID: 1141, updated on 5 Jan. 2013 muscle-specific kinase MUSK:
Gene ID: 4593, updated on 8 Jan. 2013, Isoform 1 [UniParc]. Last modified Jan. 1, 1998. Version 1. Checksum: 3DDC20E179FA010C, O15146-1/2, Isoform 1/2 voltage-gated calcium channel (P/Q-type):
Gene ID: 773, updated on 5 Jan. 2013; Isoform 1 (1A-1) (BI-1-GGCAG) [UniParc]. Last modified Jul. 15, 1999. Version 2. Checksum: 2F2F378ACE02FD56, O00555-1/2/3/4/5/6/7, Isoforms 1-7, Gene ID: 25398, updated on 11 Jan. 2013, J3KP41 [UniParc]. Last modified Oct. 3, 2012. Version 1. Checksum: AEDF4D2A5E49263F voltage-gated potassium channel (VGKC):
Gene ID: 3737, updated on 30 Dec. 2012, Gene ID: 3736, updated on 8 Jan. 2013, Gene ID: 3742, updated on 8 Jan. 2013

N-methyl-D-aspartate receptor (NMDA):
Gene ID: 2904, updated on 5 Jan. 2013, Q13224 [UniParc]. Last modified Jun. 20, 2001. Version 3. Checksum: 40AEB12BE6E50CEF; Gene ID: 2902, updated on 30 Dec. 2012, Isoform 3 (Long) (NR1-3) [UniParc]. Last modified Jun. 1, 1994. Version 1. Checksum: CDF5402769E530AB, Q05586-1/2/3/4/5, Isoforms 1-5

TSHR: Gene ID: 7253, updated on 4 Jan. 2013, Isoform Long [UniParc]. Last modified Mar. 29, 2005. Version 2. Checksum: D2EE9CEBFD64A65F, P16473-1/2/3, Isoforms 1-3

Amphiphysin:
Gene ID: 273, updated on 8 Jan. 2013, Isoform 1 (128 kDa) [UniParc].
Last modified Feb. 1, 1996. Version 1, Checksum: 78B4F75AB75BA357, P49418-1/2, Isoform 1-2 ganglioside GQ1B: Gene ID: 29906, updated on 30 Dec. 2012

GD3: Gene ID: 117189, updated on 22 Jun. 2012

Ca-125: Gene ID: 94025, updated on 30 Dec. 2012, Q8WXI7 [UniParc]. Last modified Mar. 1, 2003. Version 2. Checksum: B3E7BDF19997A440

Her-2/neu: Gene ID: 2064, updated on 13 Jan. 2013, 4. Protein=P04626-1/2/3/4=Isoform 1-4, Last modified Aug. 13, 1987. Version 1.

gross cystic disease fluid protein 15; Gene ID: 5304, updated on 30 Dec. 2012

CD117: Gene ID: 3815, updated on 6 Jan. 2013

CD30: Gene ID: 943, updated on 6 Jan. 2013; Isoform Long [UniParc]. Last modified Dec. 1, 1992. Version 1. Checksum: 7A407CC78A6E0BC8, P28908-1/2, Isoform 1/2

Platelet derived growth factor receptor PDGFR alpha:
Gene ID: 5159, updated on 13 Jan. 2013, Gene ID: 5156, updated on 13 Jan. 2013, Isoform 1 [UniParc]. Last modified Apr. 1, 1990. Version 1. Checksum: 5E3FB9940ACD1BE8, P16234-1/2/3, Isoforms 1-3; P09619 [UniParc]. Last modified Jul. 1, 1989. Version 1. Checksum: 038C15E531D6E89D Melanoma associated marker/Mart 1:
Gene ID: 2315, updated on 30 Dec. 2012; Q16655 [UniParc]. Last modified Nov. 1, 1996. Version 1. Checksum: B755BFF39CFCB16E CD133: Gene ID: 8842, updated on 13 Jan. 2013; Isoform 1 (AC133-1) (S2) [UniParc].
Last modified Jun. 1, 1998. Version 1. Checksum: D21CBC05ADB2DEDF, O43490-1/2/3/4/5/6/7, Isoforms 1-7

In the following, reference is made to the examples which are given to illustrate, not to limit the present invention.

EXAMPLES

Example 1

Cloning of Recombinant Antibody Constructs

DNA sequences derived from hybridoma cells and coding for the variable domains of anti-CD3, anti-CD45 and anti-HLA A2 antibodies, respectively, were used to generate the antibody constructs depicted in FIG. 3 by standard methods of molecular biology (see, e.g. Sambrook et al., Molecular Cloning: A Laboratory Manual, Cold Spring Harbor Laboratory Press, New York (2001)). The constructs were designed to carry different affinity tags to facilitate identification and purification upon expression of recombinant proteins (Myc-, Flag, His-Tag). For details on domain arrangement, affinity tags and linkers of the constructs, see FIG. 3.

pelB Leader codes for an amino acid sequence that directs a protein expressed in bacteria to the bacterial periplasm. The leader sequence is cleaved by bacterial enzymes and the protein can be isolated.

Example 2

Expression and Purification of Recombinant Antibodies

Periplasmic Protein Expression:
Recombinant antibody constructs were expressed in the periplasm of E. coli strain TG1 using an appropriate prokaryotic expression vector. Two litres of 2×TY medium including 0.1% glucose and 100 µg/ml ampicillin were inoculated with 20 ml of an overnight culture of transformed TG1 and grown to exponential phase (OD600 0.8-0.9) at 37° C. Since the antibody fragments are under control of the lactose promotor, protein expression was induced by addition of 1 mM IPTG followed by incubation at RT (room temperature) with shaking for additional 3 h. Cells were harvested by centrifugation for 10 min at 2,750×g and 4° C. and were resuspended in 100 ml or an appropriate buffer. Cell lysis was performed by adding 50 µg/ml freshly dissolved lysozyme [Roche Diagnostics] and incubating for 25 min on ice. Following, 10 mM $MgSO_4$ were added to stabilise spheroblasts, and cells were centrifuged for 10 min at 6,200×g and 4° C. Finally, the supernatant obtained, containing the periplasmic protein, was dialysed against PBS overnight at 4° C. and was centrifuged again for 15 min as stated above. Afterwards, recombinant proteins were purified by Ni-NTA-IMAC (Nickel Nitrilo-triacetic acid Immobilised Metal Affinity Chromatography).

Immobilised-Metal Affinity Chromatography (IMAC):

For purification of recombinant proteins with a $His_6$ tag, an IMAC was performed by means of immobilised nickel-nitrilotriacetic acid (NTA) agarose beads [Qiagen]. First, a column of 1 ml Ni-NTA agarose needed to be equilibrated with approximately 10 ml of sterile PBS or a sodium phosphate buffered solution with 20 mM imidazole. Then, crude protein, either precipitated from cytoplasmic expression or dialysed from periplasmic expression, was gradually applied to the column. After washing with about 20 ml of an appropriate IMAC wash buffer (sodium phosphate buffered solution containing 20-35 mM imidazole) until no more protein was detectable in the flow, bound protein was eluted from the column in 500 µl fractions with a sodium phosphate-buffered solution including 250 mM imidazole.

All collected wash and elution fractions were tested for presence of protein by a qualitative Bradford assay by adding 10 µl of each sample to 90 µl of 1× Bradford solution. Verification of the purification process was performed by an SDS-PAGE analysis. For this purpose, eluted fractions were run in parallel with crude protein, flow, and wash fraction under reducing conditions. Finally, positive fractions determined by the colorimetric reaction were pooled into peak and minor fractions and dialysed against PBS overnight at 4° C. For usage in stimulation assays, purified proteins needed to be sterile filtrated, and their concentration has been determined. In addition, after protein quantification, 2 µg of further used fractions were also analysed by SDS-PAGE and Western blotting under reducing and non-reducing conditions.

In an alternative of Example 2, DNA coding for $(V_H)$ CD3-EGFR$(V_H-V_L)$, $(V_H)$CD3-CEA$(V_H-V_L)$, $(V_H)$CD3-Her2$(V_H-V_L)$, $(V_H)$CD3-HLA-A2$(V_H-V_L)$, $(V_H)$CD3-HLA-CW6$(V_H-V_L)$ $(V_H)$CD3-CD138$(V_H-V_L)$, $(V_H)$ antiDig-EGFR$(V_H-V_L)$, $(V_H)$antiHis–HLA-A2$(V_H-V_L)$, $(V_L)$CD3-CEA$(V_H-V_L)$, $(V_L)$CD3-EpCAM$(V_H-V_L)$, $(V_L)$ antiDig-EpCAM$(V_H-V_L)$, $(V_L)$CD3-CD45$(V_H-V_L)$ were synthesised and proteins were produced and isolated by GenScript (Piscataway, N.J., USA). The DNA was codon optimized for *E. coli* expression (vector E3), expression optimized, grown in 2 litres standard LB-medium, protein was obtained from inclusion bodies or periplasm (pelB leader) in one step by Ni-HiTrap column. Bacterial endotoxins were removed by dialysis against 5 litres 1× phosphate buffered saline (PBS). The concentration was measured by Bradford protein assay with bovine serum albumin (BSA) as standard. The purity was estimated by densitometric analysis of a Coomassie Blue-stained SDS-PAGE gel. Aliquots were stored at −80° C. or +4° C. Storage buffer was used 1×PBS, 5% Glycerol, 0.5% sodium lauroyl sarcosine, pH 7.4.

Example 3

Cell Culture Techniques

Cell Cultivation:

Mammalian cells were cultivated in T75 tissue culture flasks in 20 ml of the appropriate culture medium at 37° C. with 5% $CO_2$. Cells were split every 2-3 days. Adherent cells first needed to be detached with 1× trypsin-EDTA. Cells were counted using a vital stain, eosin or trypan blue. For storage, cells of 60-80% confluence were harvested by centrifugation for 5 min at 450×g, resuspended in FCS with 10% DMSO, aliquoted in cryovials, and gradually frozen to a temperature of −80° C. Cells were thawed quickly at 37° C. in a water bath and cautiously added to 5 ml medium. In order to remove DMSO, cells were centrifuged again, resuspended in fresh medium and transferred into a tissue culture flask.

Preparation of Peripheral Blood Mononuclear Cells (PBMC):

PBMC, comprising lymphocytes and monocytes, were previously isolated from the buffy coat of a healthy human donor by density centrifugation using the Ficoll based lymphocyte separation solution LSM 1077 (PAA Laboratories, Pasching, Austria). Since, during usage, these PBMC nevertheless appeared as an inhomogeneous cell population, the separation from remaining erythrocytes, granulocytes, and thrombocytes was repeated as follows. Thawed PBMC, resuspended in 30 ml RPMI 1640 medium containing 10% FCS and Pen-Strep, were cautiously layered onto 10 ml of LSM 1077 and centrifuged for 5 min at 800×g without braking. After discarding the upper phase, PBMC concentrated in the interphase were transferred into a fresh tube, resuspended in 30 ml of medium, and centrifuged for 5 min at 450×g. Monocytes were removed by cultivating PBMC in a Ø10 cm tissue culture plate overnight, allowing adherence of monocytes to the plate. Finally, PBMC, remaining in solution, were harvested.

Figure 29:
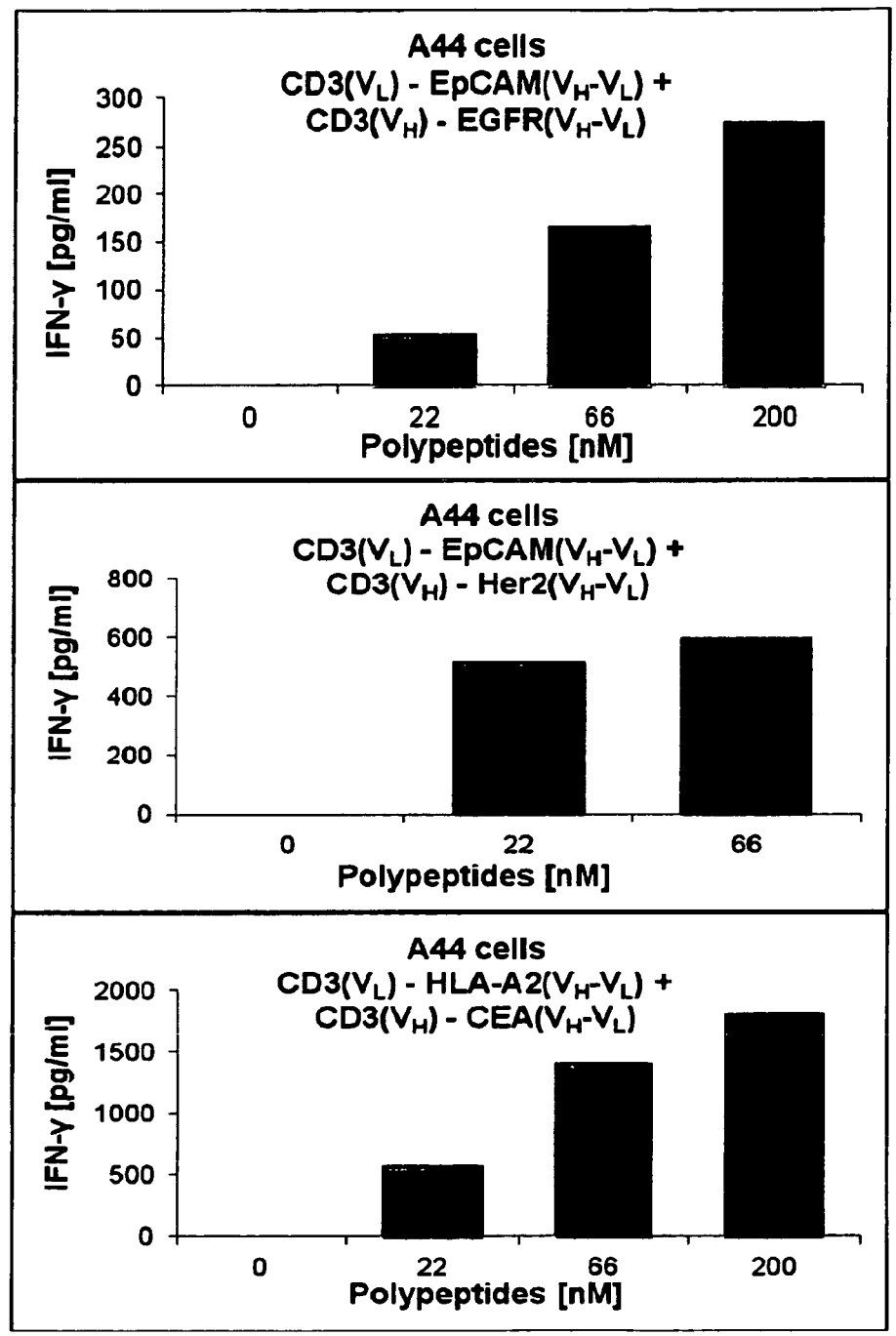
Figure 30:
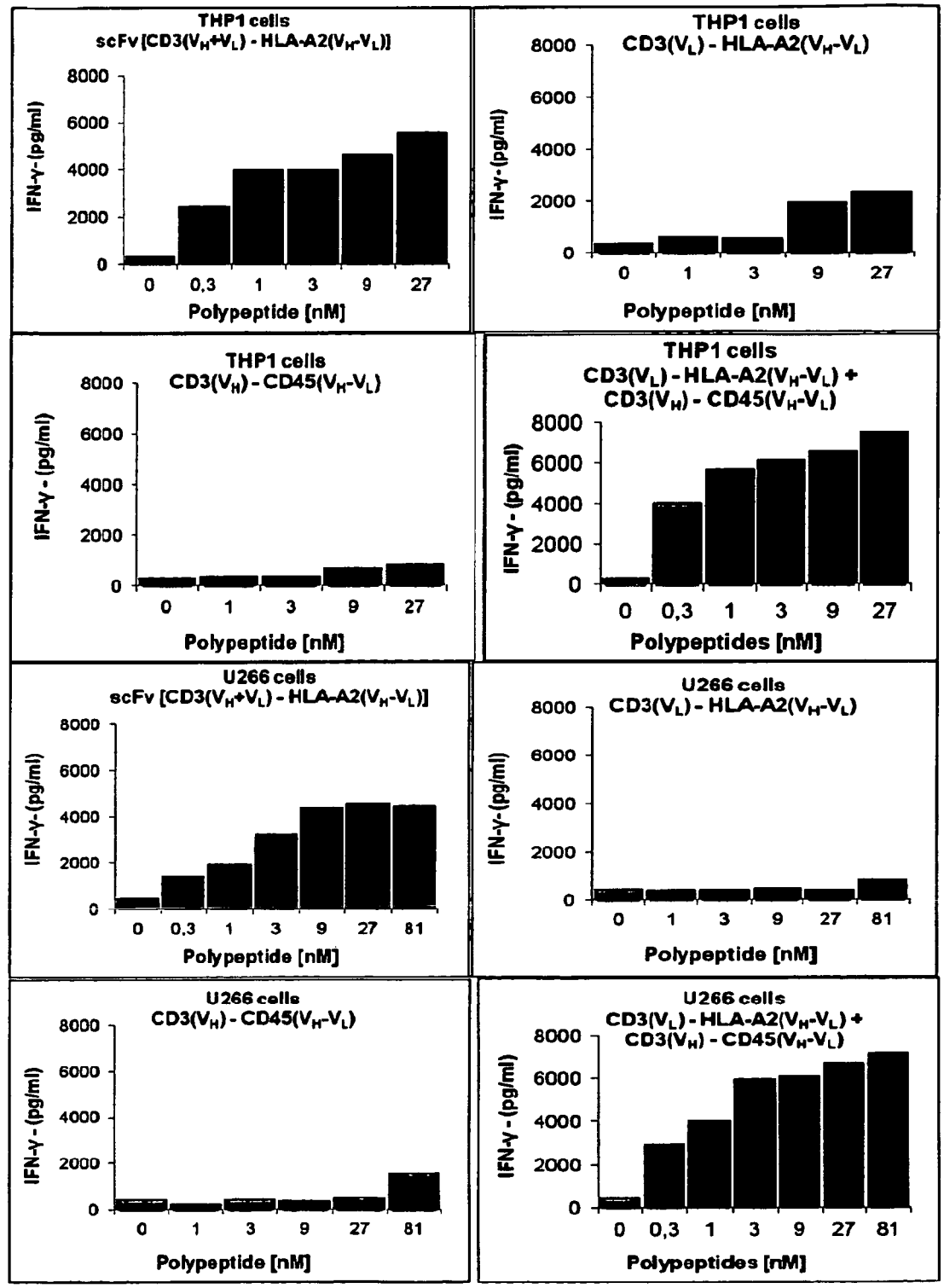

In an alternative of Example 3, Primary human cancer cells from a patient with metastatic pancreatic cancer were extracted from the ascites bags of the patient (FIG. 29). 4 litres with fresh collected malignant ascites were stored in 2 litres glass bottles at 4° C. over night. The next day the cell pellet from the glass bottom was washed in 1×PBS and resuspended in culture medium (DMED supplemented with 200 µM l-glutamine, 10% heat inactivated FBS, penicillin (200 U/mL), streptomycin (200 µg/mL) and sodium pyruvate (1 mM) (GIBCO®)). Adherend cells were cultured in incubator 36° C., 5% $CO_2$, 90% humidity. The same day the ascites was collected from the patient, 20 ml peripheral blood for PBMC extraction was collected. Primary leukemic cells were obtained from a 71 year old male patient with T-cell-prolymphocytic leukemia (T-PLL) (FIG. 11A) relapsing 32 days after matched allogeneic stem cell transplantation. The leukemic T-PLL cells were extracted as PBMCs from the peripheral blood of the patients. At the time the sample was drawn the patient had >90% leukemic blast in his blood count in routine clinic diagnostic. From all patients an informed consent, approved by the University hospital of Würzburg ethical committee, was signed.

In an alternative of Example 3, generation of cytomegalievirus (CMV)-specific human T-cells: Briefly, dendritic cells (DC) were generated from plastic adherent monocytes from PBMC of HLA-A0201 negative, B0702+ donor. After 72 h of culture in GM-CSF/IL4-containing DC medium (Cellgenix), DC were matured in medium containing IL4 (100 ng/ml), GM-CSF (800 IU/ml), LPS (10 ng/ml) and IFNγ (100 U/ml) plus 2.5 ug/ml CMV pp65 derived peptide TPRVTGGG (SEQ ID NO:201). After 16 h, DC were irradiated (30Gy) and co-incubated with CD45RO−, CD57− naïve CD8+ T-cells at a 1:4 ratio in medium containing 5% AB serum and IL21 (long/ml). Fresh medium, IL7 and IL15 was added on days 3, 5 and 7 of culture, before evaluation on day 10-12. Cells were cultured in Cellgenix DC medium. Human AB serum was used from PAA. One single batch was used throughout all experiments. IL4, IL7, IL15, IL21 were either purchased from Peprotech or Cellgenix (with identical results). GM-CSF was purchased from Gentaur. LPS (*E. coli* O:15) was purchased from Sigma. The HLA-B0702-restricted CMV-specific peptide TPRVTGGG (SEQ ID NO:201) was purchased from jpt. For in vivo experiments, CMV-specific T-cells were further purified using APC-labelled MHC-multimers (Immudex). MHC multimer staining was performed at room temperature, followed by isolation of MHC-multimer+ T-cells with anti-APC-beads (Miltenyi).

Example 4

Functional Assays

Flow Cytometry:

Binding of antibody fusion proteins to antigen-presenting tumour cells and/or T lymphocytes was tested by flow cytometry. For this purpose, $2.5-5 \times 10^5$ cells were incubated with 10 μg/ml of scFv or 0.004-4 μg/ml of titrated fusion proteins in 100 μl of a suitable buffer solution (such as PBS+bovine serum albumin, or other acceptable buffer solution) per well on a 96-well V-shaped plate at 4° C. for 2 h. After washing three times with 150 μl of a suitable buffer solution, cells were incubated with FITC-conjugated anti-His$_6$ tag or anti-Flag Tag or anti-myc Tag antibody at RT for 30 min and washed again two times. For gating and testing for background staining, additionally two samples of each cell type were prepared, one of unstained cells and one stained with FITC-conjugated anti-His$_6$ tag antibody without any protein. Finally, cells were resuspended in 500 μl of a suitable buffer solution, transferred into FACS tubes, and analysed by flow cytometry.

PBMC Stimulation Assay:

Stimulatory properties of recombinant proteins were tested in a cell-based stimulation assay. Thereby, T-cell activation mediated by bispecific antibodies and "tridomain constructs" was determined by measuring PBMC stimulation in terms of the IL-2 release induced.

Measurement of stimulatory Activity of Constructs:

CD45 pos/HLA A2 myeloma cell line U266 were seeded in a flat-bottomed 96-well cell culture plate at a density of 105 cells per well in 100 μl of culture medium. Titrated stimulatory proteins were added as indicated in 100 μl medium per well and were preincubated for 1 h at 37° C. and 5% CO2 to ensure sufficient binding. Unstimulated PBMC, thawed and isolated the day before, were then added at indicated density and incubated for 24 h at 37° C. and 5% $CO_2$. Finally, plates were centrifuged for 5 min at 450×g to harvest cell-free supernatants for IL-2 quantification in ELISA.

IL-2 Sandwich ELISA:

As an indicator for the stimulatory activity, T-cell activation induced by bispecific antibodies was measured in terms of the IL-2 release. Upon PBMC stimulation, concentration of secreted IL-2 in the supernatant was determined by an IL-2 sandwich ELISA.

First, a 96-well ELISA plate was coated with 400 ng/100 μl per well of mouse anti-human IL-2 antibody overnight at 4° C., followed by saturation of nonspecific binding sites with a suitable blocking buffer for 2 h at RT. In the meantime, serial 1:2 dilutions of an IL-2 standard were prepared in duplicate in reagent diluent starting with a maximum IL-2 concentration of 1,000 pg/ml. Then, supernatants containing IL-2 were 1:3 diluted in RPMI 1640 medium containing 10% FCS and Pen-Strep (Penicillin-Streptomycine). Both diluted supernatants and standards were transferred into the ELISA plate and incubated for 2 h at RT. Following, IL-2 was detected by incubation with 17.5 ng/100 μl per well of biotinylated goat anti-human IL-2 antibody for 2 h at RT. Finally, 100 μl of HRP-conjugated streptavidin, 1:200 diluted in reagent diluent, was added per well and incubated for 20 min at RT. Each plate was developed using a TMB substrate solution. In order to achieve a background signal, at least 2 wells on each plate were incubated with reagent diluent or medium only and the detecting antibody plus TMB. Between each incubation step, the plate was washed three times with PBS containing 0.05% Tween-20 and once with PBS only.

A seven point standard curve was created by plotting the absorbance signals of each standard sample against the IL-2 concentration. Thus, the amount of IL-2 of each supernatant could be determined by interpolation of the standard curve fitted with the nonlinear regression equation for one phase exponential association using GraphPad Prism®.

IFN-γ ELISA (Alternative of Example 4):

In 100 μl cell culture supernatant the IFN-γ concentration was measured using the human IFN-γ ELISA Kit (Invitrogen™) after manufacturer's protocol. Briefly 50 μL of Incubation Buffer was added to each well of a precoated 96-well plat. 50 μL of the Standard Diluent Buffer to zero wells. 50 μL of standards and samples to each well. 50 μL of biotinylated Hu IFN-γ Biotin Conjugate solution into each well. Taped gently on the side of the plate to mix. Covered plate with plate cover and incubate for 1 hour and 30 minutes at room temperature. Thoroughly aspirated solution from wells and discarded the liquid. Washed wells 4 times. Added 100 μL Streptavidin-HRP Working Solution to each well. Covered plate with the plate cover and incubated for 45 minutes at room temperature. Thoroughly aspirated solution from wells and discarded the liquid. Added 100 μL of Stabilized Chromogen to each well. The liquid in wells turned blue. We incubated for 15-30 minutes at room temperature and in the dark. Added 100 μL of Stop Solution to each well. Taped side of plate gently to mix. The solution in the wells changed from blue to yellow. The absorbance of each well was read with a BioRad plate reader at 450 nm.

Cytotoxicity Assay:

The HLA-A2/CD45 positive cell line U266 or myeloma cell line U266 was labelled with 10 μM CFSE (Invitrogen Vybrant CFDA SE Cell Tracer Kit) in 350 μl PBS for 10 min at room temperature (RT) in the dark. The labelling reaction was stopped by the addition of 5 ml fetal calf serum (FCS), followed by a 1-minute incubation at RT. After 2 washes, the CFSE-labelled target cells were resuspended in assay medium and co-incubated with Peripheral Blood Mononuclear Cells (PBMC) from a HLA-A2 negative healthy donor at a ration of 1:10 ($5*10^5$ U266 and $5*10^6$ PBMCs in 2 ml) and 27 nM of antibody constructs as indicated. A sample treated with Triton was used as positive control (100% lysis) and a sample without antibody construct as negative control (0% lysis). After 24 h, apoptotic cells were visualized by 7AAD stain (Biozol, 10 min at RT) and % specific Lysis of CFSE labelled U266 cells was calculated employing flow cytometry techniques.

Caspase-3 Assay (Alternative of Example 4):

Staining was performed after co-incubating of the target cells with T-cells (tumor cells: T-cells ratio 2:1) with or without the specific polypeptides for 4 h. Surface staining for HLA-A2 and CD45 was performed first, followed by fixation and permeabilization (Fix+Perm, BD Biosciences). Activated Caspase-3 antibody was then added for 30 min. (BD Biosciences). Cells were washed with 1×PBS+5% human serum (HS, PAA Laboratories) and analyzed on a BD-FACS Canto-II. % specific apoptosis was calculated as (% experimental value−spontaneous release)/(100%−% spontaneous release)*100.

ALAMARBLUE® Assay (Alternative of Example 4):

The ALAMARBLUE® assay (Abd Serotec) was used to measure proliferation and viability of cells after exposure to toxins. Briefly, cells were grown in 100 µl cell culture medium per well (96 well plate). For analysis 10 µl ALAMARBLUE® was added per well and incubated in the incubator for 30-120 minutes. The absorbance was read with a BioRad plate reader at 570 nM and 600 nM. For blank media only was used. The percent difference in reduction of cell proliferation between the different polypeptide groups was calculated as indicated by the manufacturer, using cells growing in culture without toxin as control.

Digoxigenin Assay (Alternative of Example 4):

First peroxidase from horseradish (HRP, Sigma-Aldrich Chemie gmbH) was labelled with digoxigenin NETS-ester (Sigma-Aldrich Chemie gmbH) in a 1/3 molar ratio. Dig-HRP was cleaned up with micro Bio-Spin™ chromatography columns (BioRad and and stored at 4° C. in the dark. Colo-206F cells were first incubated with indicated polypeptides at various concentrations for 90 minutes. Cells were washed with PBS and resuspended in cell culture medium with Dig-HRP and incubated for 30 minutes. Afterward cells were washed twice with PBS and resuspended in 50 µl PBS. 50 µL of Stabilized Chromogen (Invitrogen™) was added for 15-30 minutes at room temperature in the dark. 50 µL of Stop Solution was added and the absorbance was read with a BioRad plate reader at 450 nm.

Mice (Alternative of Example 4):

The HLA.A2 transgenic, immunodeficient mice (NodScid IL-2rg−/−HLA.A2/B2m tg; Stock number 14570, The Jackson Laboratory, Bar Harbor, Me., USA) for the in vivo experiment (FIG. 12A) were maintained in our certified animal facility (ZEMM, Center for experimental molecular medicine, University hospital Würzburg) in accordance with European guidelines. Female Mice, 6-10 weeks old, were divided into five groups, six mice per group (n=30). $5 \times 10^6$ THP-1 cells, $1.25 \times 10^5$ CMV specific CD8+ T-cells (tumour cell: T-cell ratio 40/1) and the 0.5 µg of the polypeptides were injected intraperitoneally (i.p.) as indicated. After injection, mice were monitored by daily inspection. A second injection of $1.16 \times 10^5$ CMV-specific CD8+ T-cells/mouse was given at day 13 and injections of the polypeptides were repeated every three days a week. The animals were sacrificed when the increase in body weight was greater 80% or if they appeared moribund according to institutional guidelines.

Domain structure, affinity tags and linkers of the constructs or polypeptides used in Examples 5-9 or FIG. 4-FIG. 11 are shown in FIG. 3. These constructs and all constructs or polypeptides used in FIG. 4-FIG. 30 were prepared as described in Examples 1 and 2. Cell culture and functional assays in Examples 5-9 and culture, functional assays and in vivo work as to FIG. 4-FIG. 30 were carried out as described in Examples 3 and 4.

Example 5

The CD45 and HLA A2 positive myeloma target cell line U266 was co-incubated with HLA A2 negative T cells (monocyte depleted PBMCs (peripheral blood mononuclear cells) from a healthy donor and varying amounts of HLA A2 and CD3 bispecific antibody constructs as indicated (Numbers 85, 82, 75 and 71). PHA-L (phytohemagglutinin, a lectin that causes unspecific stimulation of T cells; 1 µg/ml final concentration) was used as positive control and single chain scFv constructs with specificity for HLA A2 (Number 4) or CD3 (Number 36) were investigated. IL2 (Interleukin-2) production by T cells was measured by ELISA techniques. No IL2 production was found in experimental situations without any constructs. Data obtained is depicted in FIG. 4.

Example 6

The CD45 and HLA A2 positive myeloma target cell line U266 was co-incubated with HLA A2 negative T cells (monocyte depleted PBMCs) from a healthy donor and varying amounts of "tridomain constructs" added either separately (Numbers 42, 45, 55; numbers referring to constructs as depicted in FIG. 3) or in combinations (42+45 or 42+55). PHA-L and single chain scFv constructs with specificity for CD45 (Numbers 46 and 17) were given as controls. IL2 production by T cells was measured by ELISA techniques. No IL production was found in experimental situations without any constructs. Data obtained is depicted in FIG. 5.

Example 7

The CD45 and HLA A2 positive myeloma target cell line U266 was co-incubated with HLA A2 negative T cells (monocyte depleted PBMCs) from a healthy donor and the HLA A2 and CD3 bispecific antibody construct alone (number 71, 27 nM) or in combination with single chain scFv constructs that block the antigenic epitopes on HLA A2 (Number 4, hundredfold excess compared to the concentration of construct 71, i.e. 2700 nM) or CD3 (Number 36, ninefold excess compared to the concentration of construct 71, i.e. 243 nM). IL2 production by T cells was measured by ELISA techniques and PHA-L is given as control. Data obtained is depicted in FIG. 6.

Example 8

The CD45 and HLA A2 positive myeloma target cell line U266 was co-incubated with HLA A2 negative T cells (monocyte depleted PBMCs) from a healthy donor and the combination of constructs 42 and 45. T cell stimulatory function was blocked by single chain constructs specific for HLA A2 (number 4) or CD45 (number 46). Complementation of T cell stimulatory function was tested by assaying constructs 42 and 45 separately or the single chain scFv construct directed against CD3 (number 36). IL2 production by T cells was measured by ELISA techniques and PHA-L is given as control. Concentration of constructs was 27 nM, unless indicated otherwise. ("9×" indicates a concentration of 243 nM, "100×" a concentration of 2700 nM.) Data obtained is depicted in FIG. 7.

Example 9

The CD45 and HLA A2 positive myeloma target cell line U266 was co-incubated with HLA A2 negative T cells (monocyte depleted PBMCs) from a healthy donor and the combination of constructs 42 and 55. T cell stimulatory function was blocked by single chain constructs specific for HLA A2 (number 4) or CD45 (number 46). Complementation of T cell stimulatory function was tested by assaying constructs 42 and 55 separately or the single chain scFv construct directed against CD3 (number 36). IL2 production by T cells was measured by ELISA techniques and PHA-L is given as control. Concentration of constructs was 27 nM, unless indicated otherwise. ("9×" indicates a concentration of 243 nM, "100×" a concentration of 2700 nM.) Data obtained is depicted in FIG. 8.

The results of the preceding Examples clearly demonstrate that two constructs (42+45) or (42+55) first have to bind their ligands on the surface of a single cell in order to subsequently complement T cell engaging function.

Example 10

Lysis of the CD45 and HLA A2 positive myeloma target cell line U266 by HLA A2 negative T cells (monocyte depleted PBMCs) in the presence of $V_L$CD3–scFvHLA A2 (27 nMol) or $V_H$–scFvCD45 (27 nMol) or the combination of both of these constructs (27 nMol each) was determined using flow cytometry based techniques. Percent lysis was calculated by apoptotic U266 cells divided through total U266 cells and background apoptosis was subtracted. Data obtained is depicted in FIG. 9.

Example 11

As parts of the final bipartite construct, two polypeptides were designed, each composed of an antigen-binding single-chain variable fragment (scFv) and either the variable light ($V_L$) or variable heavy chain ($V_H$) domain of a T cell-activating anti-CD3 antibody (FIG. 10). When these two polypeptides bind their respective antigens on the surface of a single cell, the $V_L$ and $V_H$ domains interact with each other to reconstitute the original anti-CD3 binding site. The thus on-target formed trispecific heterodimer engages and stimulates T cells for tumor cell destruction.

This scenario is fully validated in vitro when T lymphocytes are confronted with target cells that have been incubated with the two different polypeptides. As proof of principle, major histocompatibility antigen HLA-A2 and the hematopoetic lineage marker CD45 were targeted as first and second antigens, which both are expressed on U266 myeloma cells, primary cells from a patient with pro-lymphocytic leukemia of the T cell lineage (T-PLL), and THP-1 acute myeloid leukemic blasts (FIG. 11). Due to the described $V_L/V_H$ interaction, the now trispecific heterodimer potently stimulates T cells to secrete interleukin-2 (IL-2) (FIG. 11A) and to lyse the labeled tumor cells at nanomolar concentration (FIG. 11B), the cytotoxic efficacy being quite similar to that of a bispecific T cell-activating antibody, which was employed as a positive control (FIG. 11A, left panel), Mack, 1995, Proc Natl Acad Sci 92, 7021-7025. When the polypeptides were added separately from each other, they did not induce T lymphocytes to lyse target cells. These results are in line with structural data indicating that both, $V_H$ and $V_L$ domains are required to confer sufficient affinity to the target antigen (FIG. 11A, FIG. 11B), Colman, 1987, Nature 326, 358-363; Amit, 1986, Science 233, 747-753. Moreover, the results reveal that possible homodimerization of either $V_H$ or $V_L$ arms results in a negligible measurable biological effect.

Figure 11C:
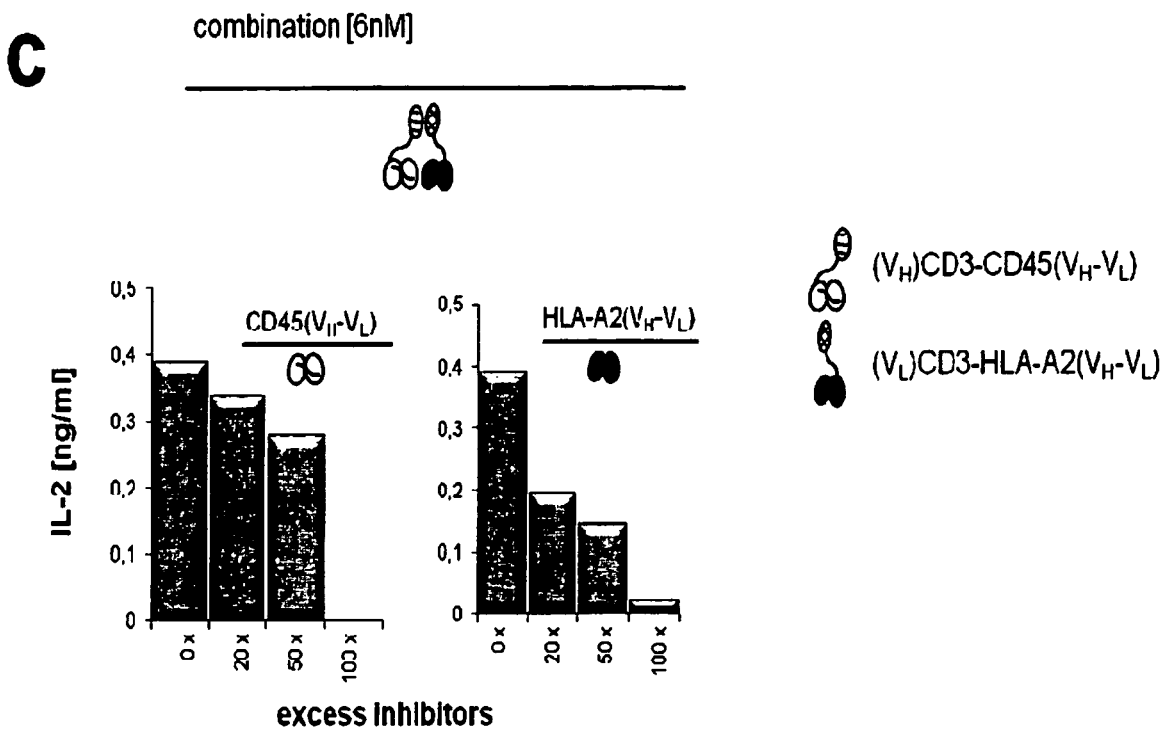
Figure 11D:
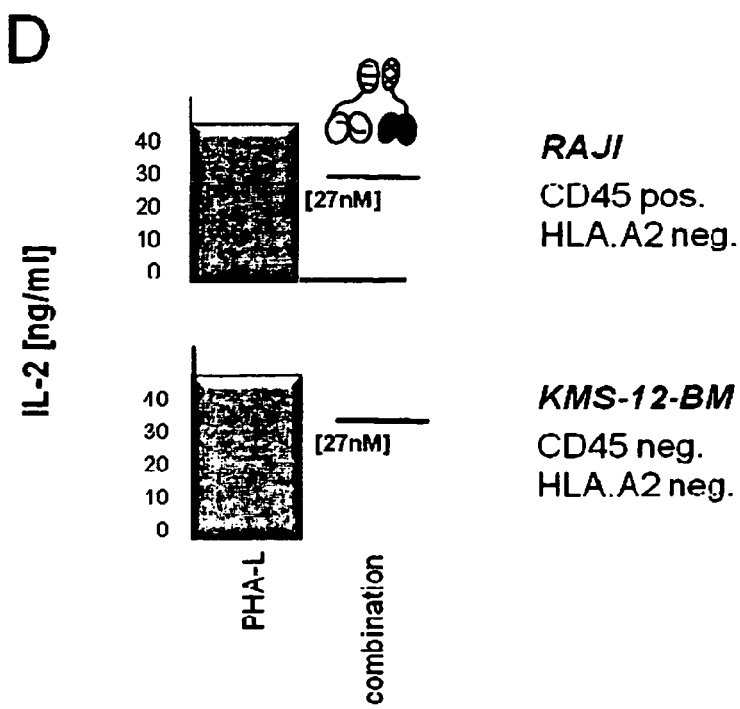

To demonstrate that the two molecules must first bind their antigens on the surface of the target cell for $V_H/V_L$ heterodimerization to occur, single-chain variable fragments specific for HLA-A2 and CD45 were used to block the respective epitopes on the target. As shown in FIG. 11C, when present in great excess, these inhibitors prevented the two polypeptides from triggering T cells in a dose-dependent manner. Furthermore, T cells were not stimulated when the target cells were omitted (data not shown) or when target cells were probed that express CD45 only (RAJI cells, FIG. 11D) or neither target molecule (KMS-12-BM, FIG. 11D).

Example 12

For in vivo proof of concept, a model of allogeneic mismatch stem cell transplantation was resorted in which a patient's residual leukemic and hematopoietic cells, all HLA-A2 and CD45-positive, must be eliminated to give the allogeneic donor stem cells (HLA-A2-negative, CD45-positive) a chance to engraft and to reconstitute hematopoiesis (see FIG. 2). To put the specificity of the bipartite construct to the test, immunodeficient mice expressing the human HLA-A2 transgene on virtually all nucleated cells were used, the question being whether HLA-A2-positive but CD45-negative murine tissues would suffer collateral damage. THP-1 cells were injected intraperitoneally with or without CD8 T lymphocytes from an HLA-A2-negative donor, which had been selected for specificity to cytomegalovirus (CMV) to avoid human anti-murine immune reactivity. Intraperitoneal tumors developed rapidly in mice that did not receive the polypeptides, and in mice treated either with single molecule types or with the combination of both polypeptides but without T cells. In all instances, fatal disseminated disease developed within 3 to 4 weeks (FIG. 12A). In stark contrast, all tumor-bearing mice treated with T cells and repeated injections of both polypeptides survived the end of the experiment on day 31, albeit with palpable tumors at the injection site. These results clearly show that the bipartite construct truly redirects T cells irrespective of their specificity at tumor cells that simultaneously express both target molecules (HLA-A2 and CD45) in vivo. As an aside, a T cell recruiting bispecific antibodies against HLA-A2 would wreak havoc by redirecting T cells against all HLA-A2 positive murine tissues. Likewise, a CD45-binding bispecific antibody would have mediated lysis of all hematopoietic cells, including THP-1 leukemic blasts and T cells from the donor. In our set-up, however, injection of HLA-A2-specific polypeptide into the HLA-A2 transgenic animals caused no apparent toxicity.

To further examine possible toxicity to bystanders, we employed a highly sensitive apoptosis assay on THP-1 cells and HLA-A2-negative but CD45-positive monocytes, the latter representing the healthy bystander compartment. As depicted in FIG. 12B, we observed caspase-3 activation in THP-1 cells but not in monocytes treated in the same well with the combination of the polypeptides or the bispecific positive control and donor T cells. THP-1 cells cultured with T cells and individual polypeptides were unaffected. These observations again clearly show initiation of apoptosis exclusively in the double antigen positive target population, while the HLA-A2-negative bystander cells are spared.

These experiments model quite accurately the dire clinical situation of leukemia patients with a HLA-mismatched stem cell transplant. The combinatorial approach of using a distinctive HLA molecule and CD45 aims at enhancing the desired graft versus leukemia effects by retargeting the donor's T cells against leukemic blasts of both, myeloid and lymphoid origin.

Example 13

To venture into solid tumors, we targeted the combinatorial approach to epithelial cell adhesion molecule (EpCAM) and epidermal growth factor receptor (EGFR) antigens. Both antigens are over-expressed in various carcinomas and have been extensively studied in clinical phase II and III trials. The expression of EGFR is closely associated with cell proliferation, while EpCAM is present at the basolateral surface of virtually all simple epithelia and was recently found to act like a signaling protein in the Wnt pathway, Maetzel, 2009, *Nat Cell Biol* 11, 162-171. As FIG. 13A illustrates, the two polypeptides trigger the release of interferon-γ (IFNγ) from co-incubated donor lymphocytes and mediate apoptosis of the double-positive cancer cell line COLO-206F at nanomolar concentrations (FIG. 13a, b), but only when given in combination and not with either part alone. As a descendant of neuroepithelial tissue, the melanoma cell line FM-55 lacks EpCAM, and therefore was completely resistant to the polypeptides (FIG. 13a, b). Though the expression of EGFR and EpCAM overlaps broadly on proliferating carcinoma cells, non-proliferating epithelial cells, e.g., of liver and pancreas solely expressing EGFR or EpCAM antigens, respectively, should be less susceptible to or protected from the two-pronged attack. Notably, hepatic and pancreatic toxicities have been dose-limiting for high-affinity monoclonal EpCAM antibodies in clinical trials (for review see, Munz, 2010, *Cancer Cell Int* 10:44).

Example 14

The further validation of the bipartite functional complementation strategy was performed by extensive in vitro experiments, using a combination of different polypeptides, targeting various cell surface antigens on different human cell lines.

The HLA A2 positive human tumor cell lines FM-55 (myeloma), Colo-206F (colon cancer) and OVCAR (ovarian cancer) were co-incubated with HLA-A2 negative PBMCs from a healthy donor, polypeptide against HLA-A2 (CD3 ($V_L$)-HLA-A2($V_H$-$V_L$)) and with a second polypeptide targeting either CEA (CD3($V_H$)-CEA($V_H$-$V_L$)), EGFR (CD3($V_H$)-EGFR($V_H$-$V_L$)) or Her2 (CD3($V_H$)-Her2($V_H$-$V_L$)). IL2 or IFN-γ production by lymphocytes was measured by ELISA techniques. These data demonstrate that (i) a specific combination of antigens, an antigen signature, can be expressed on carcinomas of various origin (skin, neuroepithelial, gut and ovary tissue), (ii) the antigen signature is approachable with our bipartite functional complementation strategy using a set of polypeptides specific for the antigen signature. Data obtained are depicted in FIG. 14, FIG. 15 and FIG. 16.

Example 15

To demonstrate the exchangeability of the functional domain, the fragments F1 and F2 of a set of polypeptides were exchanged with each other, retaining their specific complementation ability for on target restoration of their original antibody domain to engage T cells. Therefore the set of polypeptides against the CD45 and HLA-A2 target antigen was used. The polypeptide against CD45 had CD3($V_L$) as fragment F1 and the polypeptide against HLA-A2 had CD3($V_H$) as fragment F2. The CD45 and HLA-A2 positive myeloma cell line U266 was co-incubated with HLA-A2 negative T cells from a healthy donor and polypeptides against CD45 (CD3($V_L$)-CD45($V_H$-$V_L$)) and HLA-A2 (CD3($V_H$)-HLA-A2($V_H$-$V_L$)) in varying amounts. T cell engagement was assessed by reactive IFNγ production, measured by ELISA techniques. No IFNγ production was found in experimental situations without any polypeptides. Data obtained is depicted in FIG. 17.

Example 16

The bipartite functional complementation strategy was further tested by targeting a set of antigens, already used as targets for antibody therapy of cancer (EGFR, EpCAM and Her2) (Her2 is a target for Trastuzumab in breast cancer, EGFR is a target for Cetuximab in colorectal cancer and EpCAM is a target for Catumazumab for the treatment of neoplastic ascites). The EGFR, EpCAM and Her2 positive cells (Colo-206F, CX-1 and OVCAR) were co-incubated with PBMCs from a healthy donor and the combination of polypeptides against EGFR (CD3($V_H$)-EGFR($V_H$+$V_L$)), EpCAM (CD3($V_L$)-EpCAM($V_H$+$V_L$)) and Her2 (CD3($V_H$)-Her2($V_H$+$V_L$)). Complementation of lymphocyte stimulatory function was assessed by reactive IFNγ production, measured by ELISA techniques. No IFNγ production was found in experimental situations without any polypeptides. Data obtained is depicted in FIG. 18 and FIG. 19.

Example 17

To test an antigen combination with close clinical correlation, the combination CD45 and CD138 was used to target human multiple myeloma (MM) cells. The majority of human MM cells are positive for CD45 and CD138. A T cell recruiting bispecific antibodies against CD45 would kill all hematopoetic cells of a patient and against CD138 would cause severe side effects because of its expression on various normal tissues (epithelial cells, endothelia, trophoblastic cells and glandular cells of the GI tract, The Human Protein Atlas, Version: 10.0, Atlas updated: 2012 Sep. 12). In contrast the combination of CD45 and CD138 is found exclusively on plasma cells and MM cells and is therefore a good antigen signature for the targeted therapy approach. The CD45 and CD138 positive human multiple myeloma cell line AMO-1 was co-incubated with PBMCs from a healthy donor and the combination of polypeptides against CD45 (CD3($V_L$)-CD45($V_H$+$V_L$)) and CD138 (CD3($V_H$)-CD138($V_H$+$V_L$)). Complementation of lymphocyte stimulatory function was assessed by reactive IFNγ production, measured by ELISA techniques. No IFNγ production was found in experimental situations with single polypeptides or without any polypeptides. Data obtained is depicted in FIG. 20.

Example 18

A further application of the bipartite functional complementation strategy is to target single antigens on the cell surface and to kill single antigen positive tumor cells. One major drawback for T cell recruiting bispecific antibodies with functional antiCD3 binding sides are severe side effects caused by unspecific T-cell activation and cytokine release (Linke, R. et al. Catumaxomab: clinical development and future directions. MAbs 2, 129-136 (2010)). The advantage of this bipartite functional complementation strategy is the fact, antibodies that the T-cell activating antiCD3 functional domain is exclusively restored on the target cell. Without the target cell, no T-cell activating domain is present. The CD45 and CD138 positive human multiple myeloma cells AMO-1 and U266 were co-incubated with PBMCs from a healthy donor and the combination of polypeptides against a single target antigen, either CD138 (CD3($V_H$)–CD138($V_H$+$V_L$)+CD3($V_L$)–CD138($V_H$+$V_L$)) or CD45 (CD3($V_H$)–CD45($V_H$+$V_L$)+CD3($V_L$)–CD45($V_H$+$V_L$)). Complementation of lymphocyte stimulatory function was assessed by reactive IFNγ production, measured by ELISA techniques. No IFNγ production was found in experimental situations with single polypeptides or without any polypeptides. Data obtained are depicted in FIG. 21 and FIG. 22. In FIG. 23 the single antigen approach is illustrated, by using a set of polypeptides targeting two different epitopes (upper part) or the same epitope (lower part) on the target antigen A1.

Example 19

Figure 31:
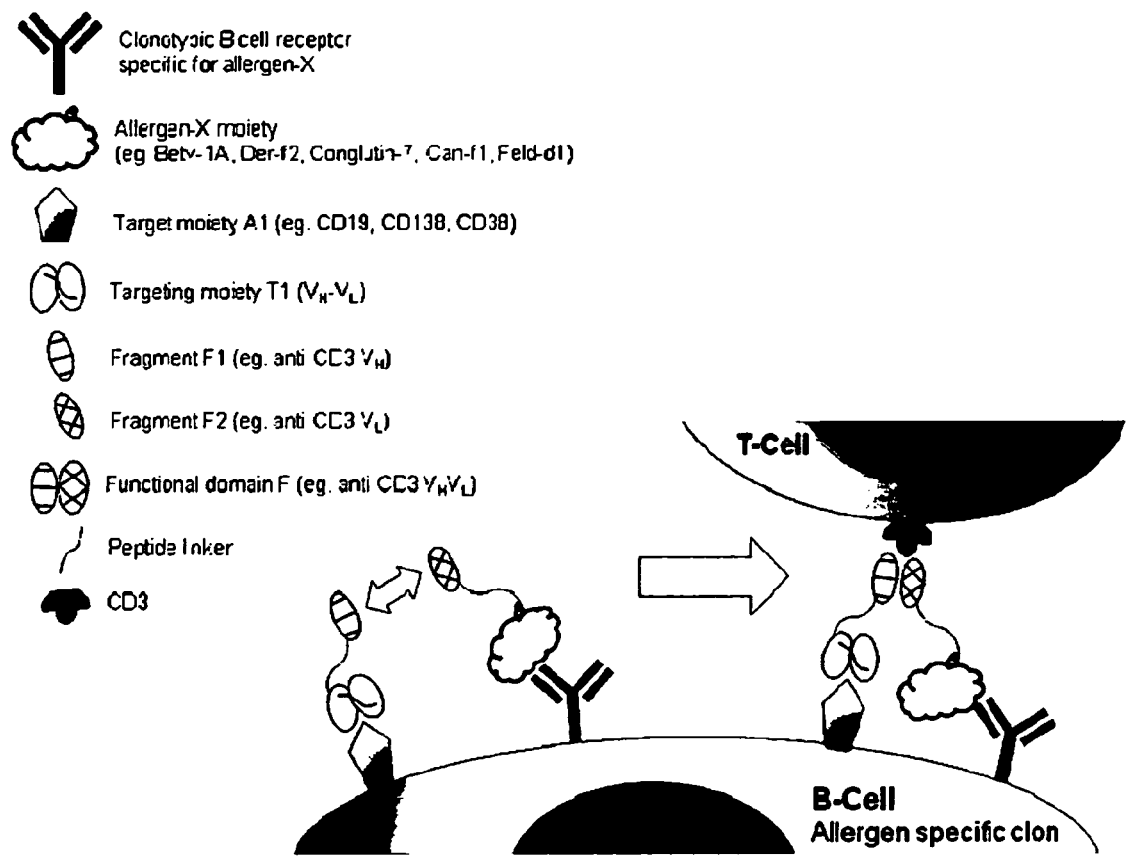
Figure 31:
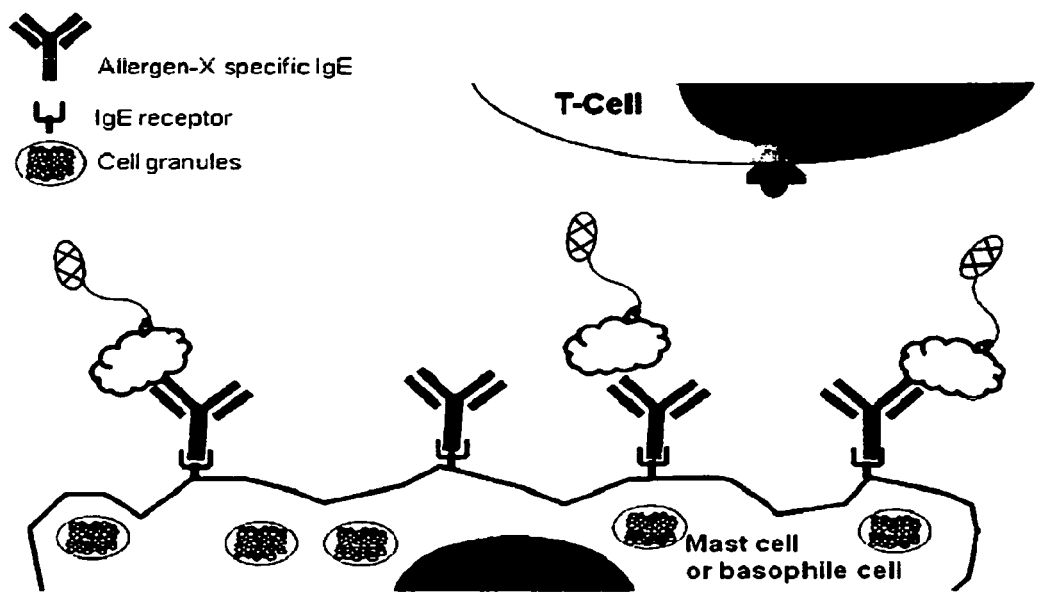

This is an example to demonstrate that the functional complementation strategy can be further elaborated for targeted payload delivery and that different effector ways are possible to kill a target cell. By complementing the F1 and F2 fragments of a set of bound polypeptides on target, the newly formed antibody binding site can bind any molecule it is specific for. In order to direct a HIS-tagged payload precisely to a target cell, the $V_H$ and $V_L$ fragments of an anti-HIS(hexa-histidine)-antibody were used. After simultaneous binding of polypeptide 1 (antiHis($V_L$)–CD45($V_H$–$V_L$) and polypeptide 2 (antiHis($V_H$)–HLA-A2($V_H$–$V_L$) to their specific target antigens CD45 and HLA-A2, a hexa-histidine binding site is complemented on target that binds histidine labeled payloads with high high affinity. The payload be a HIS-tagged toxin as given in this example here. The CD45 and HLA-A2 positive cells THP-1 were co-incubated with a histidine(His)-tagged *Clostridium perfringens* Iota toxin component Ia (FIG. 24) or a histidine(His)-tagged Shiga toxin subunit A (FIG. 25, FIG. 26) in combination with polypeptides against CD45 (antiHis($V_L$)–CD45($V_H$–$V_L$)) and HLA-A2 (antiHis($V_H$)–HLA-A2($V_H$–$V_L$)). Complementation of his-tagged toxin binding and subsequent target cell killing was assessed by measuring cell viability using an ALAMARBLUE® assay. At the highest concentration of polypeptides used (80 nM), a clear difference in target cell killing, measured as reduction in cell viability, was found in experimental situations with a combination of both polypeptides compared to single polypeptides.

Example 20

To further demonstrate the versatility, flexibility and the exchangeability of the bipartite functional complementation strategy, the $V_H$ and $V_L$ fragments of an anti-Digoxigenin antibody were used to identify and mark double antigen positive cells with Digoxigenin-labeled HRP (horse raddish peroxidase). EGFR and EpCAM positive Colo-206F cells were co-incubated with polypeptides against EGFR (antiDig($V_H$)–EGFR($V_H$+$V_L$)) and EpCAM (antiDig($V_L$)–EpCAM($V_H$+$V_L$)). On target complementation of the functional domain anti-Digoxigenin, indicated by Digoxigenin-HRP labelling of Colo-206F cells, was assessed by measuring the peroxidase activity, using a standard ELISA Kit (Invitrogen™). A clear difference in Dig-HRP labeled target cells was found in experimental situation with a combination of both polypeptides compared to single polypeptides. Data obtained are depicted in FIG. 27.

Example 21

Using the human leukocytic antigens (HLA) as one arm for dual antigen restricted bipartite functional complementation, this haplotype strategy was further validated by exchanging the functional domains of the polypeptides with $V_H$ and $V_L$ fragments of an anti-HLA-Cw6 antibody. HLA-Cw6 positive primary patient PBMCs were co-incubated with HLA-Cw6 negative PBMCs from a healthy donor, polypeptide against CD45 (CD3($V_L$)–CD45($V_H$–$V_L$)) and HLA-Cw6 (CD3($V_H$)–HLA-Cw6($V_H$–$V_L$)). IFNγ production by lymphocytes was measured by ELISA techniques. These data demonstrate that hematopoietic cells of patients with other haplotypes than HLA-A2 can be targeted simply by exchanging one targeting domain (anti HLA-A2, FIG. 5, FIG. 7-FIG. 9, FIG. 11-FIG. 12) by another (anti HLA-Cw6). Data obtained are depicted in FIG. 28.

Example 22

The dual antigen-induced bipartite functional complementation strategy was further validated in an in vitro patient assay, using freshly isolated primary patient cancer cells and antigen targets already used for cancer therapy in clinic or clinical trials (EGFR, EpCAM, CEA and Her2). Malignant cells of a 48 years old male patient with metastatic pancreatic cancer were co-incubated with the patients own peripheral blood lymphocytes and the combination of polypeptides against EGFR (CD3($V_H$)–EGFR($V_H$+$V_L$)), EpCAM (CD3($V_L$)–EpCAM($V_H$+$V_L$)), Her2 (CD3($V_H$)–Her2($V_H$+$V_L$)), CEA (CD3($V_H$)–CEA($V_H$–$V_L$)) and HLA-A2 (CD3($V_L$)–HLA-A2($V_H$–$V_L$)). Complementation of lymphocyte stimulatory function was assessed by reactive IFNγ production, measured by ELISA techniques. No IFNγ production was found in experimental situations without any polypeptides. These data demonstrate the potential of this strategy to use patients own immune cells to target and kill his malignant transformed cells. Data obtained are depicted in FIG. 29.

Example 23

A highly enriched CD3/CD8 positive CMV restricted T-cell population was used to show that any T cell, irrespective of its specificity, can serve as effector cell an kill double antigen positive tumor cells by this complementation strategy. The CD45 and HLA-A2 positive U266 and THP-1 cells were co-incubated with cytomegalievirus (CMV) specific T-cells from a HLA-A2 negative healthy donor and polypeptides against CD45 (CD3($V_H$)–CD45($V_H$–$V_L$)) and HLA-A2 (CD3($V_L$)–HLA-A2($V_H$–$V_L$)) in varying amounts. The bispecific tandem scFv (CD3($V_H$–$V_L$)×HLA-A2($V_H$–$V_L$))-antibody was used as a positive control. T cell engagement was assessed by reactive IFNγ production, measured by ELISA techniques. No IFNγ production was found in experimental situations with single polypeptides or without any polypeptides. Data obtained are depicted in FIG. 30. Cells from the same frozen aliquot batch, CMV specific T-cells and THP-1 cells, were used for the in vivo murine model (FIG. 12A).

Example 24

This illustration depicts the potential to target allergen/autoimmune specific B-cell clones with the bipartite functional complementation strategy. By using a synthetic allergen as targeting moiety, the allergen linked polypeptide will bind specifically to its clonotypic B-cell receptor expressed on the surface of the allergen specific B-cell clone. The second arm of the bipartite strategy will use a B-cell specific polypeptide (CD19, CD20, CD38, CD138), restricting the followed complementation of the effector domain with subsequent target cell killing to the allergen specific B-cell clone. The ultimate goal of this strategy is to eliminate the B cell clone that causes and allergic or autoimmune disease (upper part of FIG. 31) whilst sparing B cells with other specificities or cells other than B cells (eg. mast cells or basophilic cells) which bind the antibody responsible for the disease via Fc-receptors (lower part of FIG. 31).

The features of the present invention disclosed in the specification, the claims, and/or in the accompanying drawings may, both separately and in any combination thereof, be material for realizing the invention in various forms thereof.

The invention claimed is:

1. A method of treatment by dual antigen-induced bipartite functional complementation, said method comprising a step of administering to a subject in need thereof a pharmaceutically effective amount of a set of polypeptides comprising:
   a first polypeptide P1 comprising
      (i) a targeting moiety T1,
         wherein said targeting moiety T1 specifically binds to an antigen A1, and
      (ii) a fragment F1 of a functional domain F,
   wherein neither said fragment F1 by itself nor said polypeptide P1 by itself is functional with respect to the function of said functional domain F,
   and
   a second polypeptide P2 comprising
      (i) a targeting moiety T2,
         wherein said targeting moiety T2 specifically binds to an antigen A2, and
      (ii) a fragment F2 of said functional domain F,
   wherein neither said fragment F2 by itself nor said polypeptide P2 by itself is functional with respect to the function of said functional domain F,
   wherein said antigen A1 is different from said antigen A2,
   wherein said polypeptide P1 and said polypeptide P2 are not associated with each other in the absence of a cell that carries both antigens A1 and A2 at its surface, wherein, upon dimerization of said fragment F1 of said polypeptide P1 with said fragment F2 of said polypeptide P2, the resulting dimer is functional with respect to the function of said functional domain F, wherein said fragment F1 comprises a $V_H$ domain of an antibody and said fragment F2 comprises a $V_L$ domain of the same antibody, wherein said targeting moiety T1 comprises an immunoglobulin module, wherein said targeting moiety T2 comprises an immunoglobulin module, wherein said functional domain F specifically binds or is capable of specifically binding to an antigen, wherein said antigen is different from antigen A1 and antigen A2, and wherein said polypeptide P1 comprises the amino acid sequence SEQ ID NO: 124 and said polypeptide P2 comprises the amino acid sequence SEQ ID NO: 125.

2. The method according to claim 1, wherein said cell that carries both antigens A1 and A2 at its surface induces dimerization of the fragment F1 of said polypeptide P1 with the fragment F2 of said polypeptide P2, whereas a cell which does not carry both antigens A1 and A2 at its cell surface does not induce dimerization of the fragment F1 of said polypeptide P1 with the fragment F2 of said polypeptide P2.

3. The method according to claim 1, wherein said polypeptides P1 and P2 have, in the absence of said cell that carries both antigens A1 and A2 at its surface, a dissociation constant $K_D$ with each other in the range of $10^{-7}$ M to $10^{-3}$ M.

4. The method according to claim 1, wherein said antigen A1 and said antigen A2 are expressed on the surface of cells of a tumour or on the surface of progenitor/precursor cells of a tumour.

5. The method according to claim 1, wherein said antigen A1 is HLA-A2 and antigen A2 is CD45.

6. The method according to claim 1, wherein said targeting moiety T1 comprises an immunoglobulin module I1 comprising a $V_L$ domain linked to a $V_H$ domain; and wherein said targeting moiety T2 comprises an immunoglobulin module I2 comprising a $V_L$ domain linked to a $V_H$ domain.

7. The method according to claim 6, wherein said immunoglobulin module I1 comprises a single-chain variant fragment (scFv) of an antibody; and wherein said immunoglobulin module I2 comprises an scFv of an antibody.

8. The method according to claim 1, wherein said functional domain F is or comprises an immunoglobulin module.

9. The method according to claim 8, wherein said functional domain F is or comprises a variant fragment (Fv) of an antibody.

10. The method according to claim 1, wherein said fragment F1 comprises a $V_H$ domain of an anti-CD3 antibody and said fragment F2 comprises a $V_L$ domain of the same antibody.

11. The method of claim 1, wherein the method comprises treating a patient who is suffering from cancer and/or a tumour.

12. The method of claim 1, wherein said antigen specifically bound by said functional domain F is present on cells of the human immune system.

13. The method of claim 1, wherein said binding of said functional domain F to said antigen activates cells of the human immune system.

14. The method of claim 1, wherein said functional domain F comprises a T cell engaging domain.

15. The method of claim 1, wherein said functional domain F comprises a T cell engaging domain specifically binding to CD3; or a T cell engaging domain specifically binding to CD3ε.

16. The method of claim 1, wherein said polypeptide P1 and said polypeptide P2 have, in the absence of said cell that carries both antigens A1 and A2 at its surface, a dissociation constant $K_D$ of above $10^{-7}$ M.

* * * * *

UNITED STATES PATENT AND TRADEMARK OFFICE
CERTIFICATE OF CORRECTION

PATENT NO. : 11,427,644 B2
APPLICATION NO. : 16/289798
DATED : August 30, 2022
INVENTOR(S) : Gernot Stuhler It is certified that error appears in the above-identified patent and that said Letters Patent is hereby corrected as shown below:

On the Title Page

The name of the Assignee (item (73)), 'JULIUS-MAXMILLIANS-UNIVERSITÄT WÜRZBURG' should read --JULIUS-MAXIMILIANS-UNIVERSITÄT WÜRZBURG--.

In the Abstract (item (57)), the 'Λ' should read --A--.

In the Claims

In Claim 3, Line 56, '$K_D$' should read --$K_D$--.

In Claim 6, Line 66: '$V_L$' should read --$V_L$--.

In Claim 6, Line 67: '$V_H$' should read --$V_H$--.

In Claim 16, Line 18: '$K_D$' should read --$K_D$--.

Signed and Sealed this
Fourteenth Day of March, 2023

Katherine Kelly Vidal
*Director of the United States Patent and Trademark Office*

SEQUENCE LISTING

```
<160> NUMBER OF SEQ ID NOS: 201

<210> SEQ ID NO 1
<211> LENGTH: 119
<212> TYPE: PRT
<213> ORGANISM: Artificial Sequence
<220> FEATURE:
<223> OTHER INFORMATION: VH anti-CD3

<400> SEQUENCE: 1

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: VL anti-CD3

<400> SEQUENCE: 2

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys Gly Ser Ala Ala Ala
            100                 105                 110
```

<210> SEQ ID NO 3
<211> LENGTH: 119
<212> TYPE: PRT
<213> ORGANISM: Artificial Sequence
<220> FEATURE:
<223> OTHER INFORMATION: VH anti-CD3

<400> SEQUENCE: 3

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115
```

<210> SEQ ID NO 4
<211> LENGTH: 106
<212> TYPE: PRT
<213> ORGANISM: Artificial Sequence
<220> FEATURE:
<223> OTHER INFORMATION: VL anti-CD3

<400> SEQUENCE: 4

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105
```

<210> SEQ ID NO 5
<211> LENGTH: 122
<212> TYPE: PRT
<213> ORGANISM: Artificial Sequence
<220> FEATURE:
<223> OTHER INFORMATION: huMAb anti-CD variant 9 VH

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
```

```
                20                  25                  30
Thr Met Asn Trp Val Arg Gln Ala Pro Gly Lys Gly Leu Glu Trp Val
            35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
            115                 120

<210> SEQ ID NO 6
<211> LENGTH: 113
<212> TYPE: PRT
<213> ORGANISM: Artificial Sequence
<220> FEATURE:
<223> OTHER INFORMATION: huMAb anti-CD variant 1 VL

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Ile Lys Arg
            100                 105                 110

Thr

<210> SEQ ID NO 7
<211> LENGTH: 119
<212> TYPE: PRT
<213> ORGANISM: Artificial Sequence
<220> FEATURE:
<223> OTHER INFORMATION: Anti-CD3 VH (L2K)

<400> SEQUENCE: 7

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
```

```
                         85                  90                  95
Ala Arg Tyr Tyr Asp Asp His Tyr Cys Leu Asp Tyr Trp Gly Gln Gly
                100                 105                 110

Thr Thr Leu Thr Val Ser Ser
            115

<210> SEQ ID NO 8
<211> LENGTH: 106
<212> TYPE: PRT
<213> ORGANISM: Artificial Sequence
<220> FEATURE:
<223> OTHER INFORMATION: Anti-CD3 VL (L2K)

<400> SEQUENCE: 8

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 9
<211> LENGTH: 119
<212> TYPE: PRT
<213> ORGANISM: Artificial Sequence
<220> FEATURE:
<223> OTHER INFORMATION: Anti-CD3 VH (145.2C11)

<400> SEQUENCE: 9

Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
                100                 105                 110

Thr Val Ser Ser Ala Lys Thr
            115

<210> SEQ ID NO 10
<211> LENGTH: 110
<212> TYPE: PRT
<213> ORGANISM: Artificial Sequence
<220> FEATURE:
```

<223> OTHER INFORMATION: Anti-CD3 VL (145.2C11)

<400> SEQUENCE: 10

Asp Ile Gln Met Thr Gln Ser Pro Ser Ser Leu Pro Ala Ser Leu Gly
1               5                   10                  15

Asp Arg Val Thr Ile Asn Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Asn Lys Leu Ala Asp Gly Val Pro Ser Arg Phe Ser Gly
    50                  55                  60

Ser Gly Ser Gly Arg Asp Ser Ser Phe Thr Ile Ser Ser Leu Glu Ser
65                  70                  75                  80

Glu Asp Ile Gly Ser Tyr Tyr Cys Gln Gln Tyr Tyr Asn Tyr Pro Trp
                85                  90                  95

Thr Phe Gly Pro Gly Thr Lys Leu Glu Ile Lys Arg Ala Asp
            100                 105                 110

<210> SEQ ID NO 11
<211> LENGTH: 114
<212> TYPE: PRT
<213> ORGANISM: Artificial Sequence
<220> FEATURE:
<223> OTHER INFORMATION: Anti-HIS VH

<400> SEQUENCE: 11

Gln Val Gln Leu Gln Gln Ser Gly Pro Glu Asp Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser Pro Gly Lys Gly Leu Glu Trp Ile
        35                  40                  45

Gly Asp Ile Asn Pro Asn Asn Gly Gly Thr Ser Tyr Asn Gln Lys Phe
    50                  55                  60

Lys Gly Arg Ala Thr Leu Thr Val Asp Lys Ser Ser Ser Thr Ala Tyr
65                  70                  75                  80

Met Glu Leu Arg Ser Leu Thr Ser Glu Asp Ser Ser Val Tyr Tyr Cys
                85                  90                  95

Glu Ser Gln Ser Gly Ala Tyr Trp Gly Gln Gly Thr Thr Val Thr Val
            100                 105                 110

Ser Ala

<210> SEQ ID NO 12
<211> LENGTH: 116
<212> TYPE: PRT
<213> ORGANISM: Artificial Sequence
<220> FEATURE:
<223> OTHER INFORMATION: Anti-HIS VL

<400> SEQUENCE: 12

Asp Tyr Lys Asp Ile Leu Met Thr Gln Thr Pro Ser Ser Leu Pro Val
1               5                   10                  15

Ser Leu Gly Asp Gln Ala Ser Ile Ser Cys Arg Ser Ser Gln Ser Ile
            20                  25                  30

Val His Ser Asn Gly Asn Thr Tyr Leu Glu Trp Tyr Leu Gln Lys Pro
        35                  40                  45

Gly Gln Ser Pro Lys Leu Leu Ile Tyr Lys Val Ser Asn Arg Phe Ser
    50                  55                  60

```
Gly Val Pro Asp Arg Phe Ser Gly Ser Gly Thr Asp Phe Thr
65                  70                  75                  80

Leu Lys Ile Ser Arg Val Glu Ala Glu Asp Leu Gly Val Tyr Tyr Cys
                85                  90                  95

Phe Gln Gly Ser His Val Pro Phe Thr Phe Gly Ser Gly Thr Lys Leu
            100                 105                 110

Glu Ile Lys Arg
        115

<210> SEQ ID NO 13
<211> LENGTH: 128
<212> TYPE: PRT
<213> ORGANISM: Artificial Sequence
<220> FEATURE:
<223> OTHER INFORMATION: Anti-DIG VH

<400> SEQUENCE: 13

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asp Tyr
            20                  25                  30

Ala Met Ser Trp Ile Arg Gln Thr Pro Glu Asn Arg Leu Glu Trp Val
        35                  40                  45

Ala Ser Ile Asn Ile Gly Ala Thr Tyr Ala Tyr Tyr Pro Asp Ser Val
    50                  55                  60

Lys Gly Arg Phe Thr Ile Ser Arg Asp Asn Ala Lys Asn Thr Leu Phe
65                  70                  75                  80

Leu Gln Met Ser Ser Leu Gly Ser Glu Asp Thr Ala Met Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Pro Gly Thr Ser Val Thr Val Ser Ser Ala Lys Thr
        115                 120                 125

<210> SEQ ID NO 14
<211> LENGTH: 118
<212> TYPE: PRT
<213> ORGANISM: Artificial Sequence
<220> FEATURE:
<223> OTHER INFORMATION: Anti-DIG VL

<400> SEQUENCE: 14

Asp Val Gln Met Thr Gln Ser Ser Ser Leu Ser Ala Ser Leu Gly
1               5                   10                  15

Asp Arg Val Thr Ile Ser Cys Arg Ala Ser Gln Asp Ile Lys Asn Tyr
            20                  25                  30

Leu Asn Trp Tyr Gln Gln Lys Pro Gly Gly Thr Val Lys Leu Leu Ile
        35                  40                  45

Tyr Tyr Ser Ser Thr Leu Leu Ser Gly Val Pro Ser Arg Phe Ser Gly
    50                  55                  60

Arg Gly Ser Gly Thr Asp Phe Ser Leu Thr Ile Thr Asn Leu Glu Arg
65                  70                  75                  80

Glu Asp Ile Ala Thr Tyr Phe Cys Gln Gln Ser Ile Thr Leu Pro Pro
                85                  90                  95

Thr Phe Gly Gly Gly Thr Lys Leu Glu Ile Lys Arg Ala Asp Ala Ala
            100                 105                 110

Pro Thr Val Ser Ile Phe
```

```
<210> SEQ ID NO 15
<211> LENGTH: 10
<212> TYPE: PRT
<213> ORGANISM: Artificial Sequence
<220> FEATURE:
<223> OTHER INFORMATION: Anti-CD3 VH CDR1 (WT)

<400> SEQUENCE: 15

Gly Tyr Thr Phe Thr Arg Tyr Thr Met His
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Anti-CD3 VH CDR2 (VH5)

<400> SEQUENCE: 16

Tyr Ile Asn Pro Ser Arg Gly Tyr Thr Asn Tyr Ala Asp Ser Val Lys
1               5                   10                  15

Gly

<210> SEQ ID NO 17
<211> LENGTH: 10
<212> TYPE: PRT
<213> ORGANISM: Artificial Sequence
<220> FEATURE:
<223> OTHER INFORMATION: Anti-CD3 VH CDR3 (WT)

<400> SEQUENCE: 17

Tyr Tyr Asp Asp His Tyr Cys Leu Asp Tyr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Anti-CD3 VK CDR1 (WT)

<400> SEQUENCE: 18

Arg Ala Ser Gln Ser Val Ser Tyr Met Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Anti-CD3 VK CDR2 (WT)

<400> SEQUENCE: 19

Asp Thr Ser Lys Val Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Anti-CD3 VK CDR3 (WT)

<400> SEQUENCE: 20
```

Gln Gln Trp Ser Ser Asn Pro Leu Thr
1               5

<210> SEQ ID NO 21
<211> LENGTH: 10
<212> TYPE: PRT
<213> ORGANISM: Artificial Sequence
<220> FEATURE:
<223> OTHER INFORMATION: Anti-CD3 VH CDR1 (WT)

<400> SEQUENCE: 21

Gly Tyr Thr Phe Thr Arg Tyr Thr Met His
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Anti-CD3 VH CDR2 (WT)

<400> SEQUENCE: 22

Tyr Ile Asn Pro Ser Arg Gly Tyr Thr Asn Tyr Asn Gln Lys Phe Lys
1               5                   10                  15

Asp

<210> SEQ ID NO 23
<211> LENGTH: 10
<212> TYPE: PRT
<213> ORGANISM: Artificial Sequence
<220> FEATURE:
<223> OTHER INFORMATION: Anti-CD3 VH CDR3 (WT)

<400> SEQUENCE: 23

Tyr Tyr Asp Asp His Tyr Cys Leu Asp Tyr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Anti-CD3 VK CDR1 (WT)

<400> SEQUENCE: 24

Arg Ala Ser Ser Ser Val Ser Tyr Met Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Anti-CD3 VK CDR2 (WT)

<400> SEQUENCE: 25

Asp Thr Ser Lys Val Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Anti-CD3 VK CDR3 (WT)

<400> SEQUENCE: 26

```
Gln Gln Trp Ser Ser Asn Pro Leu Thr
1               5

<210> SEQ ID NO 27
<211> LENGTH: 10
<212> TYPE: PRT
<213> ORGANISM: Artificial Sequence
<220> FEATURE:
<223> OTHER INFORMATION: Anti-CD3 VH CDR1 (UCHT-1)

<400> SEQUENCE: 27

Gly Tyr Ser Phe Thr Gly Tyr Thr Met Asn
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Anti-CD3 VH CDR2 (UCHT-1)

<400> SEQUENCE: 28

Leu Ile Asn Pro Tyr Lys Gly Val Ser Thr Tyr Asn Gln Lys Phe Lys
1               5                   10                  15

Asp

<210> SEQ ID NO 29
<211> LENGTH: 11
<212> TYPE: PRT
<213> ORGANISM: Artificial Sequence
<220> FEATURE:
<223> OTHER INFORMATION: Anti-CD3 VH CDR3 (UCHT-1)

<400> SEQUENCE: 29

Tyr Tyr Gly Asp Ser Asp Trp Tyr Phe Asp Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Anti-CD3 VL CDR1 (UCHT-1)

<400> SEQUENCE: 30

Arg Ala Ser Gln Asp Ile Arg Asn Tyr Leu Asn
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Anti-CD3 VL CDR2 (UCHT-1)

<400> SEQUENCE: 31

Tyr Thr Ser Arg Leu Glu Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Anti-CD3 VL CDR3 (UCHT-1)
```

```
<400> SEQUENCE: 32

Gln Gln Gly Asn Thr Leu Pro Trp Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Anti-CD3 VH CDR 1 (L2K)

<400> SEQUENCE: 33

Gly Tyr Thr Phe Thr Arg Tyr Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Anti-CD3 VH CDR 2 (L2K)

<400> SEQUENCE: 34

Ile Asn Pro Ser Arg Gly Tyr Thr
1               5

<210> SEQ ID NO 35
<211> LENGTH: 12
<212> TYPE: PRT
<213> ORGANISM: Artificial Sequence
<220> FEATURE:
<223> OTHER INFORMATION: Anti-CD3 VH CDR 3 (L2K)

<400> SEQUENCE: 35

Ala Arg Tyr Tyr Asp Asp His Tyr Cys Leu Asp Tyr
1               5                   10

<210> SEQ ID NO 36
<211> LENGTH: 5
<212> TYPE: PRT
<213> ORGANISM: Artificial Sequence
<220> FEATURE:
<223> OTHER INFORMATION: Anti-CD3 VL CDR 1 (L2K)

<400> SEQUENCE: 36

Ser Ser Val Ser Tyr
1               5

<210> SEQ ID NO 37
<211> LENGTH: 9
<212> TYPE: PRT
<213> ORGANISM: Artificial Sequence
<220> FEATURE:
<223> OTHER INFORMATION: Anti-CD3 VL CDR 3 (L2K)

<400> SEQUENCE: 37

Gln Gln Trp Ser Ser Asn Pro Leu Thr
1               5

<210> SEQ ID NO 38
<211> LENGTH: 8
<212> TYPE: PRT
<213> ORGANISM: Artificial Sequence
<220> FEATURE:
<223> OTHER INFORMATION: Anti-CD3 VH CDR 1 (145-2C11)

<400> SEQUENCE: 38
```

```
Gly Phe Thr Phe Ser Gly Tyr Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Anti-CD3 VH CDR 2 (145-2C11)

<400> SEQUENCE: 39

Ile Thr Ser Ser Ser Ile Asn Ile
1               5

<210> SEQ ID NO 40
<211> LENGTH: 9
<212> TYPE: PRT
<213> ORGANISM: Artificial Sequence
<220> FEATURE:
<223> OTHER INFORMATION: Anti-CD3 VH CDR 3 (145-2C11)

<400> SEQUENCE: 40

Ala Arg Phe Asp Trp Asp Lys Asn Tyr
1               5

<210> SEQ ID NO 41
<211> LENGTH: 6
<212> TYPE: PRT
<213> ORGANISM: Artificial Sequence
<220> FEATURE:
<223> OTHER INFORMATION: Anti-CD3 VL CDR 1 (145-2C11)

<400> SEQUENCE: 41

Gln Asp Ile Ser Asn Tyr
1               5

<210> SEQ ID NO 42
<211> LENGTH: 9
<212> TYPE: PRT
<213> ORGANISM: Artificial Sequence
<220> FEATURE:
<223> OTHER INFORMATION: Anti-CD3 VL CDR 3 (145-2C11)

<400> SEQUENCE: 42

Gln Gln Tyr Tyr Asn Tyr Pro Trp Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Anti-HIS VH CDR1

<400> SEQUENCE: 43

Gly Tyr Thr Phe Thr Asp Tyr Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: Anti-HIS VH CDR2

<400> SEQUENCE: 44
```

```
Ile Asn Pro Asn Asn Gly Gly Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Anti-HIS VH CDR3

<400> SEQUENCE: 45

Glu Ser Gln Ser Gly Ala Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: Anti-HIS VL CDR1

<400> SEQUENCE: 46

Gln Ser Ile Val His Ser Asn Gly Asn Thr Tyr
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Anti-HIS VL CDR3

<400> SEQUENCE: 47

Phe Gln Gly Ser His Val Pro Phe Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Anti-DIG VH CDR1

<400> SEQUENCE: 48

Gly Phe Thr Phe Ser Asp Tyr Ala
1               5

<210> SEQ ID NO 49
<211> LENGTH: 8
<212> TYPE: PRT
<213> ORGANISM: Artificial Sequence
<220> FEATURE:
<223> OTHER INFORMATION: Anti-DIG VH CDR2

<400> SEQUENCE: 49

Ile Asn Ile Gly Ala Thr Tyr Ala
1               5

<210> SEQ ID NO 50
<211> LENGTH: 6
<212> TYPE: PRT
<213> ORGANISM: Artificial Sequence
<220> FEATURE:
<223> OTHER INFORMATION: Anti-DIG VL CDR1

<400> SEQUENCE: 50

Gln Asp Ile Lys Asn Tyr
```

<210> SEQ ID NO 51
<211> LENGTH: 123
<212> TYPE: PRT
<213> ORGANISM: Artificial Sequence
<220> FEATURE:
<223> OTHER INFORMATION: Anti-HLA-A2 VH

<400> SEQUENCE: 51

Gln Val Gln Leu Val Gln Ser Gly Gly Gly Val Gln Pro Gly Gly
1               5                   10                  15

Ser Leu Arg Val Ser Cys Ala Ala Ser Gly Val Thr Leu Ser Asp Tyr
            20                  25                  30

Gly Met His Trp Val Arg Gln Ala Pro Gly Lys Gly Leu Glu Trp Met
        35                  40                  45

Ala Phe Ile Arg Asn Asp Gly Ser Asp Lys Tyr Tyr Ala Asp Ser Val
    50                  55                  60

Lys Gly Arg Phe Thr Ile Ser Arg Asp Asn Ser Lys Lys Thr Val Ser
65                  70                  75                  80

Leu Gln Met Ser Ser Leu Arg Ala Glu Asp Thr Ala Val Tyr Tyr Cys
                85                  90                  95

Ala Lys Asn Gly Glu Ser Gly Pro Leu Asp Tyr Trp Tyr Phe Asp Leu
            100                 105                 110

Trp Gly Arg Gly Thr Leu Val Thr Val Ser Ser
        115                 120

<210> SEQ ID NO 52
<211> LENGTH: 108
<212> TYPE: PRT
<213> ORGANISM: Artificial Sequence
<220> FEATURE:
<223> OTHER INFORMATION: Anti-HLA-A2 VL

<400> SEQUENCE: 52

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr Ser Ser Phe Pro Leu
                85                  90                  95

Thr Phe Gly Gly Gly Thr Lys Val Asp Ile Lys Arg
            100                 105

<210> SEQ ID NO 53
<211> LENGTH: 118
<212> TYPE: PRT
<213> ORGANISM: Artificial Sequence
<220> FEATURE:
<223> OTHER INFORMATION: Anti-HLA-Cw6 VH

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Phe Ser Trp Phe Asp Val Trp Gly Gln Gly Thr Leu
            100                 105                 110

Val Thr Val Ser Ser Ala
            115

<210> SEQ ID NO 54
<211> LENGTH: 108
<212> TYPE: PRT
<213> ORGANISM: Artificial Sequence
<220> FEATURE:
<223> OTHER INFORMATION: Anti-HLA-Cw6 VL

<400> SEQUENCE: 54

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Asn Phe Asp Ser Pro
                85                  90                  95

Val Phe Gly Gly Gly Thr Lys Leu Thr Val Leu Gly
            100                 105

<210> SEQ ID NO 55
<211> LENGTH: 120
<212> TYPE: PRT
<213> ORGANISM: Artificial Sequence
<220> FEATURE:
<223> OTHER INFORMATION: Anti-EpCAM VH

<400> SEQUENCE: 55

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe

```
                    85                  90                  95
Cys Ala Arg Leu Arg Asn Trp Asp Glu Pro Met Asp Tyr Trp Gly Gln
                100                 105                 110

Gly Thr Thr Val Thr Val Ser Ser
            115                 120

<210> SEQ ID NO 56
<211> LENGTH: 113
<212> TYPE: PRT
<213> ORGANISM: Artificial Sequence
<220> FEATURE:
<223> OTHER INFORMATION: Anti-EpCAM VL

<400> SEQUENCE: 56

Glu Leu Val Met Thr Gln Ser Pro Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
                100                 105                 110

Lys

<210> SEQ ID NO 57
<211> LENGTH: 120
<212> TYPE: PRT
<213> ORGANISM: Artificial Sequence
<220> FEATURE:
<223> OTHER INFORMATION: Anti-HER2 VH

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 58
<211> LENGTH: 107
<212> TYPE: PRT
```

```
<213> ORGANISM: Artificial Sequence
<220> FEATURE:
<223> OTHER INFORMATION: Anti-HER2 VL

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 59
<211> LENGTH: 119
<212> TYPE: PRT
<213> ORGANISM: Artificial Sequence
<220> FEATURE:
<223> OTHER INFORMATION: Anti-EGFR-1 VH

<400> SEQUENCE: 59

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: Anti-EGFR-1 VL

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 61
<211> LENGTH: 127
<212> TYPE: PRT
<213> ORGANISM: Artificial Sequence
<220> FEATURE:
<223> OTHER INFORMATION: Anti-CEA VH

<400> SEQUENCE: 61

Ser Arg Val Ala Gln Val Gln Leu Gln Gln Ser Gly Ala Glu Leu Ala
 1               5                  10                  15

Arg Pro Gly Ala Ser Val Lys Met Ser Cys Lys Ala Ser Gly Tyr Thr
                20                  25                  30

Phe Thr Thr Tyr Thr Ile His Trp Val Arg Gln Arg Pro Gly His Asp
            35                  40                  45

Leu Glu Trp Ile Gly Tyr Ile Asn Pro Ser Ser Gly Tyr Ser Asp Tyr
        50                  55                  60

Asn Gln Asn Phe Lys Gly Lys Thr Thr Leu Thr Ala Asp Lys Ser Ser
 65                  70                  75                  80

Asn Thr Ala Tyr Met Gln Leu Asn Ser Leu Thr Ser Glu Asp Ser Ala
                85                  90                  95

Val Tyr Tyr Cys Ala Arg Arg Ala Asp Tyr Gly Asn Tyr Glu Tyr Thr
            100                 105                 110

Trp Phe Ala Tyr Trp Gly Gln Gly Thr Thr Val Thr Val Ser Ser
        115                 120                 125

<210> SEQ ID NO 62
<211> LENGTH: 110
<212> TYPE: PRT
<213> ORGANISM: Artificial Sequence
<220> FEATURE:
<223> OTHER INFORMATION: Anti-CEA VL

<400> SEQUENCE: 62

Asp Ile Glu Leu Thr Gln Ser Pro Lys Phe Met Ser Thr Ser Val Gly
 1               5                  10                  15

Asp Arg Val Asn Val Thr Tyr Lys Ala Ser Gln Asn Val Gly Thr Asn
                20                  25                  30

Val Ala Trp Phe Gln Gln Lys Pro Gly Gln Ser Pro Lys Val Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr His Thr Tyr Pro Leu
                85                  90                  95

Thr Phe Gly Gly Gly Thr Lys Leu Glu Ile Lys Arg Ala Asp
            100                 105                 110
```

-continued

```
<210> SEQ ID NO 63
<211> LENGTH: 120
<212> TYPE: PRT
<213> ORGANISM: Artificial Sequence
<220> FEATURE:
<223> OTHER INFORMATION: Anti-CD45 VH

<400> SEQUENCE: 63

Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser
        115                 120

<210> SEQ ID NO 64
<211> LENGTH: 111
<212> TYPE: PRT
<213> ORGANISM: Artificial Sequence
<220> FEATURE:
<223> OTHER INFORMATION: Anti-CD45 VL

<400> SEQUENCE: 64

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
            100                 105                 110

<210> SEQ ID NO 65
<211> LENGTH: 121
<212> TYPE: PRT
<213> ORGANISM: Artificial Sequence
<220> FEATURE:
<223> OTHER INFORMATION: VH anti-CD138

<400> SEQUENCE: 65

Gln Val Gln Leu Gln Gln Ser Gly Ser Glu Leu Met Pro Gly Ala Ser
1               5                   10                  15

Val Lys Ile Ser Cys Lys Ala Thr Gly Tyr Thr Phe Ser Asn Tyr Trp
            20                  25                  30
```

Ile Glu Trp Val Lys Gln Arg Pro Gly His Gly Leu Glu Trp Ile Gly
            35                  40                  45

Glu Ile Leu Pro Gly Thr Gly Arg Thr Ile Tyr Asn Glu Lys Phe Lys
        50                  55                  60

Gly Lys Ala Thr Phe Thr Ala Asp Ile Ser Ser Asn Thr Val Gln Met
65                  70                  75                  80

Gln Leu Ser Ser Leu Thr Ser Glu Asp Ser Ala Val Tyr Tyr Cys Ala
                85                  90                  95

Arg Glu Gln Tyr Tyr Gly Asn Phe Tyr Tyr Ala Met Asp Tyr Trp Gly
            100                 105                 110

Gln Gly Thr Ser Val Thr Val Ser Ser
        115                 120

<210> SEQ ID NO 66
<211> LENGTH: 110
<212> TYPE: PRT
<213> ORGANISM: Artificial Sequence
<220> FEATURE:
<223> OTHER INFORMATION: VL anti-CD138

<400> SEQUENCE: 66

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Arg Thr Val
            100                 105                 110

<210> SEQ ID NO 67
<211> LENGTH: 246
<212> TYPE: PRT
<213> ORGANISM: Artificial Sequence
<220> FEATURE:
<223> OTHER INFORMATION: Anti-HLA-A2 scFv

<400> SEQUENCE: 67

Gln Val Gln Leu Val Gln Ser Gly Gly Gly Val Val Gln Pro Gly Gly
1               5                   10                  15

Ser Leu Arg Val Ser Cys Ala Ala Ser Gly Val Thr Leu Ser Asp Tyr
            20                  25                  30

Gly Met His Trp Val Arg Gln Ala Pro Gly Lys Gly Leu Glu Trp Met
        35                  40                  45

Ala Phe Ile Arg Asn Asp Gly Ser Asp Lys Tyr Tyr Ala Asp Ser Val
    50                  55                  60

Lys Gly Arg Phe Thr Ile Ser Arg Asp Asn Ser Lys Lys Thr Val Ser
65                  70                  75                  80

Leu Gln Met Ser Ser Leu Arg Ala Glu Asp Thr Ala Val Tyr Tyr Cys
                85                  90                  95

Ala Lys Asn Gly Glu Ser Gly Pro Leu Asp Tyr Trp Tyr Phe Asp Leu

```
                100             105             110
Trp Gly Arg Gly Thr Leu Val Thr Val Ser Ser Gly Gly Gly Ser
            115             120             125
Gly Gly Gly Gly Ser Gly Gly Gly Ser Asp Val Met Thr Gln
            130             135             140
Ser Pro Ser Ser Leu Ser Ala Ser Val Gly Asp Arg Val Thr Ile Thr
145             150             155             160
Cys Gln Ala Ser Gln Asp Ile Ser Asn Tyr Leu Asn Trp Tyr Gln Gln
            165             170             175
Lys Pro Gly Lys Ala Pro Lys Leu Leu Ile Tyr Asp Ala Ser Asn Leu
            180             185             190
Glu Thr Gly Val Pro Ser Arg Phe Ser Gly Ser Gly Ser Gly Thr Asp
            195             200             205
Phe Thr Phe Thr Ile Ser Ser Leu Gln Pro Glu Asp Phe Ala Thr Tyr
            210             215             220
Tyr Cys Gln Gln Tyr Ser Ser Phe Pro Leu Thr Phe Gly Gly Gly Thr
225             230             235             240
Lys Val Asp Ile Lys Arg
            245

<210> SEQ ID NO 68
<211> LENGTH: 245
<212> TYPE: PRT
<213> ORGANISM: Artificial Sequence
<220> FEATURE:
<223> OTHER INFORMATION: Anti-HLA-Cw6 scFv

<400> SEQUENCE: 68

Glu Val Gln Leu Val Glu Ser Gly Gly Gly Leu Val Gln Pro Gly Gly
1               5               10              15
Ser Leu Arg Leu Ser Cys Ala Ala Ser Gly Phe Thr Phe Ser Ser Tyr
            20              25              30
Ala Met Ser Trp Val Arg Gln Ala Pro Gly Lys Gly Leu Glu Trp Val
            35              40              45
Ser Ala Ile Ser Gly Ser Gly Gly Ser Thr Tyr Tyr Ala Asp Ser Val
            50              55              60
Lys Gly Arg Phe Thr Ile Ser Arg Asp Asn Ser Lys Asn Thr Leu Tyr
65              70              75              80
Leu Gln Met Asn Ser Leu Arg Ala Glu Asp Thr Ala Val Tyr Tyr Cys
            85              90              95
Ala Arg Tyr Ser Phe Ser Trp Phe Asp Val Trp Gly Gln Gly Thr Leu
            100             105             110
Val Thr Val Ser Ser Ala Gly Gly Ser Gly Gly Gly Gly Ser Gly
            115             120             125
Gly Gly Ser Gly Gly Gly Ser Asp Ile Glu Leu Thr Gln Pro
            130             135             140
Pro Ser Val Ser Val Ala Pro Gly Gln Thr Ala Arg Ile Ser Cys Ser
145             150             155             160
Gly Asp Ala Leu Gly Asp Lys Tyr Ala Ser Trp Tyr Gln Gln Lys Pro
            165             170             175
Gly Gln Ala Pro Val Leu Val Ile Tyr Asp Asp Ser Asp Arg Pro Ser
            180             185             190
Gly Ile Pro Glu Arg Phe Ser Gly Ser Asn Ser Gly Asn Thr Ala Thr
            195             200             205
Leu Thr Ile Ser Gly Thr Gln Ala Glu Asp Glu Ala Asp Tyr Tyr Cys
```

Gln Ser Tyr Asp Asn Phe Asp Ser Pro Val Phe Gly Gly Gly Thr Lys
225                 230                 235                 240

Leu Thr Val Leu Gly
            245

<210> SEQ ID NO 69
<211> LENGTH: 248
<212> TYPE: PRT
<213> ORGANISM: Artificial Sequence
<220> FEATURE:
<223> OTHER INFORMATION: Anti-EpCAM scFv

<400> SEQUENCE: 69

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Met Thr Gln Ser Pro Ser
        130                 135                 140

Ser Leu Thr Val Thr Ala Gly Glu Lys Val Thr Met Ser Cys Lys Ser
145                 150                 155                 160

Ser Gln Ser Leu Leu Asn Ser Gly Asn Gln Lys Asn Tyr Leu Thr Trp
                165                 170                 175

Tyr Gln Gln Lys Pro Gly Gln Pro Pro Lys Leu Leu Ile Tyr Trp Ala
            180                 185                 190

Ser Thr Arg Glu Ser Gly Val Pro Asp Arg Phe Thr Gly Ser Gly Ser
        195                 200                 205

Gly Thr Asp Phe Thr Leu Thr Ile Ser Ser Val Gln Ala Glu Asp Leu
        210                 215                 220

Ala Val Tyr Tyr Cys Gln Asn Asp Tyr Ser Tyr Pro Leu Thr Phe Gly
225                 230                 235                 240

Ala Gly Thr Lys Leu Glu Ile Lys
            245

<210> SEQ ID NO 70
<211> LENGTH: 242
<212> TYPE: PRT
<213> ORGANISM: Artificial Sequence
<220> FEATURE:
<223> OTHER INFORMATION: Anti-HER2 scFv

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Gly Gly Gly Ser Gly Gly Gly
        115                 120                 125

Gly Ser Gly Gly Gly Ser Asp Ile Gln Met Thr Gln Ser Pro Ser
        130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
210                 215                 220

Gln His Tyr Thr Thr Pro Pro Thr Phe Gly Gln Gly Thr Lys Val Glu
225                 230                 235                 240

Ile Lys

<210> SEQ ID NO 71
<211> LENGTH: 241
<212> TYPE: PRT
<213> ORGANISM: Artificial Sequence
<220> FEATURE:
<223> OTHER INFORMATION: Anti-EGFR(1) scFv

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser

```
            130                 135                 140
Leu Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
            195                 200                 205

Ile Ser Ser Leu Gln Pro Glu Asp Ile Ala Thr Tyr Phe Cys Gln His
            210                 215                 220

Phe Asp His Leu Pro Leu Ala Phe Gly Gly Gly Thr Lys Val Glu Ile
225                 230                 235                 240

Lys

<210> SEQ ID NO 72
<211> LENGTH: 252
<212> TYPE: PRT
<213> ORGANISM: Artificial Sequence
<220> FEATURE:
<223> OTHER INFORMATION: Anti-CEA scFv

<400> SEQUENCE: 72

Ser Arg Val Ala Gln Val Gln Leu Gln Gln Ser Gly Ala Glu Leu Ala
1               5                   10                  15

Arg Pro Gly Ala Ser Val Lys Met Ser Cys Lys Ala Ser Gly Tyr Thr
            20                  25                  30

Phe Thr Thr Tyr Thr Ile His Trp Val Arg Gln Arg Pro Gly His Asp
            35                  40                  45

Leu Glu Trp Ile Gly Tyr Ile Asn Pro Ser Ser Gly Tyr Ser Asp Tyr
        50                  55                  60

Asn Gln Asn Phe Lys Gly Lys Thr Thr Leu Thr Ala Asp Lys Ser Ser
65              70                  75                  80

Asn Thr Ala Tyr Met Gln Leu Asn Ser Leu Thr Ser Glu Asp Ser Ala
                85                  90                  95

Val Tyr Tyr Cys Ala Arg Arg Ala Asp Tyr Gly Asn Tyr Glu Tyr Thr
            100                 105                 110

Trp Phe Ala Tyr Trp Gly Gln Gly Thr Thr Val Thr Val Ser Ser Gly
            115                 120                 125

Gly Gly Gly Ser Gly Gly Gly Gly Ser Gly Gly Gly Gly Ser Asp Ile
        130                 135                 140

Glu Leu Thr Gln Ser Pro Lys Phe Met Ser Thr Ser Val Gly Asp Arg
145                 150                 155                 160

Val Asn Val Thr Tyr Lys Ala Ser Gln Asn Val Gly Thr Asn Val Ala
                165                 170                 175

Trp Phe Gln Gln Lys Pro Gly Gln Ser Pro Lys Val Leu Ile Tyr Ser
            180                 185                 190

Ala Ser Tyr Arg Tyr Ser Gly Val Pro Asp Arg Phe Thr Gly Ser Gly
            195                 200                 205

Ser Gly Thr Asp Phe Thr Leu Thr Ile Ser Asn Val Gln Ser Glu Asp
            210                 215                 220

Leu Ala Glu Tyr Phe Cys Gln Gln Tyr His Thr Tyr Pro Leu Thr Phe
225                 230                 235                 240

Gly Gly Gly Thr Lys Leu Glu Ile Lys Arg Ala Asp
                245                 250
```

<210> SEQ ID NO 73
<211> LENGTH: 250
<212> TYPE: PRT
<213> ORGANISM: Artificial Sequence
<220> FEATURE:
<223> OTHER INFORMATION: Anti-CD45 scFv

<400> SEQUENCE: 73

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Lys
            100                 105                 110

Ile Ser Gly Gly Gly Gly Ser Gly Gly Gly Ser Gly Gly Gly Gly
        115                 120                 125

Ser Ser Gln Val Gln Leu Val Glu Ser Gly Gly Gly Leu Val Gln Pro
    130                 135                 140

Gly Gly Ser Leu Lys Leu Ser Cys Ala Ala Ser Gly Phe Asp Phe Ser
145                 150                 155                 160

Arg Tyr Trp Met Ser Trp Val Arg Gln Ala Pro Gly Lys Gly Leu Glu
                165                 170                 175

Trp Ile Gly Glu Ile Asn Pro Thr Ser Ser Thr Ile Asn Phe Thr Pro
            180                 185                 190

Ser Leu Lys Asp Lys Val Phe Ile Ser Arg Asp Asn Ala Lys Asn Thr
        195                 200                 205

Leu Tyr Leu Gln Met Ser Lys Val Arg Ser Glu Asp Thr Ala Leu Tyr
    210                 215                 220

Tyr Cys Ala Arg Gly Asn Tyr Tyr Arg Tyr Gly Asp Ala Met Asp Tyr
225                 230                 235                 240

Trp Gly Gln Gly Thr Ser Val Thr Val Ser
                245                 250
```

<210> SEQ ID NO 74
<211> LENGTH: 246
<212> TYPE: PRT
<213> ORGANISM: Artificial Sequence
<220> FEATURE:
<223> OTHER INFORMATION: Anti-CD138 scFv

<400> SEQUENCE: 74

```
Gln Val Gln Leu Gln Gln Ser Gly Ser Glu Leu Met Pro Gly Ala Ser
1               5                   10                  15

Val Lys Ile Ser Cys Lys Ala Thr Gly Tyr Thr Phe Ser Asn Tyr Trp
            20                  25                  30

Ile Glu Trp Val Lys Gln Arg Pro Gly His Gly Leu Glu Trp Ile Gly
        35                  40                  45

Glu Ile Leu Pro Gly Thr Gly Arg Thr Ile Tyr Asn Glu Lys Phe Lys
```

```
                        50                  55                  60
Gly Lys Ala Thr Phe Thr Ala Asp Ile Ser Ser Asn Thr Val Gln Met
 65                  70                  75                  80

Gln Leu Ser Ser Leu Thr Ser Glu Asp Ser Ala Val Tyr Tyr Cys Ala
                 85                  90                  95

Arg Glu Gln Tyr Tyr Gly Asn Phe Tyr Tyr Ala Met Asp Tyr Trp Gly
            100                 105                 110

Gln Gly Thr Ser Val Thr Val Ser Ser Gly Gly Gly Ser Gly Gly
        115                 120                 125

Gly Gly Ser Gly Gly Gly Ser Asp Ile Gln Met Thr Gln Ser Thr
    130                 135                 140

Ser Ser Leu Ser Ala Ser Leu Gly Asp Arg Val Thr Ile Ser Cys Ser
145                 150                 155                 160

Ala Ser Gln Gly Ile Asn Asn Tyr Leu Asn Trp Tyr Gln Gln Lys Pro
                165                 170                 175

Asp Gly Thr Val Glu Leu Leu Ile Tyr Tyr Thr Ser Thr Leu Gln Ser
            180                 185                 190

Gly Val Pro Ser Arg Phe Ser Gly Ser Gly Ser Gly Thr Asp Tyr Ser
        195                 200                 205

Leu Thr Ile Ser Asn Leu Glu Pro Glu Asp Ile Gly Thr Tyr Tyr Cys
    210                 215                 220

Gln Gln Tyr Ser Lys Leu Pro Arg Thr Phe Gly Gly Gly Thr Lys Leu
225                 230                 235                 240

Glu Ile Lys Arg Thr Val
                245

<210> SEQ ID NO 75
<211> LENGTH: 8
<212> TYPE: PRT
<213> ORGANISM: Artificial Sequence
<220> FEATURE:
<223> OTHER INFORMATION: Anti-HLA-A2 VH CDR1

<400> SEQUENCE: 75

Gly Val Thr Leu Ser Asp Tyr Gly
1               5

<210> SEQ ID NO 76
<211> LENGTH: 8
<212> TYPE: PRT
<213> ORGANISM: Artificial Sequence
<220> FEATURE:
<223> OTHER INFORMATION: Anti-HLA-A2 VH CDR2

<400> SEQUENCE: 76

Ile Arg Asn Asp Gly Ser Asp Lys
1               5

<210> SEQ ID NO 77
<211> LENGTH: 16
<212> TYPE: PRT
<213> ORGANISM: Artificial Sequence
<220> FEATURE:
<223> OTHER INFORMATION: Anti-HLA-A2 VH CDR3

<400> SEQUENCE: 77

Ala Lys Asn Gly Glu Ser Gly Pro Leu Asp Tyr Trp Tyr Phe Asp Leu
1               5                   10                  15

<210> SEQ ID NO 78
```

```
<211> LENGTH: 6
<212> TYPE: PRT
<213> ORGANISM: Artificial Sequence
<220> FEATURE:
<223> OTHER INFORMATION: Anti-HLA-A2 VL CDR1

<400> SEQUENCE: 78

Gln Asp Ile Ser Asn Tyr
1               5

<210> SEQ ID NO 79
<211> LENGTH: 9
<212> TYPE: PRT
<213> ORGANISM: Artificial Sequence
<220> FEATURE:
<223> OTHER INFORMATION: Anti-HLA-A2 VL CDR3

<400> SEQUENCE: 79

Gln Gln Tyr Ser Ser Phe Pro Leu Thr
1               5

<210> SEQ ID NO 80
<211> LENGTH: 8
<212> TYPE: PRT
<213> ORGANISM: Artificial Sequence
<220> FEATURE:
<223> OTHER INFORMATION: Anti-HLA-Cw6 VH CDR1

<400> SEQUENCE: 80

Gly Phe Thr Phe Ser Ser Tyr Ala
1               5

<210> SEQ ID NO 81
<211> LENGTH: 8
<212> TYPE: PRT
<213> ORGANISM: Artificial Sequence
<220> FEATURE:
<223> OTHER INFORMATION: Anti-HLA-Cw6 VH CDR2

<400> SEQUENCE: 81

Ile Ser Gly Ser Gly Gly Ser Thr
1               5

<210> SEQ ID NO 82
<211> LENGTH: 10
<212> TYPE: PRT
<213> ORGANISM: Artificial Sequence
<220> FEATURE:
<223> OTHER INFORMATION: Anti-HLA-Cw6 VH CDR3

<400> SEQUENCE: 82

Ala Arg Tyr Ser Phe Ser Trp Phe Asp Val
1               5                   10

<210> SEQ ID NO 83
<211> LENGTH: 6
<212> TYPE: PRT
<213> ORGANISM: Artificial Sequence
<220> FEATURE:
<223> OTHER INFORMATION: Anti-HLA-Cw6 VL CDR1

<400> SEQUENCE: 83

Ala Leu Gly Asp Lys Tyr
1               5

<210> SEQ ID NO 84
<211> LENGTH: 10
```

```
<212> TYPE: PRT
<213> ORGANISM: Artificial Sequence
<220> FEATURE:
<223> OTHER INFORMATION: Anti-HLA-Cw6 VL CDR3

<400> SEQUENCE: 84

Gln Ser Tyr Asp Asn Phe Asp Ser Pro Val
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Anti-EpCAM CDR1 VH

<400> SEQUENCE: 85

Gly Tyr Ala Phe Thr Asn Tyr Trp
1               5

<210> SEQ ID NO 86
<211> LENGTH: 8
<212> TYPE: PRT
<213> ORGANISM: Artificial Sequence
<220> FEATURE:
<223> OTHER INFORMATION: Anti-EpCAM CDR2 VH

<400> SEQUENCE: 86

Ile Phe Pro Gly Ser Gly Asn Ile
1               5

<210> SEQ ID NO 87
<211> LENGTH: 12
<212> TYPE: PRT
<213> ORGANISM: Artificial Sequence
<220> FEATURE:
<223> OTHER INFORMATION: Anti-EpCAM CDR3 VH

<400> SEQUENCE: 87

Ala Arg Leu Arg Asn Trp Asp Glu Pro Met Asp Tyr
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Anti-EpCAM CDR1 VL

<400> SEQUENCE: 88

Gln Ser Leu Leu Asn Ser Gly Asn Gln Lys Asn Tyr
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Anti-EpCAM CDR3 VL

<400> SEQUENCE: 89

Gln Asn Asp Tyr Ser Tyr Pro Leu Thr
1               5

<210> SEQ ID NO 90
<211> LENGTH: 8
<212> TYPE: PRT
```

```
<213> ORGANISM: Artificial Sequence
<220> FEATURE:
<223> OTHER INFORMATION: Anti-HER2 VH CDR1

<400> SEQUENCE: 90

Gly Phe Asn Ile Lys Asp Thr Tyr
1               5

<210> SEQ ID NO 91
<211> LENGTH: 8
<212> TYPE: PRT
<213> ORGANISM: Artificial Sequence
<220> FEATURE:
<223> OTHER INFORMATION: Anti-HER2 VH CDR2

<400> SEQUENCE: 91

Ile Tyr Pro Thr Asn Gly Tyr Thr
1               5

<210> SEQ ID NO 92
<211> LENGTH: 13
<212> TYPE: PRT
<213> ORGANISM: Artificial Sequence
<220> FEATURE:
<223> OTHER INFORMATION: Anti-HER2 VH CDR3

<400> SEQUENCE: 92

Ser Arg Trp Gly Gly Asp Gly Phe Tyr Ala Met Asp Tyr
1               5                   10

<210> SEQ ID NO 93
<211> LENGTH: 6
<212> TYPE: PRT
<213> ORGANISM: Artificial Sequence
<220> FEATURE:
<223> OTHER INFORMATION: Anti-HER2 VL CDR1

<400> SEQUENCE: 93

Gln Asp Val Asn Thr Ala
1               5

<210> SEQ ID NO 94
<211> LENGTH: 9
<212> TYPE: PRT
<213> ORGANISM: Artificial Sequence
<220> FEATURE:
<223> OTHER INFORMATION: Anti-HER2 VL CDR3

<400> SEQUENCE: 94

Gln Gln His Tyr Thr Thr Pro Pro Thr
1               5

<210> SEQ ID NO 95
<211> LENGTH: 10
<212> TYPE: PRT
<213> ORGANISM: Artificial Sequence
<220> FEATURE:
<223> OTHER INFORMATION: Anti-EGFR-1 VH CDR1

<400> SEQUENCE: 95

Gly Gly Ser Val Ser Ser Gly Asp Tyr Tyr
1               5                   10

<210> SEQ ID NO 96
<211> LENGTH: 7
<212> TYPE: PRT
<213> ORGANISM: Artificial Sequence
```

```
<220> FEATURE:
<223> OTHER INFORMATION: Anti-EGFR-1 VH CDR2

<400> SEQUENCE: 96

Ile Tyr Tyr Ser Gly Asn Thr
1               5

<210> SEQ ID NO 97
<211> LENGTH: 11
<212> TYPE: PRT
<213> ORGANISM: Artificial Sequence
<220> FEATURE:
<223> OTHER INFORMATION: Anti-EGFR-1 VH CDR3

<400> SEQUENCE: 97

Val Arg Asp Arg Val Thr Gly Ala Phe Asp Ile
1               5                   10

<210> SEQ ID NO 98
<211> LENGTH: 6
<212> TYPE: PRT
<213> ORGANISM: Artificial Sequence
<220> FEATURE:
<223> OTHER INFORMATION: Anti-EGFR-1 VL CDR1

<400> SEQUENCE: 98

Gln Asp Ile Ser Asn Tyr
1               5

<210> SEQ ID NO 99
<211> LENGTH: 9
<212> TYPE: PRT
<213> ORGANISM: Artificial Sequence
<220> FEATURE:
<223> OTHER INFORMATION: Anti-EGFR-1 VL CDR3

<400> SEQUENCE: 99

Gln His Phe Asp His Leu Pro Leu Ala
1               5

<210> SEQ ID NO 100
<211> LENGTH: 8
<212> TYPE: PRT
<213> ORGANISM: Artificial Sequence
<220> FEATURE:
<223> OTHER INFORMATION: Anti-CEA VH CDR1

<400> SEQUENCE: 100

Gly Tyr Thr Phe Thr Thr Tyr Thr
1               5

<210> SEQ ID NO 101
<211> LENGTH: 8
<212> TYPE: PRT
<213> ORGANISM: Artificial Sequence
<220> FEATURE:
<223> OTHER INFORMATION: Anti-CEA VH CDR2

<400> SEQUENCE: 101

Ile Asn Pro Ser Ser Gly Tyr Ser
1               5

<210> SEQ ID NO 102
<211> LENGTH: 16
<212> TYPE: PRT
<213> ORGANISM: Artificial Sequence
<220> FEATURE:
```

<223> OTHER INFORMATION: Anti-CEA VH CDR3

<400> SEQUENCE: 102

Ala Arg Arg Ala Asp Tyr Gly Asn Tyr Glu Tyr Thr Trp Phe Ala Tyr
1               5                   10                  15

<210> SEQ ID NO 103
<211> LENGTH: 6
<212> TYPE: PRT
<213> ORGANISM: Artificial Sequence
<220> FEATURE:
<223> OTHER INFORMATION: Anti-CEA VL CDR1

<400> SEQUENCE: 103

Gln Asn Val Gly Thr Asn
1               5

<210> SEQ ID NO 104
<211> LENGTH: 9
<212> TYPE: PRT
<213> ORGANISM: Artificial Sequence
<220> FEATURE:
<223> OTHER INFORMATION: Anti-CEA VL CDR3

<400> SEQUENCE: 104

Gln Gln Tyr His Thr Tyr Pro Leu Thr
1               5

<210> SEQ ID NO 105
<211> LENGTH: 5
<212> TYPE: PRT
<213> ORGANISM: Artificial Sequence
<220> FEATURE:
<223> OTHER INFORMATION: Anti-CD45 VH CDR1

<400> SEQUENCE: 105

Gly Phe Asp Phe Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Anti-CD45 VH CDR2

<400> SEQUENCE: 106

Glu Ile Asn Pro Thr Ser Ser Thr Ile
1               5

<210> SEQ ID NO 107
<211> LENGTH: 10
<212> TYPE: PRT
<213> ORGANISM: Artificial Sequence
<220> FEATURE:
<223> OTHER INFORMATION: Anti-CD45 VL CDR1

<400> SEQUENCE: 107

Lys Ser Val Ser Thr Ser Gly Tyr Ser Tyr
1               5                   10

<210> SEQ ID NO 108
<211> LENGTH: 9
<212> TYPE: PRT
<213> ORGANISM: Artificial Sequence
<220> FEATURE:
<223> OTHER INFORMATION: Anti-CD45 VL CDR3

<400> SEQUENCE: 108

Gln His Ser Arg Glu Leu Pro Phe Thr
1               5

<210> SEQ ID NO 109
<211> LENGTH: 8
<212> TYPE: PRT
<213> ORGANISM: Artificial Sequence
<220> FEATURE:
<223> OTHER INFORMATION: Anti-CD138 VH CDR1

<400> SEQUENCE: 109

Gly Tyr Thr Phe Ser Asn Tyr Trp
1               5

<210> SEQ ID NO 110
<211> LENGTH: 8
<212> TYPE: PRT
<213> ORGANISM: Artificial Sequence
<220> FEATURE:
<223> OTHER INFORMATION: Anti-CD138 VH CDR2

<400> SEQUENCE: 110

Ile Leu Pro Gly Thr Gly Arg Thr
1               5

<210> SEQ ID NO 111
<211> LENGTH: 15
<212> TYPE: PRT
<213> ORGANISM: Artificial Sequence
<220> FEATURE:
<223> OTHER INFORMATION: Anti-CD138 VH CDR3

<400> SEQUENCE: 111

Ala Arg Glu Gln Tyr Tyr Gly Asn Phe Tyr Tyr Ala Met Asp Tyr
1               5                   10                  15

<210> SEQ ID NO 112
<211> LENGTH: 6
<212> TYPE: PRT
<213> ORGANISM: Artificial Sequence
<220> FEATURE:
<223> OTHER INFORMATION: Anti-CD138 VL CDR1

<400> SEQUENCE: 112

Gln Gly Ile Asn Asn Tyr
1               5

<210> SEQ ID NO 113
<211> LENGTH: 9
<212> TYPE: PRT
<213> ORGANISM: Artificial Sequence
<220> FEATURE:
<223> OTHER INFORMATION: Anti-CD138 VL CDR3

<400> SEQUENCE: 113

Gln Gln Tyr Ser Lys Leu Pro Arg Thr
1               5

<210> SEQ ID NO 114
<211> LENGTH: 388
<212> TYPE: PRT
<213> ORGANISM: Artificial Sequence
<220> FEATURE:
<223> OTHER INFORMATION: pelB-CD3VL-scFvEPCAM(VH-VL)-6His

<400> SEQUENCE: 114

```
Met Lys Tyr Leu Leu Pro Thr Ala Ala Gly Leu Leu Leu Ala
1               5                   10                  15

Ala Gln Pro Ala Met Ala Asp Ile Gln Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Ser Val Ser Tyr Met Asn Trp Tyr Gln Gln Lys Ser Gly Thr Ser
    50                  55                  60

Pro Lys Arg Trp Ile Tyr Asp Thr Ser Lys Val Ala Ser Gly Val Pro
65                  70                  75                  80

Tyr Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

Ser Gly Gly Gly Gly Ser Glu Val Gln Leu Leu Glu Gln Ser Gly Ala
130                 135                 140

Glu Leu Val Arg Pro Gly Thr Ser Val Lys Ile Ser Cys Lys Ala Ser
145                 150                 155                 160

Gly Tyr Ala Phe Thr Asn Tyr Trp Leu Gly Trp Val Lys Gln Arg Pro
                165                 170                 175

Gly His Gly Leu Glu Trp Ile Gly Asp Ile Phe Pro Gly Ser Gly Asn
            180                 185                 190

Ile His Tyr Asn Glu Lys Phe Lys Gly Lys Ala Thr Leu Thr Ala Asp
        195                 200                 205

Lys Ser Ser Ser Thr Ala Tyr Met Gln Leu Ser Ser Leu Thr Phe Glu
210                 215                 220

Asp Ser Ala Val Tyr Phe Cys Ala Arg Leu Arg Asn Trp Asp Glu Pro
225                 230                 235                 240

Met Asp Tyr Trp Gly Gln Gly Thr Thr Val Thr Val Ser Ser Gly Gly
                245                 250                 255

Gly Gly Ser Gly Gly Gly Gly Ser Gly Gly Gly Gly Ser Glu Leu Val
            260                 265                 270

Met Thr Gln Ser Pro Ser Ser Leu Thr Val Thr Ala Gly Glu Lys Val
        275                 280                 285

Thr Met Ser Cys Lys Ser Ser Gln Ser Leu Leu Asn Ser Gly Asn Gln
290                 295                 300

Lys Asn Tyr Leu Thr Trp Tyr Gln Gln Lys Pro Gly Gln Pro Pro Lys
305                 310                 315                 320

Leu Leu Ile Tyr Trp Ala Ser Thr Arg Glu Ser Gly Val Pro Asp Arg
                325                 330                 335

Phe Thr Gly Ser Gly Ser Gly Thr Asp Phe Thr Leu Thr Ile Ser Ser
            340                 345                 350

Val Gln Ala Glu Asp Leu Ala Val Tyr Tyr Cys Gln Asn Asp Tyr Ser
        355                 360                 365

Tyr Pro Leu Thr Phe Gly Ala Gly Thr Lys Leu Glu Ile Lys His His
    370                 375                 380

His His His His
385
```

<210> SEQ ID NO 115

<211> LENGTH: 404
<212> TYPE: PRT
<213> ORGANISM: Artificial Sequence
<220> FEATURE:
<223> OTHER INFORMATION: pelB-CD3VH-scFvHer2-6HIS

<400> SEQUENCE: 115

```
Met Lys Tyr Leu Leu Pro Thr Ala Ala Ala Gly Leu Leu Leu Leu Ala
1               5                   10                  15
Ala Gln Pro Ala Met Ala Asp Ile Lys Leu Gln Gln Ser Gly Ala Glu
            20                  25                  30
Leu Ala Arg Pro Gly Ala Ser Val Lys Met Ser Cys Lys Thr Ser Gly
        35                  40                  45
Tyr Thr Phe Thr Arg Tyr Thr Met His Trp Val Lys Gln Arg Pro Gly
    50                  55                  60
Gln Gly Leu Glu Trp Ile Gly Tyr Ile Asn Pro Ser Arg Gly Tyr Thr
65                  70                  75                  80
Asn Tyr Asn Gln Lys Phe Lys Asp Lys Ala Thr Leu Thr Thr Asp Lys
                85                  90                  95
Ser Ser Ser Thr Ala Tyr Met Gln Leu Ser Ser Leu Thr Ser Glu Asp
            100                 105                 110
Ser Ala Val Tyr Tyr Cys Ala Arg Tyr Tyr Asp Asp His Tyr Cys Leu
        115                 120                 125
Asp Tyr Trp Gly Gln Gly Thr Thr Leu Thr Val Ser Ser Gly Gly Gly
    130                 135                 140
Gly Ser Gly Gly Gly Gly Ser Gly Gly Gly Gly Ser Glu Val Gln Leu
145                 150                 155                 160
Val Glu Ser Gly Gly Gly Leu Val Gln Pro Gly Gly Ser Leu Arg Leu
                165                 170                 175
Ser Cys Ala Ala Ser Gly Phe Asn Ile Lys Asp Thr Tyr Ile His Trp
            180                 185                 190
Val Arg Gln Ala Pro Gly Lys Gly Leu Glu Trp Val Ala Arg Ile Tyr
        195                 200                 205
Pro Thr Asn Gly Tyr Thr Arg Tyr Ala Asp Ser Val Lys Gly Arg Phe
    210                 215                 220
Thr Ile Ser Ala Asp Thr Ser Lys Asn Thr Ala Tyr Leu Gln Met Asn
225                 230                 235                 240
Ser Leu Arg Ala Glu Asp Thr Ala Val Tyr Tyr Cys Ser Arg Trp Gly
                245                 250                 255
Gly Asp Gly Phe Tyr Ala Met Asp Tyr Trp Gly Gln Gly Thr Leu Val
            260                 265                 270
Thr Val Ser Ser Gly Gly Gly Gly Ser Gly Gly Gly Gly Ser Gly Gly
        275                 280                 285
Gly Gly Ser Asp Ile Gln Met Thr Gln Ser Pro Ser Ser Leu Ser Ala
    290                 295                 300
Ser Val Gly Asp Arg Val Thr Ile Thr Cys Arg Ala Ser Gln Asp Val
305                 310                 315                 320
Asn Thr Ala Val Ala Trp Tyr Gln Gln Lys Pro Gly Lys Ala Pro Lys
                325                 330                 335
Leu Leu Ile Tyr Ser Ala Ser Phe Leu Tyr Ser Gly Val Pro Ser Arg
            340                 345                 350
Phe Ser Gly Ser Arg Ser Gly Thr Asp Phe Thr Leu Thr Ile Ser Ser
        355                 360                 365
Leu Gln Pro Glu Asp Phe Ala Thr Tyr Tyr Cys Gln Gln His Tyr Thr
    370                 375                 380
```

Thr Pro Pro Thr Phe Gly Gln Gly Thr Lys Val Glu Ile Lys His His
385                 390                 395                 400

His His His His

<210> SEQ ID NO 116
<211> LENGTH: 403
<212> TYPE: PRT
<213> ORGANISM: Artificial Sequence
<220> FEATURE:
<223> OTHER INFORMATION: pelB-CD3VH-scFvEGFR(1)-6HIS

<400> SEQUENCE: 116

Met Lys Tyr Leu Leu Pro Thr Ala Ala Ala Gly Leu Leu Leu Leu Ala
1               5                   10                  15

Ala Gln Pro Ala Met Ala Asp Ile Lys Leu Gln Gln Ser Gly Ala Glu
            20                  25                  30

Leu Ala Arg Pro Gly Ala Ser Val Lys Met Ser Cys Lys Thr Ser Gly
        35                  40                  45

Tyr Thr Phe Thr Arg Tyr Thr Met His Trp Val Lys Gln Arg Pro Gly
50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Tyr Tyr Asp Asp His Tyr Cys Leu
        115                 120                 125

Asp Tyr Trp Gly Gln Gly Thr Thr Leu Thr Val Ser Ser Gly Gly Gly
130                 135                 140

Gly Ser Gly Gly Gly Gly Ser Gly Gly Gly Gly Ser Gln Val Gln Leu
145                 150                 155                 160

Gln Glu Ser Gly Pro Gly Leu Val Lys Pro Ser Glu Thr Leu Ser Leu
                165                 170                 175

Thr Cys Thr Val Ser Gly Gly Ser Val Ser Ser Gly Asp Tyr Tyr Trp
            180                 185                 190

Thr Trp Ile Arg Gln Ser Pro Gly Lys Gly Leu Glu Trp Ile Gly His
        195                 200                 205

Ile Tyr Tyr Ser Gly Asn Thr Asn Tyr Asn Pro Ser Leu Lys Ser Arg
210                 215                 220

Leu Thr Ile Ser Ile Asp Thr Ser Lys Thr Gln Phe Ser Leu Lys Leu
225                 230                 235                 240

Ser Ser Val Thr Ala Ala Asp Thr Ala Ile Tyr Tyr Cys Val Arg Asp
                245                 250                 255

Arg Val Thr Gly Ala Phe Asp Ile Trp Gly Gln Gly Thr Met Val Thr
            260                 265                 270

Val Ser Ser Gly Gly Gly Gly Ser Gly Gly Gly Gly Ser Gly Gly Gly
        275                 280                 285

Gly Ser Asp Ile Gln Met Thr Gln Ser Pro Ser Ser Leu Ser Ala Ser
290                 295                 300

Val Gly Asp Arg Val Thr Ile Thr Cys Gln Ala Ser Gln Asp Ile Ser
305                 310                 315                 320

Asn Tyr Leu Asn Trp Tyr Gln Gln Lys Pro Gly Lys Ala Pro Lys Leu
                325                 330                 335

```
Leu Ile Tyr Asp Ala Ser Asn Leu Glu Thr Gly Val Pro Ser Arg Phe
            340                 345                 350

Ser Gly Ser Gly Ser Gly Thr Asp Phe Thr Phe Thr Ile Ser Ser Leu
            355                 360                 365

Gln Pro Glu Asp Ile Ala Thr Tyr Phe Cys Gln His Phe Asp His Leu
        370                 375                 380

Pro Leu Ala Phe Gly Gly Gly Thr Lys Val Glu Ile Lys His His His
385                 390                 395                 400

His His His
```

<210> SEQ ID NO 117
<211> LENGTH: 414
<212> TYPE: PRT
<213> ORGANISM: Artificial Sequence
<220> FEATURE:
<223> OTHER INFORMATION: pelB-CD3VH-scFvCEA-6HIS

<400> SEQUENCE: 117

```
Met Lys Tyr Leu Leu Pro Thr Ala Ala Ala Gly Leu Leu Leu Leu Ala
1               5                   10                  15

Ala Gln Pro Ala Met Ala Asp Ile Lys Leu Gln Gln Ser Gly Ala Glu
            20                  25                  30

Leu Ala Arg Pro Gly Ala Ser Val Lys Met Ser Cys Lys Thr Ser Gly
        35                  40                  45

Tyr Thr Phe Thr Arg Tyr Thr Met His Trp Val Lys Gln Arg Pro Gly
    50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Tyr Tyr Asp Asp His Tyr Cys Leu
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Ser Arg Val Ala
145                 150                 155                 160

Gln Val Gln Leu Gln Gln Ser Gly Ala Glu Leu Ala Arg Pro Gly Ala
                165                 170                 175

Ser Val Lys Met Ser Cys Lys Ala Ser Gly Tyr Thr Phe Thr Thr Tyr
            180                 185                 190

Thr Ile His Trp Val Arg Gln Arg Pro Gly His Asp Leu Glu Trp Ile
        195                 200                 205

Gly Tyr Ile Asn Pro Ser Ser Gly Tyr Ser Asp Tyr Asn Gln Asn Phe
    210                 215                 220

Lys Gly Lys Thr Thr Leu Thr Ala Asp Lys Ser Ser Asn Thr Ala Tyr
225                 230                 235                 240

Met Gln Leu Asn Ser Leu Thr Ser Glu Asp Ser Ala Val Tyr Tyr Cys
                245                 250                 255

Ala Arg Arg Ala Asp Tyr Gly Asn Tyr Glu Tyr Thr Trp Phe Ala Tyr
            260                 265                 270

Trp Gly Gln Gly Thr Thr Val Thr Val Ser Ser Gly Gly Gly Gly Ser
        275                 280                 285

Gly Gly Gly Gly Ser Gly Gly Gly Gly Ser Asp Ile Glu Leu Thr Gln
```

```
                290                 295                 300
Ser Pro Lys Phe Met Ser Thr Ser Val Gly Asp Arg Val Asn Val Thr
305                 310                 315                 320

Tyr Lys Ala Ser Gln Asn Val Gly Thr Asn Val Ala Trp Phe Gln Gln
                325                 330                 335

Lys Pro Gly Gln Ser Pro Lys Val Leu Ile Tyr Ser Ala Ser Tyr Arg
                340                 345                 350

Tyr Ser Gly Val Pro Asp Arg Phe Thr Gly Ser Gly Ser Gly Thr Asp
                355                 360                 365

Phe Thr Leu Thr Ile Ser Asn Val Gln Ser Glu Asp Leu Ala Glu Tyr
            370                 375                 380

Phe Cys Gln Gln Tyr His Thr Tyr Pro Leu Thr Phe Gly Gly Gly Thr
385                 390                 395                 400

Lys Leu Glu Ile Lys Arg Ala Asp His His His His His His
                405                 410
```

<210> SEQ ID NO 118
<211> LENGTH: 392
<212> TYPE: PRT
<213> ORGANISM: Artificial Sequence
<220> FEATURE:
<223> OTHER INFORMATION: pelB-CD3VL-scFvCEA-6HIS

<400> SEQUENCE: 118

```
Met Lys Tyr Leu Leu Pro Thr Ala Ala Ala Gly Leu Leu Leu Leu Ala
1               5                   10                  15

Ala Gln Pro Ala Met Ala Asp Ile Gln Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Ser Val Ser Tyr Met Asn Trp Tyr Gln Gln Lys Ser Gly Thr Ser
    50                  55                  60

Pro Lys Arg Trp Ile Tyr Asp Thr Ser Lys Val Ala Ser Gly Val Pro
65                  70                  75                  80

Tyr Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

Ser Gly Gly Gly Ser Ser Arg Val Ala Gln Val Gln Leu Gln Gln
    130                 135                 140

Ser Gly Ala Glu Leu Ala Arg Pro Gly Ala Ser Val Lys Met Ser Cys
145                 150                 155                 160

Lys Ala Ser Gly Tyr Thr Phe Thr Thr Tyr Thr Ile His Trp Val Arg
                165                 170                 175

Gln Arg Pro Gly His Asp Leu Glu Trp Ile Gly Tyr Ile Asn Pro Ser
            180                 185                 190

Ser Gly Tyr Ser Asp Tyr Asn Gln Asn Phe Lys Gly Lys Thr Thr Leu
        195                 200                 205

Thr Ala Asp Lys Ser Ser Asn Thr Ala Tyr Met Gln Leu Asn Ser Leu
    210                 215                 220

Thr Ser Glu Asp Ser Ala Val Tyr Tyr Cys Ala Arg Arg Ala Asp Tyr
225                 230                 235                 240

Gly Asn Tyr Glu Tyr Thr Trp Phe Ala Tyr Trp Gly Gln Gly Thr Thr
```

```
                      245                 250                 255
Val Thr Val Ser Ser Gly Gly Gly Ser Gly Gly Gly Ser Gly
                260                 265                 270

Gly Gly Gly Ser Asp Ile Glu Leu Thr Gln Ser Pro Lys Phe Met Ser
                275                 280                 285

Thr Ser Val Gly Asp Arg Val Asn Val Thr Tyr Lys Ala Ser Gln Asn
            290                 295                 300

Val Gly Thr Asn Val Ala Trp Phe Gln Gln Lys Pro Gly Gln Ser Pro
305                 310                 315                 320

Lys Val Leu Ile Tyr Ser Ala Ser Tyr Arg Tyr Ser Gly Val Pro Asp
                325                 330                 335

Arg Phe Thr Gly Ser Gly Ser Gly Thr Asp Phe Thr Leu Thr Ile Ser
                340                 345                 350

Asn Val Gln Ser Glu Asp Leu Ala Glu Tyr Phe Cys Gln Gln Tyr His
                355                 360                 365

Thr Tyr Pro Leu Thr Phe Gly Gly Gly Thr Lys Leu Glu Ile Lys Arg
            370                 375                 380

Ala Asp His His His His His His
385                 390

<210> SEQ ID NO 119
<211> LENGTH: 414
<212> TYPE: PRT
<213> ORGANISM: Artificial Sequence
<220> FEATURE:
<223> OTHER INFORMATION: pelB-(aCD3)VH-scFvHLA-Cw6-myc-6His

<400> SEQUENCE: 119

Met Lys Tyr Leu Leu Pro Thr Ala Ala Ala Gly Leu Leu Leu Leu Ala
1                   5                   10                  15

Ala Gln Pro Ala Met Ala Asp Ile Lys Leu Gln Gln Ser Gly Ala Glu
                20                  25                  30

Leu Ala Arg Pro Gly Ala Ser Val Lys Met Ser Cys Lys Thr Ser Gly
            35                  40                  45

Tyr Thr Phe Thr Arg Tyr Thr Met His Trp Val Lys Gln Arg Pro Gly
        50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Tyr Tyr Asp Asp His Tyr Cys Leu
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Phe Thr Phe Ser Ser Tyr Ala Met Ser Trp Val Arg Gln
            180                 185                 190

Ala Pro Gly Lys Gly Leu Glu Trp Val Ser Ala Ile Ser Gly Ser Gly
        195                 200                 205

Gly Ser Thr Tyr Tyr Ala Asp Ser Val Lys Gly Arg Phe Thr Ile Ser
```

```
            210                 215                 220
Arg Asp Asn Ser Lys Asn Thr Leu Tyr Leu Gln Met Asn Ser Leu Arg
225                 230                 235                 240

Ala Glu Asp Thr Ala Val Tyr Tyr Cys Ala Arg Tyr Ser Phe Ser Trp
                245                 250                 255

Phe Asp Val Trp Gly Gln Gly Thr Leu Val Thr Val Ser Ser Ala Gly
                260                 265                 270

Gly Gly Ser Gly Gly Gly Ser Gly Gly Gly Ser Gly Gly Gly
            275                 280                 285

Gly Ser Asp Ile Glu Leu Thr Gln Pro Pro Ser Val Ser Val Ala Pro
290                 295                 300

Gly Gln Thr Ala Arg Ile Ser Cys Ser Gly Asp Ala Leu Gly Asp Lys
305                 310                 315                 320

Tyr Ala Ser Trp Tyr Gln Gln Lys Pro Gly Gln Ala Pro Val Leu Val
                325                 330                 335

Ile Tyr Asp Asp Ser Asp Arg Pro Ser Gly Ile Pro Glu Arg Phe Ser
                340                 345                 350

Gly Ser Asn Ser Gly Asn Thr Ala Thr Leu Thr Ile Ser Gly Thr Gln
                355                 360                 365

Ala Glu Asp Glu Ala Asp Tyr Tyr Cys Gln Ser Tyr Asp Asn Phe Asp
                370                 375                 380

Ser Pro Val Phe Gly Gly Gly Thr Lys Leu Thr Val Leu Gly Glu Gln
385                 390                 395                 400

Lys Leu Ile Ser Glu Glu Asp Leu His His His His His His
                405                 410

<210> SEQ ID NO 120
<211> LENGTH: 391
<212> TYPE: PRT
<213> ORGANISM: Artificial Sequence
<220> FEATURE:
<223> OTHER INFORMATION: pelB-CD3VL-scFvCD138-6His

<400> SEQUENCE: 120

Met Lys Tyr Leu Leu Pro Thr Ala Ala Ala Gly Leu Leu Leu Leu Ala
1               5                   10                  15

Ala Gln Pro Ala Met Ala Asp Ile Gln Leu Thr Gln Ser Pro Ala Ile
                20                  25                  30

Met Ser Ala Ser Pro Gly Glu Lys Val Thr Met Thr Cys Arg Ala Ser
            35                  40                  45

Ser Ser Val Ser Tyr Met Asn Trp Tyr Gln Gln Lys Ser Gly Thr Ser
        50                  55                  60

Pro Lys Arg Trp Ile Tyr Asp Thr Ser Lys Val Ala Ser Gly Val Pro
65                  70                  75                  80

Tyr Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

Ser Gly Gly Gly Gly Ser Gly Gly Gly Ser Gln Val Gln Leu Gln
    130                 135                 140

Gln Ser Gly Ser Glu Leu Met Pro Gly Ala Ser Val Lys Ile Ser Cys
145                 150                 155                 160

Lys Ala Thr Gly Tyr Thr Phe Ser Asn Tyr Trp Ile Glu Trp Val Lys
```

```
                165                 170                 175
Gln Arg Pro Gly His Gly Leu Glu Trp Ile Gly Glu Ile Leu Pro Gly
                180                 185                 190

Thr Gly Arg Thr Ile Tyr Asn Glu Lys Phe Lys Gly Lys Ala Thr Phe
                195                 200                 205

Thr Ala Asp Ile Ser Ser Asn Thr Val Gln Met Gln Leu Ser Ser Leu
            210                 215                 220

Thr Ser Glu Asp Ser Ala Val Tyr Tyr Cys Ala Arg Glu Gln Tyr Tyr
225                 230                 235                 240

Gly Asn Phe Tyr Tyr Ala Met Asp Tyr Trp Gly Gln Gly Thr Ser Val
                245                 250                 255

Thr Val Ser Ser Gly Gly Gly Ser Gly Gly Gly Ser Gly Gly
            260                 265                 270

Gly Gly Ser Asp Ile Gln Met Thr Gln Ser Thr Ser Ser Leu Ser Ala
            275                 280                 285

Ser Leu Gly Asp Arg Val Thr Ile Ser Cys Ser Ala Ser Gln Gly Ile
            290                 295                 300

Asn Asn Tyr Leu Asn Trp Tyr Gln Gln Lys Pro Asp Gly Thr Val Glu
305                 310                 315                 320

Leu Leu Ile Tyr Tyr Thr Ser Thr Leu Gln Ser Gly Val Pro Ser Arg
                325                 330                 335

Phe Ser Gly Ser Gly Ser Gly Thr Asp Tyr Ser Leu Thr Ile Ser Asn
            340                 345                 350

Leu Glu Pro Glu Asp Ile Gly Thr Tyr Tyr Cys Gln Gln Tyr Ser Lys
            355                 360                 365

Leu Pro Arg Thr Phe Gly Gly Gly Thr Lys Leu Glu Ile Lys Arg Thr
            370                 375                 380

Val His His His His His
385                 390

<210> SEQ ID NO 121
<211> LENGTH: 408
<212> TYPE: PRT
<213> ORGANISM: Artificial Sequence
<220> FEATURE:
<223> OTHER INFORMATION: pelB-CD3VH-scFvCD138-6His

<400> SEQUENCE: 121

Met Lys Tyr Leu Leu Pro Thr Ala Ala Ala Gly Leu Leu Leu Leu Ala
1               5                   10                  15

Ala Gln Pro Ala Met Ala Asp Ile Lys Leu Gln Gln Ser Gly Ala Glu
            20                  25                  30

Leu Ala Arg Pro Gly Ala Ser Val Lys Met Ser Cys Lys Thr Ser Gly
        35                  40                  45

Tyr Thr Phe Thr Arg Tyr Thr Met His Trp Val Lys Gln Arg Pro Gly
    50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Tyr Tyr Asp Asp His Tyr Cys Leu
        115                 120                 125

Asp Tyr Trp Gly Gln Gly Thr Thr Leu Thr Val Ser Ser Gly Gly Gly
```

```
            130                 135                 140
Gly Ser Gly Gly Gly Ser Gly Gly Gly Ser Gln Val Gln Leu
145                 150                 155                 160

Gln Gln Ser Gly Ser Glu Leu Met Pro Gly Ala Ser Val Lys Ile Ser
                165                 170                 175

Cys Lys Ala Thr Gly Tyr Thr Phe Ser Asn Tyr Trp Ile Glu Trp Val
                180                 185                 190

Lys Gln Arg Pro Gly His Gly Leu Glu Trp Ile Gly Glu Ile Leu Pro
                195                 200                 205

Gly Thr Gly Arg Thr Ile Tyr Asn Glu Lys Phe Lys Gly Lys Ala Thr
    210                 215                 220

Phe Thr Ala Asp Ile Ser Ser Asn Thr Val Gln Met Gln Leu Ser Ser
225                 230                 235                 240

Leu Thr Ser Glu Asp Ser Ala Val Tyr Tyr Cys Ala Arg Glu Gln Tyr
                245                 250                 255

Tyr Gly Asn Phe Tyr Tyr Ala Met Asp Tyr Trp Gly Gln Gly Thr Ser
                260                 265                 270

Val Thr Val Ser Ser Gly Gly Gly Gly Ser Gly Gly Gly Gly Ser Gly
    275                 280                 285

Gly Gly Ser Asp Ile Gln Met Thr Gln Ser Thr Ser Ser Leu Ser
    290                 295                 300

Ala Ser Leu Gly Asp Arg Val Thr Ile Ser Cys Ser Ala Ser Gln Gly
305                 310                 315                 320

Ile Asn Asn Tyr Leu Asn Trp Tyr Gln Gln Lys Pro Asp Gly Thr Val
                325                 330                 335

Glu Leu Leu Ile Tyr Tyr Thr Ser Thr Leu Gln Ser Gly Val Pro Ser
                340                 345                 350

Arg Phe Ser Gly Ser Gly Ser Gly Thr Asp Tyr Ser Leu Thr Ile Ser
                355                 360                 365

Asn Leu Glu Pro Glu Asp Ile Gly Thr Tyr Tyr Cys Gln Gln Tyr Ser
    370                 375                 380

Lys Leu Pro Arg Thr Phe Gly Gly Gly Thr Lys Leu Glu Ile Lys Arg
385                 390                 395                 400

Thr Val His His His His His
            405

<210> SEQ ID NO 122
<211> LENGTH: 404
<212> TYPE: PRT
<213> ORGANISM: Artificial Sequence
<220> FEATURE:
<223> OTHER INFORMATION: pelB-(aHis)VH-scFvHLA-A2(VH-VL)-myc

<400> SEQUENCE: 122

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Pro Glu
                20                  25                  30

Asp Val Lys Pro Gly Ala Ser Val Lys Ile Ser Cys Lys Ala Ser Gly
            35                  40                  45

Tyr Thr Phe Thr Asp Tyr Tyr Met Asn Trp Val Lys Gln Ser Pro Gly
    50                  55                  60

Lys Gly Leu Glu Trp Ile Gly Asp Ile Asn Pro Asn Asn Gly Gly Thr
65              70                  75                  80

Ser Tyr Asn Gln Lys Phe Lys Gly Arg Ala Thr Leu Thr Val Asp Lys
```

85                  90                  95
Ser Ser Ser Thr Ala Tyr Met Glu Leu Arg Ser Leu Thr Ser Glu Asp
                100                 105                 110

Ser Ser Val Tyr Tyr Cys Glu Ser Gln Ser Gly Ala Tyr Trp Gly Gln
            115                 120                 125

Gly Thr Thr Val Thr Val Ser Ala Gly Gly Gly Ser Gly Gly Gly
        130                 135                 140

Gly Ser Gly Gly Gln Val Gln Leu Val Gln Ser Gly Gly Val Val
145                 150                 155                 160

Gln Pro Gly Gly Ser Leu Arg Val Ser Cys Ala Ala Ser Gly Val Thr
                165                 170                 175

Leu Ser Asp Tyr Gly Met His Trp Val Arg Gln Ala Pro Gly Lys Gly
                180                 185                 190

Leu Glu Trp Met Ala Phe Ile Arg Asn Asp Gly Ser Asp Lys Tyr Tyr
                195                 200                 205

Ala Asp Ser Val Lys Gly Arg Phe Thr Ile Ser Arg Asp Asn Ser Lys
            210                 215                 220

Lys Thr Val Ser Leu Gln Met Ser Ser Leu Arg Ala Glu Asp Thr Ala
225                 230                 235                 240

Val Tyr Tyr Cys Ala Lys Asn Gly Glu Ser Gly Pro Leu Asp Tyr Trp
                245                 250                 255

Tyr Phe Asp Leu Trp Gly Arg Gly Thr Leu Val Thr Val Ser Ser Gly
            260                 265                 270

Gly Gly Gly Ser Gly Gly Gly Gly Ser Gly Gly Gly Gly Ser Asp Val
            275                 280                 285

Val Met Thr Gln Ser Pro Ser Ser Leu Ser Ala Ser Val Gly Asp Arg
        290                 295                 300

Val Thr Ile Thr Cys Gln Ala Ser Gln Asp Ile Ser Asn Tyr Leu Asn
305                 310                 315                 320

Trp Tyr Gln Gln Lys Pro Gly Lys Ala Pro Lys Leu Leu Ile Tyr Asp
                325                 330                 335

Ala Ser Asn Leu Glu Thr Gly Val Pro Ser Arg Phe Ser Gly Ser Gly
            340                 345                 350

Ser Gly Thr Asp Phe Thr Phe Thr Ile Ser Ser Leu Gln Pro Glu Asp
        355                 360                 365

Phe Ala Thr Tyr Tyr Cys Gln Gln Tyr Ser Ser Phe Pro Leu Thr Phe
    370                 375                 380

Gly Gly Gly Thr Lys Val Asp Ile Lys Arg Glu Gln Lys Leu Ile Ser
385                 390                 395                 400

Glu Glu Asp Leu

<210> SEQ ID NO 123
<211> LENGTH: 410
<212> TYPE: PRT
<213> ORGANISM: Artificial Sequence
<220> FEATURE:
<223> OTHER INFORMATION: pelB-(aHis)VL-scFvCD45(VL-VH)-myc

<400> SEQUENCE: 123

Met Lys Tyr Leu Leu Pro Thr Ala Ala Ala Gly Leu Leu Leu Leu Ala
1               5                   10                  15

Ala Gln Pro Ala Met Ala Asp Tyr Lys Asp Ile Leu Met Thr Gln Thr
            20                  25                  30

Pro Ser Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Phe Thr Phe
            115                 120                 125

Gly Ser Gly Thr Lys Leu Glu Ile Lys Arg Gly Gly Gly Gly Ser Gly
130                 135                 140

Gly Gly Gly Ser Gly Gly Asp Ile Val Leu Thr Gln Ser Pro Ala Ser
145                 150                 155                 160

Leu Ala Val Ser Leu Gly Gln Arg Ala Thr Ile Ser Cys Arg Ala Ser
                165                 170                 175

Lys Ser Val Ser Thr Ser Gly Tyr Ser Tyr Leu His Trp Tyr Gln Gln
            180                 185                 190

Lys Pro Gly Gln Pro Pro Lys Leu Leu Ile Tyr Leu Ala Ser Asn Leu
        195                 200                 205

Glu Ser Gly Val Pro Ala Arg Phe Ser Gly Ser Gly Ser Gly Thr Asp
210                 215                 220

Phe Thr Leu Asn Ile His Pro Val Glu Glu Glu Asp Ala Ala Thr Tyr
225                 230                 235                 240

Tyr Cys Gln His Ser Arg Glu Leu Pro Phe Thr Phe Gly Ser Gly Thr
                245                 250                 255

Lys Leu Glu Ile Lys Lys Ile Ser Gly Gly Gly Gly Ser Gly Gly Gly
            260                 265                 270

Gly Ser Gly Gly Gly Ser Ser Gln Val Gln Leu Val Glu Ser Gly
        275                 280                 285

Gly Gly Leu Val Gln Pro Gly Gly Ser Leu Lys Leu Ser Cys Ala Ala
290                 295                 300

Ser Gly Phe Asp Phe Ser Arg Tyr Trp Met Ser Trp Val Arg Gln Ala
305                 310                 315                 320

Pro Gly Lys Gly Leu Glu Trp Ile Gly Glu Ile Asn Pro Thr Ser Ser
                325                 330                 335

Thr Ile Asn Phe Thr Pro Ser Leu Lys Asp Lys Val Phe Ile Ser Arg
            340                 345                 350

Asp Asn Ala Lys Asn Thr Leu Tyr Leu Gln Met Ser Lys Val Arg Ser
        355                 360                 365

Glu Asp Thr Ala Leu Tyr Tyr Cys Ala Arg Gly Asn Tyr Tyr Arg Tyr
370                 375                 380

Gly Asp Ala Met Asp Tyr Trp Gly Gln Gly Thr Ser Val Thr Val Ser
385                 390                 395                 400

Glu Gln Lys Leu Ile Ser Glu Glu Asp Leu
            405                 410

<210> SEQ ID NO 124
<211> LENGTH: 415
<212> TYPE: PRT
<213> ORGANISM: Artificial Sequence
<220> FEATURE:
<223> OTHER INFORMATION: pelB-(aCD3)VH-scFvHLA-A2(VH-VL)-myc-6His

<400> SEQUENCE: 124

```
Met Lys Tyr Leu Leu Pro Thr Ala Ala Ala Gly Leu Leu Leu Ala
 1               5                  10                  15

Ala Gln Pro Ala Met Ala Asp Ile Lys Leu Gln Gln Ser Gly Ala Glu
            20                  25                  30

Leu Ala Arg Pro Gly Ala Ser Val Lys Met Ser Cys Lys Thr Ser Gly
        35                  40                  45

Tyr Thr Phe Thr Arg Tyr Thr Met His Trp Val Lys Gln Arg Pro Gly
    50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Tyr Tyr Asp Asp His Tyr Cys Leu
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gln Val Gln Leu Val Gln Ser
145                 150                 155                 160

Gly Gly Gly Val Val Gln Pro Gly Gly Ser Leu Arg Val Ser Cys Ala
                165                 170                 175

Ala Ser Gly Val Thr Leu Ser Asp Tyr Gly Met His Trp Val Arg Gln
            180                 185                 190

Ala Pro Gly Lys Gly Leu Glu Trp Met Ala Phe Ile Arg Asn Asp Gly
        195                 200                 205

Ser Asp Lys Tyr Tyr Ala Asp Ser Val Lys Gly Arg Phe Thr Ile Ser
    210                 215                 220

Arg Asp Asn Ser Lys Lys Thr Val Ser Leu Gln Met Ser Ser Leu Arg
225                 230                 235                 240

Ala Glu Asp Thr Ala Val Tyr Tyr Cys Ala Lys Asn Gly Glu Ser Gly
                245                 250                 255

Pro Leu Asp Tyr Trp Tyr Phe Asp Leu Trp Gly Arg Gly Thr Leu Val
            260                 265                 270

Thr Val Ser Ser Gly Gly Gly Ser Gly Gly Gly Gly Ser Gly Gly
        275                 280                 285

Gly Gly Ser Asp Val Val Met Thr Gln Ser Pro Ser Ser Leu Ser Ala
        290                 295                 300

Ser Val Gly Asp Arg Val Thr Ile Thr Cys Gln Ala Ser Gln Asp Ile
305                 310                 315                 320

Ser Asn Tyr Leu Asn Trp Tyr Gln Gln Lys Pro Gly Lys Ala Pro Lys
                325                 330                 335

Leu Leu Ile Tyr Asp Ala Ser Asn Leu Glu Thr Gly Val Pro Ser Arg
            340                 345                 350

Phe Ser Gly Ser Gly Ser Gly Thr Asp Phe Thr Phe Thr Ile Ser Ser
        355                 360                 365

Leu Gln Pro Glu Asp Phe Ala Thr Tyr Tyr Cys Gln Gln Tyr Ser Ser
    370                 375                 380

Phe Pro Leu Thr Phe Gly Gly Gly Thr Lys Val Asp Ile Lys Arg Glu
385                 390                 395                 400

Gln Lys Leu Ile Ser Glu Glu Asp Leu His His His His His
                405                 410                 415
```

<210> SEQ ID NO 125
<211> LENGTH: 406
<212> TYPE: PRT
<213> ORGANISM: Artificial Sequence
<220> FEATURE:
<223> OTHER INFORMATION: pelB-(aCD3)VL-scFvCD45(VL-VH)-myc-6His

<400> SEQUENCE: 125

```
Met Lys Tyr Leu Leu Pro Thr Ala Ala Ala Gly Leu Leu Leu Leu Ala
1               5                   10                  15

Ala Gln Pro Ala Met Ala Asp Ile Gln Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Ser Val Ser Tyr Met Asn Trp Tyr Gln Gln Lys Ser Gly Thr Ser
    50                  55                  60

Pro Lys Arg Trp Ile Tyr Asp Thr Ser Lys Val Ala Ser Gly Val Pro
65                  70                  75                  80

Tyr Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

Gly Gly Gly Gly Ser Gly Gly Gly Ser Gly Gly Asp Ile Val Leu
    130                 135                 140

Thr Gln Ser Pro Ala Ser Leu Ala Val Ser Leu Gly Gln Arg Ala Thr
145                 150                 155                 160

Ile Ser Cys Arg Ala Ser Lys Ser Val Ser Thr Ser Gly Tyr Ser Tyr
                165                 170                 175

Leu His Trp Tyr Gln Gln Lys Pro Gly Gln Pro Pro Lys Leu Leu Ile
            180                 185                 190

Tyr Leu Ala Ser Asn Leu Glu Ser Gly Val Pro Ala Arg Phe Ser Gly
        195                 200                 205

Ser Gly Ser Gly Thr Asp Phe Thr Leu Asn Ile His Pro Val Glu Glu
    210                 215                 220

Glu Asp Ala Ala Thr Tyr Tyr Cys Gln His Ser Arg Glu Leu Pro Phe
225                 230                 235                 240

Thr Phe Gly Ser Gly Thr Lys Leu Glu Ile Lys Lys Ile Ser Gly Gly
                245                 250                 255

Gly Gly Ser Gly Gly Gly Ser Gly Gly Gly Ser Ser Gln Val
        260                 265                 270

Gln Leu Val Glu Ser Gly Gly Gly Leu Val Gln Pro Gly Gly Ser Leu
    275                 280                 285

Lys Leu Ser Cys Ala Ala Ser Gly Phe Asp Phe Ser Arg Tyr Trp Met
290                 295                 300

Ser Trp Val Arg Gln Ala Pro Gly Lys Gly Leu Glu Trp Ile Gly Glu
305                 310                 315                 320

Ile Asn Pro Thr Ser Ser Thr Ile Asn Phe Thr Pro Ser Leu Lys Asp
                325                 330                 335

Lys Val Phe Ile Ser Arg Asp Asn Ala Lys Asn Thr Leu Tyr Leu Gln
            340                 345                 350

Met Ser Lys Val Arg Ser Glu Asp Thr Ala Leu Tyr Tyr Cys Ala Arg
        355                 360                 365
```

```
Gly Asn Tyr Tyr Arg Tyr Gly Asp Ala Met Asp Tyr Trp Gly Gln Gly
    370             375                 380

Thr Ser Val Thr Val Ser Glu Gln Lys Leu Ile Ser Glu Glu Asp Leu
385             390                 395                 400

His His His His His His
                405

<210> SEQ ID NO 126
<211> LENGTH: 415
<212> TYPE: PRT
<213> ORGANISM: Artificial Sequence
<220> FEATURE:
<223> OTHER INFORMATION: pelB-VHaDIG-scFvEGFR-FLAG-6HIS

<400> SEQUENCE: 126

Met Lys Tyr Leu Leu Pro Thr Ala Ala Gly Leu Leu Leu Leu Ala
1               5                   10                  15

Ala Gln Pro Ala Met Ala Glu Val Gln Leu Val Glu Ser Gly Gly Gly
                20                  25                  30

Leu Val Lys Pro Gly Gly Ser Leu Lys Leu Ser Cys Ala Val Ser Gly
            35                  40                  45

Phe Thr Phe Ser Asp Tyr Ala Met Ser Trp Ile Arg Gln Thr Pro Glu
    50                  55                  60

Asn Arg Leu Glu Trp Val Ala Ser Ile Asn Ile Gly Ala Thr Tyr Ala
65                  70                  75                  80

Tyr Tyr Pro Asp Ser Val Lys Gly Arg Phe Thr Ile Ser Arg Asp Asn
                85                  90                  95

Ala Lys Asn Thr Leu Phe Leu Gln Met Ser Ser Leu Gly Ser Glu Asp
            100                 105                 110

Thr Ala Met Tyr Tyr Cys Ala Arg Pro Gly Ser Pro Tyr Glu Tyr Asp
        115                 120                 125

Lys Ala Tyr Tyr Ser Met Ala Tyr Trp Gly Pro Gly Thr Ser Val Thr
    130                 135                 140

Val Ser Ser Ala Lys Thr Gly Gly Gly Gly Ser Gly Gly Gly Gly Ser
145                 150                 155                 160

Gln Val Gln Leu Gln Glu Ser Gly Pro Gly Leu Val Lys Pro Ser Glu
                165                 170                 175

Thr Leu Ser Leu Thr Cys Thr Val Ser Gly Gly Ser Val Ser Ser Gly
            180                 185                 190

Asp Tyr Tyr Trp Thr Trp Ile Arg Gln Ser Pro Gly Lys Gly Leu Glu
        195                 200                 205

Trp Ile Gly His Ile Tyr Tyr Ser Gly Asn Thr Asn Tyr Asn Pro Ser
    210                 215                 220

Leu Lys Ser Arg Leu Thr Ile Ser Ile Asp Thr Ser Lys Thr Gln Phe
225                 230                 235                 240

Ser Leu Lys Leu Ser Ser Val Thr Ala Ala Asp Thr Ala Ile Tyr Tyr
                245                 250                 255

Cys Val Arg Asp Arg Val Thr Gly Ala Phe Asp Ile Trp Gly Gln Gly
            260                 265                 270

Thr Met Val Thr Val Ser Ser Gly Gly Gly Gly Ser Gly Gly Gly Gly
        275                 280                 285

Ser Gly Gly Gly Gly Ser Asp Ile Gln Met Thr Gln Ser Pro Ser Ser
    290                 295                 300

Leu Ser Ala Ser Val Gly Asp Arg Val Thr Ile Thr Cys Gln Ala Ser
305                 310                 315                 320
```

Gln Asp Ile Ser Asn Tyr Leu Asn Trp Tyr Gln Gln Lys Pro Gly Lys
            325                 330                 335

Ala Pro Lys Leu Leu Ile Tyr Asp Ala Ser Asn Leu Glu Thr Gly Val
        340                 345                 350

Pro Ser Arg Phe Ser Gly Ser Gly Ser Gly Thr Asp Phe Thr Phe Thr
        355                 360                 365

Ile Ser Ser Leu Gln Pro Glu Asp Ile Ala Thr Tyr Phe Cys Gln His
    370                 375                 380

Phe Asp His Leu Pro Leu Ala Phe Gly Gly Gly Thr Lys Val Glu Ile
385                 390                 395                 400

Lys Asp Tyr Lys Asp Asp Asp Lys His His His His His
                405                 410                 415

<210> SEQ ID NO 127
<211> LENGTH: 412
<212> TYPE: PRT
<213> ORGANISM: Artificial Sequence
<220> FEATURE:
<223> OTHER INFORMATION: pelB-VLaDIG-scFvEpCAM-myc-6HIS

<400> SEQUENCE: 127

Met Lys Tyr Leu Leu Pro Thr Ala Ala Ala Gly Leu Leu Leu Leu Ala
1               5                   10                  15

Ala Gln Pro Ala Met Ala Asp Val Gln Met Thr Gln Ser Thr Ser Ser
            20                  25                  30

Leu Ser Ala Ser Leu Gly Asp Arg Val Thr Ile Ser Cys Arg Ala Ser
        35                  40                  45

Gln Asp Ile Lys Asn Tyr Leu Asn Trp Tyr Gln Gln Lys Pro Gly Gly
    50                  55                  60

Thr Val Lys Leu Leu Ile Tyr Tyr Ser Ser Thr Leu Leu Ser Gly Val
65                  70                  75                  80

Pro Ser Arg Phe Ser Gly Arg Gly Ser Gly Thr Asp Phe Ser Leu Thr
                85                  90                  95

Ile Thr Asn Leu Glu Arg Glu Asp Ile Ala Thr Tyr Phe Cys Gln Gln
            100                 105                 110

Ser Ile Thr Leu Pro Pro Thr Phe Gly Gly Gly Thr Lys Leu Glu Ile
        115                 120                 125

Lys Arg Ala Asp Ala Ala Pro Thr Val Ser Ile Phe Gly Gly Ser Gly
    130                 135                 140

Gly Gly Gly Ser Glu Val Gln Leu Leu Glu Gln Ser Gly Ala Glu Leu
145                 150                 155                 160

Val Arg Pro Gly Thr Ser Val Lys Ile Ser Cys Lys Ala Ser Gly Tyr
                165                 170                 175

Ala Phe Thr Asn Tyr Trp Leu Gly Trp Val Lys Gln Arg Pro Gly His
            180                 185                 190

Gly Leu Glu Trp Ile Gly Asp Ile Phe Pro Gly Ser Gly Asn Ile His
        195                 200                 205

Tyr Asn Glu Lys Phe Lys Gly Lys Ala Thr Leu Thr Ala Asp Lys Ser
    210                 215                 220

Ser Ser Thr Ala Tyr Met Gln Leu Ser Ser Leu Thr Phe Glu Asp Ser
225                 230                 235                 240

Ala Val Tyr Phe Cys Ala Arg Leu Arg Asn Trp Asp Glu Pro Met Asp
                245                 250                 255

Tyr Trp Gly Gln Gly Thr Thr Val Thr Val Ser Ser Gly Gly Gly Gly
            260                 265                 270

```
Ser Gly Gly Gly Gly Ser Gly Gly Gly Ser Glu Leu Val Met Thr
            275                 280             285
Gln Ser Pro Ser Ser Leu Thr Val Thr Ala Gly Glu Lys Val Thr Met
    290                 295                 300
Ser Cys Lys Ser Gln Ser Leu Leu Asn Ser Gly Asn Gln Lys Asn
305                 310                 315                 320
Tyr Leu Thr Trp Tyr Gln Gln Lys Pro Gly Gln Pro Pro Lys Leu Leu
                325                 330                 335
Ile Tyr Trp Ala Ser Thr Arg Glu Ser Gly Val Pro Asp Arg Phe Thr
                340                 345                 350
Gly Ser Gly Ser Gly Thr Asp Phe Thr Leu Thr Ile Ser Ser Val Gln
            355                 360                 365
Ala Glu Asp Leu Ala Val Tyr Tyr Cys Gln Asn Asp Tyr Ser Tyr Pro
    370                 375                 380
Leu Thr Phe Gly Ala Gly Thr Lys Leu Glu Ile Lys Glu Gln Lys Leu
385                 390                 395                 400
Ile Ser Glu Glu Asp Leu His His His His His His
                405                 410

<210> SEQ ID NO 128
<211> LENGTH: 400
<212> TYPE: PRT
<213> ORGANISM: Artificial Sequence
<220> FEATURE:
<223> OTHER INFORMATION: pelB-murineCD3VH-scFvEpCAM-6His

<400> SEQUENCE: 128

Met Lys Tyr Leu Leu Pro Thr Ala Ala Ala Gly Leu Leu Leu Leu Ala
1               5                   10                  15
Ala Gln Pro Ala Met Ala Glu Val Gln Leu Val Glu Ser Gly Gly Gly
            20                  25                  30
Leu Val Gln Pro Gly Lys Ser Leu Lys Leu Ser Cys Glu Ala Ser Gly
        35                  40                  45
Phe Thr Phe Ser Gly Tyr Gly Met His Trp Val Arg Gln Ala Pro Gly
    50                  55                  60
Arg Gly Leu Glu Ser Val Ala Tyr Ile Thr Ser Ser Ile Asn Ile
65                  70                  75                  80
Lys Tyr Ala Asp Ala Val Lys Gly Arg Phe Thr Val Ser Arg Asp Asn
                85                  90                  95
Ala Lys Asn Leu Leu Phe Leu Gln Met Asn Ile Leu Lys Ser Glu Asp
            100                 105                 110
Thr Ala Met Tyr Tyr Cys Ala Arg Phe Asp Trp Asp Lys Asn Tyr Trp
        115                 120                 125
Gly Gln Gly Thr Met Val Thr Val Ser Ser Ala Lys Thr Ser Ser Gly
    130                 135                 140
Gly Gly Glu Val Gln Leu Leu Glu Gln Ser Gly Ala Glu Leu Val Arg
145                 150                 155                 160
Pro Gly Thr Ser Val Lys Ile Ser Cys Lys Ala Ser Gly Tyr Ala Phe
                165                 170                 175
Thr Asn Tyr Trp Leu Gly Trp Val Lys Gln Arg Pro Gly His Gly Leu
            180                 185                 190
Glu Trp Ile Gly Asp Ile Phe Pro Gly Ser Gly Asn Ile His Tyr Asn
        195                 200                 205
Glu Lys Phe Lys Gly Lys Ala Thr Leu Thr Ala Asp Lys Ser Ser Ser
    210                 215                 220
```

```
Thr Ala Tyr Met Gln Leu Ser Ser Leu Thr Phe Glu Asp Ser Ala Val
225                 230                 235                 240

Tyr Phe Cys Ala Arg Leu Arg Asn Trp Asp Glu Pro Met Asp Tyr Trp
                245                 250                 255

Gly Gln Gly Thr Thr Val Thr Val Ser Ser Gly Gly Gly Gly Ser Gly
            260                 265                 270

Gly Gly Ser Gly Gly Gly Ser Glu Leu Val Met Thr Gln Ser
275                 280                 285

Pro Ser Ser Leu Thr Val Thr Ala Gly Glu Lys Val Thr Met Ser Cys
        290                 295                 300

Lys Ser Ser Gln Ser Leu Leu Asn Ser Gly Asn Gln Lys Asn Tyr Leu
305                 310                 315                 320

Thr Trp Tyr Gln Gln Lys Pro Gly Gln Pro Lys Leu Leu Ile Tyr
                325                 330                 335

Trp Ala Ser Thr Arg Glu Ser Gly Val Pro Asp Arg Phe Thr Gly Ser
                340                 345                 350

Gly Ser Gly Thr Asp Phe Thr Leu Thr Ile Ser Ser Val Gln Ala Glu
            355                 360                 365

Asp Leu Ala Val Tyr Tyr Cys Gln Asn Asp Tyr Ser Tyr Pro Leu Thr
370                 375                 380

Phe Gly Ala Gly Thr Lys Leu Glu Ile Lys His His His His His His
385                 390                 395                 400

<210> SEQ ID NO 129
<211> LENGTH: 384
<212> TYPE: PRT
<213> ORGANISM: Artificial Sequence
<220> FEATURE:
<223> OTHER INFORMATION: pelB-murineCD3VL-scFvEGFR1-6His

<400> SEQUENCE: 129

Met Lys Tyr Leu Leu Pro Thr Ala Ala Ala Gly Leu Leu Leu Leu Ala
1               5                   10                  15

Ala Gln Pro Ala Met Ala Asp Ile Gln Met Thr Gln Ser Pro Ser Ser
                20                  25                  30

Leu Pro Ala Ser Leu Gly Asp Arg Val Thr Ile Asn Cys Gln Ala Ser
            35                  40                  45

Gln Asp Ile Ser Asn Tyr Leu Asn Trp Tyr Gln Gln Lys Pro Gly Lys
50                  55                  60

Ala Pro Lys Leu Leu Ile Tyr Tyr Thr Asn Lys Leu Ala Asp Gly Val
65                  70                  75                  80

Pro Ser Arg Phe Ser Gly Ser Gly Ser Gly Arg Asp Ser Ser Phe Thr
                85                  90                  95

Ile Ser Ser Leu Glu Ser Glu Asp Ile Gly Ser Tyr Tyr Cys Gln Gln
            100                 105                 110

Tyr Tyr Asn Tyr Pro Trp Thr Phe Gly Pro Gly Thr Lys Leu Glu Ile
            115                 120                 125

Lys Arg Ala Asp Ser Ser Gly Gly Gln Val Gln Leu Gln Glu Ser
130                 135                 140

Gly Pro Gly Leu Val Lys Pro Ser Glu Thr Leu Ser Leu Thr Cys Thr
145                 150                 155                 160

Val Ser Gly Gly Ser Val Ser Ser Gly Asp Tyr Tyr Trp Thr Trp Ile
                165                 170                 175

Arg Gln Ser Pro Gly Lys Gly Leu Glu Trp Ile Gly His Ile Tyr Tyr
            180                 185                 190
```

```
Ser Gly Asn Thr Asn Tyr Asn Pro Ser Leu Lys Ser Arg Leu Thr Ile
            195                 200                 205

Ser Ile Asp Thr Ser Lys Thr Gln Phe Ser Leu Lys Leu Ser Ser Val
    210                 215                 220

Thr Ala Ala Asp Thr Ala Ile Tyr Tyr Cys Val Arg Asp Arg Val Thr
225                 230                 235                 240

Gly Ala Phe Asp Ile Trp Gly Gln Gly Thr Met Val Thr Val Ser Ser
                245                 250                 255

Gly Gly Gly Gly Ser Gly Gly Gly Ser Gly Gly Gly Gly Ser Asp
                260                 265                 270

Ile Gln Met Thr Gln Ser Pro Ser Ser Leu Ser Ala Ser Val Gly Asp
            275                 280                 285

Arg Val Thr Ile Thr Cys Gln Ala Ser Gln Asp Ile Ser Asn Tyr Leu
290                 295                 300

Asn Trp Tyr Gln Gln Lys Pro Gly Lys Ala Pro Lys Leu Leu Ile Tyr
305                 310                 315                 320

Asp Ala Ser Asn Leu Glu Thr Gly Val Pro Ser Arg Phe Ser Gly Ser
                325                 330                 335

Gly Ser Gly Thr Asp Phe Thr Phe Thr Ile Ser Ser Leu Gln Pro Glu
                340                 345                 350

Asp Ile Ala Thr Tyr Phe Cys Gln His Phe Asp His Leu Pro Leu Ala
                355                 360                 365

Phe Gly Gly Gly Thr Lys Val Glu Ile Lys His His His His His His
                370                 375                 380

<210> SEQ ID NO 130
<211> LENGTH: 558
<212> TYPE: PRT
<213> ORGANISM: Artificial Sequence
<220> FEATURE:
<223> OTHER INFORMATION: pelB-ta(DIG*EpCAM)-Myc-6HIS

<400> SEQUENCE: 130

Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Glu Ser Gly Gly Gly
            20                  25                  30

Leu Val Lys Pro Gly Gly Ser Leu Lys Leu Ser Cys Ala Val Ser Gly
        35                  40                  45

Phe Thr Phe Ser Asp Tyr Ala Met Ser Trp Ile Arg Gln Thr Pro Glu
    50                  55                  60

Asn Arg Leu Glu Trp Val Ala Ser Ile Asn Ile Gly Ala Thr Tyr Ala
65                  70                  75                  80

Tyr Tyr Pro Asp Ser Val Lys Gly Arg Phe Thr Ile Ser Arg Asp Asn
                85                  90                  95

Ala Lys Asn Thr Leu Phe Leu Gln Met Ser Ser Leu Gly Ser Glu Asp
            100                 105                 110

Thr Ala Met Tyr Tyr Cys Ala Arg Pro Gly Ser Pro Tyr Glu Tyr Asp
        115                 120                 125

Lys Ala Tyr Tyr Ser Met Ala Tyr Trp Gly Pro Gly Thr Ser Val Thr
    130                 135                 140

Val Ser Ser Ala Lys Thr Ser Ser Gly Gly Gly Ser Gly Gly Gly
145                 150                 155                 160

Gly Ser Gly Gly Gly Ser Gly Asp Val Gln Met Thr Gln Ser Thr
                165                 170                 175
```

Ser Ser Leu Ser Ala Ser Leu Gly Asp Arg Val Thr Ile Ser Cys Arg
            180                 185                 190

Ala Ser Gln Asp Ile Lys Asn Tyr Leu Asn Trp Tyr Gln Gln Lys Pro
        195                 200                 205

Gly Gly Thr Val Lys Leu Leu Ile Tyr Tyr Ser Ser Thr Leu Leu Ser
    210                 215                 220

Gly Val Pro Ser Arg Phe Ser Gly Arg Gly Ser Gly Thr Asp Phe Ser
225                 230                 235                 240

Leu Thr Ile Thr Asn Leu Glu Arg Glu Asp Ile Ala Thr Tyr Phe Cys
                245                 250                 255

Gln Gln Ser Ile Thr Leu Pro Pro Thr Phe Gly Gly Gly Thr Lys Leu
            260                 265                 270

Glu Ile Lys Arg Ala Asp Ala Ala Pro Thr Val Ser Ile Phe Gly Gly
        275                 280                 285

Ser Gly Gly Gly Ser Glu Val Gln Leu Leu Glu Gln Ser Gly Ala
    290                 295                 300

Glu Leu Val Arg Pro Gly Thr Ser Val Lys Ile Ser Cys Lys Ala Ser
305                 310                 315                 320

Gly Tyr Ala Phe Thr Asn Tyr Trp Leu Gly Trp Val Lys Gln Arg Pro
                325                 330                 335

Gly His Gly Leu Glu Trp Ile Gly Asp Ile Phe Pro Gly Ser Gly Asn
            340                 345                 350

Ile His Tyr Asn Glu Lys Phe Lys Gly Lys Ala Thr Leu Thr Ala Asp
        355                 360                 365

Lys Ser Ser Ser Thr Ala Tyr Met Gln Leu Ser Ser Leu Thr Phe Glu
370                 375                 380

Asp Ser Ala Val Tyr Phe Cys Ala Arg Leu Arg Asn Trp Asp Glu Pro
                390                 395                 400
385

Met Asp Tyr Trp Gly Gln Gly Thr Thr Val Thr Val Ser Ser Gly Gly
            405                 410                 415

Gly Gly Ser Gly Gly Gly Ser Gly Gly Gly Ser Glu Leu Val
        420                 425                 430

Met Thr Gln Ser Pro Ser Ser Leu Thr Val Thr Ala Gly Glu Lys Val
    435                 440                 445

Thr Met Ser Cys Lys Ser Ser Gln Ser Leu Leu Asn Ser Gly Asn Gln
450                 455                 460

Lys Asn Tyr Leu Thr Trp Tyr Gln Gln Lys Pro Gly Gln Pro Pro Lys
465                 470                 475                 480

Leu Leu Ile Tyr Trp Ala Ser Thr Arg Glu Ser Gly Val Pro Asp Arg
                485                 490                 495

Phe Thr Gly Ser Gly Ser Gly Thr Asp Phe Thr Leu Thr Ile Ser Ser
            500                 505                 510

Val Gln Ala Glu Asp Leu Ala Val Tyr Tyr Cys Gln Asn Asp Tyr Ser
        515                 520                 525

Tyr Pro Leu Thr Phe Gly Ala Gly Thr Lys Leu Glu Ile Lys Glu Gln
    530                 535                 540

Lys Leu Ile Ser Glu Glu Asp Leu His His His His His His
545                 550                 555

<210> SEQ ID NO 131
<211> LENGTH: 9
<212> TYPE: PRT
<213> ORGANISM: Artificial Sequence
<220> FEATURE:
<223> OTHER INFORMATION: Anti-DIG VL CDR3

<400> SEQUENCE: 131

Gln Gln Ser Ile Thr Leu Pro Pro Thr
1               5

<210> SEQ ID NO 132
<211> LENGTH: 8
<212> TYPE: PRT
<213> ORGANISM: Artificial Sequence
<220> FEATURE:
<223> OTHER INFORMATION: Anti-CD45 VH CDR1

<400> SEQUENCE: 132

Gly Phe Asp Phe Ser Arg Tyr Trp
1               5

<210> SEQ ID NO 133
<211> LENGTH: 8
<212> TYPE: PRT
<213> ORGANISM: Artificial Sequence
<220> FEATURE:
<223> OTHER INFORMATION: Anti-CD45 VH CDR2

<400> SEQUENCE: 133

Ile Asn Pro Thr Ser Ser Thr Ile
1               5

<210> SEQ ID NO 134
<211> LENGTH: 14
<212> TYPE: PRT
<213> ORGANISM: Artificial Sequence
<220> FEATURE:
<223> OTHER INFORMATION: Anti-CD45 VH CDR3

<400> SEQUENCE: 134

Ala Arg Gly Asn Tyr Tyr Arg Tyr Gly Asp Ala Met Asp Tyr
1               5                   10

<210> SEQ ID NO 135
<211> LENGTH: 1167
<212> TYPE: DNA
<213> ORGANISM: Artificial Sequence
<220> FEATURE:
<223> OTHER INFORMATION: Nucleotide sequence encoding pelB-CD3VL-
      scFvEPCAM(VH-VL)-6His

<400> SEQUENCE: 135

| | | | |
|---|---|---|---|
| atgaaatacc tgctgccgac cgctgctgct ggtctgctgc tcctcgctgc ccagccggcg | 60 |
| atggccgaca ttcagctgac ccagtctcca gcaatcatgt ctgcatctcc aggggagaag | 120 |
| gtcaccatga cctgcagagc cagttcaagt gtaagttaca tgaactggta ccagcagaag | 180 |
| tcaggcaccct cccccaaaag atggatttat gacacatcca agtggcttc tggagtccct | 240 |
| tatcgcttca gtggcagtgg gtctgggacc tcatactctc tcacaatcag cagcatggag | 300 |
| gctgaagatg ctgccactta ttactgccaa cagtggagta gtaacccgct cacgttcggt | 360 |
| gctgggacca agctggagct gaaatccgga ggtggtggat ccgaggtgca gctgctcgag | 420 |
| cagtctggag ctgagctggt aaggcctggg acttcagtga agatatcctg caaggcttct | 480 |
| ggatacgcct tcactaacta ctggctaggt tgggtaaagc agaggcctgg acatggactt | 540 |
| gagtggattg agatattttt ccctggaagt ggtaatatcc actacaatga aagttcaag | 600 |
| ggcaaagcca cactgactgc agacaaatct tcgagcacag cctatatgca gctcagtagc | 660 |
| ctgacatttg aggactctgc tgtctatttc tgtgcaagac tgaggaactg ggacgagcct | 720 |

```
atggactact ggggccaagg gaccacggtc accgtctcct caggtggtgg tggttctggc    780
ggcggcggct ccggtggtgg tggttctgag ctcgtgatga cacagtctcc atcctccctg    840
actgtgacag caggagagaa ggtcactatg agctgcaagt ccagtcagag tctgttaaac    900
agtgaaatca aaagaacta cttgacctgg taccagcaga aaccagggca gcctcctaaa    960
ctgttgatct actgggcatc cactagggaa tctggggtcc ctgatcgctt cacaggcagt   1020
ggatctggaa cagatttcac tctcaccatc agcagtgtgc aggctgaaga cctggcagtt   1080
tattactgtc agaatgatta tagttatccg ctcacgttcg gtgctgggac caagcttgag   1140
atcaaacatc atcaccatca tcattag                                        1167
```

<210> SEQ ID NO 136
<211> LENGTH: 1215
<212> TYPE: DNA
<213> ORGANISM: Artificial Sequence
<220> FEATURE:
<223> OTHER INFORMATION: Nucleotide sequence encoding pelB-CD3VH-scFvHer2/neu-6HIS

<400> SEQUENCE: 136

```
atgaaatacc tgctgccgac cgctgctgct ggtctgctgc tcctcgctgc ccagccggcg     60
atggccgata tcaaactgca gcagtcaggg gctgaactgg caagacctgg ggcctcagtg    120
aagatgtcct gcaagacttc tggctacacc tttactaggt acacgatgca ctgggtaaaa    180
cagaggcctg gacagggtct ggaatggatt ggatacatta atcctagccg tggttatact    240
aattacaatc agaagttcaa ggacaaggcc acattgacta cagacaaatc ctccagcaca    300
gcctacatgc aactgagcag cctgacatct gaggactctg cagtctatta ctgtgcaaga    360
tattatgatg atcattactg ccttgactac tggggccaag gcaccactct cacagtctcc    420
tcaggtggtg gtggttctgg cggcggcggc tccggtggtg gtggttctga ggttcagctg    480
gtggagtctg gcggtggcct ggtgcagcca ggggggctcac tccgtttgtc ctgtgcagct    540
tctggcttca acattaaaga cacctatata cactgggtgc gtcaggcccc gggtaagggc    600
ctggaatggg ttgcaaggat ttatcctacg aatggttata ctagatatgc cgatagcgtc    660
aagggccgtt tcactataag cgcagacaca tccaaaaaca cagcctacct gcagatgaac    720
agcctgcgtc tgaggacac tgccgtctat tattgttcta ggtggggagg gacggcttc    780
tatgctatgg actattgggg tcaaggaacc ctggtcactg tctcctccgg tggtggtggt    840
tctggcggcg gcggctccgg tggtggtggt tctgatatcc agatgaccca gtccccgagc    900
tccctgtccg cctctgtggg cgataggtc accatcacct gccgtgccag tcaggatgtg    960
aatactgctg tagcctggta tcaacagaaa ccaggaaaag ctccgaaact actgatttac   1020
tcggcatcct tcctctactc tggagtccct tctcgcttct ctggatccag atctgggacg   1080
gatttcactc tgaccatcag cagtctgcag ccggaagact cgcaacttta ttactgtcag   1140
caacattata ctactcctcc cacgttcgga cagggtacca aggtggagat caaacatcat   1200
caccatcatc attag                                                    1215
```

<210> SEQ ID NO 137
<211> LENGTH: 1212
<212> TYPE: DNA
<213> ORGANISM: Artificial Sequence
<220> FEATURE:
<223> OTHER INFORMATION: Nucleotide sequence encoding pelB-CD3VH-scFvEGFR1-6HIS

<400> SEQUENCE: 137

```
atgaaatacc tgctgccgac cgctgctgct ggtctgctgc tcctcgctgc ccagccggcg      60
atggccgata tcaaactgca gcagtcaggg gctgaactgg caagacctgg ggcctcagtg     120
aagatgtcct gcaagacttc tggctacacc tttactaggt acacgatgca ctgggtaaaa     180
cagaggcctg gacagggtct ggaatggatt ggatacatta atcctagccg tggttatact     240
aattacaatc agaagttcaa ggacaaggcc acattgacta cagacaaatc ctccagcaca     300
gcctacatgc aactgagcag cctgacatct gaggactctg cagtctatta ctgtgcaaga     360
tattatgatg atcattactg ccttgactac tggggccaag gcaccactct cacagtctcc     420
tcaggtggtg gtggttctgg cggcggcggc tccggtggtg gtggttctca ggtgcagctg     480
caggagtcgg gcccaggact ggtgaagcct tcggagaccc tgtccctcac ctgcactgtc     540
tctggtggct ccgtcagcag tggtgattac tactggacct ggatccggca gtccccaggg     600
aagggactgg agtggattgg acacatctat acagtggga acaccaatta taaccccctcc    660
ctcaagagcc gactcaccat atcaattgac acgtccaaga ctcagttctc cctgaagctg     720
agttctgtga ccgctgcgga cacggccatt tattactgtg tgcgagatcg agtgactggt     780
gcttttgata tctggggcca agggacaatg gtcaccgtct cttccggtgg tggtggttct     840
ggcggcggcg gctccggtgg tggtggttct gacatccaga tgacccagtc tccatcctcc     900
ctgtctgcat ctgtcggaga cagagtcacc atcacttgcc aggcgagtca ggacatcagc     960
aactatttaa attggtatca gcagaaacca gggaaagccc ctaaactcct gatctacgat    1020
gcatccaatt tggaaacagg ggtcccatca aggttcagtg aagtggatc tgggacagat    1080
tttactttca ccatcagcag cctgcagcct gaagatattg caacatattt ctgtcaacac    1140
tttgatcatc tcccgctcgc tttcggcgga gggaccaagg tggagatcaa acatcatcac    1200
catcatcatt ag                                                       1212
```

<210> SEQ ID NO 138
<211> LENGTH: 1245
<212> TYPE: DNA
<213> ORGANISM: Artificial Sequence
<220> FEATURE:
<223> OTHER INFORMATION: Nucleotide sequence encoding pelB-CD3VH-
    scFvCEA-6HIS

<400> SEQUENCE: 138

```
atgaaatacc tgctgccgac cgctgctgct ggtctgctgc tcctcgctgc ccagccggcg      60
atggccgata tcaaactgca gcagtcaggg gctgaactgg caagacctgg ggcctcagtg     120
aagatgtcct gcaagacttc tggctacacc tttactaggt acacgatgca ctgggtaaaa     180
cagaggcctg gacagggtct ggaatggatt ggatacatta atcctagccg tggttatact     240
aattacaatc agaagttcaa ggacaaggcc acattgacta cagacaaatc ctccagcaca     300
gcctacatgc aactgagcag cctgacatct gaggactctg cagtctatta ctgtgcaaga     360
tattatgatg atcattactg ccttgactac tggggccaag gcaccactct cacagtctcc     420
tcaggtggtg gtggttctgg cggcggcggc tccggtggtg gtggttcttc tagagtggcc     480
caggtgcaac tgcagcagtc aggggctgag ctggctagac tgggggcttc agtgaagatg     540
tcctgcaagg cttctggcta cacctttact acctacacaa tacactgggt aagacagagg     600
cctggacacg atctggaatg gattggatac attaatccta gcagtggata ttctgactac     660
aatcaaaact tcaagggcaa gaccacattg actgcagaca agtcctccaa cacagcctac     720
```

| | |
|---|---|
| atgcaactga acagcctgac atctgaggac tctgcggtct attactgtgc aagaagagcg | 780 |
| gactatggta actacgaata tacctggttt gcttactggg gccaagggac cacggtcacc | 840 |
| gtctcctcag gtggaggcgg ttcaggcgga ggtggctctg gcggtggcgg atcggacatc | 900 |
| gagctcactc agtctccaaa attcatgtcc acatcagtag agacagggt caacgtcacc | 960 |
| tacaaggcca gtcagaatgt gggtactaat gtagcctggt tcaacaaaa accagggcaa | 1020 |
| tctcctaaag ttctgattta ctcggcatct taccgataca gtggagtccc tgatcgcttc | 1080 |
| acaggcagtg gatctggaac agatttcact ctcaccatca gcaatgtgca gtctgaagac | 1140 |
| ttggcagagt atttctgtca gcaatatcac acctatcctc tcacgttcgg agggggcacc | 1200 |
| aagctggaaa tcaaacgggc ggatcatcat caccatcatc attag | 1245 |

<210> SEQ ID NO 139
<211> LENGTH: 1179
<212> TYPE: DNA
<213> ORGANISM: Artificial Sequence
<220> FEATURE:
<223> OTHER INFORMATION: Nucleotide sequence encoding pelB-CD3VL-scFvCEA-6HIS

<400> SEQUENCE: 139

| | |
|---|---|
| atgaaatacc tgctgccgac cgctgctgct ggtctgctgc tcctcgctgc ccagccggcg | 60 |
| atggccgaca ttcagctgac ccagtctcca gcaatcatgt ctgcatctcc aggggagaag | 120 |
| gtcaccatga cctgcagagc cagttcaagt gtaagttaca tgaactggta ccagcagaag | 180 |
| tcaggcacct cccccaaaag atggatttat gacacatcca agtggcttc tggagtccct | 240 |
| tatcgcttca gtggcagtgg gtctgggacc tcatactctc tcacaatcag cagcatggag | 300 |
| gctgaagatg ctgccactta ttactgccaa cagtggagta gtaacccgct cacgttcggt | 360 |
| gctgggacca agctggagct gaaatccgga ggtggtggat cctctagagt ggcccaggtg | 420 |
| caactgcagc agtcagggc tgagctggct agacctgggg cttcagtgaa gatgtcctgc | 480 |
| aaggcttctg gctacacctt tactacctac acaatacact gggtaagaca gaggcctgga | 540 |
| cacgatctgg aatggattgg atacattaat cctagcagtg gatattctga ctacaatcaa | 600 |
| aacttcaagg gcaagaccac attgactgca gacaagtcct ccaacacagc ctacatgcaa | 660 |
| ctgaacagcc tgacatctga ggactctgcg gtctattact gtgcaagaag agcggactat | 720 |
| ggtaactacg aatatacctg gtttgcttac tggggccaag gaccacggt caccgtctcc | 780 |
| tcaggtggag gcggttcagg cggaggtggc tctggcggtg gcggatcgga catcgagctc | 840 |
| actcagtctc caaaattcat gtccacatca gtaggagaca gggtcaacgt cacctacaag | 900 |
| gccagtcaga atgtgggtac taatgtagcc tggtttcaac aaaaaccagg gcaatctcct | 960 |
| aaagttctga tttactcggc atcttaccga tacagtggag tccctgatcg cttcacaggc | 1020 |
| agtggatctg gaacagattt cactctcacc atcagcaatg tgcagtctga gacttggca | 1080 |
| gagtatttct gtcagcaata tcacacctat cctctcacgt tcggaggggg caccaagctg | 1140 |
| gaaatcaaac gggcggatca tcatcaccat catcattag | 1179 |

<210> SEQ ID NO 140
<211> LENGTH: 1245
<212> TYPE: DNA
<213> ORGANISM: Artificial Sequence
<220> FEATURE:
<223> OTHER INFORMATION: Nucleotide sequence encoding pelB-(aCD3)VH-scFvHLA-Cw6-myc-6His

<400> SEQUENCE: 140

```
atgaaatacc tgctgccgac cgctgctgct ggtctgctgc tcctcgctgc ccagccggcg      60
atggccgata tcaaactgca gcagtcaggg gctgaactgg caagacctgg ggcctcagtg     120
aagatgtcct gcaagacttc tggctacacc tttactaggt acacgatgca ctgggtaaaa     180
cagaggcctg gacagggtct ggaatggatt ggatacatta atcctagccg tggttatact     240
aattacaatc agaagttcaa ggacaaggcc acattgacta cagacaaatc ctccagcaca     300
gcctacatgc aactgagcag cctgacatct gaggactctg cagtctatta ctgtgcaaga     360
tattatgatg atcattactg ccttgactac tggggccaag gcaccactct cacagtctcc     420
tcaggcggcg gcggcagcgg cggcggcggc agcggcggcg aagtgcagct ggtggaaagc     480
ggcggcggcc tggtgcagcc gggcggcagc ctgcgcctga gctgcgcggc gagcggcttt     540
acctttagca gctatgcgat gagctgggtg cgccaggcgc cgggcaaagg cctggaatgg     600
gtgagcgcga ttagcggcag cggcggcagc acctatatg cggatagcgt gaaaggccgc      660
tttaccatta ccgcgataa cagcaaaaac accctgtatc tgcagatgaa cagcctgcgc     720
gcggaagata ccgcggtgta ttattgcgcg cgctatagct ttagctggtt tgatgtgtgg     780
ggccagggca ccctggtgac cgtgagcagc gcggcggcg cagcggcgg cggcggcagc      840 ggcggcggcg cagcggcgg cggcggcagc gatattgaac tgacccagcc gccgagcgtg     900
agcgtggcgc cggccagac cgcgcgcatt agctgcagcg gcgatgcgct gggcgataaa     960
tatgcgagct ggtatcagca gaaaccgggc caggcgccgg tgctggtgat ttatgatgat    1020
agcgatcgcc cgagcggcat tccggaacgc tttagcggca gcaacagcgg caacaccgcg    1080
accctgacca ttagcggcac ccaggcggaa gatgaagcgg attattattg ccagagctat    1140
gataactttg atagcccggt gtttggcggc ggcaccaaac tgaccgtgct gggcgaacaa    1200
aaactcatct cagaagagga tctgcatcat caccatcatc attag                    1245
```

<210> SEQ ID NO 141
<211> LENGTH: 1176
<212> TYPE: DNA
<213> ORGANISM: Artificial Sequence
<220> FEATURE:
<223> OTHER INFORMATION: Nucleotide sequence encoding pelB-CD3VL-scFvCD138-6His

<400> SEQUENCE: 141

```
atgaaatacc tgctgccgac cgctgctgct ggtctgctgc tcctcgctgc ccagccggcg      60
atggccgaca ttcagctgac ccagtctcca gcaatcatgt ctgcatctcc aggggagaag     120
gtcaccatga cctgcagagc cagttcaagt gtaagttaca tgaactggta ccagcagaag     180
tcaggcacct cccccaaaag atggatttat gacacatcca agtggcttc tggagtccct      240 tatcgcttca gtggcagtgg gtctgggacc tcatactctc tcacaatcag cagcatggag     300
gctgaagatg ctgccactta ttactgccaa cagtggagta gtaacccgct cacgttcggt     360
gctgggacca agctggagct gaaatccgga ggtggtggat ccgaggtgg tggatcccag     420 gtgcagctgc agcagagcgg cagcgaactg atgccgggcg cgagcgtgaa aattagctgc     480
aaagcgaccg gctataccct tagcaactat tggattgaat gggtgaaaca gcgcccgggc     540
catggcctgg aatggattgg cgaaattctg ccgggcaccg gcgcaccat ttataacgaa      600 aaatttaaag gcaaagcgac ctttaccgcg gatattagca gcaacaccgt gcagatgcag     660
ctgagcagcc tgaccagcga agatagcgcg gtgtattatt gcgcgcgcga acagtattat     720
ggcaactttt attatgcgat ggattattgg ggccagggca ccagcgtgac cgtgagcagc     780
```

```
ggcggcggcg gcagcggcgg cggcggcagc ggcggcggcg gcagcgatat tcagatgacc      840
cagagcacca gcagcctgag cgcgagcctg ggcgatcgcg tgaccattag ctgcagcgcg      900
agccagggca ttaacaacta tctgaactgg tatcagcaga aaccggatgg caccgtggaa      960
ctgctgattt attataccag caccctgcag agcggcgtgc cgagccgctt tagcggcagc     1020
ggcagcggca ccgattatag cctgaccatt agcaacctgg aaccggaaga tattggcacc     1080
tattattgcc agcagtatag caaactgccg cgcacctttg gcggcggcac caaactggaa     1140
attaaacgca ccgtgcatca tcaccatcat cattag                               1176
```

<210> SEQ ID NO 142
<211> LENGTH: 1227
<212> TYPE: DNA
<213> ORGANISM: Artificial Sequence
<220> FEATURE:
<223> OTHER INFORMATION: Nucleotide sequence encoding pelB-CD3VH-
      scFvCD138-6His

<400> SEQUENCE: 142

```
atgaaatacc tgctgccgac cgctgctgct ggtctgctgc tcctcgctgc ccagccggcg       60
atggccgata tcaaactgca gcagtcaggg gctgaactgg caagacctgg ggcctcagtg      120
aagatgtcct gcaagacttc tggctacacc tttactaggt acacgatgca ctgggtaaaa      180
cagaggcctg gacagggtct ggaatggatt ggatacatta atcctagccg tggttatact      240
aattacaatc agaagttcaa ggacaaggcc acattgacta cagacaaatc ctccagcaca      300
gcctacatgc aactgagcag cctgacatct gaggactctg cagtctatta ctgtgcaaga      360
tattatgatg atcattactg ccttgactac tggggccaag gcaccactct cacagtctcc      420
tcaggtggtg gtggttctgg cggcggcggc tccgtggtg gtggttctca ggtgcagctg      480
cagcagagcg gcagcgaact gatgccgggc gcgagcgtga aaattagctg caaagcgacc      540
ggctatacct ttagcaacta ttggattgaa tgggtgaaac agcgcccggg ccatggcctg      600
gaatggattg gcgaaattct gccgggcacc ggccgcacca tttataacga aaaatttaaa      660
ggcaaagcga cctttaccgc ggatattagc agcaacaccg tgcagatgca gctgagcagc      720
ctgaccagcg aagatagcgc ggtgtattat tgcgcgcgcg aacagtatta tggcaacttt      780
tattatgcga tggattattg gggccagggc accagcgtga ccgtgagcag cggcggcggc      840
ggcagcggcg gcggcggcag cggcggcggc ggcagcgata ttcagatgac ccagagcacc      900
agcagcctga gcgcgagcct gggcgatcgc gtgaccatta gctgcagcgc gagccagggc      960
attaacaact atctgaactg gtatcagcag aaaccggatg gcaccgtgga actgctgatt     1020
tattatacca gcaccctgca gagcggcgtg ccgagccgct ttagcggcag cggcagcggc     1080
accgattata gcctgaccat tagcaacctg gaaccggaag atattggcac ctattattgc     1140
cagcagtata gcaaactgcc gcgcaccttt ggcggcggca ccaaactgga aattaaacgc     1200
accgtgcatc atcaccatca tcattag                                         1227
```

<210> SEQ ID NO 143
<211> LENGTH: 1212
<212> TYPE: DNA
<213> ORGANISM: Artificial Sequence
<220> FEATURE:
<223> OTHER INFORMATION: Nucleotide sequence encoding pelB-(aHis)VH-
      scFvHLA-A2(VH-VL)-myc

<400> SEQUENCE: 143

| | |
|---|---|
| atgaaatacc tgctgccgac cgctgctgct ggtctgctgc tcctcgctgc ccagccggcg | 60 |
| atggcccagg tgcagctgca gcagagcggc ccggaagatg tgaaaccggg cgcgagcgtg | 120 |
| aaaattagct gcaaagcgag cggctatacc tttaccgatt attatatgaa ctgggtgaaa | 180 |
| cagagcccgg gcaaaggcct ggaatggatt ggcgatatta cccgaacaa cggcggcacc | 240 |
| agctataacc agaaatttaa aggccgcgcg accctgaccg tggataaaag cagcagcacc | 300 |
| gcgtatatgg aactgcgcag cctgaccagc gaagatagca gcgtgtatta ttgcgaaagc | 360 |
| cagagcggcg cgtattgggg ccagggcacc accgtgaccg tgagcgcggg cggcggcggc | 420 |
| agcggcggcg gcggcagcgg cggccaggtg cagctggtgc agtctggggg aggcgtggtc | 480 |
| cagcctgggg ggtccctgag agtctcctgt gcagcgtctg gggtcaccct cagtgattat | 540 |
| ggcatgcatt gggtccgcca ggctccaggc aaggggctgg agtggatggc ttttatacgg | 600 |
| aatgatggaa gtgataaata ttatgcagac tccgtgaagg gccgattcac catctccaga | 660 |
| gacaactcca agaaaacagt gtctctgcaa atgagcagtc tcagagctga agacacggct | 720 |
| gtgtattact gtgcgaaaaa tggcgaatct gggccttggg actactggta cttcgatctc | 780 |
| tggggccgtg gcaccctggt caccgtgtcg agtggtggag cggttcagg cggaggtggc | 840 |
| tctggcggtg gcggatcgga tgttgtgatg actcagtctc catcctccct gtctgcatct | 900 |
| gtaggagaca gagtcaccat cacttgccag gcgagtcagg acattagcaa ctatttaaat | 960 |
| tggtatcagc agaaaccagg gaaagcccct aagctcctga tctacgatgc atccaatttg | 1020 |
| gaaacagggg tcccatcaag gttcagtgga agtggatctg ggacagattt tactttcacc | 1080 |
| atcagcagcc tgcagcctga ggattttgca acttattact gccaacaata tagtagtttt | 1140 |
| ccgctcactt tcggcggagg gaccaaagtg gatatcaaac gtgaacaaaa actcatctca | 1200 |
| gaagaggatc tg | 1212 |

<210> SEQ ID NO 144
<211> LENGTH: 1230
<212> TYPE: DNA
<213> ORGANISM: Artificial Sequence
<220> FEATURE:
<223> OTHER INFORMATION: Nucleotide sequence encoding pelB-(aHis)VL-
     scFvCD45(VL-VH)-myc

<400> SEQUENCE: 144

| | |
|---|---|
| atgaaatacc tgctgccgac cgctgctgct ggtctgctgc tcctcgctgc ccagccggcg | 60 |
| atggccgatt ataaagatat tctgatgacc cagacccga gcagcctgcc ggtgagcctg | 120 |
| ggcgatcagg cgagcattag ctgccgcagc agccagagca ttgtgcatag caacggcaac | 180 |
| acctatctgg aatggtatct gcagaaaccg ggccagagcc cgaaactgct gatttataaa | 240 |
| gtgagcaacc gctttagcgg cgtgccggat cgctttagcg gcagcggcag cggcaccgat | 300 |
| tttaccctga aaattagccg cgtggaagcg gaagatctgg gcgtgtatta ttgctttcag | 360 |
| ggcagccatg tgccgtttac ctttggcagc ggcaccaaac tggaaattaa acgcggcggc | 420 |
| ggcggcagcg gcggcggcgg cagcggcggc gatattgttc tgacccagag cccggcgagc | 480 |
| ctggcggtta gcctgggtca gcgtgccacc attagctgcc gtgcgagcaa aagcgtgagc | 540 |
| accagcggct atagctatct gcattggtat cagcagaaac cggccagcc tccaaaactg | 600 |
| ctgatttatc tggccagcaa cctggaaagc ggtgtgccgg cccgttttag cggcagcggc | 660 |
| agcggtaccg attttaccct gaacattcat ccggtgaag aagaagatgc ggcgacctat | 720 |
| tattgccagc atagccgtga actgccgttt acctttggca gcggcaccaa actggaaatt | 780 |

```
aaaaagatct ctggtggcgg cggctcgggt ggtggtgggt cgggcggcgg cggctcgagc    840
caggtgcagc tggtggaaag cggtggcgga ctggtgcagc cgggcggcag cctgaaactg    900
agctgtgccg ccagcggttt tgattttagc cgttattgga tgagctgggt gcgtcaggcg    960
ccgggcaaag gcctggaatg gattggcgaa attaacccga ccagcagcac cattaacttt    1020
accccgagcc tgaaagataa agtgtttatt agccgtgata cgcgaaaaa caccctgtat    1080 ctgcagatga gcaaagtgcg tagcgaagat accgcgctgt attattgcgc gcgtggcaac    1140
tattatcgtt atggcgatgc gatggattat tggggccagg gcaccagcgt gaccgtgagc    1200
gaacaaaaac tcatctcaga gaggatctg                                      1230

<210> SEQ ID NO 145
<211> LENGTH: 1248
<212> TYPE: DNA
<213> ORGANISM: Artificial Sequence
<220> FEATURE:
<223> OTHER INFORMATION: Nucleotide sequence encoding
      pelB-(aCD3)VH-scFvHLA-A2(VH-VL)-myc-6His

<400> SEQUENCE: 145
atgaaatacc tgctgccgac cgctgctgct ggtctgctgc tcctcgctgc ccagccggcg    60
atggccgata tcaaactgca gcagtcaggg gctgaactgg caagacctgg ggcctcagtg    120
aagatgtcct gcaagacttc tggctacacc tttactaggt acacgatgca ctgggtaaaa    180
cagaggcctg gacagggtct ggaatggatt ggatacatta atcctagccg tggttatact    240
aattacaatc agaagttcaa ggacaaggcc acattgacta cagacaaatc ctccagcaca    300
gcctacatgc aactgagcag cctgacatct gaggactctg cagtctatta ctgtgcaaga    360
tattatgatg atcattactg ccttgactac tggggccaag gcaccactct cacagtctcc    420
tcaggcggcg gcggcagcgg cggcggcggc agcgcggcc aggtgcagct ggtgcagtct    480
gggggaggcg tggtccagcc tggggggtcc ctgagagtct cctgtgcagc gtctggggtc    540
accctcagtg attatggcat gcattgggtc cgccaggctc caggcaaggg gctggagtgg    600
atggctttta cggaatga tggaagtgat aaatattatg cagactccgt gaagggccga    660
ttcaccatct ccagagacaa ctccaagaaa acagtgtctc tgcaaatgag cagtctcaga    720
gctgaagaca cggctgtgta ttactgtgcg aaaaatggcg aatctgggcc tttggactac    780
tggtacttcg atctctgggg ccgtggcacc ctggtcaccg tgtcgagtgg tggaggcggt    840
tcaggcggag gtggctctgg cggtggcgga tcggatgttg tgatgactca gtctccatcc    900
tccctgtctg catctgtagg agacagagtc accatcactt gccaggcgag tcaggacatt    960
agcaactatt taaattggta tcagcagaaa ccagggaaag cccctaagct cctgatctac    1020
gatgcatcca atttggaaac aggggtccca tcaaggttca gtggaagtgg atctgggaca    1080
gattttactt tcaccatcag cagcctgcag cctgaggatt ttgcaactta ttactgccaa    1140
caatatagta gttttccgct cactttcggc ggagggacca agtggatat caaacgtgaa    1200 caaaaactca tctcagaaga ggatctgcat catcaccatc atcattag                 1248

<210> SEQ ID NO 146
<211> LENGTH: 1221
<212> TYPE: DNA
<213> ORGANISM: Artificial Sequence
<220> FEATURE:
<223> OTHER INFORMATION: Nucleotide sequence encoding
      pelB-(aCD3)VL-scFvCD45(VL-VH)-myc-6His

<400> SEQUENCE: 146
```

```
atgaaatacc tgctgccgac cgctgctgct ggtctgctgc tcctcgctgc ccagccggcg    60
atggccgaca ttcagctgac ccagtctcca gcaatcatgt ctgcatctcc aggggagaag   120
gtcaccatga cctgcagagc cagttcaagt gtaagttaca tgaactggta ccagcagaag   180
tcaggcacct cccccaaaag atggatttat gacacatcca agtggcttc tggagtccct    240 tatcgcttca gtggcagtgg gtctgggacc tcatactctc tcacaatcag cagcatggag   300
gctgaagatg ctgccactta ttactgccaa cagtggagta gtaacccgct cacgttcggt   360
gctgggacca agctggagct gaaaggcggc ggcggcagcg gcggcggcgg cagcggcggc   420
gatattgttc tgacccagag cccggcgagc ctggcggtta gcctgggtca gcgtgccacc   480
attagctgcc gtgcgagcaa agcgtgagc accagcggct atagctatct gcattggtat    540
cagcagaaac cgggccagcc tccaaaactg ctgatttatc tggccagcaa cctgaaagc   600 ggtgtgccgg cccgttttag cggcagcggc agcggtaccg attttacccct gaacattcat  660 ccggtggaag aagaagatgc ggcgacctat tattgccagc atagccgtga actgccgttt  720
acctttggca gcggcaccaa actggaaatt aaaaagatct ctggtggcgg cggctcgggt  780
ggtggtgggt cgggcggcgg cggctcgagc caggtgcagc tggtgaaag cggtggcgga   840 ctggtgcagc cgggcggcag cctgaaactg agctgtgccg ccagcggttt tgattttagc   900
cgttattgga tgagctgggt gcgtcaggcg ccgggcaaag cctgaatg gattggcgaa    960 attaacccga ccagcagcac cattaacttt accccgagcc tgaaagataa agtgtttatt  1020
agccgtgata cgcgaaaaa cacctgtat ctgcagatga gcaaagtgcg tagcgaagat   1080
accgcgctgt attattgcgc gcgtggcaac tattatcgtt atggcgatgc gatggattat  1140
tggggccagg gcaccagcgt gaccgtgagc gaacaaaaac tcatctcaga gaggatctg   1200 catcatcacc atcatcatta g                                            1221
```

<210> SEQ ID NO 147
<211> LENGTH: 1248
<212> TYPE: DNA
<213> ORGANISM: Artificial Sequence
<220> FEATURE:
<223> OTHER INFORMATION: Nucleotide sequence encoding pelB-VHaDIG-
      scFvEGFR-FLAG-6HIS

<400> SEQUENCE: 147

```
atgaaatacc tgctgccgac cgctgctgct ggtctgctgc tcctcgctgc ccagccggcg    60
atggccgaag tgcagctggt ggaaagcggc ggcggcctgg tgaaaccggg cggcagcctg   120
aaactgagct gcgcggtgag cggctttacc tttagcgatt atgcgatgag ctggattcgc   180
cagaccccgg aaaaccgcct ggaatgggtg gcgagcatta acattggcgc gacctatgcg   240
tattatccgg atagcgtgaa aggccgcttt accattagcc gcgataacgc gaaaaacacc   300
ctgtttctgc agatgagcag cctgggcagc gaagataccg cgatgtatta ttgcgcgcgc   360
ccgggcagcc gtatgaata tgataaagcg tattatagca tggcgtattg gggcccgggc    420
accagcgtga ccgtgagcag cgcgaaaacc ggtggtggtg gttctggcgg cggcggctcc   480
caggtgcagc tgcaggagtc gggcccagga ctggtgaagc cttcggagac cctgtccctc   540
acctgcactg tctctggtgg ctccgtcagc agtggtgatt actactggac ctggatccgg   600
cagtccccag ggaagggact ggagtggatt ggacacatct attacagtgg gaacaccaat   660
tataacccct ccctcaagag ccgactcacc atatcaattg acacgtccaa gactcagttc   720
tccctgaagc tgagttctgt gaccgctgcg gacacggcca tttattactg tgtgcgagat   780
```

```
cgagtgactg gtgcttttga tatctggggc caagggacaa tggtcaccgt ctcttccggt      840
ggtggtggtt ctggcggcgg cggctccggt ggtggtggtt ctgacatcca gatgacccag      900
tctccatcct ccctgtctgc atctgtcgga gacagagtca ccatcacttg ccaggcgagt      960
caggacatca gcaactattt aaattggtat cagcagaaac cagggaaagc ccctaaactc     1020
ctgatctacg atgcatccaa tttggaaaca ggggtcccat caaggttcag tggaagtgga     1080
tctgggacag attttacttt caccatcagc agcctgcagc ctgaagatat tgcaacatat     1140
ttctgtcaac actttgatca tctcccgctc gctttcggcg agggaccaa  ggtggagatc     1200 aaagactaca aggatgacga tgacaaacat catcaccatc atcattag               1248
```

<210> SEQ ID NO 148
<211> LENGTH: 1239
<212> TYPE: DNA
<213> ORGANISM: Artificial Sequence
<220> FEATURE:
<223> OTHER INFORMATION: Nucleotide sequence encoding pelB-VLaDIG-
       scFvEpCAM-myc-6HIS

<400> SEQUENCE: 148

```
atgaaatacc tgctgccgac cgctgctgct ggtctgctgc tcctcgctgc ccagccggcg       60
atggccgatg tgcagatgac ccagagcacc agcagcctga gcgcgagcct gggcgatcgc      120
gtgaccatta gctgccgcgc gagccaggat attaaaaact atctgaactg gtatcagcag      180
aaaccgggcg caccgtgaa  actgctgatt tattatagca gcaccctgct gagcggcgtg      240
ccgagccgct ttagcggccg cggcagcggc accgatttta gctgaccat  taccaacctg      300 gaacgcgaag atattgcgac ctatttttgc cagcagagca ttaccctgcc gccgaccttt      360
ggcggcggca ccaaactgga aattaaacgc gcggatgcgg cgccgaccgt gagcattttt      420
ggtggttccg gaggtggtgg atccgaggtg cagctgctcg agcagtctgg agctgagctg      480
gtaaggcctg gacttcagt  gaagatatcc tgcaaggctt ctggatacgc cttcactaac      540
tactggctag gttgggtaaa gcagaggcct ggacatggac ttgagtggat tggagatatt      600
ttccctggaa gtggtaatat ccactacaat gagaagttca agggcaaagc cacactgact      660
gcagacaaat cttcgagcac agcctatatg cagctcagta gcctgacatt tgaggactct      720
gctgtctatt tctgtgcaag actgaggaac tgggacgagc ctatggacta ctggggccaa      780
gggaccacgg tcaccgtctc ctcaggtggt ggtggttctg gcggcggcgg ctccggtggt      840 ggtggtctg  agctcgtgat gacacagtct ccatcctccc tgactgtgac agcaggagag      900
aaggtcacta tgagctgcaa gtccagtcag agtctgttaa acagtggaaa tcaaaagaac      960
tacttgacct ggtaccagca gaaaccaggg cagcctccta aactgttgat ctactgggca     1020
tccactaggg aatctggggt ccctgatcgc ttcacaggca gtggatctgg aacagatttc     1080
actctcacca tcagcagtgt gcaggctgaa gacctggcag tttattactg tcagaatgat     1140
tatagttatc cgctcacgtt cggtgctggg accaagcttg agatcaaaga acagaaactg     1200
atctctgaag aagacctgca tcatcaccat catcattag                           1239
```

<210> SEQ ID NO 149
<211> LENGTH: 1203
<212> TYPE: DNA
<213> ORGANISM: Artificial Sequence
<220> FEATURE:
<223> OTHER INFORMATION: Nucleotide sequence encoding pelB-murineCD3VH-
       scFvEpCaAM-6His

<400> SEQUENCE: 149

```
atgaaatatc tgctgccgac cgcggcggcg ggcctgctgc tgctggcggc gcagccggcg      60
atggcggaag tgcagctggt ggaaagcggc ggcggcctgg tgcagccggg caaaagcctg     120
aaactgagct gcgaagcgag cggctttacc tttagcggct atggcatgca ttgggtgcgc     180
caggcgccgg gccgcggcct ggaaagcgtg gcgtatatta ccagcagcag cattaacatt     240
aaatatgcgg atgcggtgaa aggccgcttt accgtgagcc gcgataacgc gaaaaacctg     300
ctgtttctgc agatgaacat tctgaaaagc gaagataccg cgatgtatta ttgcgcgcgc     360
tttgattggg ataaaaacta ttggggccag ggcaccatgg tgaccgtgag cagcgcgaaa     420
accagcagcg gcggcggcga ggtgcagctg ctcgagcagt ctggagctga gctggtaagg     480
cctgggactt cagtgaagat atcctgcaag gcttctggat acgccttcac taactactgg     540
ctaggttggg taaagcagag gcctggacat ggacttgagt ggattggaga tattttccct     600
ggaagtggta atatccacta caatgagaag ttcaagggca agccacact gactgcagac      660
aaatcttcga gcacagccta tatgcagctc agtagcctga catttgagga ctctgctgtc     720
tatttctgtg caagactgag gaactgggac gagcctatgg actactgggg ccaagggacc     780
acggtcaccg tctcctcagg tggtggtggt tctggcggcg gcggctccgg tggtggtggt     840
tctgagctcg tgatgacaca gtctccatcc tccctgactg tgacagcagg agagaaggtc     900
actatgagct gcaagtccag tcagagtctg ttaaacagtg gaaatcaaaa gaactacttg     960
acctggtacc agcagaaacc agggcagcct cctaaactgt tgatctactg ggcatccact    1020
agggaatctg ggtccctga tcgcttcaca ggcagtggat ctggaacaga tttcactctc    1080
accatcagca gtgtgcaggc tgaagacctg gcagtttatt actgtcagaa tgattatagt    1140
tatccgctca cgttcggtgc tgggaccaag cttgagatca acatcatca ccatcatcat    1200
tag                                                                   1203
```

<210> SEQ ID NO 150
<211> LENGTH: 1155
<212> TYPE: DNA
<213> ORGANISM: Artificial Sequence
<220> FEATURE:
<223> OTHER INFORMATION: Nucleotide sequence encoding pelB-murineCD3VL-scFvEGFR-6His

<400> SEQUENCE: 150

```
atgaaatatc tgctgccgac cgcggcggcg ggcctgctgc tgctggcggc gcagccggcg      60
atggcggata ttcagatgac ccagagcccg agcagcctgc cggcgagcct gggcgatcgc     120
gtgaccatta cctgccaggc gagccaggat attagcaact atctgaactg gtatcagcag     180
aaacgggca aagcgccgaa actgctgatt tattatacca caaaactggc ggatggcgtg     240
ccgagccgct ttagcggcag cggcagcggc cgcgatagca gctttaccat tagcagcctg     300
gaaagcgaag atattggcag ctattattgc cagcagtatt ataactatcc gtggaccttt     360
ggcccgggca ccaaactgga aattaaacgc gcggatagca gcggcggcgg ccaggtgcag     420
ctgcaggagt cgggcccagg actggtgaag ccttcggaga cccctgtccct cacctgcact     480
gtctctggtg gctccgtcag cagtggtgat tactactgga cctggatccg gcagtcccca     540
gggaagggac tggagtggat tggacacatc tattacagtg gaacaccaa ttataacccc     600
tccctcaaga gccgactcac catatcaatt gacacgtcca agactcagtt ctccctgaag    660
ctgagttctg tgaccgctgc ggacacggcc atttattact gtgtgcgaga tcgagtgact     720
```

```
ggtgcttttg atatctgggg ccaagggaca atggtcaccg tctcttccgg tggtggtggt    780
tctggcggcg gcggctccgg tggtggtggt tctgacatcc agatgaccca gtctccatcc    840
tccctgtctg catctgtcgg agacagagtc accatcactt gccaggcgag tcaggacatc    900
agcaactatt taaattggta tcagcagaaa ccagggaaag cccctaaact cctgatctac    960
gatgcatcca atttggaaac aggggtccca tcaaggttca gtggaagtgg atctgggaca   1020 gatttttactt tcaccatcag cagcctgcag cctgaagata ttgcaacata tttctgtcaa   1080
cactttgatc atctcccgct cgctttcggc ggagggacca aggtggagat caaacatcat   1140
caccatcatc attag                                                    1155

<210> SEQ ID NO 151
<211> LENGTH: 1677
<212> TYPE: DNA
<213> ORGANISM: Artificial Sequence
<220> FEATURE:
<223> OTHER INFORMATION: Nucleotide sequence encoding pelB-
      ta(DIG*EpCAM)-Myc-6HIS

<400> SEQUENCE: 151
atgaaatacc tgctgccgac cgctgctgct ggtctgctgc tcctcgctgc ccagccggcg     60
atggccgaag tgcagctggt ggaaagcggc ggcggcctgg tgaaaccggg cggcagcctg    120
aaactgagct gcgcggtgag cggctttacc tttagcgatt atgcgatgag ctggattcgc    180
cagaccccgg aaaaccgcct ggaatgggtg gcgagcatta acattggcgc gacctatgcg    240
tattatccgg atagcgtgaa aggccgcttt accattagcc gcgataacgc gaaaaacacc    300
ctgtttctgc agatgagcag cctgggcagc gaagataccg cgatgtatta ttgcgcgcgc    360
ccgggcagcc gtatgaata tgataaagcg tattatagca tggcgtattg gggcccgggc    420
accagcgtga ccgtgagcag cgcgaaaacc tcctcaggtg gtggtggttc tggcggcggc    480
ggctccggtg gtggtggttc tggtgatgtg cagatgaccc agagcaccag cagcctgagc    540
gcgagcctgg gcgatcgcgt gaccattagc tgccgcgcga gccaggatat taaaaactat    600
ctgaactggt atcagcagaa accgggcggc accgtgaaaac tgctgattta ttatagcagc    660
accctgctga gcggcgtgcc gagccgcttt agcggccgcg gcagcggcac cgatttttagc    720 ctgaccatta ccaacctgga acgcgaagat attgcgacct attttttgcca gcagagcatt    780 accctgccgc cgacctttgg cggcggcacc aaactgaaa ttaaacgcgc ggatgcggcg    840
ccgaccgtga gcattttttgg tggttccgga ggtggtggat ccgaggtgca gctgctcgag    900
cagtctggag ctgagctggt aaggcctggg acttcagtga agatatcctg caaggcttct    960
ggatacgcct tcactaacta ctggctaggt tgggtaaagc agaggcctgg acatggactt   1020
gagtggattg agatattttt ccctggaagt ggtaatatcc actacaatga aagttcaag    1080 ggcaaagcca cactgactgc agacaaatct tcgagcacag cctatatgca gctcagtagc   1140
ctgacatttg aggactctgc tgtctatttc tgtcaagac tgaggaactg ggacgagcct   1200
atggactact ggggccaagg gaccacggtc accgtctcct caggtggtgg tggttctggc   1260
ggcggcggct ccggtggtgg tggttctgag ctcgtgatga cacagtctcc atcctccctg   1320
actgtgacag caggagagaa ggtcactatg agctgcaagt ccagtcagag tctgttaaac   1380
agtggaaatc aaaagaacta cttgacctgg taccagcaga accagggca gcctcctaaa   1440 ctgttgatct actgggcatc cactaggaa tctggggtcc ctgatcgctt cacaggcagt   1500
ggatctggaa cagatttcac tctcaccatc agcagtgtgc aggctgaaga cctggcagtt   1560
```

-continued

```
tattactgtc agaatgatta tagttatccg ctcacgttcg gtgctgggac caagcttgag    1620
atcaaagaac agaaactgat ctctgaagaa gacctgcatc atcaccatca tcattag       1677
```

<210> SEQ ID NO 152
<211> LENGTH: 124
<212> TYPE: PRT
<213> ORGANISM: Artificial Sequence
<220> FEATURE:
<223> OTHER INFORMATION: Anti-CD19 VH

<400> SEQUENCE: 152

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 153
<211> LENGTH: 112
<212> TYPE: PRT
<213> ORGANISM: Artificial Sequence
<220> FEATURE:
<223> OTHER INFORMATION: Anti-CD19 VL

<400> SEQUENCE: 153

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Ser
            100                 105                 110

<210> SEQ ID NO 154
<211> LENGTH: 251
<212> TYPE: PRT
<213> ORGANISM: Artificial Sequence
<220> FEATURE:
<223> OTHER INFORMATION: scFv anti CD19 (VH-linker-VL)

<400> SEQUENCE: 154

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
            85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Gly Gly Gly Gly
            115                 120                 125

Ser Gly Gly Gly Ser Gly Gly Gly Ser Asp Ile Gln Leu Thr
            130                 135                 140

Gln Ser Pro Ala Ser Leu Ala Val Ser Leu Gly Gln Arg Ala Thr Ile
145                 150                 155                 160

Ser Cys Lys Ala Ser Gln Ser Val Asp Tyr Asp Gly Asp Ser Tyr Leu
                165                 170                 175

Asn Trp Tyr Gln Gln Ile Pro Gly Gln Pro Pro Lys Leu Leu Ile Tyr
                180                 185                 190

Asp Ala Ser Asn Leu Val Ser Gly Ile Pro Pro Arg Phe Ser Gly Ser
            195                 200                 205

Gly Ser Gly Thr Asp Phe Thr Leu Asn Ile His Pro Val Glu Lys Val
    210                 215                 220

Asp Ala Ala Thr Tyr His Cys Gln Gln Ser Thr Glu Asp Pro Trp Thr
225                 230                 235                 240

Phe Gly Gly Gly Thr Lys Leu Glu Ile Lys Ser
                245                 250

<210> SEQ ID NO 155
<211> LENGTH: 8
<212> TYPE: PRT
<213> ORGANISM: Artificial Sequence
<220> FEATURE:
<223> OTHER INFORMATION: Anti-CD19 VH CDR1

<400> SEQUENCE: 155

Gly Tyr Ala Phe Ser Ser Tyr Trp
1               5

<210> SEQ ID NO 156
<211> LENGTH: 8
<212> TYPE: PRT
<213> ORGANISM: Artificial Sequence
<220> FEATURE:
<223> OTHER INFORMATION: Anti-CD19 VH CDR2

<400> SEQUENCE: 156

Ile Trp Pro Gly Asp Gly Asp Thr
1               5

<210> SEQ ID NO 157
<211> LENGTH: 17
<212> TYPE: PRT
<213> ORGANISM: Artificial Sequence
<220> FEATURE:
<223> OTHER INFORMATION: Anti-CD19 VH CDR3

<400> SEQUENCE: 157

Ala Arg Arg Glu Thr Thr Thr Val Gly Arg Tyr Tyr Tyr Ala Met Asp
1               5                   10                  15

Tyr

<210> SEQ ID NO 158
<211> LENGTH: 10
<212> TYPE: PRT
<213> ORGANISM: Artificial Sequence
<220> FEATURE:
<223> OTHER INFORMATION: Anti-CD19 VL CDR1

<400> SEQUENCE: 158

Gln Ser Val Asp Tyr Asp Gly Asp Ser Tyr
1               5                   10

<210> SEQ ID NO 159
<211> LENGTH: 9
<212> TYPE: PRT
<213> ORGANISM: Artificial Sequence
<220> FEATURE:
<223> OTHER INFORMATION: Anti-CD19 VL CDR3

<400> SEQUENCE: 159

Gln Gln Ser Thr Glu Asp Pro Trp Thr
1               5

<210> SEQ ID NO 160
<211> LENGTH: 451
<212> TYPE: PRT
<213> ORGANISM: Artificial Sequence
<220> FEATURE:
<223> OTHER INFORMATION: Clostridium perfringens Iota toxin component Ia
      (a.a.23-454) 6x histidine tag two protease cleavage sites

<400> SEQUENCE: 160

Met Ala Ser Thr Thr His His His His His His Asp Thr Asp Ile Pro
1               5                   10                  15

Thr Thr Gly Gly Gly Ser Arg Pro Asp Asp Asp Lys Glu Asn Leu
            20                  25                  30

Tyr Phe Gln Gly His Met Ala Phe Ile Glu Arg Pro Glu Asp Phe Leu
        35                  40                  45

Lys Asp Lys Glu Asn Ala Ile Gln Trp Glu Lys Lys Glu Ala Glu Arg
    50                  55                  60

Val Glu Lys Asn Leu Asp Thr Leu Glu Lys Glu Ala Leu Glu Leu Tyr
65                  70                  75                  80

Lys Lys Asp Ser Glu Gln Ile Ser Asn Tyr Ser Gln Thr Arg Gln Tyr
                85                  90                  95

Phe Tyr Asp Tyr Gln Ile Glu Ser Asn Pro Arg Glu Lys Glu Tyr Lys
            100                 105                 110

Asn Leu Arg Asn Ala Ile Ser Lys Asn Lys Ile Asp Lys Pro Ile Asn
        115                 120                 125

Val Tyr Tyr Phe Glu Ser Pro Glu Lys Phe Ala Phe Asn Lys Glu Ile
    130                 135                 140

Arg Thr Glu Asn Gln Asn Glu Ile Ser Leu Glu Lys Phe Asn Glu Leu
145                 150                 155                 160

Lys Glu Thr Ile Gln Asp Lys Leu Phe Lys Gln Asp Gly Phe Lys Asp
                165                 170                 175

```
Val Ser Leu Tyr Glu Pro Gly Asn Gly Asp Glu Lys Pro Thr Pro Leu
            180                 185                 190

Leu Ile His Leu Lys Leu Pro Lys Asn Thr Gly Met Leu Pro Tyr Ile
            195                 200                 205

Asn Ser Asn Asp Val Lys Thr Leu Ile Glu Gln Asp Tyr Ser Ile Lys
            210                 215                 220

Ile Asp Lys Ile Val Arg Ile Val Glu Gly Lys Gln Tyr Ile Lys
225                 230                 235                 240

Ala Glu Ala Ser Ile Val Asn Ser Leu Asp Phe Lys Asp Val Ser
            245                 250                 255

Lys Gly Asp Leu Trp Gly Lys Glu Asn Tyr Ser Asp Trp Ser Asn Lys
            260                 265                 270

Leu Thr Pro Asn Glu Leu Ala Asp Val Asn Asp Tyr Met Arg Gly Gly
            275                 280                 285

Tyr Thr Ala Ile Asn Asn Tyr Leu Ile Ser Asn Gly Pro Leu Asn Asn
            290                 295                 300

Pro Asn Pro Glu Leu Asp Ser Lys Val Asn Asn Ile Glu Asn Ala Leu
305                 310                 315                 320

Lys Leu Thr Pro Ile Pro Ser Asn Leu Ile Val Tyr Arg Arg Ser Gly
                    325                 330                 335

Pro Gln Glu Phe Gly Leu Thr Leu Thr Ser Pro Glu Tyr Asp Phe Asn
            340                 345                 350

Lys Ile Glu Asn Ile Asp Ala Phe Lys Glu Lys Trp Glu Gly Lys Val
                355                 360                 365

Ile Thr Tyr Pro Asn Phe Ile Ser Thr Ser Ile Gly Ser Val Asn Met
            370                 375                 380

Ser Ala Phe Ala Lys Arg Lys Ile Ile Leu Arg Ile Asn Ile Pro Lys
385                 390                 395                 400

Asp Ser Pro Gly Ala Tyr Leu Ser Ala Ile Pro Gly Tyr Ala Gly Glu
                405                 410                 415

Tyr Glu Val Leu Leu Asn His Gly Ser Lys Phe Lys Ile Asn Lys Val
            420                 425                 430

Asp Ser Tyr Lys Asp Gly Thr Val Thr Lys Leu Ile Leu Asp Ala Thr
            435                 440                 445

Leu Ile Asn
    450

<210> SEQ ID NO 161
<211> LENGTH: 300
<212> TYPE: PRT
<213> ORGANISM: Artificial Sequence
<220> FEATURE:
<223> OTHER INFORMATION: Burkholderia sp. CCGE1002 Shiga toxin subunit A
      (a.a.24-285) 6x histidine tag two protease cleavage sites

<400> SEQUENCE: 161

Met Ala Ser Thr Thr His His His His His Asp Thr Asp Ile Pro
1               5                   10                  15

Thr Thr Gly Gly Gly Ser Arg Pro Asp Asp Asp Lys Glu Asn Leu
            20                  25                  30

Tyr Phe Gln Gly His Met Glu Phe Ser Val Asp Phe Thr Ser Pro Gln
            35                  40                  45

Lys Tyr Val Gln Ser Leu Gly Ala Ile Arg Ala Met Gly Asp Ala
            50                  55                  60

Met Ser Leu Thr Asn Ile Pro Gly Asn Lys Ile Leu Tyr Gln Leu Arg
```

```
             65                  70                  75                  80
Pro Asp Ala Ser Asn Ile Val Glu Gly Val Thr Ile Glu Ile Ile Gly
                85                  90                  95

Val Gly Arg Asn Asn Ser Pro Ser Asn Arg Asp Val Arg Phe Val Ile
            100                 105                 110

Asn Pro Ser Asp Leu Tyr Leu Thr Gly Phe Ile Val Gly Arg Ile Phe
        115                 120                 125

Tyr Arg Phe Ser Asp Phe Ser Asp Thr Ala Ser Gly Arg Val Gln Val
    130                 135                 140

Asn Ala Pro Arg His Leu Val Asp Phe Thr Ile Asp Met Thr Val Asp
145                 150                 155                 160

Ser Ser Tyr Leu Ser Leu Ala Arg Ser Ala Gly Val Ser Ala Asp Arg
                165                 170                 175

Thr Asp Leu Ser Ile Asp Arg Tyr Ser Leu Met Lys Gly Tyr Arg Asp
            180                 185                 190

Leu Ile Asn His Val Ser Ser Thr Arg Thr Ile Asn Gly Ala Glu Ala
        195                 200                 205

Arg Ala Leu Leu Ser Tyr Ala Thr Val Leu Ser Glu Ala Val Arg Phe
    210                 215                 220

Arg Ser Ile Gln Gly Asn Phe Ala Ser Thr Ala Leu Gly Asp Asp Ala
225                 230                 235                 240

Phe Thr Pro Tyr Arg Leu Ser Leu Glu Asp Ser Asn Arg Thr Thr Arg
                245                 250                 255

Trp Asp Arg Leu Ser Asp Glu Ile Arg Lys Ala His Tyr Gly Ala Ile
            260                 265                 270

Lys Ile Ala Thr His Gly Ala Ala Pro Ile Leu Leu Ala Asn Val Arg
        275                 280                 285

Asp Val Phe Gly Met Thr Thr Cys Thr Ser Lys Lys
    290                 295                 300

<210> SEQ ID NO 162
<211> LENGTH: 521
<212> TYPE: PRT
<213> ORGANISM: Artificial Sequence
<220> FEATURE:
<223> OTHER INFORMATION: Anthrax lethal factor endopeptidase no
      PA-binding region (34-295) 6x histidine tag

<400> SEQUENCE: 162

Gln Arg Met Leu Ala Arg Tyr Glu Lys Trp Glu Lys Ile Lys Gln His
1               5                  10                  15

Tyr Gln His Trp Ser Asp Ser Leu Ser Glu Glu Gly Arg Gly Leu Leu
            20                  25                  30

Lys Lys Leu Gln Ile Pro Ile Glu Pro Lys Lys Asp Asp Ile Ile His
        35                  40                  45

Ser Leu Ser Gln Glu Glu Lys Glu Leu Leu Lys Arg Ile Gln Ile Asp
    50                  55                  60

Ser Ser Asp Phe Leu Ser Thr Glu Glu Lys Glu Phe Leu Lys Lys Leu
65                  70                  75                  80

Gln Ile Asp Ile Arg Asp Ser Leu Ser Glu Glu Glu Lys Glu Leu Leu
                85                  90                  95

Asn Arg Ile Gln Val Asp Ser Ser Asn Pro Leu Ser Glu Lys Glu Lys
            100                 105                 110

Glu Phe Leu Lys Lys Leu Lys Leu Asp Ile Gln Pro Tyr Asp Ile Asn
        115                 120                 125
```

Gln Arg Leu Gln Asp Thr Gly Gly Leu Ile Asp Ser Pro Ser Ile Asn
130                 135                 140

Leu Asp Val Arg Lys Gln Tyr Lys Arg Asp Ile Gln Asn Ile Asp Ala
145                 150                 155                 160

Leu Leu His Gln Ser Ile Gly Ser Thr Leu Tyr Asn Lys Ile Tyr Leu
            165                 170                 175

Tyr Glu Asn Met Asn Ile Asn Asn Leu Thr Ala Thr Leu Gly Ala Asp
            180                 185                 190

Leu Val Asp Ser Thr Asp Asn Thr Lys Ile Asn Arg Gly Ile Phe Asn
            195                 200                 205

Glu Phe Lys Lys Asn Phe Lys Tyr Ser Ile Ser Ser Asn Tyr Met Ile
210                 215                 220

Val Asp Ile Asn Glu Arg Pro Ala Leu Asp Asn Glu Arg Leu Lys Trp
225                 230                 235                 240

Arg Ile Gln Leu Ser Pro Asp Thr Arg Ala Gly Tyr Leu Glu Asn Gly
                245                 250                 255

Lys Leu Ile Leu Gln Arg Asn Ile Gly Leu Glu Ile Lys Asp Val Gln
                260                 265                 270

Ile Ile Lys Gln Ser Glu Lys Glu Tyr Ile Arg Ile Asp Ala Lys Val
            275                 280                 285

Val Pro Lys Ser Lys Ile Asp Thr Lys Ile Gln Glu Ala Gln Leu Asn
            290                 295                 300

Ile Asn Gln Glu Trp Asn Lys Ala Leu Gly Leu Pro Lys Tyr Thr Lys
305                 310                 315                 320

Leu Ile Thr Phe Asn Val His Asn Arg Tyr Ala Ser Asn Ile Val Glu
                325                 330                 335

Ser Ala Tyr Leu Ile Leu Asn Glu Trp Lys Asn Asn Ile Gln Ser Asp
                340                 345                 350

Leu Ile Lys Lys Val Thr Asn Tyr Leu Val Asp Gly Asn Gly Arg Phe
            355                 360                 365

Val Phe Thr Asp Ile Thr Leu Pro Asn Ile Ala Glu Gln Tyr Thr His
            370                 375                 380

Gln Asp Glu Ile Tyr Glu Gln Val His Ser Lys Gly Leu Tyr Val Pro
385                 390                 395                 400

Glu Ser Arg Ser Ile Leu Leu His Gly Pro Ser Lys Gly Val Glu Leu
                405                 410                 415

Arg Asn Asp Ser Glu Gly Phe Ile His Glu Phe Gly His Ala Val Asp
                420                 425                 430

Asp Tyr Ala Gly Tyr Leu Leu Asp Lys Asn Gln Ser Asp Leu Val Thr
            435                 440                 445

Asn Ser Lys Lys Phe Ile Asp Ile Phe Lys Glu Glu Gly Ser Asn Leu
450                 455                 460

Thr Ser Tyr Gly Arg Thr Asn Glu Ala Glu Phe Phe Ala Glu Ala Phe
465                 470                 475                 480

Arg Leu Met His Ser Thr Asp His Ala Glu Arg Leu Lys Val Gln Lys
                485                 490                 495

Asn Ala Pro Lys Thr Phe Gln Phe Ile Asn Asp Gln Ile Lys Phe Ile
                500                 505                 510

Ile Asn Ser His His His His His
            515                 520

<210> SEQ ID NO 163
<211> LENGTH: 389
<212> TYPE: PRT

<213> ORGANISM: Artificial Sequence
<220> FEATURE:
<223> OTHER INFORMATION: Corynebacterium diphtheria toxin 6x histidine tag

<400> SEQUENCE: 163

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Phe Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Asp Ser Ile Ile Arg
        355                 360                 365

Thr Gly Phe Gln Gly Glu Ser Gly His Lys Thr Gln Pro His Met His
    370                 375                 380
```

His His His His His
385

<210> SEQ ID NO 164
<211> LENGTH: 506
<212> TYPE: PRT
<213> ORGANISM: Artificial Sequence
<220> FEATURE:
<223> OTHER INFORMATION: Clostridium perfringens str. 13 pfoA
      perfringolysin O 6x histidine tag

<400> SEQUENCE: 164

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
                20                  25                  30

Asp Lys Asn Gln Ser Ile Asp Ser Gly Ile Ser Ser Leu Ser Tyr Asn
            35                  40                  45

Arg Asn Glu Val Leu Ala Ser Asn Gly Asp Lys Ile Glu Ser Phe Val
50                  55                  60

Pro Lys Glu Gly Lys Lys Thr Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125

Ile Asn Ile Asn Ile Asp Leu Pro Gly Leu Lys Gly Glu Asn Ser Ile
130                 135                 140

Lys Val Asp Asp Pro Thr Tyr Gly Lys Val Ser Gly Ala Ile Asp Glu
145                 150                 155                 160

Leu Val Ser Lys Trp Asn Glu Lys Tyr Ser Ser Thr His Thr Leu Pro
                165                 170                 175

Ala Arg Thr Gln Tyr Ser Glu Ser Met Val Tyr Ser Lys Ser Gln Ile
            180                 185                 190

Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255

Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
        275                 280                 285

Asp Val Gln Ala Ala Phe Lys Ala Leu Ile Lys Asn Thr Asp Ile Lys
290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
            340                 345                 350

```
Thr Lys Asn Pro Ala Tyr Pro Ile Ser Tyr Thr Ser Val Phe Leu Lys
            355                 360                 365

Asp Asn Ser Val Ala Ala Val His Asn Lys Thr Asp Tyr Ile Glu Thr
    370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415

Lys Glu Gly Asn Glu Val Leu Thr His Lys Thr Trp Asp Gly Asn Tyr
            420                 425                 430

Gln Asp Lys Thr Ala His Tyr Ser Thr Val Ile Pro Leu Glu Ala Asn
            435                 440                 445

Ala Arg Asn Ile Arg Ile Lys Ala Arg Glu Cys Thr Gly Leu Ala Trp
        450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn His His His His His His
            500                 505

<210> SEQ ID NO 165
<211> LENGTH: 273
<212> TYPE: PRT
<213> ORGANISM: Artificial Sequence
<220> FEATURE:
<223> OTHER INFORMATION: Ricin A chain 6x histidine tag

<400> SEQUENCE: 165

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
                20                  25                  30

Thr Thr Gly Ala Asp Val Arg His Glu Ile Pro Val Leu Pro Asn Arg
            35                  40                  45

Val Gly Leu Pro Ile Asn Gln Arg Phe Ile Leu Val Glu Leu Ser Asn
    50                  55                  60

His Ala Glu Leu Ser Val Thr Leu Ala Leu Asp Val Thr Asn Ala Tyr
65                  70                  75                  80

Val Val Gly Tyr Arg Ala Gly Asn Ser Ala Tyr Phe Phe His Pro Asp
                85                  90                  95

Ala Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
    130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
            180                 185                 190

Arg Tyr Asn Arg Arg Ser Ala Pro Asp Pro Ser Val Ile Thr Leu Glu
        195                 200                 205
```

```
Asn Ser Trp Gly Arg Leu Ser Thr Ala Ile Gln Glu Ser Asn Gln Gly
        210                 215                 220

Ala Phe Ala Ser Pro Ile Gln Leu Gln Arg Arg Asn Gly Ser Lys Phe
225                 230                 235                 240

Ser Val Tyr Asp Val Ser Ile Leu Ile Pro Ile Ile Ala Leu Met Val
                245                 250                 255

Tyr Arg Cys Ala Pro Pro Ser Ser Gln Phe His His His His His
            260                 265                 270

His
```

<210> SEQ ID NO 166
<211> LENGTH: 285
<212> TYPE: PRT
<213> ORGANISM: Artificial Sequence
<220> FEATURE:
<223> OTHER INFORMATION: Ricin A chain linker peptide 6x histidine tag

<400>

<210> SEQ ID NO 167
<211> LENGTH: 256
<212> TYPE: PRT
<213> ORGANISM: Artificial Sequence
<220> FEATURE:
<223> OTHER INFORMATION: Plant RIP bouganin with reduced immunogenic potential 6x histidine tag

<400> SEQUENCE: 167

```
Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Ala Asp Arg Lys Ala Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys His His His His His His
                245                 250                 255
```

<210> SEQ ID NO 168
<211> LENGTH: 149
<212> TYPE: PRT
<213> ORGANISM: Artificial Sequence
<220> FEATURE:
<223> OTHER INFORMATION: Human RNASE3 ribonuclease (RNase A family, 3) protein without N-terminal signal peptide but with a N-terminal nuclear localisation sequence 6x histidine tag

<400> SEQUENCE: 168

```
Pro Lys Lys Lys Arg Lys Val Glu Ala Ser Arg Pro Pro Gln Phe Thr
1               5                   10                  15

Arg Ala Gln Trp Phe Ala Ile Gln His Ile Ser Leu Asn Pro Pro Arg
            20                  25                  30

Cys Thr Ile Ala Met Arg Ala Ile Asn Asn Tyr Arg Trp Arg Cys Lys
        35                  40                  45
```

```
Asn Gln Asn Thr Phe Leu Arg Thr Thr Phe Ala Asn Val Val Asn Val
 50                  55                  60

Cys Gly Asn Gln Ser Ile Arg Cys Pro His Asn Arg Thr Leu Asn Asn
 65                  70                  75                  80

Cys His Arg Ser Arg Phe Arg Val Pro Leu Leu His Cys Asp Leu Ile
                 85                  90                  95

Asn Pro Gly Ala Gln Asn Ile Ser Asn Cys Thr Tyr Ala Asp Arg Pro
            100                 105                 110

Gly Arg Arg Phe Tyr Val Val Ala Cys Asp Asn Arg Asp Pro Arg Asp
            115                 120                 125

Ser Pro Arg Tyr Pro Val Val Pro Val His Leu Asp Thr Thr Ile His
    130                 135                 140

His His His His His
145

<210> SEQ ID NO 169
<211> LENGTH: 18
<212> TYPE: PRT
<213> ORGANISM: Artificial Sequence
<220> FEATURE:
<223> OTHER INFORMATION: Antigen for human myeloma cell line U266
      antibody IgE-ND

<400> SEQUENCE: 169

Leu Ser Pro His Leu Leu Trp Asp Leu Phe Arg Val Gly Leu Pro Gly
1               5                   10                  15

Ala Ala

<210> SEQ ID NO 170
<211> LENGTH: 146
<212> TYPE: PRT
<213> ORGANISM: Dermatophagoides farinae

<400> SEQUENCE: 170

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
 50                  55                  60

Lys Thr Ala Lys Ile Glu Ile Lys Ala Ser Leu Asp Gly Leu Glu Ile
 65                  70                  75                  80

Asp Val Pro Gly Ile Asp Thr Asn Ala Cys His Phe Met Lys Cys Pro
                 85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Leu Ile
            115                 120                 125

Gly Asp Asn Gly Val Leu Ala Cys Ala Ile Ala Thr His Gly Lys Ile
    130                 135                 140

Arg Asp
145

<210> SEQ ID NO 171
<211> LENGTH: 320
```

<212> TYPE: PRT
<213> ORGANISM: Dermatophagoides pteronyssinus

<400> SEQUENCE: 171

Met Lys Ile Val Leu Ala Ile Ala Ser Leu Leu Ala Leu Ser Ala Val
1               5                   10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Cys Trp Ala Phe Ser Gly Val Ala Ala Thr Glu Ser Ala
    130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
    210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
            260                 265                 270

Val Gly Tyr Ser Asn Ala Gln Gly Val Asp Tyr Trp Ile Val Arg Asn
        275                 280                 285

Ser Trp Asp Thr Asn Trp Gly Asp Asn Gly Tyr Gly Tyr Phe Ala Ala
    290                 295                 300

Asn Ile Asp Leu Met Met Ile Glu Glu Tyr Pro Tyr Val Val Ile Leu
305                 310                 315                 320

<210> SEQ ID NO 172
<211> LENGTH: 141
<212> TYPE: PRT
<213> ORGANISM: Tyrophagus putrescentiae

<400> SEQUENCE: 172

Met Lys Phe Leu Ile Leu Phe Ala Leu Val Ala Val Ala Ala Ala Gly
1               5                   10                  15

Gln Val Lys Phe Thr Asp Cys Gly Lys Lys Glu Ile Ala Ser Val Ala
            20                  25                  30

```
Val Asp Gly Cys Glu Gly Asp Leu Cys Val Ile His Lys Ser Lys Pro
        35                  40                  45

Val His Val Ile Ala Glu Phe Thr Ala Asn Gln Asp Thr Cys Lys Ile
    50                  55                  60

Glu Val Lys Val Thr Gly Gln Leu Asn Gly Leu Glu Val Pro Ile Pro
65                  70                  75                  80

Gly Ile Glu Thr Asp Gly Cys Lys Val Leu Lys Cys Pro Leu Lys Lys
                85                  90                  95

Gly Thr Lys Tyr Thr Met Asn Tyr Ser Val Asn Val Pro Ser Val Val
                100                 105                 110

Pro Asn Ile Lys Thr Val Lys Leu Leu Ala Thr Gly Glu His Gly
            115                 120                 125

Val Leu Ala Cys Gly Ala Val Asn Thr Asp Val Lys Pro
    130                 135                 140

<210> SEQ ID NO 173
<211> LENGTH: 109
<212> TYPE: PRT
<213> ORGANISM: Felis catus

<400> SEQUENCE: 173

Met Arg Gly Ala Leu Leu Val Leu Ala Leu Leu Val Thr Gln Ala Leu
1               5                   10                  15

Gly Val Lys Met Ala Glu Thr Cys Pro Ile Phe Tyr Asp Val Phe Phe
                20                  25                  30

Ala Val Ala Asn Gly Asn Glu Leu Leu Leu Asp Leu Ser Leu Thr Lys
            35                  40                  45

Val Asn Ala Thr Glu Pro Glu Arg Thr Ala Met Lys Lys Ile Gln Asp
50                  55                  60

Cys Tyr Val Glu Asn Gly Leu Ile Ser Arg Val Leu Asp Gly Leu Val
65                  70                  75                  80

Met Thr Thr Ile Ser Ser Ser Lys Asp Cys Met Gly Glu Ala Val Gln
                85                  90                  95

Asn Thr Val Glu Asp Leu Lys Leu Asn Thr Leu Gly Arg
                100                 105

<210> SEQ ID NO 174
<211> LENGTH: 92
<212> TYPE: PRT
<213> ORGANISM: Felis catus

<400> SEQUENCE: 174

Met Lys Gly Ala Cys Val Leu Val Leu Leu Trp Ala Ala Leu Leu Leu
1               5                   10                  15

Ile Ser Gly Gly Asn Cys Glu Ile Cys Pro Ala Val Lys Arg Asp Val
                20                  25                  30

Asp Leu Phe Leu Thr Gly Thr Pro Asp Glu Tyr Val Glu Gln Val Ala
            35                  40                  45

Gln Tyr Lys Ala Leu Pro Val Val Leu Glu Asn Ala Arg Ile Leu Lys
        50                  55                  60

Asn Cys Val Asp Ala Lys Met Thr Glu Glu Asp Lys Glu Asn Ala Leu
65                  70                  75                  80

Ser Val Leu Asp Lys Ile Tyr Thr Ser Pro Leu Cys
                85                  90

<210> SEQ ID NO 175
<211> LENGTH: 146
```

```
<212> TYPE: PRT
<213> ORGANISM: Felis catus

<400> SEQUENCE: 175

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
                20                  25                  30

Val Val Leu Glu Asn Ala Arg Ile Leu Lys Asn Cys Val Asp Ala Lys
            35                  40                  45

Met Thr Glu Glu Asp Lys Glu Asn Ala Leu Ser Leu Leu Asp Lys Ile
    50                  55                  60

Tyr Thr Ser Pro Leu Cys Val Lys Met Ala Glu Thr Cys Pro Ile Phe
65                  70                  75                  80

Tyr Asp Val Phe Phe Ala Val Ala Asn Gly Asn Glu Leu Leu Leu Asp
                85                  90                  95

Leu Ser Leu Thr Lys Val Asn Ala Thr Glu Pro Glu Arg Thr Ala Met
            100                 105                 110

Lys Lys Ile Gln Asp Cys Tyr Val Glu Asn Gly Leu Ile Ser Arg Val
        115                 120                 125

Leu Asp Gly Leu Val Met Thr Thr Ile Ser Ser Lys Asp Cys Met
    130                 135                 140

Gly Glu
145

<210> SEQ ID NO 176
<211> LENGTH: 172
<212> TYPE: PRT
<213> ORGANISM: Arachis hypogaea

<400> SEQUENCE: 176

Met Ala Lys Leu Thr Ile Leu Val Ala Leu Ala Leu Phe Leu Leu Ala
1               5                   10                  15

Ala His Ala Ser Ala Arg Gln Gln Trp Glu Leu Gln Gly Asp Arg Arg
                20                  25                  30

Cys Gln Ser Gln Leu Glu Arg Ala Asn Leu Arg Pro Cys Glu Gln His
            35                  40                  45

Leu Met Gln Lys Ile Gln Arg Asp Glu Asp Ser Tyr Gly Arg Asp Pro
    50                  55                  60

Tyr Ser Pro Ser Gln Asp Pro Tyr Ser Pro Ser Gln Asp Pro Asp Arg
65                  70                  75                  80

Arg Asp Pro Tyr Ser Pro Ser Pro Tyr Asp Arg Arg Gly Ala Gly Ser
                85                  90                  95

Ser Gln His Gln Glu Arg Cys Cys Asn Glu Leu Asn Glu Phe Glu Asn
            100                 105                 110

Asn Gln Arg Cys Met Cys Glu Ala Leu Gln Gln Ile Met Glu Asn Gln
        115                 120                 125

Ser Asp Arg Leu Gln Gly Arg Gln Gln Glu Gln Gln Phe Lys Arg Glu
    130                 135                 140

Leu Arg Asn Leu Pro Gln Gln Cys Gly Leu Arg Ala Pro Gln Arg Cys
145                 150                 155                 160

Asp Leu Glu Val Glu Ser Gly Gly Arg Asp Arg Tyr
                165                 170

<210> SEQ ID NO 177
<211> LENGTH: 157
```

<212> TYPE: PRT
<213> ORGANISM: Alternaria alternata (Alternaria rot fungus)

<400> SEQUENCE: 177

Met Gln Phe Thr Thr Ile Ala Ser Leu Phe Ala Ala Gly Leu Ala
1               5                   10                  15

Ala Ala Ala Pro Leu Glu Ser Arg Gln Asp Thr Ala Ser Cys Pro Val
            20                  25                  30

Thr Thr Glu Gly Asp Tyr Val Trp Lys Ile Ser Glu Phe Tyr Gly Arg
            35                  40                  45

Lys Pro Glu Gly Thr Tyr Tyr Asn Ser Leu Gly Phe Asn Ile Lys Ala
    50                  55                  60

Thr Asn Gly Gly Thr Leu Asp Phe Thr Cys Ser Ala Gln Ala Asp Lys
65                  70                  75                  80

Leu Glu Asp His Lys Trp Tyr Ser Cys Gly Leu Asn Ser Phe Met Asp
                85                  90                  95

Phe Ser Phe Asp Ser Asp Arg Ser Gly Leu Leu Leu Lys Gln Lys Val
            100                 105                 110

Ser Asp Asp Ile Thr Tyr Val Ala Thr Ala Thr Leu Pro Asn Tyr Cys
            115                 120                 125

Arg Ala Gly Gly Asn Gly Pro Lys Asp Phe Val Cys Gln Gly Val Ala
            130                 135                 140

Asp Ala Tyr Ile Thr Leu Val Thr Leu Pro Lys Ser Ser
145                 150                 155

<210> SEQ ID NO 178
<211> LENGTH: 174
<212> TYPE: PRT
<213> ORGANISM: Canis familiaris

<400> SEQUENCE: 178

Met Lys Thr Leu Leu Leu Thr Ile Gly Phe Ser Leu Ile Ala Ile Leu
1               5                   10                  15

Gln Ala Gln Asp Thr Pro Ala Leu Gly Lys Asp Thr Val Ala Val Ser
            20                  25                  30

Gly Lys Trp Tyr Leu Lys Ala Met Thr Ala Asp Gln Glu Val Pro Glu
            35                  40                  45

Lys Pro Asp Ser Val Thr Pro Met Ile Leu Lys Ala Gln Lys Gly Gly
    50                  55                  60

Asn Leu Glu Ala Lys Ile Thr Met Leu Thr Asn Gly Gln Cys Gln Asn
65                  70                  75                  80

Ile Thr Val Val Leu His Lys Thr Ser Glu Pro Gly Lys Tyr Thr Ala
                85                  90                  95

Tyr Glu Gly Gln Arg Val Val Phe Ile Gln Pro Ser Pro Val Arg Asp
            100                 105                 110

His Tyr Ile Leu Tyr Cys Glu Gly Glu Leu His Gly Arg Gln Ile Arg
            115                 120                 125

Met Ala Lys Leu Leu Gly Arg Asp Pro Glu Gln Ser Gln Glu Ala Leu
            130                 135                 140

Glu Asp Phe Arg Glu Phe Ser Arg Ala Lys Gly Leu Asn Gln Glu Ile
145                 150                 155                 160

Leu Glu Leu Ala Gln Ser Glu Thr Cys Ser Pro Gly Gly Gln
                165                 170

<210> SEQ ID NO 179
<211> LENGTH: 286

<212> TYPE: PRT
<213> ORGANISM: Triticum aestivum

<400> SEQUENCE: 179

```
Met Lys Thr Phe Leu Ile Leu Val Leu Leu Ala Ile Val Ala Thr Thr
1               5                   10                  15

Ala Thr Thr Ala Val Arg Phe Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Gln Pro Phe Pro Pro Gln Gln Pro Tyr Pro
    50                  55                  60

Gln Pro Gln Pro Phe Pro Ser Gln Leu Pro Tyr Leu Gln Leu Gln Pro
65                  70                  75                  80

Phe Pro Gln Pro Gln Leu Pro Tyr Ser Gln Pro Gln Pro Phe Arg Pro
                85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Gln Gln Gln Ile Leu Gln Gln Ile Leu Gln Gln Gln Leu Ile
    130                 135                 140

Pro Cys Met Asp Val Val Leu Gln Gln His Asn Ile Ala His Gly Arg
145                 150                 155                 160

Ser Gln Val Leu Gln Gln Ser Thr Tyr Gln Leu Leu Gln Glu Leu Cys
                165                 170                 175

Cys Gln His Leu Trp Gln Ile Pro Glu Gln Ser Gln Cys Gln Ala Ile
            180                 185                 190

His Asn Val Val His Ala Ile Ile Leu His Gln Gln Lys Gln Gln
                195                 200                 205

Gln Gln Pro Ser Ser Gln Val Ser Phe Gln Pro Leu Gln Gln Tyr
    210                 215                 220

Pro Leu Gly Gln Gly Ser Phe Arg Pro Ser Gln Gln Asn Pro Gln Ala
225                 230                 235                 240

Gln Gly Ser Val Gln Pro Gln Gln Leu Pro Gln Phe Glu Glu Ile Arg
                245                 250                 255

Asn Leu Ala Leu Gln Thr Leu Pro Ala Met Cys Asn Val Tyr Ile Pro
            260                 265                 270

Pro Tyr Cys Thr Ile Ala Pro Phe Gly Ile Phe Gly Thr Asn
        275                 280                 285
```

<210> SEQ ID NO 180
<211> LENGTH: 491
<212> TYPE: PRT
<213> ORGANISM: Blattella germanica

<400> SEQUENCE: 180

```
Ala Ile Glu Phe Leu Asn Asn Ile His Asp Leu Leu Gly Ile Pro His
1               5                   10                  15

Ile Pro Val Thr Ala Arg Lys His His Arg Arg Gly Val Gly Ile Thr
            20                  25                  30

Gly Leu Ile Asp Asp Ile Ile Ala Ile Leu Pro Val Asp Asp Leu Tyr
        35                  40                  45

Ala Leu Phe Gln Glu Lys Leu Glu Thr Ser Pro Glu Phe Lys Ala Leu
    50                  55                  60
```

```
Tyr Asp Ala Ile Arg Ser Pro Glu Phe Gln Ser Ile Val Gly Thr Leu
 65                  70                  75                  80

Glu Ala Met Pro Glu Tyr Gln Asn Leu Ile Gln Lys Leu Lys Asp Lys
                 85                  90                  95

Gly Val Asp Val Asp His Ile Ile Glu Leu Ile His Gln Ile Phe Asn
            100                 105                 110

Ile Val Arg Asp Thr Arg Gly Leu Pro Glu Asp Leu Gln Asp Phe Leu
            115                 120                 125

Ala Leu Ile Pro Thr Asp Gln Val Leu Ala Ile Ala Ala Asp Tyr Leu
            130                 135                 140

Ala Asn Asp Ala Glu Val Lys Ala Ala Val Glu Tyr Leu Lys Ser Asp
145                 150                 155                 160

Glu Phe Glu Thr Ile Val Val Thr Val Asp Ser Leu Pro Glu Phe Lys
                165                 170                 175

Asn Phe Leu Asn Phe Leu Gln Thr Asn Gly Leu Asn Ala Ile Glu Phe
            180                 185                 190

Leu Asn Asn Ile His Asp Leu Leu Gly Ile Pro His Ile Pro Val Thr
            195                 200                 205

Ala Arg Lys His Leu Arg Arg Gly Val Gly Ile Thr Gly Leu Ile Asp
            210                 215                 220

Asp Ile Ile Ala Ile Leu Pro Val Asp Asp Leu Tyr Ala Leu Phe Gln
225                 230                 235                 240

Glu Lys Leu Glu Thr Ser Pro Glu Phe Lys Ala Leu Tyr Asp Ala Ile
                245                 250                 255

Arg Ser Pro Glu Phe Gln Ser Ile Val Glu Thr Leu Lys Ala Met Pro
            260                 265                 270

Glu Tyr Gln Ser Leu Ile Gln Lys Leu Lys Asp Lys Gly Val Asp Val
            275                 280                 285

Asp His Ile Ile Glu Leu Ile His Gln Ile Phe Asn Ile Val Arg Asp
            290                 295                 300

Thr Arg Gly Leu Pro Glu Asp Leu Gln Asp Phe Leu Ala Leu Ile Pro
305                 310                 315                 320

Ile Asp Gln Ile Leu Ala Ile Ala Ala Asp Tyr Leu Ala Asn Asp Ala
                325                 330                 335

Glu Val Gln Ala Ala Val Glu Tyr Leu Lys Ser Asp Glu Phe Glu Thr
            340                 345                 350

Ile Val Val Thr Val Asp Ser Leu Pro Glu Phe Lys Asn Phe Leu Asn
            355                 360                 365

Phe Leu Gln Thr Asn Gly Leu Asn Ala Ile Glu Phe Ile Asn Asn Ile
            370                 375                 380

His Asp Leu Leu Gly Ile Pro His Ile Pro Ala Thr Gly Arg Lys His
385                 390                 395                 400

Val Arg Arg Gly Val Gly Ile Asn Gly Leu Ile Asp Asp Val Ile Ala
                405                 410                 415

Ile Leu Pro Val Asp Glu Leu Tyr Ala Leu Phe Gln Glu Lys Leu Glu
            420                 425                 430

Ser Ser Pro Glu Phe Lys Ala Leu Tyr Asp Ala Ile Arg Ser Pro Glu
            435                 440                 445

Phe Gln Ser Ile Val Gln Thr Leu Lys Ala Met Pro Glu Tyr Gln Asp
            450                 455                 460

Leu Ile Gln Arg Leu Lys Asp Lys Gly Val Asp Val Asp His Phe Ile
465                 470                 475                 480

Glu Leu Ile Lys Lys Leu Phe Gly Leu Ser His
```

<210> SEQ ID NO 181
<211> LENGTH: 160
<212> TYPE: PRT
<213> ORGANISM: Betula pendula (Betula verrucosa)

<400> SEQUENCE: 181

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 182
<211> LENGTH: 160
<212> TYPE: PRT
<213> ORGANISM: Betula pendula (Betula verrucosa)

<400> SEQUENCE: 182

Met Gly Val Phe Asn Tyr Glu Thr Glu Ala Thr Ser Val Ile Pro Ala
1               5                   10                  15

Ala Arg Met Phe Lys Ala Phe Ile Leu Asp Gly Asp Lys Leu Val Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Asn Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Val Gly Asp Thr Leu
                85                  90                  95

Glu Lys Ile Ser Asn Glu Ile Lys Ile Val Ala Thr Pro Asp Gly Gly
            100                 105                 110

Cys Val Leu Lys Ile Ser Asn Lys Tyr His Thr Lys Gly Asn His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

```
<210> SEQ ID NO 183
<211> LENGTH: 133
<212> TYPE: PRT
<213> ORGANISM: Betula pendula (Betula verrucosa)

<400> SEQUENCE: 183

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130

<210> SEQ ID NO 184
<211> LENGTH: 263
<212> TYPE: PRT
<213> ORGANISM: Phleum pratense

<400> SEQUENCE: 184

Met Ala Ser Ser Ser Val Leu Leu Val Val Leu Phe Ala Val
1               5                   10                  15

Phe Leu Gly Ser Ala Tyr Gly Ile Pro Lys Val Pro Pro Gly Pro Asn
            20                  25                  30

Ile Thr Ala Thr Tyr Gly Asp Lys Trp Leu Asp Ala Lys Ser Thr Trp
        35                  40                  45

Tyr Gly Lys Pro Thr Gly Ala Gly Pro Lys Asp Asn Gly Gly Ala Cys
    50                  55                  60

Gly Tyr Lys Asp Val Asp Lys Pro Pro Phe Ser Gly Met Thr Gly Cys
65                  70                  75                  80

Gly Asn Thr Pro Ile Phe Lys Ser Gly Arg Gly Cys Gly Ser Cys Phe
                85                  90                  95

Glu Ile Lys Cys Thr Lys Pro Glu Ala Cys Ser Gly Glu Pro Val Val
            100                 105                 110

Val His Ile Thr Asp Asp Asn Glu Glu Pro Ile Ala Pro Tyr His Phe
        115                 120                 125

Asp Leu Ser Gly His Ala Phe Gly Ala Met Ala Lys Lys Gly Asp Glu
    130                 135                 140

Gln Lys Leu Arg Ser Ala Gly Glu Leu Glu Leu Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Tyr Val Asn Gly
            180                 185                 190

Asp Gly Asp Val Val Ala Val Asp Ile Lys Glu Lys Gly Lys Asp Lys
```

```
                195                 200                 205
Trp Ile Glu Leu Lys Glu Ser Trp Gly Ala Ile Trp Arg Ile Asp Thr
    210                 215                 220
Pro Asp Lys Leu Thr Gly Pro Phe Thr Val Arg Tyr Thr Thr Glu Gly
225                 230                 235                 240
Gly Thr Lys Thr Glu Ala Glu Asp Val Ile Pro Glu Gly Trp Lys Ala
                245                 250                 255
Asp Thr Ser Tyr Glu Ser Lys
                260

<210> SEQ ID NO 185
<211> LENGTH: 122
<212> TYPE: PRT
<213> ORGANISM: Phleum pratense

<400> SEQUENCE: 185

Met Ser Met Ala Ser Ser Ser Ser Leu Leu Ala Met Ala Val
1               5                   10                  15

Leu Ala Ala Leu Phe Ala Gly Ala Trp Cys Val Pro Lys Val Thr Phe
                20                  25                  30

Thr Val Glu Lys Gly Ser Asn Glu Lys His Leu Ala Val Leu Val Lys
            35                  40                  45

Tyr Glu Gly Asp Thr Met Ala Glu Val Glu Leu Arg Glu His Gly Ser
        50                  55                  60

Asp Glu Trp Val Ala Met Thr Lys Gly Glu Gly Val Trp Thr Phe
65                  70                  75                  80

Asp Ser Glu Glu Pro Leu Gln Gly Pro Phe Asn Phe Arg Phe Leu Thr
                85                  90                  95

Glu Lys Gly Met Lys Asn Val Phe Asp Asp Val Val Pro Glu Lys Tyr
            100                 105                 110

Thr Ile Gly Ala Thr Tyr Ala Pro Glu Glu
        115                 120

<210> SEQ ID NO 186
<211> LENGTH: 159
<212> TYPE: PRT
<213> ORGANISM: Malus domestica

<400> SEQUENCE: 186

Met Gly Val Tyr Thr Phe Glu Asn Glu Phe Thr Ser Glu Ile Pro Pro
1               5                   10                  15

Ser Arg Leu Phe Lys Ala Phe Val Leu Asp Ala Asp Asn Leu Ile Pro
                20                  25                  30

Lys Ile Ala Pro Gln Ala Ile Lys Gln Ala Glu Ile Leu Glu Gly Asn
            35                  40                  45

Gly Gly Pro Gly Thr Ile Lys Lys Ile Thr Phe Gly Glu Gly Ser Gln
        50                  55                  60

Tyr Gly Tyr Val Lys His Arg Ile Asp Ser Ile Asp Glu Ala Ser Tyr
65                  70                  75                  80

Ser Tyr Ser Tyr Thr Leu Ile Glu Gly Asp Ala Leu Thr Asp Thr Ile
                85                  90                  95

Glu Lys Ile Ser Tyr Glu Thr Lys Leu Val Ala Cys Gly Ser Gly Ser
            100                 105                 110

Thr Ile Lys Ser Ile Ser His Tyr His Thr Lys Gly Asn Ile Glu Ile
        115                 120                 125

Lys Glu Glu His Val Lys Val Gly Lys Glu Lys Ala His Gly Leu Phe
```

```
                130                 135                 140
Lys Leu Ile Glu Ser Tyr Leu Lys Asp His Pro Asp Ala Tyr Asn
145                 150                 155
```

<210> SEQ ID NO 187
<211> LENGTH: 96
<212> TYPE: PRT
<213> ORGANISM: Dactylis glomerata

<400> SEQUENCE: 187

```
Val Lys Val Thr Phe Lys Val Glu Lys Gly Ser Asp Pro Lys Lys Leu
1               5                   10                  15

Val Leu Asp Ile Lys Tyr Thr Arg Pro Gly Asp Thr Leu Ala Glu Val
                20                  25                  30

Glu Leu Arg Gln His Gly Ser Glu Glu Trp Glu Pro Leu Thr Lys Lys
            35                  40                  45

Gly Asn Leu Trp Glu Val Lys Ser Ser Lys Pro Leu Thr Gly Pro Phe
        50                  55                  60

Asn Phe Arg Phe Met Ser Lys Gly Gly Met Arg Asn Val Phe Asp Glu
65                  70                  75                  80

Val Ile Pro Thr Ala Phe Lys Ile Gly Thr Thr Tyr Thr Pro Glu Glu
                85                  90                  95
```

<210> SEQ ID NO 188
<211> LENGTH: 269
<212> TYPE: PRT
<213> ORGANISM: Phalaris aquatica

<400> SEQUENCE: 188

```
Met Met Lys Met Val Cys Ser Ser Ser Ser Ser Leu Leu Val Val
1               5                   10                  15

Ala Ala Leu Leu Ala Val Phe Val Gly Ser Ala Gln Gly Ile Ala Lys
                20                  25                  30

Val Pro Pro Gly Pro Asn Ile Thr Ala Glu Tyr Gly Asp Lys Trp Leu
            35                  40                  45

Asp Ala Lys Ser Thr Trp Tyr Gly Lys Pro Thr Gly Ala Gly Pro Lys
        50                  55                  60

Asp Asn Gly Gly Ala Cys Gly Tyr Lys Asp Val Asp Lys Ala Pro Phe
65                  70                  75                  80

Asn Gly Met Thr Gly Cys Gly Asn Thr Pro Ile Phe Lys Asp Gly Arg
                85                  90                  95

Gly Cys Gly Ser Cys Phe Glu Leu Lys Cys Ser Lys Pro Glu Ser Cys
            100                 105                 110

Ser Gly Glu Pro Ile Thr Val His Ile Thr Asp Asp Asn Glu Glu Pro
        115                 120                 125

Ile Ala Pro Tyr His Phe Asp Leu Ser Gly His Ala Phe Gly Ser Met
    130                 135                 140

Ala Lys Lys Gly Glu Glu Glu Asn Val Arg Gly Ala Gly Glu Leu Glu
145                 150                 155                 160

Leu Gln Phe Arg Arg Val Lys Cys Lys Tyr Pro Asp Gly Thr Lys Pro
                165                 170                 175

Thr Phe His Val Glu Lys Gly Ser Asn Pro Asn Tyr Leu Ala Leu Leu
            180                 185                 190

Val Lys Tyr Val Asp Gly Asp Gly Asp Val Val Ala Val Asp Ile Lys
        195                 200                 205

Glu Lys Gly Lys Asp Lys Trp Ile Glu Leu Lys Glu Ser Trp Gly Ala
```

Ile Trp Arg Ile Asp Thr Pro Asp Lys Leu Thr Gly Pro Phe Thr Val
225                 230                 235                 240

Arg Tyr Thr Thr Glu Gly Gly Thr Lys Ala Glu Phe Glu Asp Val Ile
                245                 250                 255

Pro Glu Gly Trp Lys Ala Asp Thr His Asp Ala Ser Lys
            260                 265

<210> SEQ ID NO 189
<211> LENGTH: 246
<212> TYPE: PRT
<213> ORGANISM: Cynodon dactylon

<400> SEQUENCE: 189

Ala Ile Gly Asp Lys Pro Gly Pro Asn Ile Thr Ala Thr Tyr Gly Ser
1               5                   10                  15

Lys Trp Leu Glu Ala Arg Ala Thr Phe Tyr Gly Ser Asn Pro Arg Gly
            20                  25                  30

Ala Ala Pro Asp Asp His Gly Gly Ala Cys Gly Tyr Lys Asp Val Asp
        35                  40                  45

Lys Pro Pro Phe Asp Gly Met Thr Ala Cys Gly Asn Glu Pro Ile Phe
    50                  55                  60

Lys Asp Gly Leu Gly Cys Arg Ala Cys Tyr Glu Ile Lys Cys Lys Glu
65                  70                  75                  80

Pro Val Glu Cys Ser Gly Glu Pro Val Leu Val Lys Ile Thr Asp Lys
                85                  90                  95

Asn Tyr Glu His Ile Ala Ala Tyr His Phe Asp Leu Ser Gly Lys Ala
            100                 105                 110

Phe Gly Ala Met Ala Lys Lys Gly Gln Glu Asp Lys Leu Arg Lys Ala
        115                 120                 125

Gly Glu Leu Thr Leu Gln Phe Arg Arg Val Lys Cys Lys Tyr Pro Ser
    130                 135                 140

Gly Thr Lys Ile Thr Phe His Ile Glu Lys Gly Ser Asn Asp His Tyr
145                 150                 155                 160

Leu Ala Leu Leu Val Lys Tyr Ala Ala Gly Asp Gly Asn Ile Val Ala
                165                 170                 175

Val Asp Ile Lys Pro Arg Asp Ser Asp Glu Phe Ile Pro Met Lys Ser
            180                 185                 190

Ser Trp Gly Ala Ile Trp Arg Ile Asp Pro Lys Lys Pro Leu Lys Gly
        195                 200                 205

Pro Phe Ser Ile Arg Leu Thr Ser Glu Gly Gly Ala His Leu Val Gln
    210                 215                 220

Asp Asp Val Ile Pro Ala Asn Trp Lys Pro Asp Thr Val Tyr Thr Ser
225                 230                 235                 240

Lys Leu Gln Phe Gly Ala
                245

<210> SEQ ID NO 190
<211> LENGTH: 214
<212> TYPE: PRT
<213> ORGANISM: Bos primigenius

<400> SEQUENCE: 190

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn

```
                20                  25                  30
Glu Asn Leu Leu Arg Phe Phe Val Ala Pro Phe Pro Glu Val Phe Gly
            35                  40                  45
Lys Glu Lys Val Asn Glu Leu Ser Lys Asp Ile Gly Ser Glu Ser Thr
 50                  55                  60
Glu Asp Gln Ala Met Glu Asp Ile Lys Gln Met Glu Ala Glu Ser Ile
 65                  70                  75                  80
Ser Ser Ser Glu Glu Ile Val Pro Asn Ser Val Glu Gln Lys His Ile
                85                  90                  95
Gln Lys Glu Asp Val Pro Ser Glu Arg Tyr Leu Gly Tyr Leu Glu Gln
            100                 105                 110
Leu Leu Arg Leu Lys Lys Tyr Lys Val Pro Gln Leu Glu Ile Val Pro
        115                 120                 125
Asn Ser Ala Glu Glu Arg Leu His Ser Met Lys Glu Gly Ile His Ala
    130                 135                 140
Gln Gln Lys Glu Pro Met Ile Gly Val Asn Gln Glu Leu Ala Tyr Phe
145                 150                 155                 160
Tyr Pro Glu Leu Phe Arg Gln Phe Tyr Gln Leu Asp Ala Tyr Pro Ser
                165                 170                 175
Gly Ala Trp Tyr Tyr Val Pro Leu Gly Thr Gln Tyr Thr Asp Ala Pro
            180                 185                 190
Ser Phe Ser Asp Ile Pro Asn Pro Ile Gly Ser Glu Asn Ser Glu Lys
        195                 200                 205
Thr Thr Met Pro Leu Trp
    210

<210> SEQ ID NO 191
<211> LENGTH: 142
<212> TYPE: PRT
<213> ORGANISM: Bos primigenius

<400> SEQUENCE: 191

Met Met Ser Phe Val Ser Leu Leu Val Gly Ile Leu Phe His Ala
 1               5                  10                  15
Thr Gln Ala Glu Gln Leu Thr Lys Cys Glu Val Phe Arg Glu Leu Lys
                20                  25                  30
Asp Leu Lys Gly Tyr Gly Gly Val Ser Leu Pro Glu Trp Val Cys Thr
            35                  40                  45
Thr Phe His Thr Ser Gly Tyr Asp Thr Gln Ala Ile Val Gln Asn Asn
 50                  55                  60
Asp Ser Thr Glu Tyr Gly Leu Phe Gln Ile Asn Asn Lys Ile Trp Cys
 65                  70                  75                  80
Lys Asp Asp Gln Asn Pro His Ser Ser Asn Ile Cys Asn Ile Ser Cys
                85                  90                  95
Asp Lys Phe Leu Asp Asp Asp Leu Thr Asp Asp Ile Met Cys Val Lys
            100                 105                 110
Lys Ile Leu Asp Lys Val Gly Ile Asn Tyr Trp Leu Ala His Lys Ala
        115                 120                 125
Leu Cys Ser Glu Lys Leu Asp Gln Trp Leu Cys Glu Lys Leu
    130                 135                 140

<210> SEQ ID NO 192
<211> LENGTH: 386
<212> TYPE: PRT
<213> ORGANISM: Gallus gallus
```

<400> SEQUENCE: 192

```
Met Gly Ser Ile Gly Ala Ala Ser Met Glu Phe Cys Phe Asp Val Phe
1               5                   10                  15
Lys Glu Leu Lys Val His His Ala Asn Glu Asn Ile Phe Tyr Cys Pro
            20                  25                  30
Ile Ala Ile Met Ser Ala Leu Ala Met Val Tyr Leu Gly Ala Lys Asp
        35                  40                  45
Ser Thr Arg Thr Gln Ile Asn Lys Val Val Arg Phe Asp Lys Leu Pro
    50                  55                  60
Gly Phe Gly Asp Ser Ile Glu Ala Gln Cys Gly Thr Ser Val Asn Val
65                  70                  75                  80
His Ser Ser Leu Arg Asp Ile Leu Asn Gln Ile Thr Lys Pro Asn Asp
                85                  90                  95
Val Tyr Ser Phe Ser Leu Ala Ser Arg Leu Tyr Ala Glu Glu Arg Tyr
            100                 105                 110
Pro Ile Leu Pro Glu Tyr Leu Gln Cys Val Lys Glu Leu Tyr Arg Gly
        115                 120                 125
Gly Leu Glu Pro Ile Asn Phe Gln Thr Ala Ala Asp Gln Ala Arg Glu
130                 135                 140
Leu Ile Asn Ser Trp Val Glu Ser Gln Thr Asn Gly Ile Ile Arg Asn
145                 150                 155                 160
Val Leu Gln Pro Ser Ser Val Asp Ser Gln Thr Ala Met Val Leu Val
                165                 170                 175
Asn Ala Ile Val Phe Lys Gly Leu Trp Glu Lys Ala Phe Lys Asp Glu
            180                 185                 190
Asp Thr Gln Ala Met Pro Phe Arg Val Thr Glu Gln Glu Ser Lys Pro
        195                 200                 205
Val Gln Met Met Tyr Gln Ile Gly Leu Phe Arg Val Ala Ser Met Ala
210                 215                 220
Ser Glu Lys Met Lys Ile Leu Glu Leu Pro Phe Ala Ser Gly Thr Met
225                 230                 235                 240
Ser Met Leu Val Leu Leu Pro Asp Glu Val Ser Gly Leu Glu Gln Leu
                245                 250                 255
Glu Ser Ile Ile Asn Phe Glu Lys Leu Thr Glu Trp Thr Ser Ser Asn
            260                 265                 270
Val Met Glu Glu Arg Lys Ile Lys Val Tyr Leu Pro Arg Met Lys Met
        275                 280                 285
Glu Glu Lys Tyr Asn Leu Thr Ser Val Leu Met Ala Met Gly Ile Thr
290                 295                 300
Asp Val Phe Ser Ser Ala Asn Leu Ser Gly Ile Ser Ser Ala Glu
305                 310                 315                 320
Ser Leu Lys Ile Ser Gln Ala Val His Ala Ala His Ala Glu Ile Asn
                325                 330                 335
Glu Ala Gly Arg Glu Val Val Gly Ser Ala Glu Ala Gly Val Asp Ala
            340                 345                 350
Ala Ser Val Ser Glu Glu Phe Arg Ala Asp His Pro Phe Leu Phe Cys
        355                 360                 365
Ile Lys His Ile Ala Thr Asn Ala Val Leu Phe Phe Gly Arg Cys Val
370                 375                 380
Ser Pro
385
```

<210> SEQ ID NO 193

```
<211> LENGTH: 147
<212> TYPE: PRT
<213> ORGANISM: Gallus gallus

<400> SEQUENCE: 193

Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145

<210> SEQ ID NO 194
<211> LENGTH: 187
<212> TYPE: PRT
<213> ORGANISM: Equus caballus

<400> SEQUENCE: 194

Met Lys Leu Leu Leu Leu Cys Leu Gly Leu Ile Leu Val Cys Ala Gln
1               5                   10                  15

Gln Glu Glu Asn Ser Asp Val Ala Ile Arg Asn Phe Asp Ile Ser Lys
            20                  25                  30

Ile Ser Gly Glu Trp Tyr Ser Ile Phe Leu Ala Ser Asp Val Lys Glu
        35                  40                  45

Lys Ile Glu Glu Asn Gly Ser Met Arg Val Phe Val Asp Val Ile Arg
    50                  55                  60

Ala Leu Asp Asn Ser Ser Leu Tyr Ala Glu Tyr Gln Thr Lys Val Asn
65                  70                  75                  80

Gly Glu Cys Thr Glu Phe Pro Met Val Phe Asp Lys Thr Glu Glu Asp
                85                  90                  95

Gly Val Tyr Ser Leu Asn Tyr Asp Gly Tyr Asn Val Phe Arg Ile Ser
            100                 105                 110

Glu Phe Glu Asn Asp Glu His Ile Ile Leu Tyr Leu Val Asn Phe Asp
        115                 120                 125

Lys Asp Arg Pro Phe Gln Leu Phe Glu Phe Tyr Ala Arg Glu Pro Asp
    130                 135                 140

Val Ser Pro Glu Ile Lys Glu Glu Phe Val Lys Ile Val Gln Lys Arg
145                 150                 155                 160

Gly Ile Val Lys Glu Asn Ile Ile Asp Leu Thr Lys Ile Asp Arg Cys
                165                 170                 175

Phe Gln Leu Arg Gly Asn Gly Val Ala Gln Ala
            180                 185
```

<210> SEQ ID NO 195
<211> LENGTH: 228
<212> TYPE: PRT
<213> ORGANISM: Equus caballus

<400> SEQUENCE: 195

Met Leu Lys Val Ser Cys Leu Phe Val Leu Leu Cys Gly Leu Leu Val
1               5                   10                  15

Pro Ser Ser Ala Gln Gln Ile Pro Pro Glu Val Ser Ser Gln Ile Thr
            20                  25                  30

Asp Ala Leu Thr Gln Gly Leu Leu Asp Gly Asn Phe Leu Ser Leu Leu
        35                  40                  45

Asn Ala Ile Asn Leu Glu Gly Leu Leu Asn Thr Ile Leu Asp Gln Val
    50                  55                  60

Thr Gly Leu Leu Asn Ile Leu Val Gly Pro Leu Gly Pro Ser Asp
65                  70                  75                  80

Ala Glu Ile Lys Leu Gln Asp Thr Arg Leu Leu Gln Leu Ser Leu Glu
                85                  90                  95

Phe Ser Pro Asp Ser Lys Gly Ile Asp Ile Trp Ile Pro Leu Glu Leu
            100                 105                 110

Ser Val Tyr Leu Lys Leu Leu Ile Leu Glu Pro Leu Thr Leu Tyr Val
        115                 120                 125

Arg Thr Asp Ile Arg Val Gln Leu Arg Leu Glu Ser Asp Glu Asp Gly
    130                 135                 140

Lys Tyr Arg Leu Ala Phe Gly His Cys Ser Leu Leu Pro Arg Ala Ile
145                 150                 155                 160

Glu Leu Gln Ser Gly Asn Pro Leu Ser Leu Pro Val Asn Ala Val Leu
                165                 170                 175

Gly Thr Ile Glu Asn Ala Leu Gly Asn Phe Ile Thr Glu Asp Leu Gly
            180                 185                 190

Ala Gly Leu Cys Pro Thr Leu Asn Ser Leu Val Ser Asn Leu Asp Leu
        195                 200                 205

Gln Leu Val Asn Asn Leu Ile Asn Leu Ile Leu Asp Arg Ala Asn Val
    210                 215                 220

Asp Leu Ser Val
225

<210> SEQ ID NO 196
<211> LENGTH: 558
<212> TYPE: DNA
<213> ORGANISM: Artificial Sequence
<220> FEATURE:
<223> OTHER INFORMATION: Nucleotide sequence encoding pelB-CD3(VL)-
      FLAG-BirA-U266Ant-6His

<400> SEQUENCE: 196
atgaaatacc tgctgccgac cgctgctgct ggtctgctgc tcctcgctgc ccagccggcg      60
atggccgaca ttcagctgac ccagtctcca gcaatcatgt ctgcatctcc aggggagaag     120
gtcaccatga cctgcagagc cagttcaagt gtaagttaca tgaactggta ccagcagaag     180
tcaggcacct cccccaaaag atggatttat gacacatcca agtggcttc tggagtccct     240 tatcgcttca gtggcagtgg gtctgggacc tcatactctc tcacaatcag cagcatggag     300
gctgaagatg ctgccactta ttactgccaa cagtggagta gtaacccgct cacgttcggt     360
gctgggacca agctggagct gaaatccgga ggtggtggat ccgactacaa ggatgacgat     420

```
gacaaaggcg gcggcctgaa cgatattttt gaagcgcaga aaattgaatg gcatctgagc    480
ccgcatctgc tgtgggatct gtttcgcgtg ggcctgccgg gcgcggcggg cggcggccat    540
catcaccatc atcattag                                                  558
```

<210> SEQ ID NO 197
<211> LENGTH: 185
<212> TYPE: PRT
<213> ORGANISM: Artificial Sequence
<220> FEATURE:
<223> OTHER INFORMATION: pelB-CD3(VL) - FLAG-BirA-U266Ant-6His

<400> SEQUENCE: 197

```
Met Lys Tyr Leu Leu Pro Thr Ala Ala Ala Gly Leu Leu Leu Leu Ala
1               5                   10                  15

Ala Gln Pro Ala Met Ala Asp Ile Gln Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Ser Val Ser Tyr Met Asn Trp Tyr Gln Gln Lys Ser Gly Thr Ser
    50                  55                  60

Pro Lys Arg Trp Ile Tyr Asp Thr Ser Lys Val Ala Ser Gly Val Pro
65                  70                  75                  80

Tyr Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

Ser Gly Gly Gly Gly Ser Asp Tyr Lys Asp Asp Asp Lys Gly Gly
    130                 135                 140

Gly Leu Asn Asp Ile Phe Glu Ala Gln Lys Ile Glu Trp His Leu Ser
145                 150                 155                 160

Pro His Leu Leu Trp Asp Leu Phe Arg Val Gly Leu Pro Gly Ala Ala
                165                 170                 175

Gly Gly Gly His His His His His His
            180                 185
```

<210> SEQ ID NO 198
<211> LENGTH: 18
<212> TYPE: PRT
<213> ORGANISM: Artificial Sequence
<220> FEATURE:
<223> OTHER INFORMATION: Alternative linker

<400> SEQUENCE: 198

```
Gly Glu Gly Thr Ser Thr Gly Ser Gly Gly Ser Gly Gly Ser Gly Gly
1               5                   10                  15

Ala Asp
```

<210> SEQ ID NO 199
<211> LENGTH: 4
<212> TYPE: PRT
<213> ORGANISM: Artificial Sequence
<220> FEATURE:
<223> OTHER INFORMATION: Linker sequence
<220> FEATURE:
<221> NAME/KEY: MISC_FEATURE
<222> LOCATION: (1)..(4)
<223> OTHER INFORMATION: sequence may be repeated 1, 2, 3, 4, 5 or 6
      times

```
<400> SEQUENCE: 199

Gly Gly Gly Ser
1

<210> SEQ ID NO 200
<211> LENGTH: 5
<212> TYPE: PRT
<213> ORGANISM: Artificial Sequence
<220> FEATURE:
<223> OTHER INFORMATION: Linker sequence
<220> FEATURE:
<221> NAME/KEY: MISC_FEATURE
<222> LOCATION: (1)..(5)
<223> OTHER INFORMATION: sequence may be repeated 1, 2, 3, 4, 5 or 6
      times

<400> SEQUENCE: 200

Gly Gly Gly Gly Ser
1               5

<210> SEQ ID NO 201
<211> LENGTH: 8
<212> TYPE: PRT
<213> ORGANISM: Artificial Sequence
<220> FEATURE:
<223> OTHER INFORMATION: CMV pp65 derived peptide

<400> SEQUENCE: 201

Thr Pro Arg Val Thr Gly Gly Gly
1               5
```